US009623066B2

(12) United States Patent
Hayer et al.

(10) Patent No.: US 9,623,066 B2
(45) Date of Patent: *Apr. 18, 2017

(54) COMPOSITIONS AND METHODS TO INHIBIT KIDNEY STONE GROWTH

(71) Applicant: KIDNEY STONE LABORATORIES, INC., Fort Lauderdale, FL (US)

(72) Inventors: Gregory K. Hayer, Fort Lauderdale, FL (US); Brendan Magrab, Westfield, NJ (US); Henry R. Wolfe, Jr., Glenmoore, PA (US)

(73) Assignee: KIDNEY STONE LABORATORIES, INC., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/266,464

(22) Filed: Sep. 15, 2016

(65) Prior Publication Data

US 2017/0065658 A1 Mar. 9, 2017

Related U.S. Application Data

(60) Division of application No. 15/059,644, filed on Mar. 3, 2016, now Pat. No. 9,492,491, which is a continuation-in-part of application No. 14/960,692, filed on Dec. 7, 2015, which is a continuation of application No. 14/845,612, filed on Sep. 4, 2015, now Pat. No. 9,233,135.

(51) Int. Cl.
| | |
|---|---|
| *A61K 36/00* | (2006.01) |
| *A61K 36/88* | (2006.01) |
| *A61K 31/194* | (2006.01) |
| *A61K 33/06* | (2006.01) |
| *A61K 31/6615* | (2006.01) |
| *A61K 31/4415* | (2006.01) |
| *A61K 9/00* | (2006.01) |
| *A61K 9/48* | (2006.01) |

(52) U.S. Cl.
CPC ............ *A61K 36/88* (2013.01); *A61K 9/0053* (2013.01); *A61K 9/48* (2013.01); *A61K 31/194* (2013.01); *A61K 31/4415* (2013.01); *A61K 31/6615* (2013.01); *A61K 33/06* (2013.01)

(58) Field of Classification Search
None
See application file for complete search history.

(56) References Cited

U.S. PATENT DOCUMENTS

| | | | | |
|---|---|---|---|---|
| 2013/0302448 A1* | 11/2013 | Parc | ........................ | A61K 8/55 |
| | | | | 424/725 |
| 2013/0337057 A1* | 12/2013 | Patankar | .............. | A61K 36/185 |
| | | | | 424/451 |

FOREIGN PATENT DOCUMENTS

RO 80051 A2 * 10/1982

OTHER PUBLICATIONS

"Complications from kidney stone treatments are common, costly"; Science Daily;Duke University Medical Center;Apr. 2014; http://www.sciencedaily.com/releases/2014/04/140428094257.htm [retrieved on Aug. 19, 2015]; 2 pages.
"6 Easy Ways to Prevent Kidney Stones"; National Kidney Foundation; 2015; https://www.kidney.org/atoz/content/kidneystones_prevent [retrieved on Aug. 19, 2015]; 2 pages.
"Diet for Kidney Stone Prevention"; NIH; Feb. 2013,The National Institute of Diabetes and Digestive and Kidney Diseases, NIH Publication No. 13-6425, 8 pages.
"How Can Kidney Stones Be Prevented?"; The Johns Hopkins School of Medicine; The James Buchanan Brady Urological Institute;Accessed Aug. 31, 2015; http://urology.jhu.edu/kidney/STONESprevention.php; 3 pages.
Allie-Hamdulay; Prophylactic and therapeutic properties of a sodium citrate preparation in the management of calcium oxalate urolithiasis: randomized, placebo-controlled trial; Urol Res;vol. 33; 2005; pp. 116-124.
Barcelo et al.; "Randomized Double-Blind Study of Potassium Citrate in Idiopathic Hypocitraturic Calcium Nephrolithiasis"; The Journal of Urology, vol. 150; 1993; pp. 1761-1764.
Chow et al.; "Citrate inhibits growth of residual fragments in an in vitro model of calcium oxalate renal stones"; Kidney International, vol. 65; 2004; pp. 1724-1730.
Chow et al.;"A stone farm: development of a method for simultaneous production of multiple calcium oxalate stones in vitro"; Urol Res, vol. 32; 2004; pp. 55-60.
Coe (2015); "Citrate to Prevent Calcium and Uric Acid Stones"; University of Chicago Kidney Stone Evaluation and Treatment Program; http://kidneystones.uchicago.edu/citrate-to-prevent-stones/ [retrieved on Aug. 19, 2015];8 pages.
Coe et al.; "The Pathogenesis and Treatment of Kidney Stones"; N Engl J Med, vol. 327; 1992; pp. 1141-1152 (abstract only).
Costa-Bauza et al.; "Factors affecting calcium oxalate dihydrate fragmented calculi regrowth" BMC Urology, vol. 6, No. 16, 2006; 7 pages.
Ettinger et al.; "Potassium-magnesium citrate is an effective prophylaxis against recurrent calcium oxalate nephrolithiasis"; J Urol., vol. 158; 1997; pp. 2069-2073.
Fabris et al.; "Long-Term Treatment with Potassium Citrate and Renal Stones in Medullary Sponge Kidney"; Clin J Am Soc Nephrol., vol. 5, No. 9; 2010; pp. 1663-1668.
Forbes et al.; "Effects of Dietary Phytate, Calcium and Magnesium Levels on Zinc Bioavailability to Rats"; J. Nutr., vol. 114; 1984; pp. 1421-1425.
Foster et al.; "Emergency Department Visits and Hospital Admissions for Kidney Stone Disease,2009";Healthcare Cost and Utilization Project; Statistical Brief # 139, Jul. 2012, Agency for Healthcare Research and Quality, Rockville, MD. Available at http://www.hcup-us.ahrq.gov/reports/statbriefs/sb139.pdf [retrieved on Aug. 19, 2015];10 pages.

(Continued)

*Primary Examiner* — Qiuwen Mi
(74) *Attorney, Agent, or Firm* — Cantor Colburn LLP

(57) ABSTRACT

An oral dosage form or plurality of oral dosage forms comprising as active ingredients combinations of citric acid, magnesium citrate, phytin, pyridoxine, and musa is disclosed. The oral dosage form(s) is useful for inhibiting calcium oxalate crystal growth and for treating or inhibiting growth of kidney stones. Methods of inhibiting calcium oxalate crystal growth and of treating or preventing kidney stones are also disclosed.

26 Claims, 78 Drawing Sheets

(56) References Cited

OTHER PUBLICATIONS

Gershoff et al.; "Effect of Daily MgO and Vitamin B6 Administration to Patients with Recurring Calcium Oxalate Kidney Stones"The American Journal of Clinical Nutrition; vol. 20, No. 5; 1967; pp. 393-399.

Goldberg et al. ; "Urine citrate and renal stone disease"; Canadian Medical Association Journal; vol. 141, No. 3 ; 1989; pp. 217-221.

Grases et al.; "Effects of Phytic Acid on Renal Stone Formation in Rats";Scandinavian Journal of Urology and Nephrology ; vol. 32, No. 4;1998; pp. 261-265 (Abstract Only).

Grases et al.; "Phytate (IP6) is a Powerful Agent for Preventing Calcifications in Biological Fluids: Usefulness in Renal Lithiasis Treatment";Anticancer Research, vol. 19; 1999; pp. 3717-3722.

Grases et al.; "Study of Potassium Phytate Effects on Decreasing Urinary Calcium in Rats"; Urol Int; vol. 72; 2004; pp. 237-243.

Grases et al.;"Phytate acts as an inhibitor in formation of renal calculi"; Frontiers in Bioscience, vol. 12; 2007; pp. 2580-2587.

Grubbs; "Procedures for Detecting Outlying Observations in Samples"; Technometrics; vol. 11, No. 1; Feb. 1969; 22 pages.

Hess; "Citrate determines calcium oxalate crystallization kinetics and crystal morphology-studies in the presence of Tamm-Horsfall protein of a healthy subject and a severely recurrent calcium stone former"; Nephrol Dial Transplant, vol. 15; 2000; 366-374.

Hughes et al.; "Diet and calcium stones"; Can Med Assoc J, vol. 146, No. 2; 1992; pp. 137-143.

Jahnen et al.; "Dietary fibre: the effectiveness of a high bran intake in reducing renal calcium excretion"; Urol Res; vol. 20, No. 1; 1992; pp. 3-6 (Abstract Only).

Johri et al.; "An Update and Practical Guide to Renal Stone Management";Nephron Clinical Practice,vol. 116; published online Jul. 2010; pp. 159-171.

Leumann et al.; "Efficacy of oral citrate administration in primary hyperoxaluria" Nephrol Dial Transplant, vol. 10, No. 8; 1995; pp. 14-16.

Lojanapiwat et al.; "Alkaline citrate reduces stone recurrence and regrowth after shockwave lithotripsy and percutaneous nephrolithotomy"; International Braz J Urol, vol. 37, No. 5; Sep.-Oct. 2011; pp. 611-616.

López-González; "Phytate (myo-Inositol Hexaphosphate) and Risk Factors for Osteoporosis"; J Med Food,vol. 11, No. 1; 2008; pp. 747-752.

Massey; "Dietary influences on urinary oxalate and risk of kidney stones"; Frontiers in Bioscience;vol. 8, Sections 584-594; 2003; 8 pages.

Mitwalli et al. ; "Control of hyperoxaluria with large doses of pyridoxine in patients with kidney stones"; Int Urol Nephrol., vol. 20, No. 4; 1988; pp. 353-359 (Abstract Only).

Monico et al.; "Pyridoxine effect in type I primary hyperoxaluria is associated with the most common mutant allele"; Kidney International, vol. 67; 2005; pp. 1704-1709.

Nakagawa et al. ;"Purification and Characterization of a Calcium Oxalate Monohydrate Crystal Growth Inhibitorfr om Human Kidney Tissue Culture Medium"; The Journal of Biological Chemistry, vol. 256, No. 8; 1981; pp. 3936-3944.

Ortiz-Alvarado; "Pyridoxine and Dietary Counseling for the Management of Idiopathic Hyperoxaluria in Stone-forming Patients"; Urology, vol. 77, No. 5; May 2011; pp. 1054-1058-(Abstract Only).

Pak et al.; "Long-Term Treatment of Calcium Nephrolithiasis With Potassium Citrate"; The Journal of Urology, vol. 134; 1985; pp. 11-19.

Penniston; "Citric Acid and Kidney Stones"; Department of Clinical Nutrition Services, UW Hospital and Clinics; Accessed Aug. 31, 2015;https://www.uwhealth.org/files/uwhealth/docs/pdf/kidney_citric_acid.pdf; 2 pages.

Qiu et al.; Molecular modulation of calcium oxalate crystallization by osteopontin and citrate; P.N.A.S, vol. 101, No. 7; 2004; pp. 1811-1815.

Rao et al.; "In-vitro Chemodissolution of Urinary Stones by Some Chelating Natural Acids"; Asian Journal of Chemistry, vol. 16, No. 1; 2004; pp. 59-66.

Riley et al.; "Effect of Magnesium on Calcium and Oxalate Ion Binding"; J Endourol., vol. 27, No. 12; Dec. 2013; pp. 1487-1492.

Scales et al.; "Prevalence of Kidney Stones in the United States"; European Urology, vol. 62; 2012; pp. 160-165.

Shang et al.; "Concave Urinary Crystallines: Direct Evidence of Calcium Oxalate Crystals Dissolution by Citrate In Vivo"; Bioinorg Chem Appl., DOI: 10.1155/2013/637617[retrieved Aug. 19, 2015]; 2013 (Abstract Only).

Smith; "Application of Physical, Chemical, and Metabolic Factors to the Management of Urolithiasis"; in Urolithiasis Research; Fleisch, H (Ed); Springer US, 1976; pp. 199-211(Abstract Only).

Soygür; "Effect of potassium citrate therapy on stone recurrence and residual fragments after shockwave lithotripsy in lower caliceal calcium oxalate urolithiasis: a randomized controlled trial"; J Endourol; vol. 16, No. 3; Apr. 2002; 7 pages.

Tiselius; "Epidemiology and medical management of stone disease"; BJU International, vol. 91, Issue 8; 2003; pp. 758-767.

Tomson; "Prevention of recurrent calcium stones: a rational approach"; British Journal of Urology, vol. 76; 1995; 419-424 (Abstract Only).

Türk et al.; Guidelines on Urolithiasis; European Association of Urology; 2014; [retrieved Aug. 19, 2015 from http://uroweb.org/wp-content/uploads/22-Urolithiasis_LR.pdf; 98 pages.

Watts et al.; "Studies on Some Possible Biochemical Treatments of Primary Hyperoxaluria"; QJM (1979) 48 (2):259-272 DOI: http://dx.doi.org/ 259-272 Published Online Apr. 1, 1979(Abstract Only).

Yasui et al.; "Effects of citrate on renal stone formation and osteopontin expression in rat urolithiasis model"; Urol Res, vol. 29; 2001; pp. 50-56 (Only pp. 50-51).

"Highlights of Prescribing Information:Urocit-K (Potassium Citrate)";Mission Pharmacal Company; Dec. 2009; 2 pages.

"Kidney stones";Magnesium online resource center;2007-2008;[retrieved Aug. 19, 2015 from http://www.mg12.info/articles/kidney-stones.html]; 2 pages.

Abirami J et al.; "Evaluation of Toxicity Profiles of *Musa paradisiaca* L (Pseudostem) Juice"; International Journal of Pharmacy and Pharmaceutical Sciences; vol. 6, Sup. 1; 2014; pp. 9-11.

Devi et al.; "Biochemical Effects in Normal and Stone Forming Rats Treated With the Ripe Kernel Juice of Plantain (*Musa Paradisiaca*)"; Ancient Science of Life, vol. No. XII,Nos. 3 & 4; 1993; pp. 451-461.

Duan; "Changes in urinary nanocrystallites in calcium oxalate stone formers before and after potassium citrate intake"; International Journal of Nanomedicine, vol. 8; 2013; pp. 909-918.

Ebisuno et al.; "Results of long-term rice bran treatment on stone recurrence in hypercalciuric patients"; Br J Urol.; vol. 67, No. 3; 1991; pp. 237-240 (Abstract Only).

Ebisuno et al.; "Rice-bran Treatment for Calcium Stone Formers with Idiopathic Hypercalciuria"; British Journal of Urology; vol. 58, No. 6; 1986; pp. 592-595 (Abstract Only).

Grases et al.; "Influence of Concomitant Food Intake on the Excretion of Orally Administered myo-Inositol Hexaphosphate in Humans"; J Med Food vol. 9, No. 1; 2006; pp. 72-76.

Jha U et al.;"Pharmacological Screening of Musa Paradisica Linn Against Ethylene Glycol Induced Renal Calculi"; International Journal of Research in Ayurveda & Pharmacy, vol. 2, No. 3; 2011; pp. 995-998.

Kalpana et al. ; "Inhibition of Calcium Oxalate Crystallization in Vitro by Extract of Banana Cultivar Monthan"; International Journal of Pharmacy and Pharmaceutical Sciences, vol. 5, No. 4; 2013; pp. 349-653.

Khan et al.;"Antiurolithic activity of Origanum vulgare is mediated through multiple pathways"; BMC Complementary and Alternative Medicine; vol. 11, No. 96; 2011; 16 pages.

Lindberg et al.; "Magnesium Bioavailability from Magnesium Citrate and Magnesium Oxide"; Journal of the American College of Nutrition, vol. 9, No. 1; 1990; pp. 48-55.

Massey; "Magnesium therapy for nephrolithiasis"; Magnesium Research, vol. 18, No. 2; 2005; pp. 123-126.

(56) References Cited

OTHER PUBLICATIONS

McNally et al.; "Empiric use of potassium citrate reduces kidney-stone incidence with the ketogenic diet";Pediatrics; vol. 124, No. 2; Aug. 2009; pp. 300-304 (Abstract Only).
Ogawa et al.; "Effects of sodium citrate, potassium citrate, and citric acid in preventing experimental calcium oxalate urolithiasis in rats"; Acta Urol. Jpn.; vol. 33, No. 11; 1987; pp. 1772-1777.
Patankar et al.;"A Prospective,Randomized,Controlled Study to Evaluate the Efficacy & Tolerability of Ayurvedic Formulation Varuna and Banana Stem" in the Management of Urinary Stones;J. of Alternative & Complementary Medicine; vol. 14, No. 10;2008;4pgs.
Pillai;"The Core of the Pseudostem of Musa in the Treatment of Urinary Stones"; Ancient Science of Life; vol. No. XV No. 1; 1995; pp. 2-6.
Ponnambalam et al.;ICP-MS Technique for Quantification of Potassium & Sodium in Spray-Dried Extract of Shoot Juice of Banana Plant (*Musa Balbisiana*) Responsible for Anti-Urolithiatic & Diuretic Activity;Int. J. Med. Chem.& Analys,vol. 4,No. 3;2014;p. 170-174.
Poonguzhali PK et al.; "The influence of banana stem extract on urinary risk factors for stones in normal and hyperoxaluric rats"; Br J Urol., vol. 74, No. 1; Jul. 1994; pp. 23-25 (Abstract Only ).
Prasobh G R et al.; "A Study on the Use of *Musa* Species in the Management of Renal Calculi"; Asian Journal of Pharmaceutical and Clinical Research; vol. 7, No. 3; 2014; pp. 123-125.
Prasobh GR et al.; "Effect of MUSA Tablet on Ethylene Glycol-Induced Urolithiasis in Rats" ;International Journal of Research in Pharmaceutical and Biomedical Sciences; vol. 3, No. 3; Jul.-Sep. 2012; pp. 1251-1255.
Prieto et al.; "Effects of Mediterranean diets with low and high proportions of phytate-rich foods on the urinary phytate excretion"; Eur J Nutr;DOI 10.1007/s00394-009-0087-x; Published online Jan. 2010; 6 pages.
Rodgers; "Therapeutic action of citrate in urolithiasis explained by chemical speciation: increase in pH is the determinant factor"; Nephrol Dial Transplant; vol. 21; 2006; pp. 361-369.
Shah et al.; "Antiurolithiatic and antioxidant activity of Hordeum vulgare seeds on ethylene glycol-induced urolithiasis in rats"; Indian J Pharmacol; vol. 44, No. 6; Nov.-Dec. 2012; pp. 672-677.
Taylor et al.; "Dietary Factors and the Risk of Incident Kidney Stones in Men: New Insights after 14 Years of Follow-up"; J Am Soc Nephrol, vol. 15; 2004; pp. 3225-3232.
Thirumala et al.;"Evalution of anti urolithiatic activity of aqueous extract of stem core of Musa paradisiaca againest ethylene glycol and ammonium chloride induced urolithiasis on wistar rats";Indian J. of Res. in Pharm. & Bio.; vol. 1, No. 3;2013; p. 866-868.
Xu et al.; "Kidney Stones: an Update on Current Pharmacological Management and Future Directions"; Expert Opin Pharmacother, vol. 14, No. 4; Mar. 2013; 435-447.
Zerwekh et al.; "Reduction of renal stone risk by potassium-magnesium citrate during 5 weeks of bed rest"; J Urol., vol. 177, No. 6; Jun. 2007; pp. 2179-2184 (Abstract Only).
Prasobh et al.; "A Study on the Use of *Musa* Species in the Management of Renal Calculi"; Asian Journal of Pharmaceutical and Clinical Research, vol. 7, Issue 3, 2014, pp. 123-125.

* cited by examiner

COMPOSITIONS AND METHODS TO INHIBIT KIDNEY STONE GROWTH

CROSS-REFERENCE TO RELATED APPLICATIONS

This application is a divisional of U.S. application Ser. No. 15/059,644, filed Mar. 3, 2016 which is a continuation-in-part of U.S. application Ser. No. 14/960,692, filed Dec. 7, 2015, which is a continuation application of U.S. application Ser. No. 14/845,612, filed Sep. 4, 2015, now issued as U.S. Pat. No. 9,233,135, each of which is incorporated herein by reference in its entirety.

FIELD OF INVENTION

The disclosure relates to novel compositions comprised of active agents including vitamins, minerals, and food additives ingredients to prevent and treat kidney stone formation and promote overall improved kidney health for patients that may be susceptible to forming stones in the kidney, renal pelvis, ureter, bladder, or all other renal genitourinary areas.

BACKGROUND

Kidney stones, also called renal calculi, are solid crystal aggregations of dissolved minerals in urine. Depending on their location in the urinary tract these calculi are called by various names, e.g., kidney stones, ureteric stones, bladder stones, or urethral stones. Most kidney stones are caused by the precipitation of calcium in the form of calcium oxalate. A minority of stones may also be caused by or include precipitated calcium hydroxyl phosphate (apatite), magnesium ammonium phosphate (struvite), uric acid, or cysteine. In addition to excruciating pain, symptoms of kidney stones may also include blood in the urine due to minor damage to inside lining of kidney, ureter, and urethra; reduced urine volume caused by obstruction of the bladder or urethra by the stones; kidney infection as a result of stone blockage; abdominal distention; nausea or vomiting; and fever and chills.

Kidney stone disease is an ailment afflicting human kind for many centuries. It can affect up to a quarter of the population in certain geographic areas and hence poses a significant health problem. Approximately 85% of the stones in human are calcium stones comprising oxalate and phosphate, either alone or combined. The pathogenesis of calcium oxalate stone formation is a multi-step process and in essence includes—nucleation, crystal growth, crystal aggregation, and crystal retention. Various substances in the body have an effect on one or more of the above stone forming processes, thereby influencing a person's ability to promote or prevent stone formation. Low urine volume, low urine pH, calcium, sodium, oxalate, and urate are known to promote stone formation. Many inorganic (e.g., magnesium) and organic (e.g., urinary prothrombin fragment 1, glycosaminoglycans, osteopontin, citrate) substances are known to inhibit stone formation.

The initiation of growth of a calcium oxalate stone is thought to occur at sites of inflammation or damage within the kidney. The stones form by an initial deposition of calcium crystals at the sites of inflammation or damage and are known in the literature as Randall's plaques. These Randall's plaques then serve as nuclei for formation of calcium oxalate on top of the calcium hydroxyapatite mini-stones. Once of a certain size, stones often fragment or a break off from the Randall plaque region and can either pass out of the body or get stuck along the urinary tract, resulting in clinical symptoms such as reduced urine flow, pain or bleeding.

Prevalence of kidney stones in the United States has been estimated at 8.8% (roughly 1 in 11 people). Among men, the prevalence of stones was 10.6%, compared with 7.1% among women. Kidney stones were more common among obese than normal-weight individuals. (Eur Urol. 2012 July; 62(1):160-5.)

Reoccurrence of stones in patients has been estimated to be as high as 50 percent within 5 years of the initial event. Rates of emergency department visits for kidney stone disease have increased 20 percent between 2005 and 2009.

In 2014, one study suggested that kidney stone interventions cost an estimated $10 billion annually in the United States and patients who have an unplanned hospital visit for kidney stones incur average costs of nearly $30,000, depending on the type of procedure and the subsequent care. (Duke University Medical Center. "Complications from kidney stone treatments are common, costly" ScienceDaily. 28 Apr. 2014)

Medical treatment options depend on severity of pain, size of stone, and location of stone. Smaller stones will often pass on their own. For larger stones, some form of intervention is usually required and include: ureteroscopy and laser stone lithotripsy (the stone is located with a small camera inserted into the urethra and removed with a small basket or broken up with a laser); extracorporeal shockwave lithotripsy (ESWL; breaks up stone from the outside of the body with shockwaves that travel through a gel-like medium); Percutaneous Nephrolithotomy (PCNL; inpatient procedure for very large stones, which typically requires an overnight hospital stay). If patient has more than one kidney stone or stone occurrence, physician often recommends getting a special urine study done. A 24-hour urine study will show the composition of urine in relation to kidney stone formation. Diet can be altered or improved based on these results to help in preventing reoccurrence of a stone. Rarely patients are placed on a prescription medication as the options are very limited and can have serious side effects or risks for the patient. Sometimes pain medications are utilized as the stone is passing through the person's system. One goal in diet alteration is to try to prevent crystal formation. Common recommendations include: drink more water, often at least 6-8 glasses per day; decrease caffeine intake; eliminate colas due to phosphoric acid content; drink lemon water; decrease sodium, sugar, and red meat and oxalate-rich foods (e.g., Spinach, strawberries, nuts, tea); and increase fiber intake.

Various active agents are known to have an effect on kidney stones, including citric acid, magnesium citrate, phytin, pyridoxine, and musa, however, these active agents have not been combined in one composition, nor have they been combined in amounts that maximize the percent inhibition of crystal formation.

Thus, there remains a need for a simple and effective method and composition for preventing and treating kidney stones that optimizes the inhibition of crystal formation.

SUMMARY

Disclosed is a novel oral dosage form or a plurality of oral dosage forms.

In an embodiment, the oral dosage form or plurality of oral dosage forms comprises as active ingredients citric acid, magnesium citrate, phytin, pyridoxine, and musa.

In an embodiment, the oral dosage form or plurality of oral dosage forms comprises as active ingredients citric acid, magnesium citrate, phytin, and pyridoxine.

In an embodiment, the oral dosage form or plurality of oral dosage forms comprises as active ingredients citric acid, magnesium citrate, phytin, and musa.

In an embodiment, the oral dosage form or plurality of oral dosage forms comprises as active ingredients citric acid, magnesium citrate, pyridoxine, and musa.

In an embodiment, the oral dosage form or plurality of oral dosage forms comprises as active ingredients citric acid, phytin, pyridoxine, and musa.

In an embodiment, the oral dosage form or plurality of oral dosage forms comprises as active ingredients magnesium citrate, phytin, pyridoxine, and musa Also disclosed is a method of treating and/or inhibiting growth of kidney stones.

In an embodiment, the method comprises administering to a patient in need thereof the oral dosage form or plurality of dosage forms disclosed herein.

In an embodiment, the method comprises administering to a patient in need thereof about 101 mg to about 700 mg citric acid; about 76 mg to about 226 mg magnesium citrate; about 3 mg to about 600 mg phytin; about 0.1 mg to about 15 mg pyridoxine; and about 1 mg to about 251 mg musa.

Also disclosed is a method of inhibiting growth of calcium oxalate crystals.

In an embodiment, the method comprises contacting an aqueous solution comprising calcium oxalate with the oral dosage form or plurality of dosage forms disclosed herein.

In an embodiment, the method comprises contacting an aqueous solution comprising calcium oxalate with a composition comprising as active ingredients citric acid, magnesium citrate, phytin, pyridoxine, and musa.

In an embodiment, the method comprises contacting an aqueous solution comprising calcium oxalate with a composition comprising as active ingredients citric acid, magnesium citrate, phytin, and pyridoxine.

In an embodiment, the method comprises contacting an aqueous solution comprising calcium oxalate with a composition comprising as active ingredients citric acid, magnesium citrate, phytin, and musa.

In an embodiment, the method comprises contacting an aqueous solution comprising calcium oxalate with a composition comprising as active ingredients citric acid, magnesium citrate, pyridoxine, and musa.

In an embodiment, the method comprises contacting an aqueous solution comprising calcium oxalate with a composition comprising as active ingredients citric acid, phytin, pyridoxine, and musa.

In an embodiment, the method comprises contacting an aqueous solution comprising calcium oxalate with a composition comprising as active ingredients magnesium citrate, phytin, pyridoxine, and musa.

These and other advantages, as well as additional inventive features, will be apparent from the following Drawings, Detailed Description, Examples, and Claims.

BRIEF DESCRIPTION OF THE DRAWINGS

The following is a brief description of the drawings which are presented for the purposes of illustrating the exemplary embodiments disclosed herein and not for the purposes of limiting the same.

FIG. 119 is a graph showing absorbance at 620.6 nm as a function of time to determine the Slope for Vehicle Runs Associated with Matrix 4 for Test Solution 5.

FIG. 120 is a graph showing absorbance at 620.6 nm as a function of time for Matrix 4 for Test Solution 5.

FIG. 121 is a graph showing absorbance at 620.6 nm as a function of time to determine the Slope for Matrix 4 for Test Solution 5.

FIG. 122 is a graph showing absorbance at 620.6 nm as a function of time for Control Vehicle Runs Associated with Matrix 4 for Test Solution 6.

FIG. 123 is a graph showing absorbance at 620.6 nm as a function of time to determine the Slope for Control Vehicle Runs Associated with Matrix 4 for Test Solution 6.

FIG. 124 is a graph showing absorbance at 620.6 nm as a function of time for Matrix 4 for Test Solution 6.

FIG. 125 is a graph showing absorbance at 620.6 nm as a function of time to determine the Slope for Matrix 4 for Test Solution 6.

FIG. 126 is a graph showing absorbance at 620.6 nm as a function of time for Control Vehicle Runs Associated with Matrix 5 for Test Solution 1.

FIG. 127 is a graph showing absorbance at 620.6 nm as a function of time to determine the Slope for Control Vehicle Runs Associated with Matrix 5 for Test Solution 1.

FIG. 128 is a graph showing absorbance at 620.6 nm as a function of time for Matrix 5 for Test Solution 1.

FIG. 129 is a graph showing absorbance at 620.6 nm as a function of time to determine the Slope for Matrix 5 for Test Solution 1.

FIG. 130 is a graph showing absorbance at 620.6 nm as a function of time for Control Vehicle Runs Associated with Matrix 5 for Test Solution 2.

Figure 131:
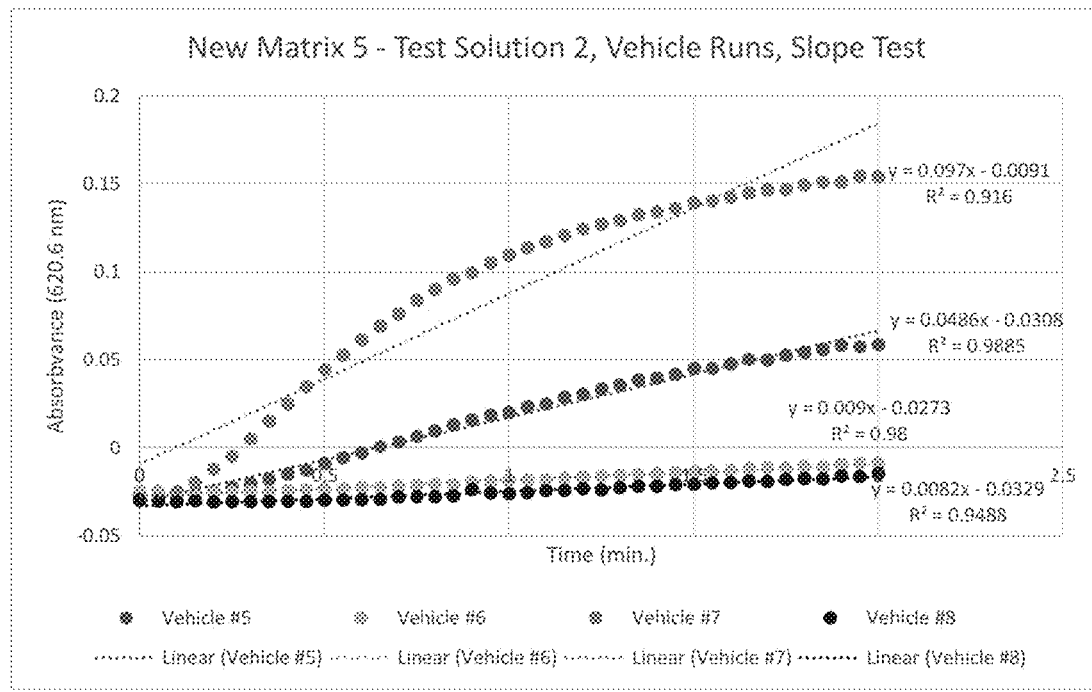

FIG. 131 is a graph showing absorbance at 620.6 nm as a function of time to determine the Slope for Control Vehicle Runs Associated with Matrix 5 for Test Solution 2.

Figure 132:
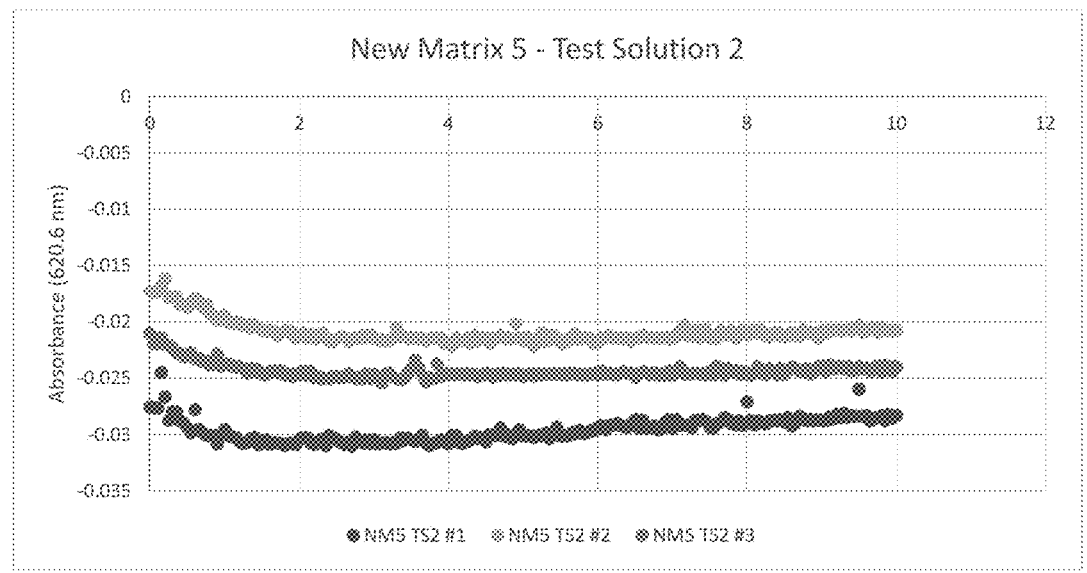

FIG. 132 is a graph showing absorbance at 620.6 nm as a function of time for Matrix 5 for Test Solution 2.

Figure 133:
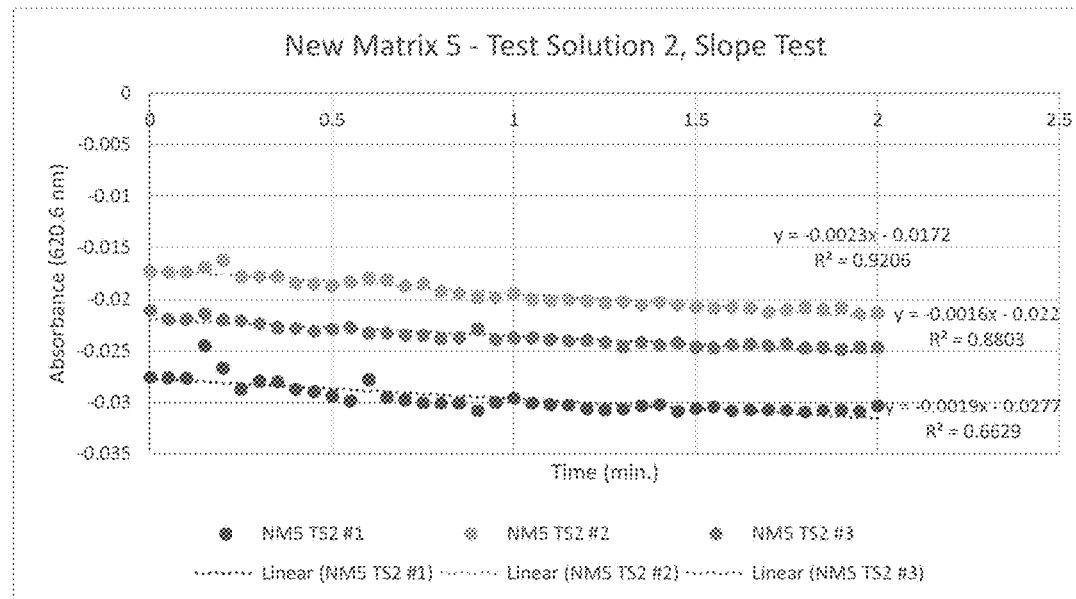

FIG. 133 is a graph showing absorbance at 620.6 nm as a function of time to determine the Slope for Matrix 5 for Test Solution 2.

Figure 134:
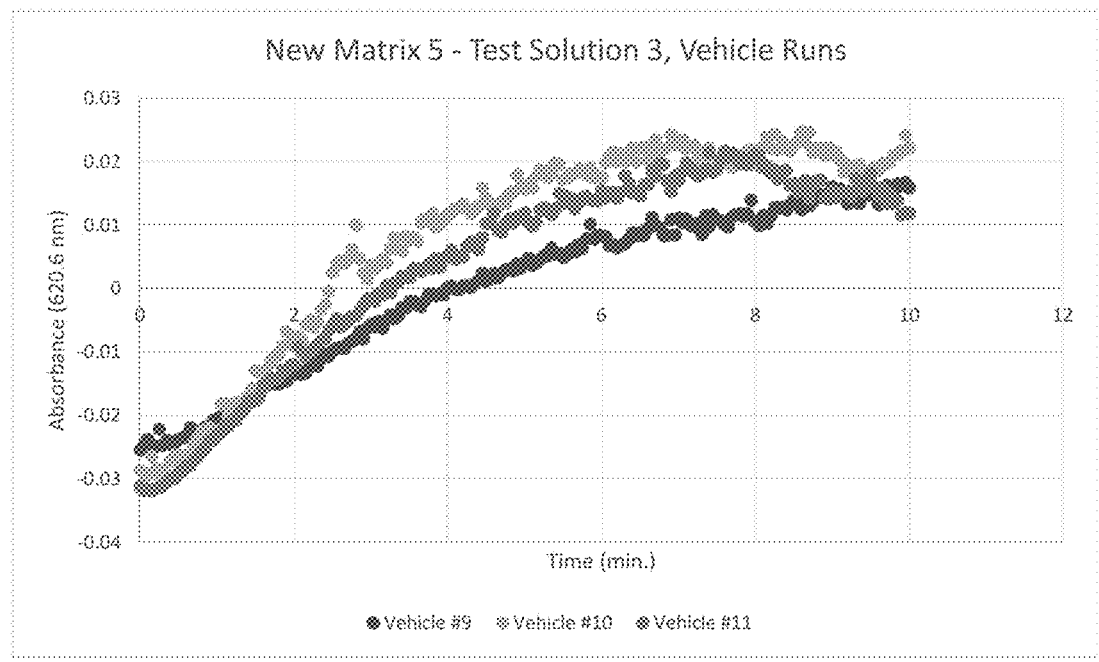

FIG. 134 is a graph showing absorbance at 620.6 nm as a function of time for Control Vehicle Runs Associated with Matrix 5 for Test Solution 3.

Figure 135:
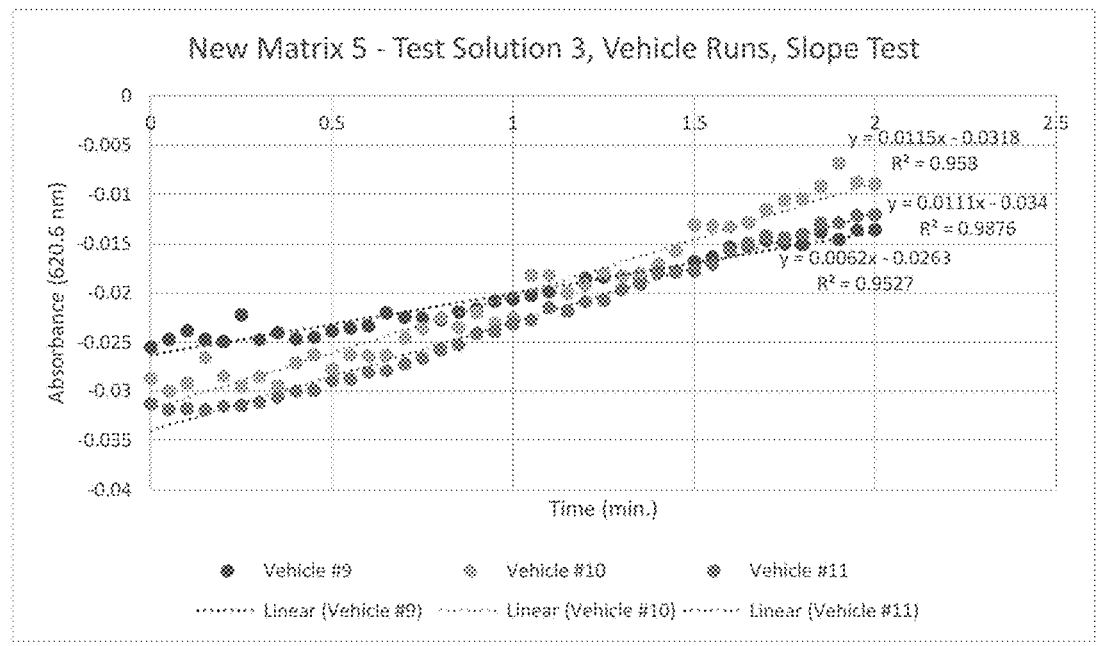

FIG. 135 is a graph showing absorbance at 620.6 nm as a function of time to determine the Slope for Control Vehicle Runs Associated with Matrix 5 for Test Solution 3.

Figure 136:
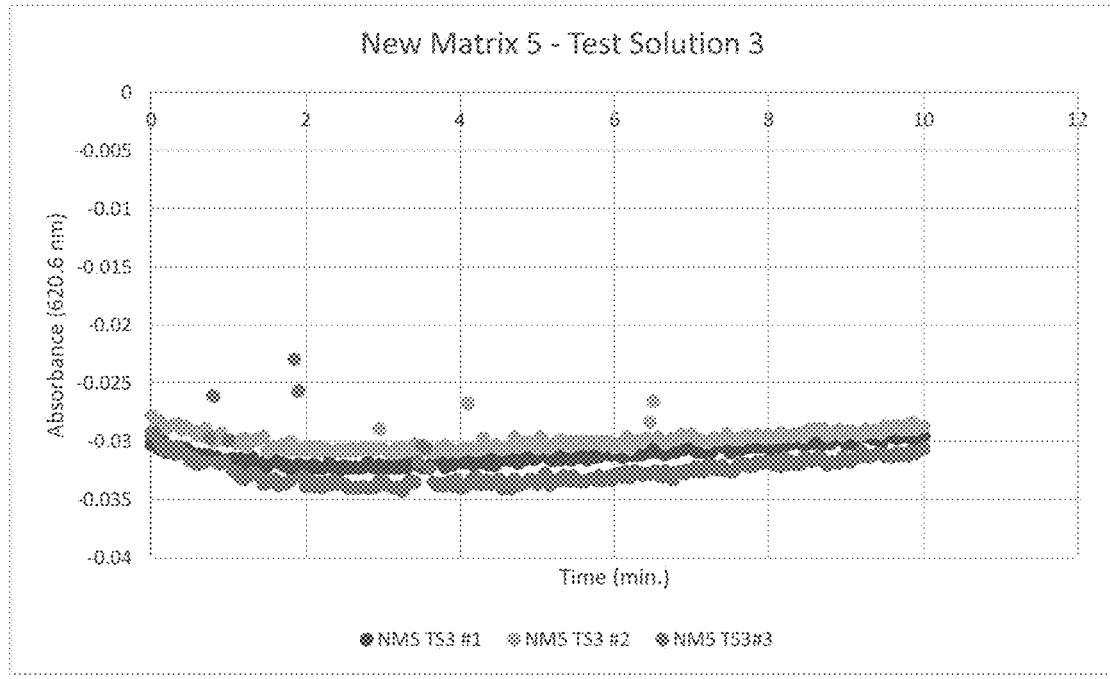

FIG. 136 is a graph showing absorbance at 620.6 nm as a function of time for Matrix 5 for Test Solution 3.

Figure 137:
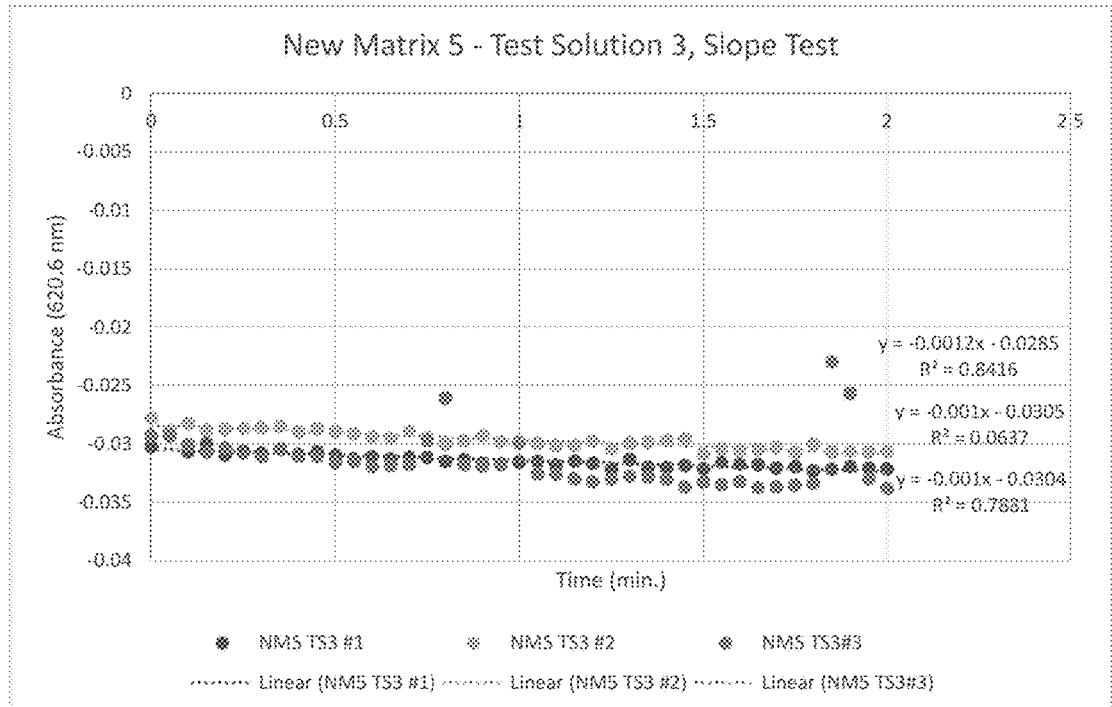

FIG. 137 is a graph showing absorbance at 620.6 nm as a function of time to determine the Slope for Matrix 5 for Test Solution 3.

Figure 138:
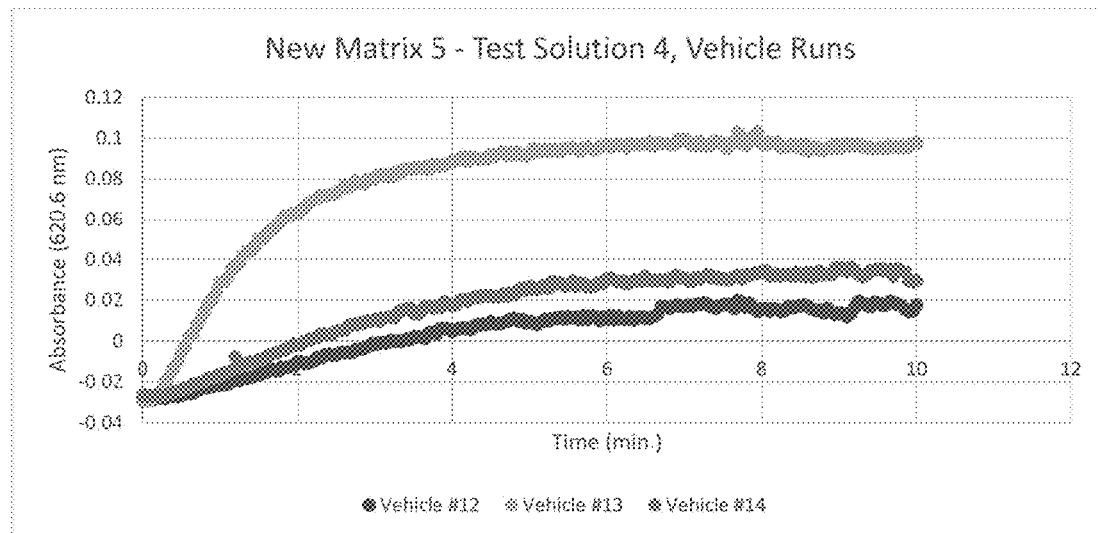

FIG. 138 is a graph showing absorbance at 620.6 nm as a function of time for Control Vehicle Runs Associated with Matrix 5 for Test Solution 4.

Figure 139:
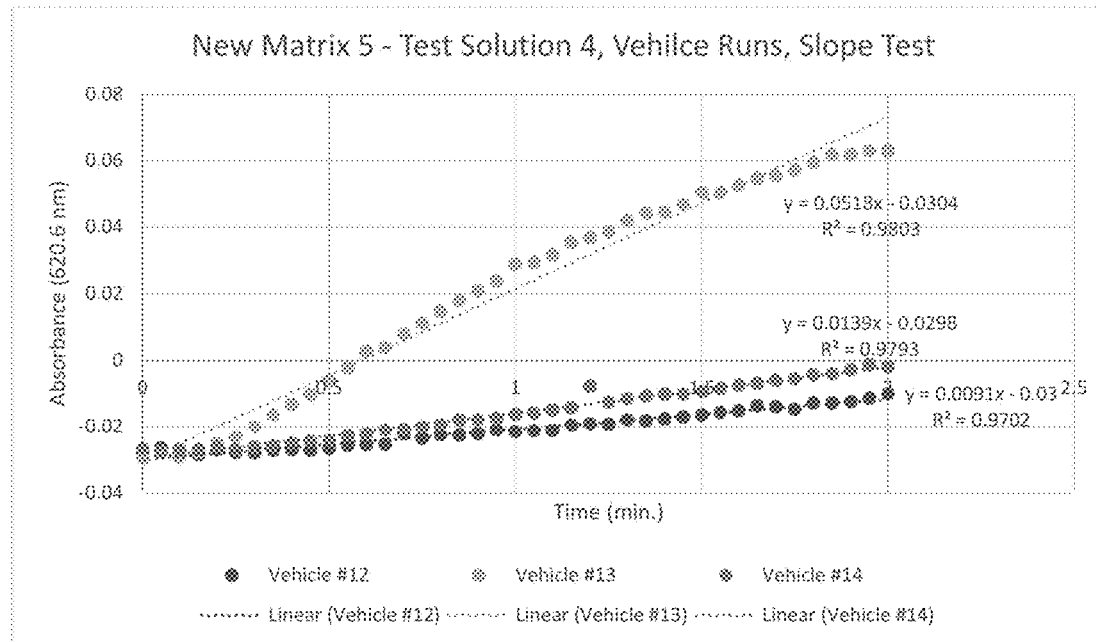

FIG. 139 is a graph showing absorbance at 620.6 nm as a function of time to determine the Slope for Control Vehicle Runs Associated with Matrix 5 for Test Solution 4.

Figure 140:
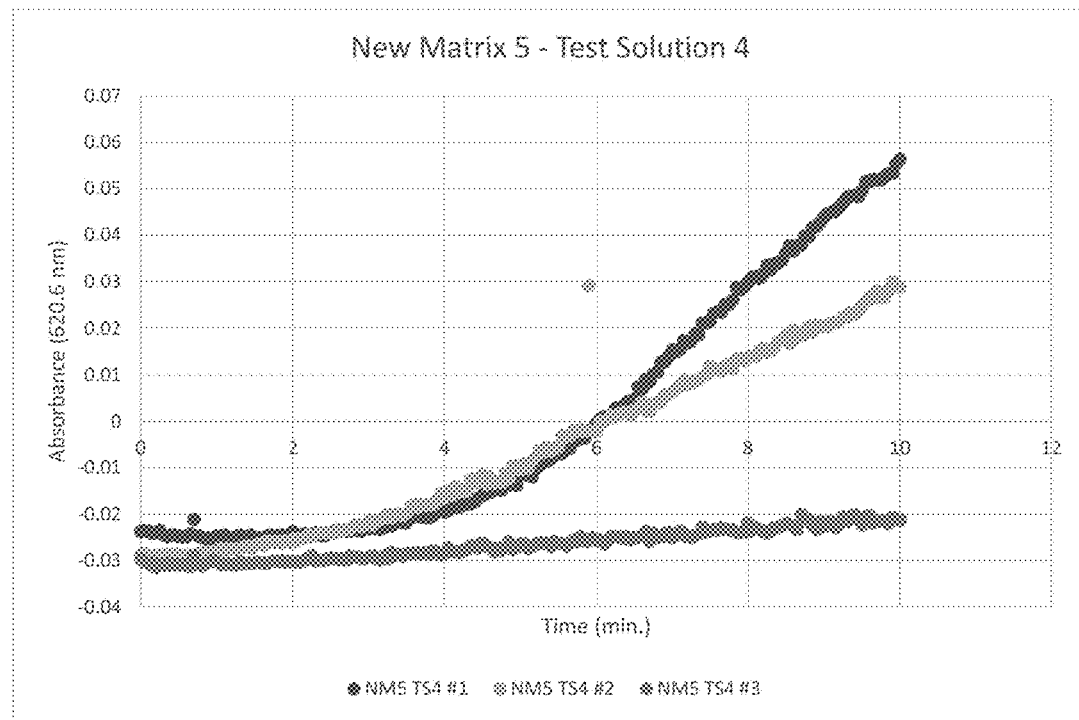

FIG. 140 is a graph showing absorbance at 620.6 nm as a function of time for Matrix 5 for Test Solution 4.

Figure 141:
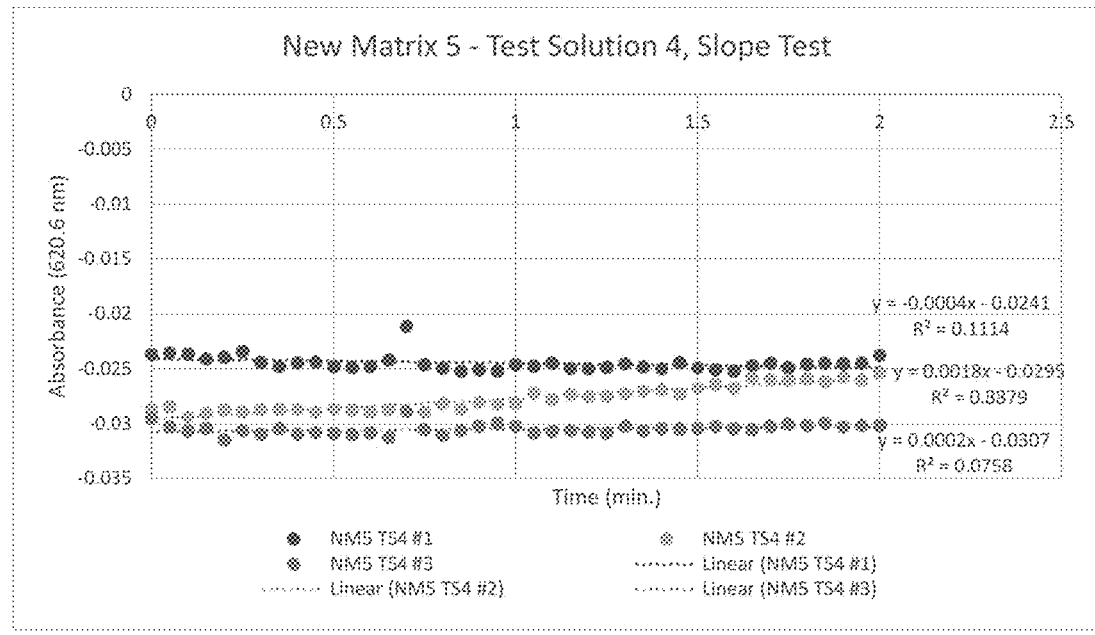

FIG. 141 is a graph showing absorbance at 620.6 nm as a function of time to determine the Slope for Matrix 5 for Test Solution 4.

Figure 142:
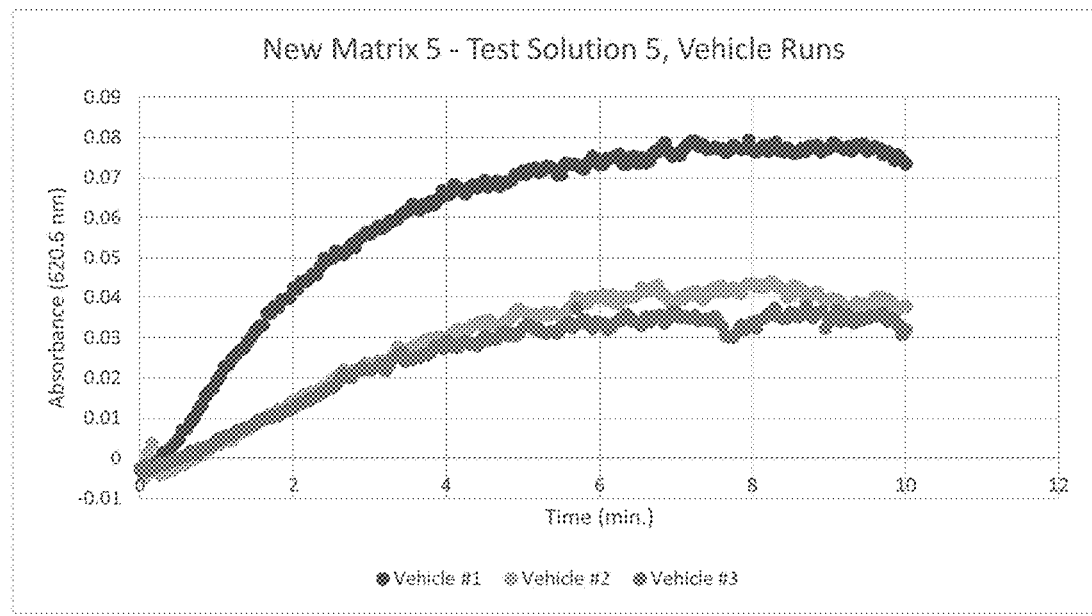

FIG. 142 is a graph showing absorbance at 620.6 nm as a function of times for Control Vehicle Runs Associated with Matrix 5 for Test Solution 5.

Figure 143:
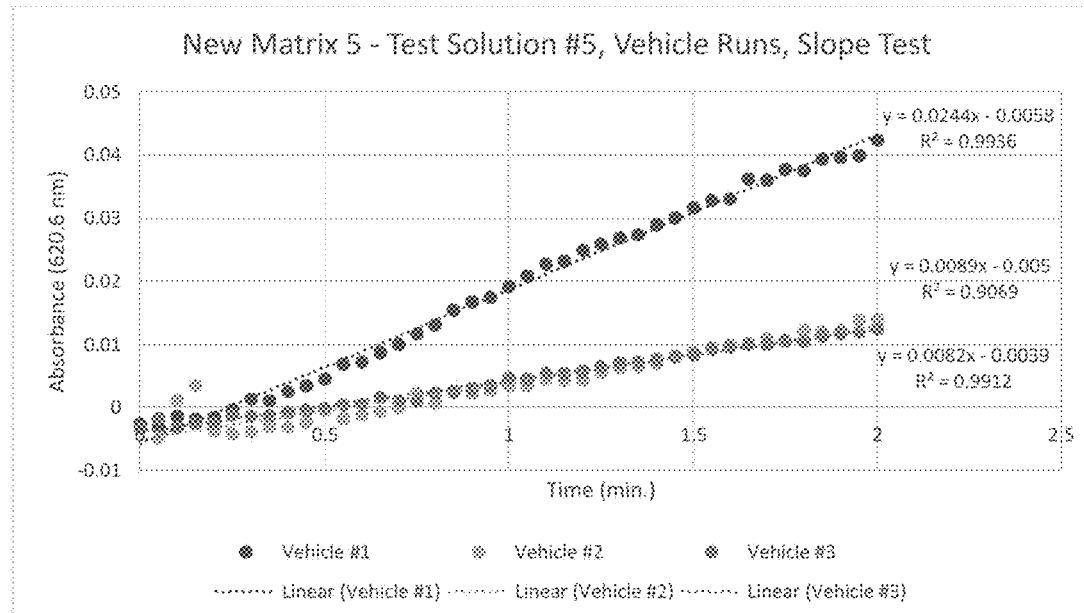

FIG. 143 is a graph showing absorbance at 620.6 nm as a function of time to determine the Slope for Vehicle Runs Associated with Matrix 5 for Test Solution 5.

Figure 144:
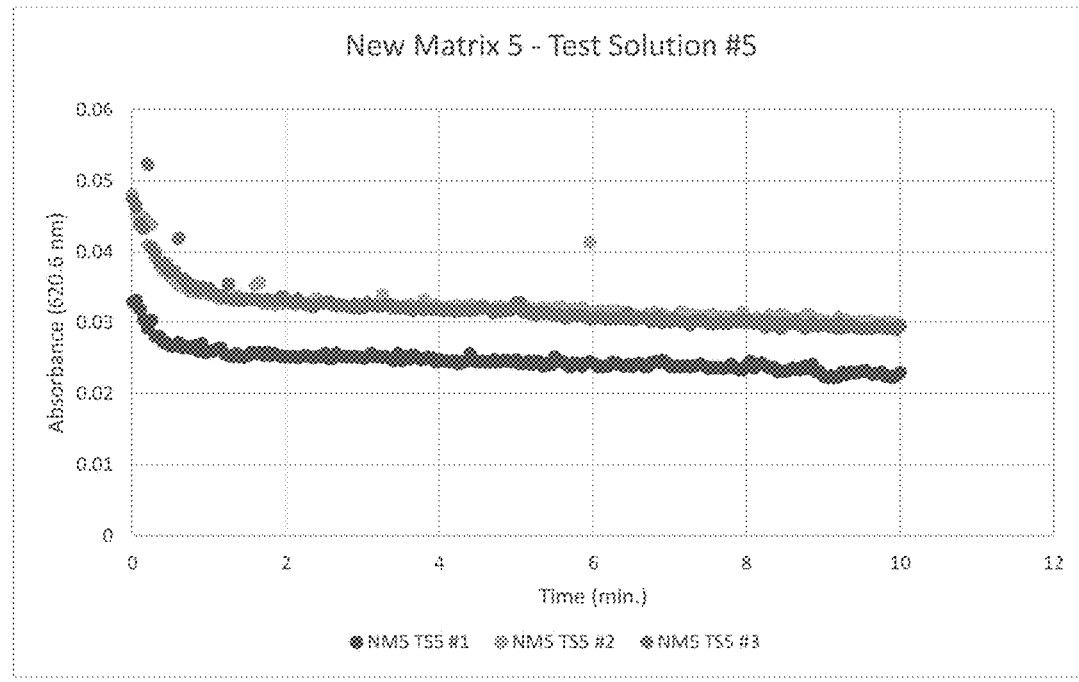

FIG. 144 is a graph showing absorbance at 620.6 nm as a function of time for Matrix 5 for Test Solution 5.

Figure 145:
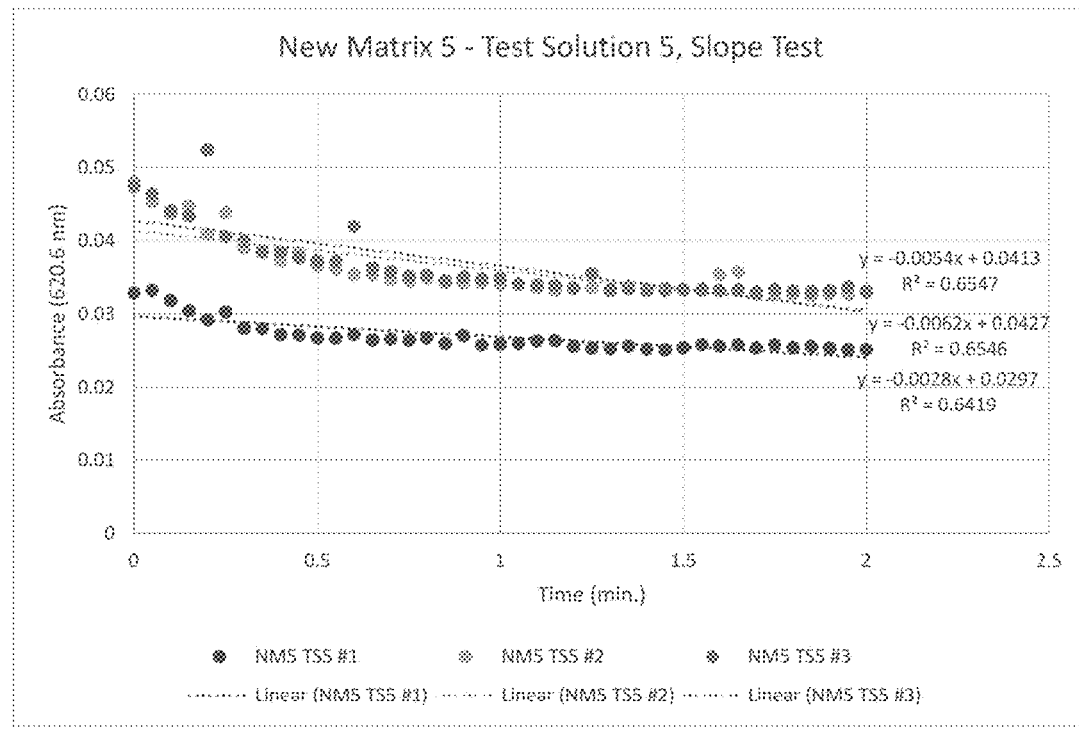

FIG. 145 is a graph showing absorbance at 620.6 nm as a function of time to determine the Slope for Matrix 5 for Test Solution 5.

Figure 146:
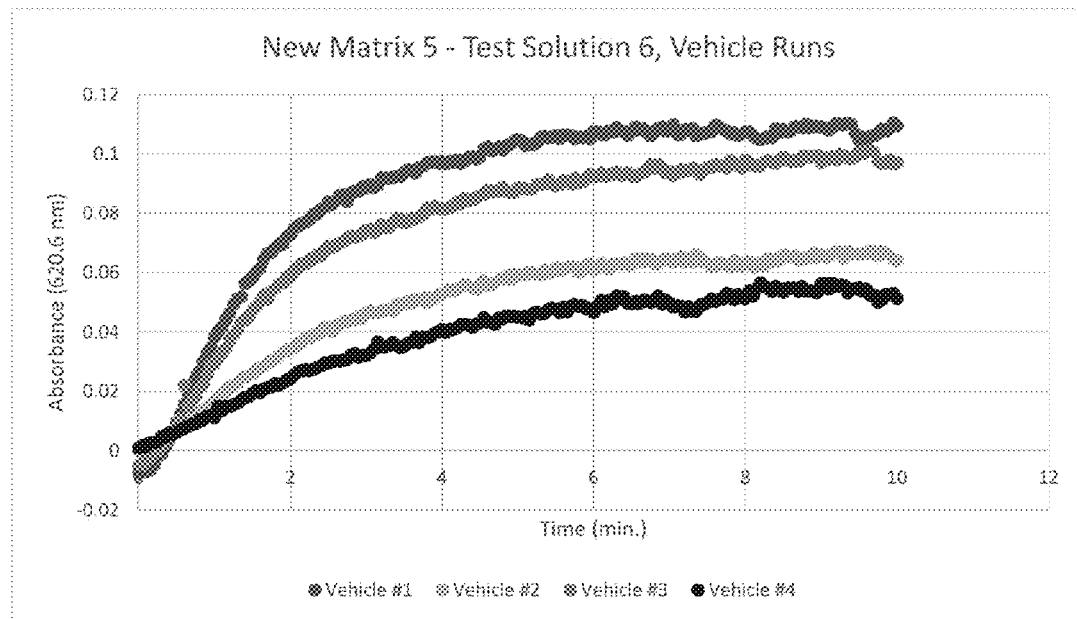

FIG. 146 is a graph showing absorbance at 620.6 nm as a function of time for Control Vehicle Runs Associated with Matrix 5 for Test Solution 6.

Figure 147:
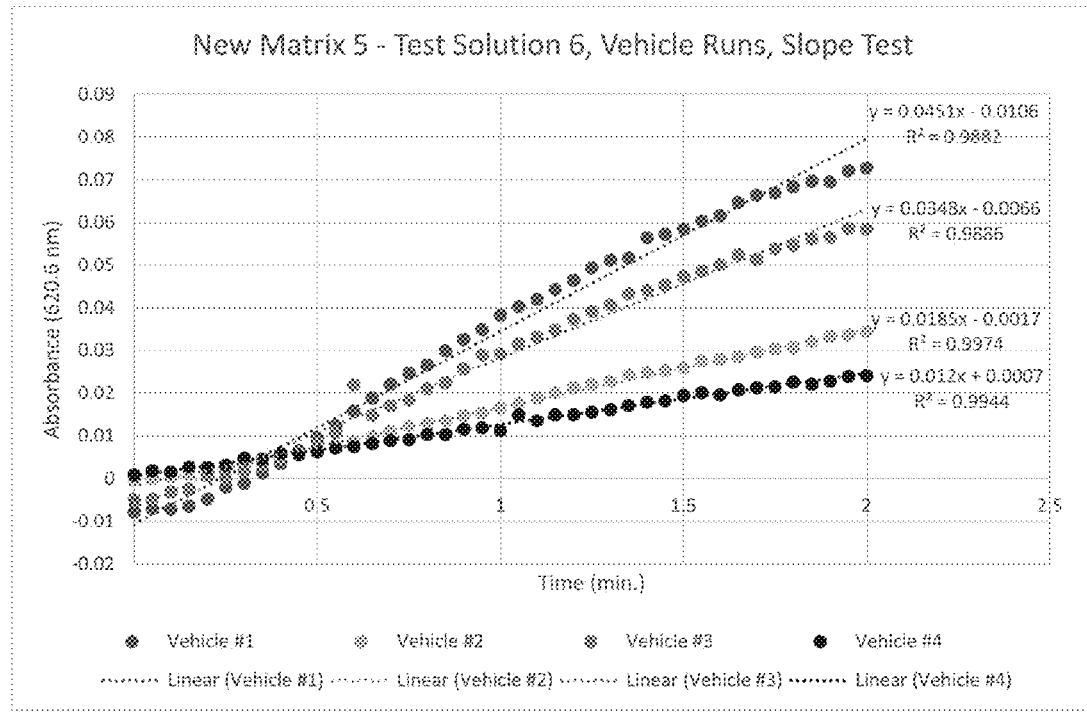

FIG. 147 is a graph showing absorbance at 620.6 nm as a function of time to determine the Slope for Control Vehicle Runs Associated with Matrix 5 for Test Solution 6.

Figure 148:
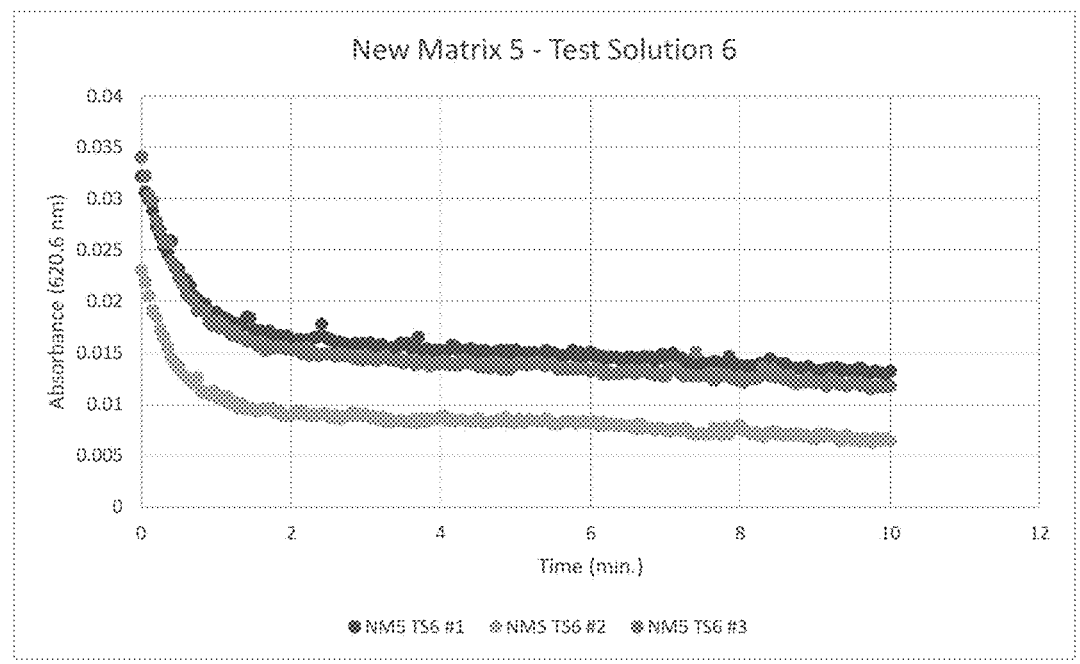

FIG. 148 is a graph showing absorbance at 620.6 nm as a function of time for Matrix 5 for Test Solution 6.

Figure 149:
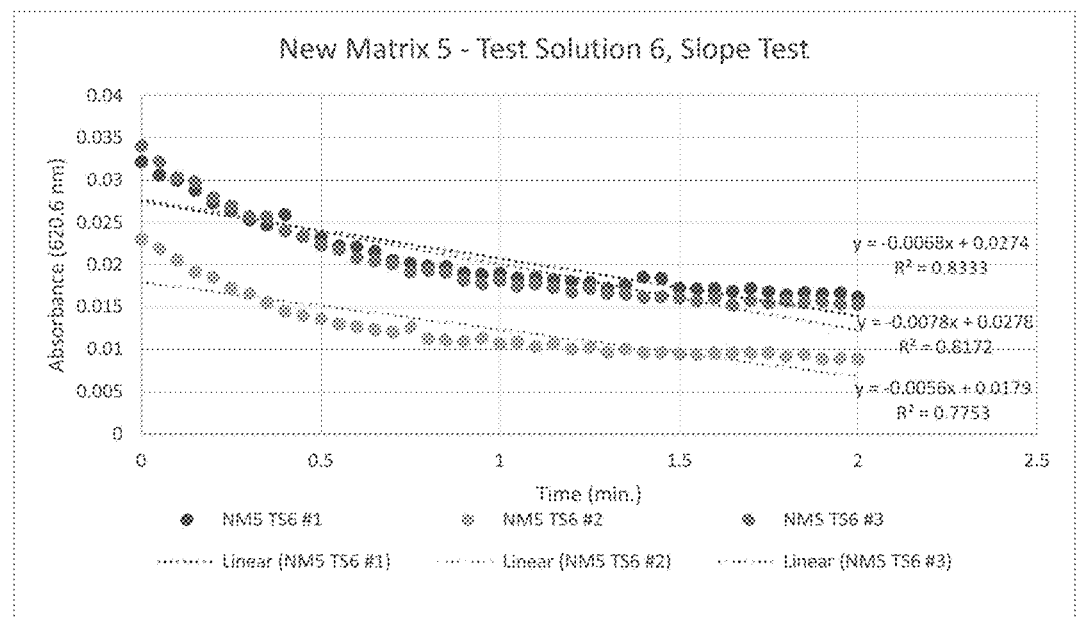

FIG. 149 is a graph showing absorbance at 620.6 nm as a function of time to determine the Slope for Matrix 5 for Test Solution 6.

Figure 150:
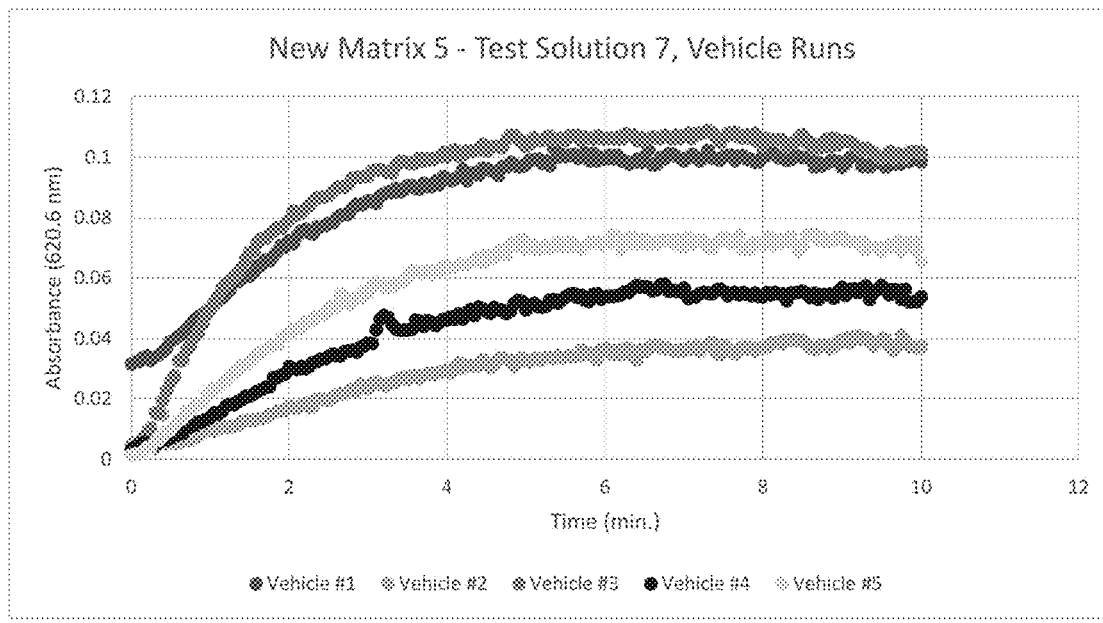

FIG. 150 is a graph showing absorbance at 620.6 nm as a function of time for Control Vehicle Runs Associated with Matrix 5 for Test Solution 7.

Figure 151:
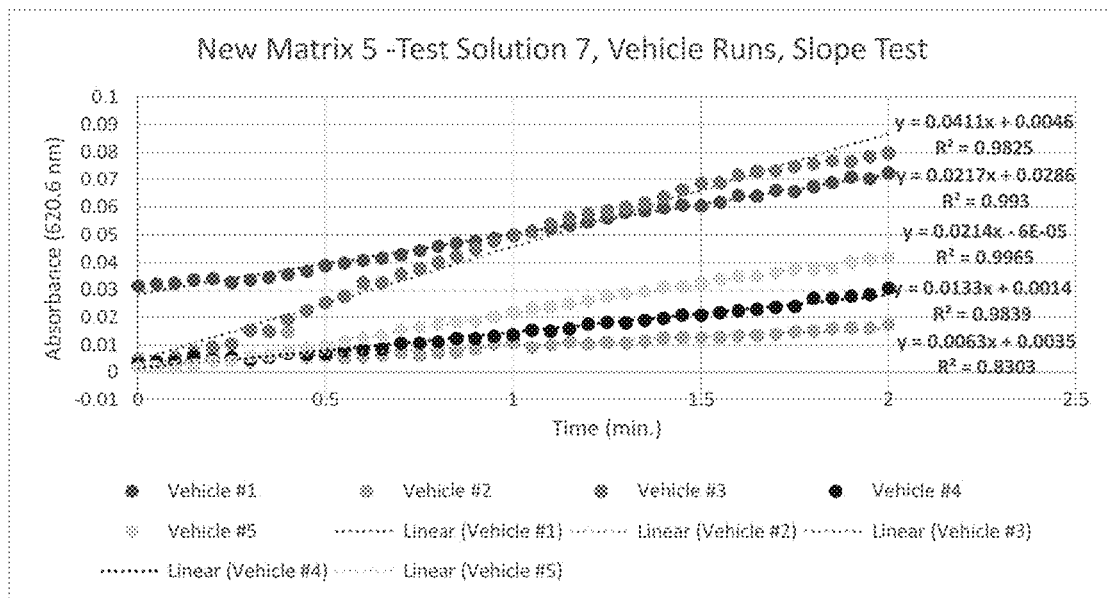

FIG. 151 is a graph showing absorbance at 620.6 nm as a function of time to determine the Slope for Control Vehicle Runs Associated with Matrix 5 for Test Solution 7.

Figure 152:
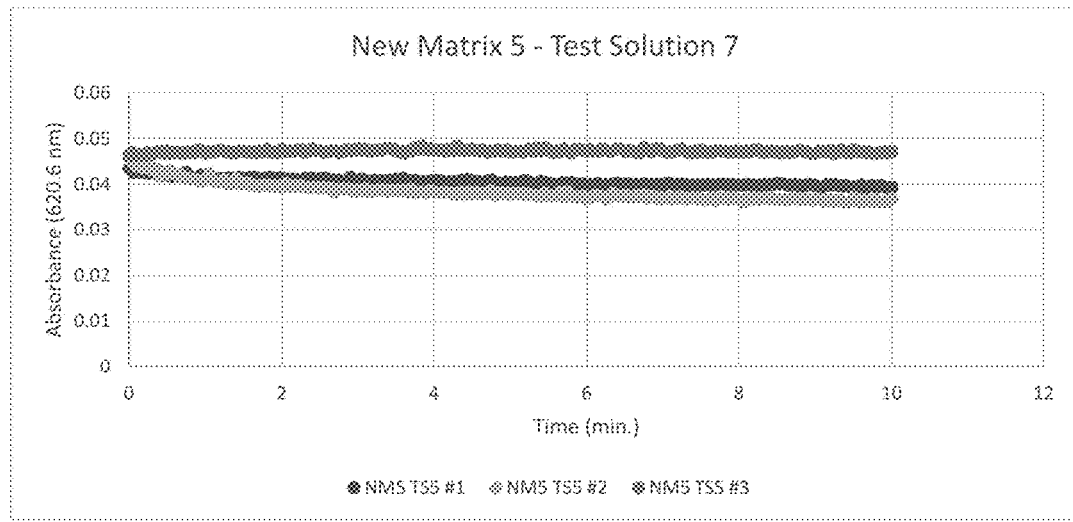

FIG. 152 is a graph showing absorbance at 620.6 nm as a function of time for Matrix 5 for Test Solution 7.

Figure 153:
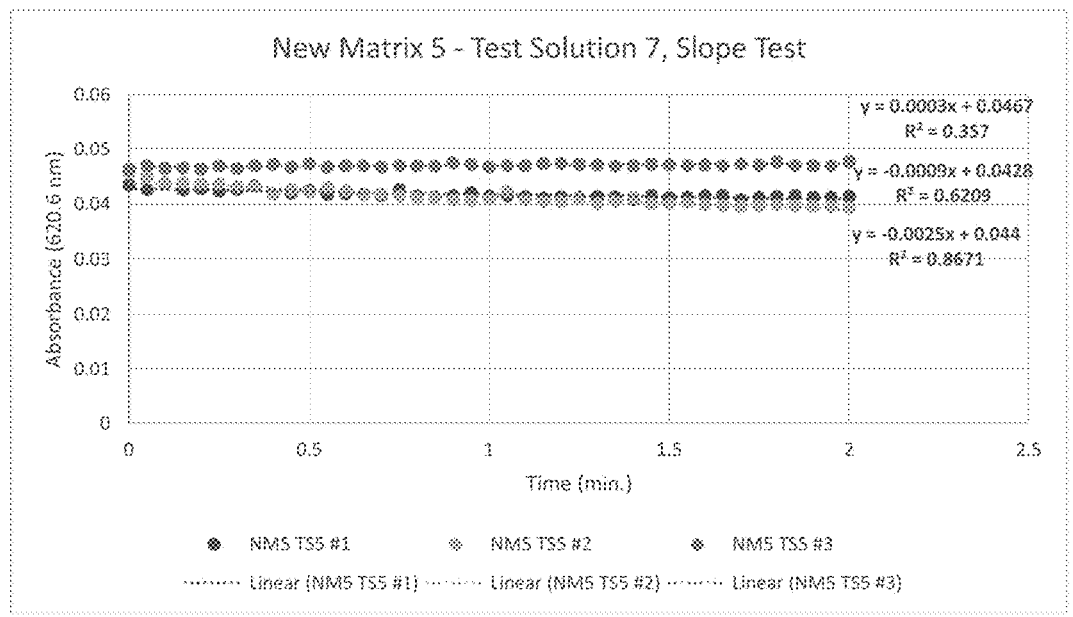

FIG. 153 is a graph showing absorbance at 620.6 nm as a function of time to determine the Slope for Matrix 5 for Test Solution 7.

DETAILED DESCRIPTION

A novel oral dosage form or a plurality of oral dosage forms comprising the ingredients citric acid, magnesium citrate, phytin, pyridoxine, and musa is disclosed herein. The disclosed oral dosage form or plurality of dosage forms is useful for treating and/or inhibiting growth of kidney stones. Methods of using the oral dosage form or plurality of dosage forms to treat or inhibit growth of kidney stones are also disclosed.

Although there is some clinical evidence that each of these ingredients individually plays a role in preventing or treating kidney stones, all five ingredients have never previously been combined in one formulation or dosing regimen for treating or inhibiting formation of kidney stones. In addition, combinations containing four of these ingredients have never been combined in one formulation or dosing regimen for treating or inhibiting formation of kidney stones.

Surprisingly, not all concentration ranges of the active ingredients in the combination provide effective inhibition of kidney stones or calcium oxalate growth. In particular, we have discovered preferred ranges in the combination of the five active ingredients that maximize the percent inhibition of kidney stones and more particularly calcium oxalate crystal growth, resulting in mean percent inhibition of the calcium oxalate crystal growth of at least about 92%. Compositions of the five active ingredients having concentrations outside the preferred ranges are unexpectedly much less effective in inhibiting calcium oxalate crystal growth. In addition, we have discovered preferred ranges in combinations containing four of the five active ingredients that maximize the percent inhibition of kidney stones and more particularly calcium oxalate crystal growth. Compositions containing four of the five active ingredients having concentrations outside the preferred ranges are unexpectedly much less effective in inhibiting calcium oxalate crystal growth.

For a dosage form or plurality of dosage forms containing all five ingredients, a preferred range for citric acid is about 101 mg to about 700 mg; and more preferably about 101 mg to about 352 mg, about 101 mg to about 176 mg, about 176 mg to about 700 mg, or about 352 mg to about 700 mg. A preferred range for magnesium citrate is about 76 mg to about 226 mg; and more preferably about 76 mg to about 201 mg, about 76 mg to about 150 mg, about 150 to about 226 mg, or about 201 mg to about 226 mg. A preferred range for phytin is about 3 mg to about 600 mg; more preferably about 3 mg to about 400 mg, about 3 mg to about 202 mg, about 3 mg to about 100 mg, about 100 mg to about 600 mg, about 201 mg to about 600 mg, or about 400 mg to about 600 mg. A preferred range for pyridoxine is about 0.2 mg to about 15 mg; more preferably about 0.2 mg to about 10.1 mg, about 0.2 mg to about 6 mg, about 0.2 mg to about 2.7 mg, about 2.7 mg to about 15 mg, about 6.0 mg to about 15 mg, or about 10 mg to about 15 mg. A preferred range for musa is about 1 mg to about 251 mg; more preferably about 1 mg to about 167 mg, about 1 mg to about 85 mg, about 1 mg to about 41 mg, about 41 mg to about 251 mg, about 85 mg to about 251 mg, or about 167 mg to about 251 mg.

Most preferred is an oral dosage form or a plurality of dosage forms comprising citric acid, magnesium citrate, phytin, pyridoxine, and musa where citric acid is present in an amount of about 350 mg, magnesium citrate is present in an amount of about 150 mg, phytin is present in an amount of about 200 mg, pyridoxine is present in an amount of about 5 mg, and musa is present in amount of about 250 mg.

For a dosage form or plurality of dosage forms containing citric acid, magnesium citrate, phytin, and pyridoxine, a preferred range for citric acid is about 101 mg to about 699 mg, magnesium citrate is about 77 mg to about 227 mg, phytin is about 3.06 mg to about 600 mg, and pyridoxine about 0.23 mg to about 15.13.

More preferably for a dosage form or plurality of dosage forms containing citric acid, magnesium citrate, phytin, and pyridoxine, citric acid is present in an amount selected from: about 101 mg to about 354 mg, about 101 mg to about 178 mg, about 178 mg to about 699 mg, about 178 mg to about 354 mg, and about 352 mg to about 699 mg; magnesium citrate is present in an amount selected from: about 77 mg to about 202 mg, about 77 mg to about 151 mg, about 151 to about 227 mg, about 151 to about 202 mg, and about 202 mg to about 227 mg; phytin is present in an amount selected from: about 3.06 mg to about 400 mg, about 3.06 mg to about 201 mg, about 3.06 mg to about 100 mg, about 100 mg to about 600 mg, about 100 mg to about 400 mg, about 100 mg to about 201 mg, about 201 mg to about 600 mg, about 201 mg to about 400 mg, and about 400 mg to about 600 mg; and pyridoxine is present in an amount selected from: about 0.23 mg to about 10.67 mg, about 0.23 mg to about 5.95 mg, about 0.23 mg to about 2.68 mg, about 2.68 mg to about 15.13 mg, about 2.68 mg to about 10.67 mg, about 2.68 mg to about 5.95 mg, about 5.45 mg to about 15.13 mg, about 5.45 mg to about 10.67 mg, and about 10.67 mg to about 15.13 mg.

Most preferred for a dosage form or plurality of dosage forms containing citric acid, magnesium citrate, phytin, and pyridoxine is one in which citric acid is present in an amount of about 350 mg, magnesium citrate is present in an amount of about 150 mg, phytin is present in an amount of about 200 mg, and pyridoxine is present in an amount of about 5 mg.

For a dosage form or plurality of dosage forms containing citric acid, magnesium citrate, phytin, and musa, a preferred range for citric acid is about 102 mg to about 1052 mg, magnesium citrate is about 2.32 mg to about 201 mg, phytin is about 100 mg to about 600 mg, and musa is about 1.51 mg to about 251 mg.

More preferably for a dosage form or plurality of dosage forms containing citric acid, magnesium citrate, phytin, and musa, citric acid is present in an amount selected from: about 102 mg to about 700 mg, about 102 mg to about 352 mg, about 102 mg to about 177 mg, about 177 mg to about 1052 mg, about 177 mg to about 700 mg, about 177 mg to about 352 mg, about 351 mg to about 1052 mg, about 351 mg to about 700 mg, and about 700 mg to about 1052 mg; magnesium citrate is present in an amount selected from: about 2.32 mg to about 201 mg, about 2.32 mg to about 151 mg, about 2.32 to about 77 mg, about 77 to about 201 mg, about 77 to about 151 mg, and about 150 mg to about 201 mg; phytin is present in an amount selected from: about 100 mg to about 401 mg, about 100 mg to about 202 mg, about 201 mg to about 600 mg, about 201 mg to about 401 mg, and about 401 mg to about 600 mg; and musa is present in an amount selected from: about 1.51 mg to about 167 mg, about 1.51 mg to about 86 mg, about 1.51 mg to about 41 mg, about 41 mg to about 251 mg, about 41 mg to about 167 mg, about 41 mg to about 86 mg, about 86 mg to about 251 mg, about 86 mg to about 167, and about 167 mg to about 251 mg.

Most preferred is an oral dosage form or a plurality of dosage forms containing citric acid, magnesium citrate, phytin, and musa where citric acid is present in an amount of about 350 mg, magnesium citrate is present in an amount of about 150 mg, phytin is present in an amount of about 200 mg, and musa is present in amount of about 250 mg.

For a dosage form or plurality of dosage forms containing citric acid, magnesium citrate, pyridoxine, and musa, a preferred range for citric acid is about 101 mg to about 1051 mg, magnesium citrate is 2.14 mg to about 226 mg, pyridoxine is 0.25 mg to about 10.23 mg, and musa is about 41.02 mg to about 252 mg.

More preferably for a dosage form or plurality of dosage forms containing citric acid, magnesium citrate, pyridoxine, and musa, citric acid is present in an amount selected from: about 101 mg to about 700 mg, about 101 mg to about 353 mg, about 101 mg to about 176 mg, about 176 mg to about 1051 mg, about 176 mg to about 700 mg, about 176 mg to about 353 mg, about 352 mg to about 1051 mg, about 352 mg to about 700 mg, and about 700 mg to about 1051 mg; magnesium citrate is present in an amount selected from: about 2.14 mg to about 202 mg, about 2.14 mg to about 153 mg, about 2.14 mg to about 77 mg, about 77 to about 226 mg, about 77 to about 202 mg, about 77 to about 153 mg, about 151 mg to about 226 mg, about 151 mg to about 202 mg, and about 202 mg to about 226 mg; pyridoxine is present in an amount selected from: about 0.25 mg to about 5.95 mg, about 0.25 mg to about 2.63 mg, about 2.63 mg to about 10.23 mg, about 2.63 mg to about 5.95 mg, and about 5.41 mg to about 10.23 mg; and musa is present in an amount selected from: about 41.02 mg to about 167 mg, about 41.02 mg to about 85 mg, about 85 mg to about 252 mg, about 85 mg to about 167 mg, and about 167 mg to about 252 mg.

Most preferred is an oral dosage form or a plurality of dosage forms comprising citric acid, magnesium citrate, pyridoxine, and musa where citric acid is present in an amount of about 350 mg, magnesium citrate is present in an amount of about 150 mg, pyridoxine is present in an amount of about 5 mg, and musa is present in an amount of about 250 mg.

For a dosage form or plurality of dosage forms containing citric acid, phytin, pyridoxine, and musa a preferred range for citric acid is about 101 mg to less than about 700 mg, phytin is about 101 mg to about 600 mg, pyridoxine is about 0.23 mg to about 15.12 mg, and musa is about 1.46 mg to about 252 mg.

More preferably for a dosage form or plurality of dosage forms containing citric acid, phytin, pyridoxine, and musa, citric acid is present in an amount selected from: about 101 mg to about 353 mg, about 101 mg to about 177 mg, about 177 mg to less than about 700 mg, about 177 mg to about 353 mg, and about 352 mg to less than about 700 mg; phytin is present in an amount selected from: about 101 mg to about 400 mg, about 101 mg to about 203 mg, about 202 mg to about 600 mg, about 202 to about 400 mg, and about 400 to about 600 mg; pyridoxine is present in an amount selected from: about 0.23 mg to about 10.20 mg, about 0.23 mg to about 6.00 mg, about 0.23 mg to about 2.69 mg, about 2.69 mg to about 15.12 mg, about 2.69 mg to about 10.20 mg, about 2.69 mg to about 6.00 mg, about 5.45 mg to about 15.12 mg, about 5.45 mg to about 10.20 mg, and about 10.20 mg to about 15.12 mg; and musa is present in an amount selected from: about 1.46 mg to about 167 mg, about 1.46 mg to about 86 mg, about 1.46 mg to about 41 mg, about 41 mg to about 252 mg, about 41 mg to about 167 mg, about 41 mg to about 86 mg, about 86 mg to about 252 mg, about 86 mg to about 167 mg, and about 167 mg to about 252 mg.

Most preferred is an oral dosage form or a plurality of dosage forms containing citric acid, phytin, pyridoxine, and musa where citric acid is present in an amount of about 350 mg, phytin is present in an amount of about 200 mg, pyridoxine is present in an amount of about 5 mg, and musa is present in amount of about 250 mg.

For a dosage form or plurality of dosage forms containing magnesium citrate, phytin, pyridoxine, and musa a preferred range for magnesium citrate is about 2.03 mg to about 203 mg, phytin is about 100 mg to about 600 mg, pyridoxine is about 0.22 mg to about 15.1 mg, and musa is about 1.46 mg to about 252 mg.

More preferably for a dosage form or plurality of dosage forms containing magnesium citrate, phytin, pyridoxine, and musa, magnesium citrate is present in an amount selected from: about 2.03 mg to about 77 mg, about 2.03 mg to about 151 mg, about 77 mg to about 151 mg, about 77 mg to about 203 mg, and about 151 mg to about 203 mg; phytin is present in an amount selected from: 100 mg to about 475 mg, 100 mg to about 400 mg, about 100 mg to about 202 mg, about 201 mg to about 600 mg, about 201 mg to about 475 mg, about 201 to about 400 mg, about 400 mg to about 600 mg, about 400 to about 475 mg, and about 475 mg to about 600 mg; pyridoxine is present in an amount selected from: about 0.22 mg to about 10.11 mg, about 0.22 mg to about 6.01 mg, about 0.22 mg to about 2.69 mg, about 2.69 mg to about 15.1 mg, about 2.69 mg to about 10.11 mg, about 2.69 mg to about 6.01 mg, about 5.4 mg to about 15.1 mg, about 5.4 mg to about 10.1120 mg, and about 10.11 mg to about 15.1 mg; and musa is present in an amount selected from: about 1.46 mg to about 168 mg, about 1.46 mg to about 85 mg, about 1.46 mg to about 42 mg, about 41 mg to about 252 mg, about 41 mg to about 168 mg, about 41 mg to about 85 mg, about 85 mg to about 252 mg, about 85 mg to about 168 mg, and about 168 mg to about 252 mg.

Most preferred is an oral dosage form or a plurality of dosage forms containing magnesium citrate, phytin, pyridoxine, and musa where magnesium citrate is present in an amount of about 150 mg, phytin is present in an amount of about 200 mg, pyridoxine is present in an amount of about 5 mg, and musa is present in amount of about 250 mg.

Also disclosed is an oral dosage form or plurality of dosage forms comprising as active ingredients citric acid, magnesium citrate, phytin, pyridoxine, and musa wherein the percent inhibition of the formation of calcium oxalate crystals caused by this combination of active ingredients is greater than about 92%, more preferably greater than about 96%, and most preferably greater than about 99%.

Also disclosed is an oral dosage form or plurality of dosage forms comprising as active ingredients citric acid, magnesium citrate, phytin, and pyridoxine wherein the percent inhibition of the formation of calcium oxalate crystals caused by this combination of active ingredients is greater than about 89%, more preferably greater than about 94%, and most preferably greater than about 98%.

Also disclosed is an oral dosage form or plurality of dosage forms comprising as active ingredients citric acid, magnesium citrate, phytin, and musa wherein the percent inhibition of the formation of calcium oxalate crystals caused by this combination of active ingredients is greater than about 92%, more preferably greater than about 96%, and most preferably greater than about 100%.

Also disclosed is an oral dosage form or plurality of dosage forms comprising as active ingredients citric acid, magnesium citrate, pyridoxine, and musa wherein the percent inhibition of the formation of calcium oxalate crystals caused by this combination of active ingredients is greater than about 59%, more preferably greater than about 62%, and most preferably greater than about 66%.

Also disclosed is an oral dosage form or plurality of dosage forms comprising as active ingredients citric acid, phytin, pyridoxine, and musa wherein the percent inhibition of the formation of calcium oxalate crystals caused by this combination of active ingredients is greater than about 88%, more preferably greater than about 100%, and most preferably greater than about 108%.

Also disclosed is an oral dosage form or plurality of dosage forms comprising as active ingredients magnesium citrate, phytin, pyridoxine, and musa wherein the percent inhibition of the formation of calcium oxalate crystals caused by this combination of active ingredients is greater than about 99%, more preferably greater than about 104%, and most preferably greater than about 106%.

Also disclosed herein are methods for treating and/or inhibiting formation of kidney stones.

In an embodiment, the method comprises administering an oral dosage form or a plurality of dosage forms disclosed herein to a patient in need thereof. The dosage form(s) can be administered to the patient one time or multiple times per day, preferably one to four times per day and more preferably twice per day. Multiple oral dosage forms can be taken per dosing, preferably one to four dosage forms, preferably one to two dosage forms, and more preferably 1 dosage form.

In an embodiment, the method comprises administering to a patient in need thereof about 101 mg to about 700 mg citric acid; about 76 mg to about 226 mg magnesium citrate; about 3 mg to about 600 mg phytin; about 0.1 mg to about 15 mg pyridoxine; and about 1 mg to about 251 mg musa. In an embodiment, the method comprises administering to the patient about 350 mg citric acid, about 150 magnesium citrate, about 200 mg phytin, about 5 mg pyridoxine, and about 250 mg musa. The administering can occur one time or multiple times per day, preferably 1 to 4 times per day, and more preferably twice per day. The combination of the citric acid, magnesium citrate, phytin, pyridoxine, and musa can be administered to the patient in form of an oral dosage form, e.g. a tablet or a capsule, preferably a capsule.

In an embodiment, the method comprises administering to a patient in need thereof any of the preferred amounts of active ingredients disclosed in the various embodiments herein.

In an embodiment, the method comprises administering to a patient in need thereof about 101 mg to about 699 mg citric acid, about 77 mg to about 227 mg magnesium citrate, about 3.06 mg to about 600 mg phytin, and about 0.23 mg to about 15.13 pyridoxine. In an embodiment, the method comprises administering to the patient about 350 mg citric acid, about 150 magnesium citrate, about 200 mg phytin, and about 5 mg pyridoxine. The combination of the citric acid, magnesium citrate, phytin, and pyridoxine, can be administered to the patient in form of an oral dosage form, e.g. a tablet or a capsule, preferably a capsule.

In an embodiment, the method comprises administering to a patient in need thereof about 102 mg to about 1052 mg citric acid, about 2.32 mg to about 201 mg magnesium citrate, about 100 mg to about 600 mg phytin, and about 1.51 mg to about 251 mg musa. In an embodiment, the method comprises administering to the patient about 350 mg citric acid, about 150 magnesium citrate, about 200 mg phytin, and about 250 mg musa. The combination of the citric acid, magnesium citrate, phytin, and musa can be administered to the patient in form of an oral dosage form, e.g. a tablet or a capsule, preferably a capsule.

In an embodiment, the method comprises administering to a patient in need thereof about 101 mg to about 1051 mg citric acid; about 2.14 mg to about 226 mg magnesium citrate; about 0.25 mg to about 10.23 mg pyridoxine; and about 41.02 mg to about 252 mg musa. In an embodiment, the method comprises administering to the patient about 350 mg citric acid, about 150 magnesium citrate, about 5 mg pyridoxine, and about 250 mg musa. The combination of the citric acid, magnesium citrate, pyridoxine, and musa can be administered to the patient in form of an oral dosage form, e.g. a tablet or a capsule, preferably a capsule.

In an embodiment, the method comprises administering to a patient in need thereof about 101 mg to less than about 700 mg citric acid; about 101 mg to about 600 mg phytin; about 0.23 mg to about 15.12 mg pyridoxine; and about 1.46 mg to about 252 mg musa. In an embodiment, the method comprises administering to the patient about 350 mg citric acid, about 200 mg phytin, about 5 mg pyridoxine, and about 250 mg musa. The combination of the citric acid, phytin, pyridoxine, and musa can be administered to the patient in form of an oral dosage form, e.g. a tablet or a capsule, preferably a capsule.

In an embodiment, the method comprises administering to the patient about 150 mg magnesium citrate, about 200 mg phytin, about 5 mg pyridoxine, and about 250 mg musa. The combination of the magnesium citrate, phytin, pyridoxine, and musa can be administered to the patient in form of an oral dosage form, e.g. a tablet or a capsule, preferably a capsule. In an embodiment, the method comprises administering to a patient in need thereof about 2.03 mg to about 203 mg magnesium citrate; about 100 mg to about 600 mg phytin; about 0.22 mg to about 15.1 mg pyridoxine; and about 1.46 mg to about 252 mg musa.

In any of the embodiments of the method for treating and/or inhibiting formation of kidney stones disclosed herein, the administering can occur one time or multiple times per day, preferably 1 to 4 times per day, and more preferably twice per day.

Also disclosed is a method of inhibiting growth of calcium oxalate crystals.

In an embodiment, the method comprises contacting an aqueous solution comprising calcium oxalate with an oral dosage form or a plurality of dosage forms disclosed herein.

In an embodiment, the method comprises contacting an aqueous solution comprising calcium oxalate with a composition comprising as active ingredients citric acid, magnesium citrate, phytin, pyridoxine, and musa. A preferred range for citric acid is about 101 mg to about 700 mg; and more preferably about 101 mg to about 352 mg, about 101 mg to about 176 mg, about 176 mg to about 700 mg, or about 352 mg to about 700 mg. A preferred range for magnesium citrate is about 76 mg to about 226 mg; and more preferably about 76 mg to about 201 mg, about 76 mg to about 150 mg, about 150 to about 226 mg, or about 201 mg to about 226 mg. A preferred range for phytin is about 3 mg to about 600 mg; more preferably about 3 mg to about 400 mg, about 3 mg to about 202 mg, about 3 mg to about 100 mg, about 100 mg to about 600 mg, about 201 mg to about 600 mg, or about 400 mg to about 600 mg. A preferred range for pyridoxine is about 0.2 mg to about 15 mg; more preferably about 0.2 mg to about 10.1 mg, about 0.2 mg to about 6 mg, about 0.2 mg to about 2.7 mg, about 2.7 mg to about 15 mg, about 6.0 mg to about 15 mg, or about 10 mg to about 15 mg. A preferred range for musa is about 1 mg to about 251 mg; more preferably about 1 mg to about 167 mg, about 1 mg to about 85 mg, about 1 mg to about 41 mg, about 41 mg to about 251 mg, about 85 mg to about 251 mg, or about 167 mg to about 251 mg. In an embodiment, the composition comprises about 101 mg to about 700 mg citric acid; about 76 mg to about 226 mg magnesium citrate; about 3 mg to about 600 mg phytin; about 0.1 mg to about 15 mg pyridoxine; and about 1 mg to about 251 mg musa; specifically, the composition comprises citric acid in an amount of about 350 mg, magnesium citrate in an amount of about 150 mg, phytin in an amount of about 200 mg, pyridoxine in an amount of about 5 mg, and musa in amount of about 250 mg.

In an embodiment, the method comprises contacting an aqueous solution comprising calcium oxalate with a composition comprising as active ingredients any four of citric acid, magnesium citrate, phytin, pyridoxine, and musa. In an embodiment, the amount of each active ingredient is any of the amounts for that active ingredient disclosed herein. In an embodiment, the method comprises contacting an aqueous solution comprising calcium oxalate with any of the preferred amounts of active ingredients disclosed in the various embodiments herein.

DEFINITIONS

Unless defined otherwise, all technical and scientific terms used herein have the same meaning as is commonly understood by one of ordinary skill in the art to which this invention belongs. In the event that there is a plurality of definitions for a term used herein, those definitions in this section shall prevail.

The terms "a" and "an" do not denote a limitation of quantity, but rather denote the presence of at least one of the referenced item.

The term "about" as used herein is inclusive of the stated value and means within the routine experimental error associated with measurement of the particular quantity (i.e., the limitations of the measurement system) or in the case of a weight, within ±10% of the stated value.

The term "active agent" or "active ingredient" as used herein includes all pharmaceutically acceptable molecules, plant extracts, vitamins, salt forms, crystalline forms, amorphous form, polymorphic forms, solvates, and hydrates that are useful for treating a medical condition.

"Administering an oral dosage form or plurality of dosage forms comprising as active ingredients citric acid, magnesium citrate, phytin, pyridoxine, and musa" or "co-administering a plurality of dosage forms comprising as active ingredients citric acid, magnesium citrate, phytin, pyridoxine, and musa" means that each active ingredient is administered simultaneously in a single dosage form, administered concomitantly in separate dosage forms, or administered in separate dosage forms separated by some amount of time that is within the time in which all of the active ingredients are within the blood stream of a patient.

The terms "comprising", "having", "including", and "containing" are to be construed as open-ended terms (i.e., meaning "including, but not limited to").

A "dosage form" means a unit of administration of an active agent. An "oral dosage form" means a unit dosage form for oral administration.

As used herein "food" means a solid food with sufficient bulk and fat content that it is not rapidly dissolved and absorbed in the stomach. More specifically, the food is a meal, such as breakfast, lunch, or dinner. An oral dosage form administered to a patient "with food" is administered to the patient between about 30 minutes prior to eating a meal to about 2 hours after eating a meal; more specifically, the dosage is administered within 15 minutes of eating a meal. The term "without food" is defined to mean the condition of the patient not having consumed solid food for about one hour prior to administration of the oral dosage form until about 2 hours after administration of the oral dosage form.

The term "kidney stone" includes a stone, crystal, calculus, or nephrolith that is formed and affects any part of the urinary tract including the kidney, bladder, and ureter.

The term "medical condition" includes disease, illness, ailment, syndrome, and/or disorder.

The term "patient" means a human or non-human animal in need of medical treatment.

The terms "treating" and "treatment" mean implementation of therapy with the intention of reducing in severity or frequency symptoms, elimination of symptoms or underlying cause, prevention of the occurrence of symptoms or their underlying cause, and improvement or remediation of damage.

By an "effective amount" or a "therapeutically effective amount" of an active agent is meant a sufficient amount of the active agent to produce a therapeutic effect in the patient. The amount that is "effective" will vary from subject to subject, depending on the age and general condition of the individual, the particular active agent, and the like. Thus, it is not always possible to specify an exact "effective amount." However, an appropriate "effective" amount in any individual case may be determined by one of ordinary skill in the art using routine experimentation.

The suffix "(s)" as used herein is intended to include both the singular and the plural of the term that it modifies, thereby including one or more of that term (e.g., the dosage form(s) includes one or more dosage forms).

Ingredients

Citric acid is a GRAS food additive that is well absorbed and is excreted into the renal tubule where it forms soluble complexes with calcium, reducing the concentration of free calcium in the urine. Citric acid can be in the form of citric acid or a citrate salt such as magnesium citrate, calcium citrate or other physiologically acceptable salts. Low urinary citrate excretion is a risk factor for the development of kidney stones. Citrate inhibits stone formation by complexing with calcium in the urine, inhibiting spontaneous nucleation, and preventing growth and agglomeration of crystals. Citric acid has been shown to inhibit the initial crystallization of calcium hydroxyapatite at Randall's plaques as well as the aggregation of calcium oxalate crystals and their attachment to urinary epithelium. For citric acid, this term is defined to include other compounds that provide the equivalent amount of citrate ion in solution as the amount available from citric acid used in the invention.

Ingestion of alkali salts (i.e. potassium and magnesium salts) reduces urine calcium excretion and increases the reabsorption of calcium in the proximal tubule reabsorption. Oral administration of potassium citrate is known to prevent the recurrence of kidney stones. Potassium citrate attaches to calcium in the urine, preventing the formation of mineral crystals that can develop into kidney stones. Potassium citrate also prevents the urine from becoming too acidic. This helps prevent uric acid or cysteine kidney stones from forming. Magnesium inhibits calcium oxalate crystallization in human urine and model systems by forming a soluble chelate with oxalate in the urine allowing for excretion. Magnesium also inhibits absorption of dietary oxalate from the gut lumen. Magnesium has been shown to inhibit crystal formation thus reducing the risk for forming kidney stones. Various forms of alkali salt can be used in the compositions of this invention. For magnesium citrate, this term is defined to include other magnesium compounds that provide the equivalent amount of free magnesium ion in solution as the amount of magnesium citrate used in the invention.

Phytin is a calcium-magnesium salt of phytic acid that occurs in plants. Phytic acid (known as inositol hexakisphosphate (IP6), inositol polyphosphate, or phytate when in salt form) has a strong binding affinity for calcium. Phytin acts by preventing crystallization of calcium salts. For phytin, this term is defined to include other compounds that provide the equivalent amount of phytate ion in solution as the amount available from phytin used in the invention.

Pyridoxine (4,5-Bis(hydroxymethyl)-2-methylpyridin-3-ol, or vitamin B6) reduces oxalate levels. It is believed that pyridoxine enhances the activity of an enzyme (alanine: glyoxylate aminotransferase) which diverts metabolites to other uses in the body rather than having them form oxalate. For pyridoxine, this term is defined to include vitamers of vitamin $B_6$, including pyridoxine (PN), pyridoxine 5'-phosphate (PNP), pyridoxal (PL), pyridoxal 5'-phosphate (PLP also known as P-5-P vitamin supplement), pyridoxamine (PM), pyridoxamine 5'-phosphate (PMP) and 4-Pyridoxic acid (PA).

Musa (extracts from the banana plant or stem) been used in traditional medicine to prevent stone growth and to aid stone passage. From a mechanistic standpoint, extracts from Musa normalize multiple abnormal urinary parameters which are known to induce stone growth, including calcium, phosphate, and oxalate. In this manner, high levels of the precipitating species that initiate stone growth are no longer excreted into the urine at high levels. Furthermore, Musa decreases the expression of liver glycolate oxidase and lactate dehydrogenase, enzymes associated with the production of oxalate in the body. In addition to these activities, Musa extracts have significant diuretic effect that aids the passage of any stones as they are generated (Devi, V. K. et al., Ancient Science of Life, 1993, 12(3&4):451-461; Pillai, R. G. Ancient Science of Life, 1995, 15(1):2-6; Patankar, S. et al., 2008, The Journal of Alternative and Complementary Medicine 14(10):1287-90; Prasobh, G. R., International Journal of Research in Pharmaceutical and Biomedical Sciences, 2012, 3(4):1251-1255). For musa, this term is defined to include all musa varieties listed in *World Checklist of Selected Plant Families*. Royal Botanic Gardens, Kew.

Formulation

Active agents used in this invention can be formulated into any oral dosage form including, solid, semi-solid, liquid, powder, sachet, and the like. Solid oral dosage forms can include, for example, a tablet, a capsule (hard or soft), or subunits, and the like. "Subunit" includes a minitablet, a bead, a spheroid, a microsphere, a seed, a pellet, a caplet, a microcapsule, a granule, a particle, and the like that can provide an oral dosage form alone or when combined with other subunits. Exemplary semi-solid or liquid dosage forms include a suspension, a solution, an emulsion, and the like.

The oral dosage form can be formulated for a specific type of release including immediate-release, controlled-release, sustained-release, or extended-release.

Exemplary solid oral dosage forms can be prepared by combining active agents with one or more pharmaceutically acceptable excipients and then forming into the dosage form. As used herein, "pharmaceutically acceptable excipient" means any other component added to the pharmaceutical formulation other than the active agent. Excipients may be added to facilitate manufacture, enhance stability, enhance product characteristics, enhance bioavailability, enhance patient acceptability, etc. Pharmaceutical excipients include carriers, fillers, binders, disintegrants, lubricants, glidants, granulating agent, compression aids, colors, sweeteners, preservatives, suspending agents, dispersing agents, film formers, flavors, printing inks, buffer agents, pH adjusters, preservatives etc. In some instances, a single material will meet two or more of the foregoing general classifications.

Exemplary pharmaceutically acceptable excipients include fillers, such as water-insoluble filler, water soluble filler, or a combination thereof. The filler may be a water-insoluble filler, such as carnauba wax, stearic acid, silicon dioxide, titanium dioxide, talc, alumina, starch, kaolin, polacrilin potassium, powdered cellulose, microcrystalline cellulose, sodium citrate, dicalcium phosphate, or a combination thereof. Exemplary water-soluble fillers include water soluble sugars and sugar alcohols, specifically lactose, glucose, fructose, sucrose, mannose, dextrose, galactose, the corresponding sugar alcohols and other sugar alcohols, such as mannitol, sorbitol, xylitol, or a combination thereof.

Exemplary binders include alginic acid, a carbomer, carboxymethylcellulose calcium, carboxymethylcellulose sodium, carrageenan, cellulose acetate phthalate, chitosan, ethyl cellulose, guar gum, hydroxyethyl cellulose, hydroxyethylmethyl cellulose, hydroxypropyl cellulose, hydroxypropyl methyl cellulose, methyl cellulose, microcrystalline cellulose, poloxamer, polyethylene oxide, polymethacrylates, povidone, a saccharide, starch, partially pregelatinized starch, and the like, or a combination thereof.

Exemplary disintegrants include alginic acid, carboxymethylcellulose calcium, carboxymethylcellulose sodium, cross-linked sodium carboxymethylcellulose (sodium croscarmellose), powdered cellulose, chitosan, croscarmellose sodium, crospovidone, guar gum, low substituted hydroxypropyl cellulose, methyl cellulose, microcrystalline cellulose, sodium alginate, sodium starch glycolate, partially pregelatinized starch, pregelatinized starch, starch, sodium carboxymethyl starch, and the like, or a combination thereof.

Exemplary lubricants include calcium stearate, magnesium stearate, glyceryl behenate, glyceryl palmitostearate, hydrogenated castor oil, light mineral oil, sodium lauryl sulfate, magnesium lauryl sulfate, sodium stearyl fumarate, stearic acid, zinc stearate, or a combination thereof.

Exemplary glidants include colloidal silica, amorphous silica, precipitated silica, talc, calcium phosphate tribasic, calcium silicate, magnesium silicate, magnesium trisilicate, or a combination thereof, and the like.

Active agents can be formulated into dosage forms using known techniques in the pharmaceutical art including dry blending and compression, wet granulation, encapsulation, dry granulation or wet granulation followed by compression or compaction, melt extrusion and spheronization, layering (e.g., spray layering suspension or solution), and the like. Examples of such techniques include direct compression, using appropriate punches and dies, the punches and dies are fitted to a suitable rotary tableting press; injection or compression molding using suitable molds fitted to a compression unit, granulation followed by compression; and extrusion in the form of a paste, into a mold or to an extrudate to be cut into lengths.

Tablets can be prepared by compression into a compressed form using conventional tableting equipment using standard techniques. Techniques and compositions for making tablets (compressed and molded) are described in Remington's Pharmaceutical Sciences, (Aurther Osol., editor), pp. 1553-1593 (1980).

Layering techniques suitable to prepare subunits include coating inert cores with a layering solution or dispersion of the active agent and a pharmaceutically acceptable excipient. Repeated layering can be used to build the subunit size and increase active agent amount.

The controlled-release dosage form can be prepared using controlled-release matrix materials, controlled-release coating materials, or a combination thereof.

The dosage forms may include functional or nonfunctional coatings. By "functional coating" is meant to include a coating that modifies the release properties of the total composition, for example, a controlled-release coating including a sustained-release or delayed-release coating. By "non-functional coating" is meant to include a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition.

Exemplary non-functional coatings include film forming polymers such as a water soluble hydroxyl cellulose (e.g. hydroxylpropyl methylcellulose, etc.), polyvinyl alcohol, and the like; optionally further including an additional pharmaceutically acceptable coating excipient such as a plasticizer, a stabilizer, an anti-tacking agent (e.g., talc), a surfactant, and the like, or a combination thereof.

Exemplary functional coatings include polymers such as cellulose esters (e.g. ethylcellulose); a polymethacrylate (e.g. copolymers of acrylic and methacrylic acid esters), and the like; optionally further including an additional pharmaceutically acceptable coating excipient such as a plasticizer, a stabilizer, a water-soluble component (e.g. pore formers), an anti-tacking agent (e.g., talc), a surfactant, and the like, or a combination thereof.

Suitable methods known in the pharmaceutical art can be used to apply the coating material. Processes such as simple or complex coacervation, interfacial polymerization, liquid drying, thermal and ionic gelation, spray drying, spray chilling, fluidized bed coating, pan coating, or electrostatic deposition may be used.

Dosing and Administration

Oral dosage forms containing active agents can be administered to prevent or treat formation of kidney stones anywhere from once to multiple times per day, preferably one to four times per day and most preferably twice per day. Multiple dosage forms can be taken per dosing, preferably one to four dosage forms and most preferably one to two dosage forms and ideally, 1 dosage form. The dosage form can be taken with or without regard to food.

EXAMPLES

Example 1

A series of tests was run to evaluate the impact that various formulations of ingredients had on the rate of calcium oxalate crystal growth. Formulations were evaluated for their ability to achieve 100% inhibition of the in vitro growth rate of calcium oxalate crystals. Initially, the growth of calcium oxalate crystals in aqueous solution was determined by UV-Visible spectroscopy and is referred to as a "Control Vehicle". Then, various formulations were evaluated for their ability to inhibit the growth rate of calcium oxalate crystals compared to the Control Vehicle.

All reagents were chemical grade or plant extracts as listed in the Reagent Table below. Other grades and sources of reagents may be used.

Reagent Table

| Reagent | Chemical Grade | Commercial Source | Lot # |
|---|---|---|---|
| Calcium chloride, dihydrate | ACS analytical grade | Mallinkrodt | G23H14 |
| Sodium oxalate | ACS Reagent ≥99.5% | Sigma-Aldrich | MKBP6508V |
| Sodium acetate | AR analytical reagent | Fisher Scientific | 7372KVND |
| Sodium Chloride | USP food grade | Mallinkrodt | 7532KVPG |
| Banana stem extract - Musa | | Acetar Biotech | TY140603 |
| Phytin | | TCI America | FFEKL-FA |
| Magnesium citrate | | BulkSupplements.com | 20141019 |
| Pyridoxine HCl | ≥98% HPLC | Sigma Aldrich | SLBK1634V |
| Citric acid | | TCI America | SVJKMIT |

Experimental Spectrophotometric Method:

The spectrophotometric method employed was based on the work of Chow (Chow, 2004b, Citrate inhibits growth of residual fragments in an in vitro model of calcium oxalate renal stones. Kidney International, 665:1724-1730) and is briefly described below. The study was conducted using a sodium acetate/sodium chloride buffer at pH 5.7 as recommended by Khan (Khan 2012, Antiurolithic activity of *Origanum vulgare* is mediated through multiple pathways BMC Complementary and Alternative Medicine 11: 96-112.).

The kinetics of calcium oxalate crystal formation in a control vehicle were characterized by the slope method of Hess (Hess, B. et al., Nephrol. Dial. Transplant, 2000, 15(3): 366-374). Briefly, 1.6 milliliters of an 8.5 mM solution of calcium chloride was added to a plastic cuvette and 1.6 milliliters of a 1.5 mM sodium oxalate solution was then added. Both of the solutions were prepared in a buffer composed of 50 mM sodium acetate and 100 mM sodium chloride at pH 5.7. Immediately upon combining the solutions, the cuvette was mixed by inversion and the kinetics of calcium oxalate crystal formation were monitored at 620 nm using a spectrophotometer. A Vernier SpectroVis spectrophotometer was used. Measurements were made in the Absorbance versus Time mode, using ten (10) minutes for a full run with an acquisition of 10 samples per minute. Other spectrophotometers, wavelengths, and methods may also be used to determine calcium oxalate crystal formation over time.

The inhibition of the kinetics of calcium oxalate crystal formation by the various Test Solutions set forth below was determined using the method described above with the following change. Before the sodium oxalate solution was added, 200 µL of the Test Solution is added to the cuvette. The remainder of the procedure was the same as described above. The inhibition of crystal growth was determined by comparison of the effect of the Test Solution on the slope of the initial velocity (compared to vehicle control, during the first two minutes), as described by Hess (Hess, 2000). Individual replicates identified as outliers by the Grubb's test were not included in the calculation (Grubbs, Frank E., 1950, Sample criteria for testing outlying observations, The Annals of Mathematical Statistics 21(1), p. 27-58.). Other methods of determining percent inhibition of calcium oxalate crystal formation, such as by individual runs or other statistical methods are also possible.

The Test Solutions were prepared by adding the following ingredients in the amounts given in Tables 1 and 11-15 in the order listed (for an ingredient not used in Matrix 1 through 5, the order remained the same but that ingredient was omitted) to a 100 mL volumetric flask:

Citric acid—added as a dry powder to a 100 mL volumetric flask;

Magnesium citrate—added as a dry powder to above volumetric flask and 50 mL distilled $H_2O$ added and vortexed until clear Phytin—added to above volumetric flask and vortexed until clear Pyridoxine—added to above volumetric flask and vortexed until clear Musa—50 mL of the prepared solution (see below) added to the above volumetric flask and made up to final volume of 100 mL with water.

The Musa samples were prepared by placing the indicated amount of Musa, as a dry powder, (see Table 1) in a 100 mL volumetric flask and making up to volume with water. The flask was vortexed intermittently for 5 minutes. At this time the sample was transferred to a centrifuge tube and centrifuged at 3000 rpm for 30 minutes. 50 mL of the supernatant was carefully transferred to a 50 mL volumetric flask and vortexed to assure complete solubility. This 50 mL homogeneous solution was transferred to the original 100 mL volumetric flask and vortexed to assure complete solubility.

For Matrix 5 test solutions, which did not include any citric acid, the entire procedure was the same except magnesium citrate was added as a dry powder to a 100 mL volumetric flask to which 40 mL distilled $H_2O$ was added and then sufficient 1 N HCl to impart a pH of between 1 and 2 to the final solution. The flask was vortexed until complete dissolution. The total volume of the magnesium citrate solution was <50 mL. Phytin, pyridoxine, and musa were added to complete the 100 mL Matrix 5 test solutions as described above. For Matrix 5 Test solution 7, magnesium citrate (203 mg) was added to a 100 mL volumetric flask to which 35 mL distilled water added and then 2.5 mL 1 N HCl was added, yielding a pH of between 1 and 2. The flask was vortexed until clear. To this volumetric flask was added 600 mg phytin and then 10 mL distilled water. The solution was vortexed, and then permitted to stand for approximately 3 minutes until the top of the liquid was clear. The pH was pH 6. An additional 2.5 mL 1 N HCl was added to yield a pH between 1 and 2. The flask was vortexed until clear. Pyridoxine and musa were then added to complete the 100 mL Matrix 5 Test Solution, as described above.

TABLE 1

Amounts of Active Ingredients in Five Ingredient Test Solutions.

| Active Ingredient | Test Solution 1 | Test Solution 2 | Test Solution 3 | Test Solution 4 | Test Solution 5 | Test Solution 6 | Test Solution 7 |
|---|---|---|---|---|---|---|---|
| Citric Acid | 352 mg | 101 mg | 1050 mg | 700 mg | 352 mg | 176 mg | 351 mg |
| Mg Citrate | 151 mg | 76 mg | 2.02 mg | 226 mg | 201 mg | 150 mg | 152 mg |
| Phytin | 202 mg | 201 mg | 100 mg | 3.03 | 600 mg | 400 mg | 200 mg |
| Pyridoxine | 5.4 mg | 10.1 mg | 5.99 mg | 2.67 | 0.2 mg | 15.1 mg | 5.3 mg |
| Musa | 251 mg | 251 mg | 167 mg | 85 mg | 41 mg | 1.4 mg | 251 mg |

Figure 1:
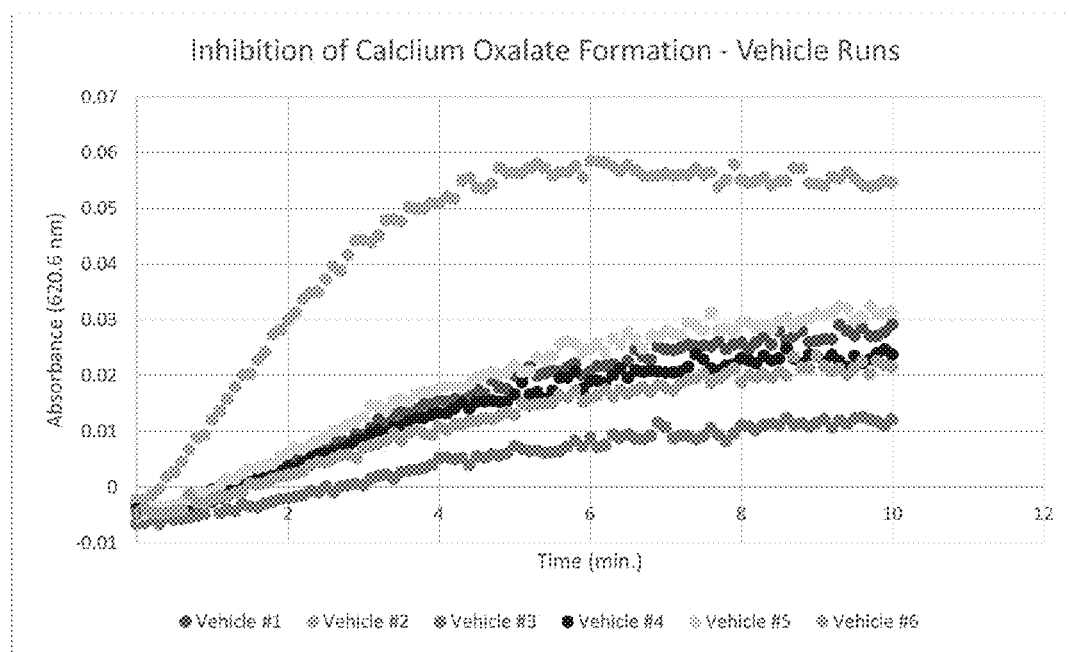
FIG. 1 is a graph showing absorbance at 620.6 nm as a function of time for Control Vehicle Runs Associated with Test Solution 1.
Figure 2:
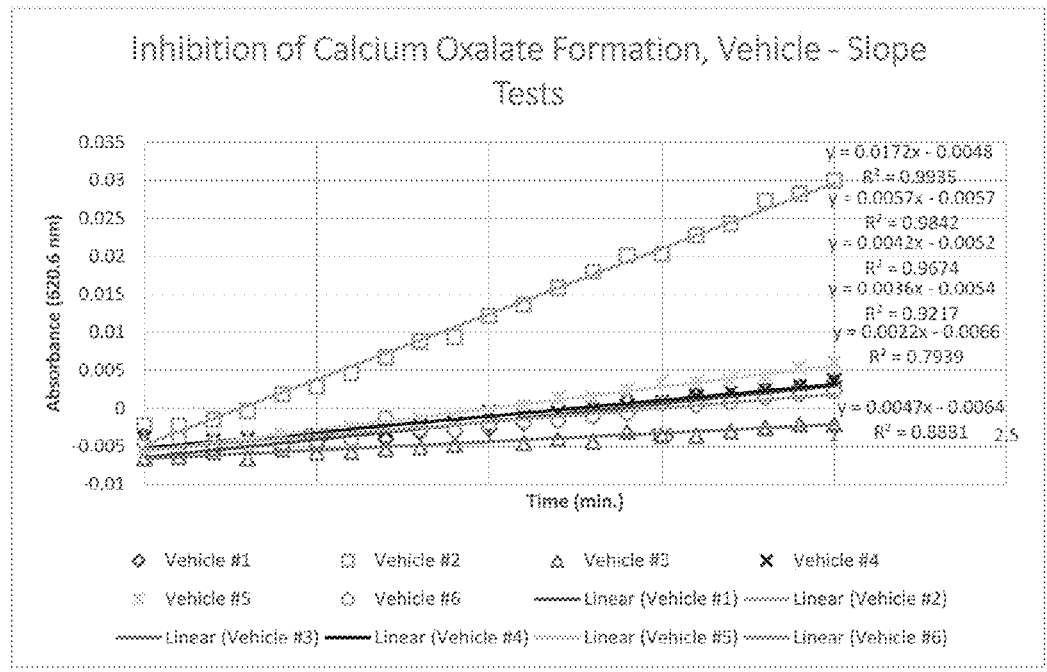
FIG. 2 is a graph showing absorbance at 620.6 nm as a function of time to determine the Slope for Control Vehicle Runs Associated with Test Solution 1.
Figure 3:
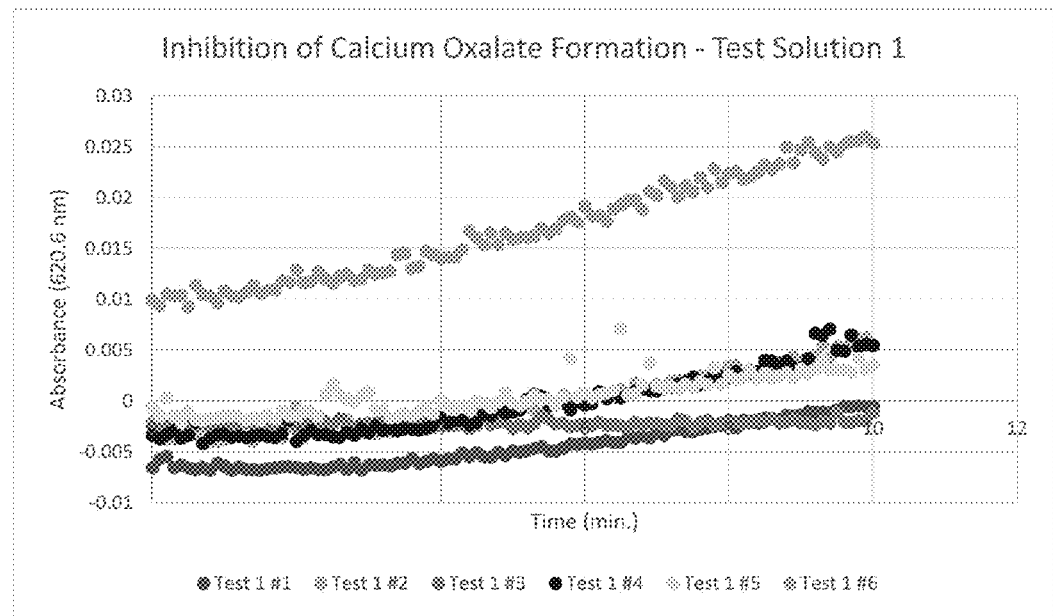
FIG. 3 is a graph showing absorbance at 620.6 nm as a function of time for Test Solution 1.
Figure 4:
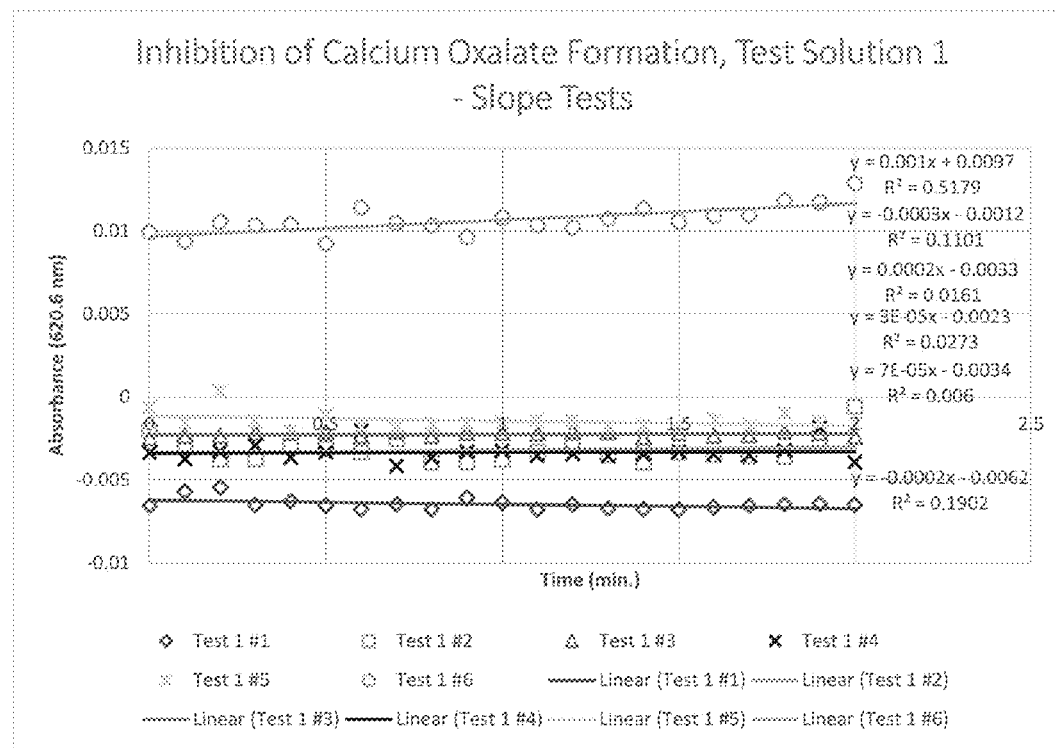
FIG. 4 is a graph showing absorbance at 620.6 nm as a function of time to determine the Slope for Test Solution 1.

FIG. 1 shows the absorbance as function of time for the first 10 minutes and measures the formation of calcium oxalate over time for the Control Vehicle runs used for Test Solution 1. From the figure it can be seen that calcium oxalate crystals are indeed forming during the ten minutes of the run. FIG. 2 shows the slopes of the curves for the initial two minutes of the runs for the Control Vehicle used for Test Solution 1. Since the data was linear ($R^2>0.95$) for the first two (2) minutes, this data was plotted for slope determination by linear regression analysis. FIG. 3 shows the absorbance as function of time for the first 10 minutes and measures the formation of calcium oxalate over time for the Control Vehicle runs used for Test Solution 1. FIG. 4 shows the slopes of the curves for the initial two minutes of the runs for Test Solution 1. Since the data was linear ($R^2>0.95$) for the first two (2) minutes, this data was plotted for slope determination by linear regression analysis.

Table 2 shows the analysis of the slopes FIGS. 2 and 4. Each run is designated as a Replicate. Outlier data identified using the Grubbs' Test (Grubbs, 1950) were not included in % inhibition calculations. The median % Inhibition was calculated according to the method of Hess (Hess, 2000) using the following equation:

% Inhibition=100%*(1−(Slope of Test Solution/ Slope of Control Vehicle)).

The mean (average) percent inhibition can also be calculated from the data. Median and mean percent inhibitions are presented in Tables 9, 11-15. In some embodiments, the median percent inhibition is the preferred measure of percent inhibition.

Figure 5:
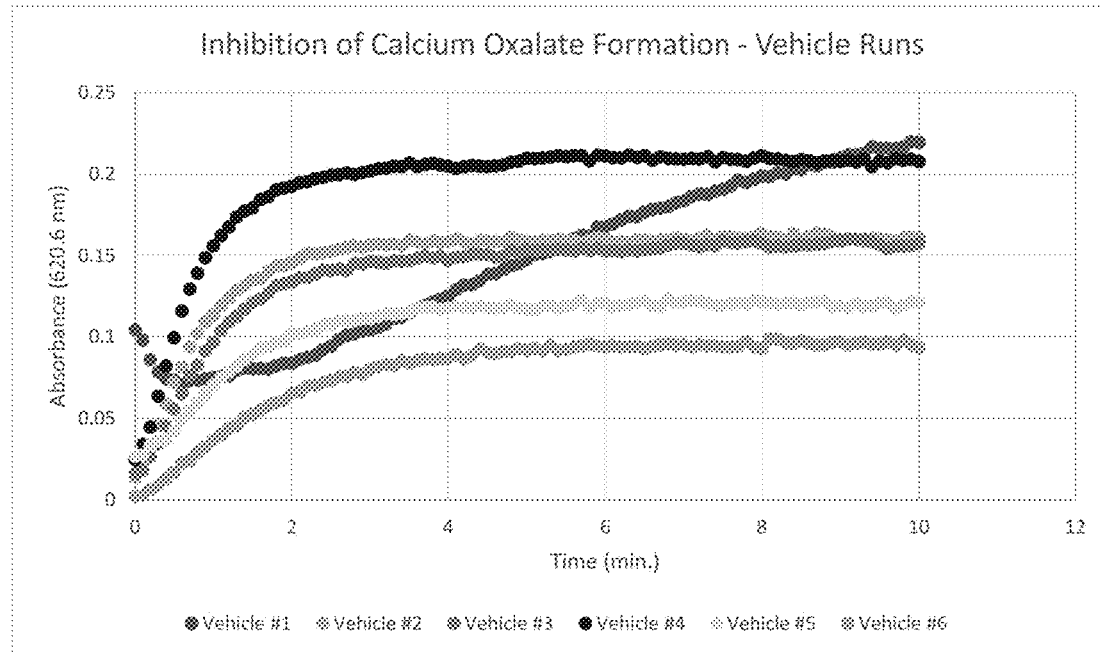
FIG. 5 is a graph showing absorbance at 620.6 nm as a function of time for Control Vehicle Runs Associated with Test Solution 2.
Figure 6:
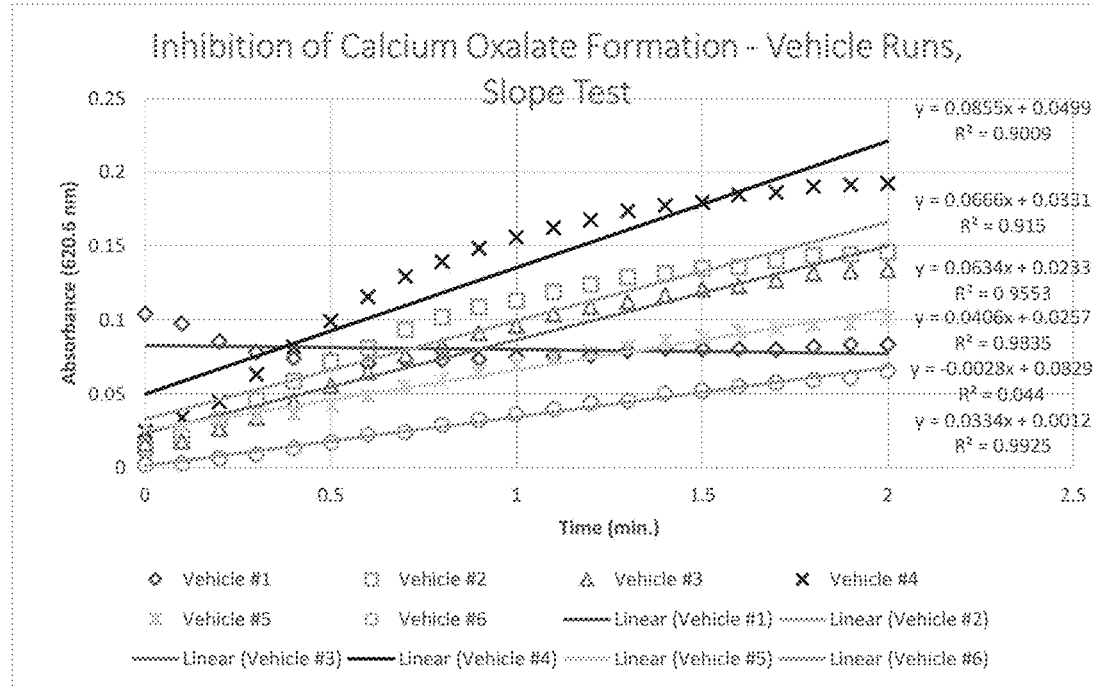
FIG. 6 is a graph showing absorbance at 620.6 nm as a function of time to determine the Slope for Control Vehicle Runs Associated with Test Solution 2.
Figure 7:
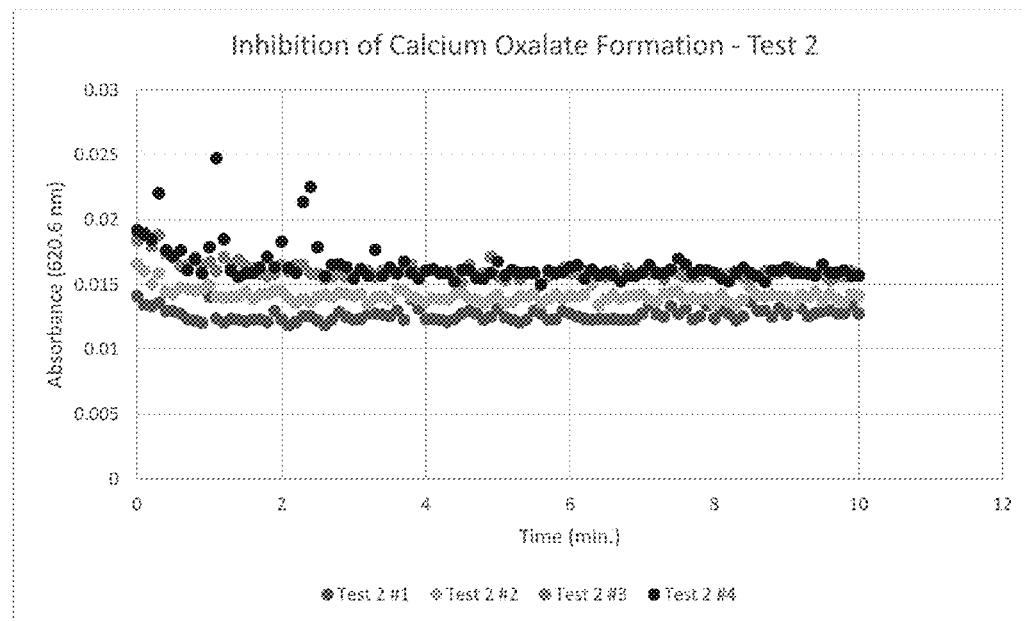
FIG. 7 is a graph showing absorbance at 620.6 nm as a function of time for Test Solution 2.
Figure 8:
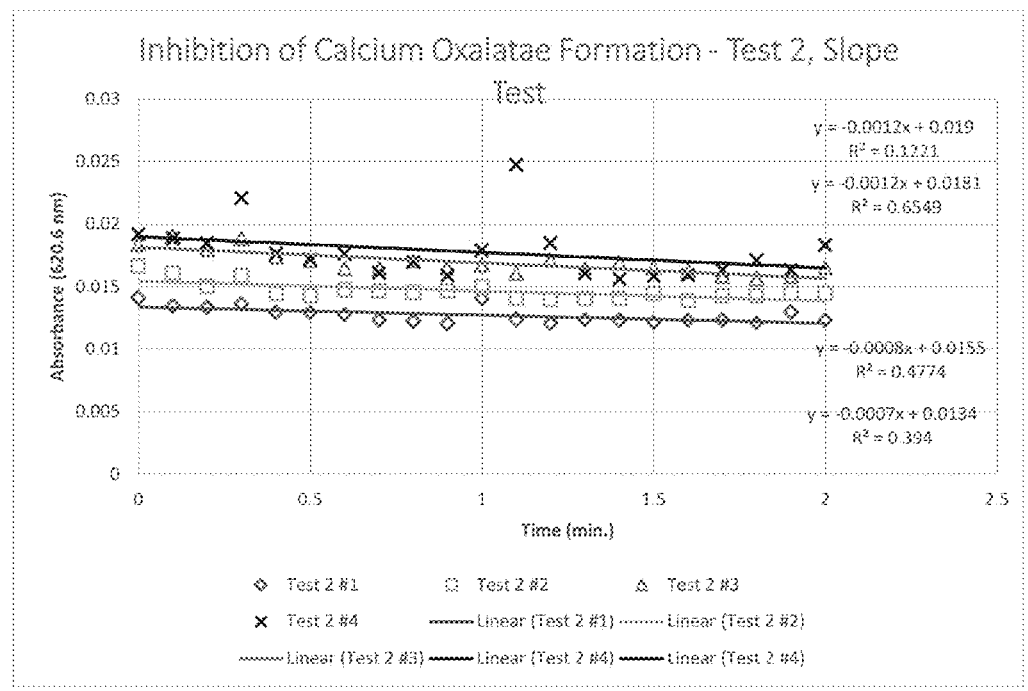
FIG. 8 is a graph showing absorbance at 620.6 nm as a function of time to determine the Slope for Test Solution 2.

FIG. 5 shows the absorbance as function of time for the first 10 minutes and measures the formation of calcium oxalate over time for the Control Vehicle runs used for Test Solution 2. From the figure it can be seen that calcium oxalate crystals are indeed forming during the ten minutes of the run. FIG. 6 shows the slopes of the curves for the initial two minutes of the runs for the Control Vehicle used for Test Solution 2. Since the data was linear ($R^2>0.95$) for the first two (2) minutes, this data was plotted for slope determination by linear regression analysis. FIG. 7 shows the absorbance as function of time for the first 10 minutes and measures the formation of calcium oxalate over time for the Control Vehicle runs used for Test Solution 1. FIG. 8 shows the slopes of the curves for the initial two minutes of the runs for Test Solution 2. Since the data was linear ($R^2>0.95$) for the first two (2) minutes, this data was plotted for slope determination by linear regression analysis. Table 3 shows the analysis of the slopes FIGS. 6 and 8. Each run is designated as a Replicate.

TABLE 3

Data Analysis for Slope Test, Control Vehicle & Test Solution 2

| | Replicate #1 | Replicate #2 | Replicate #3 | Replicate #4 | Replicate #5 | Replicate #6 | Median | Median % Inhibition |
|---|---|---|---|---|---|---|---|---|
| Control Vehicle | −0.028 | 0.0666 | 0.0634 | 0.0855 | 0.0406 | 0.0334 | 0.0634 | |
| Test Solution 2 | −0.0007 | −0.0008 | −0.0012 | −0.0012 | — | — | −0.001 | 101.5773 |

Figure 9:
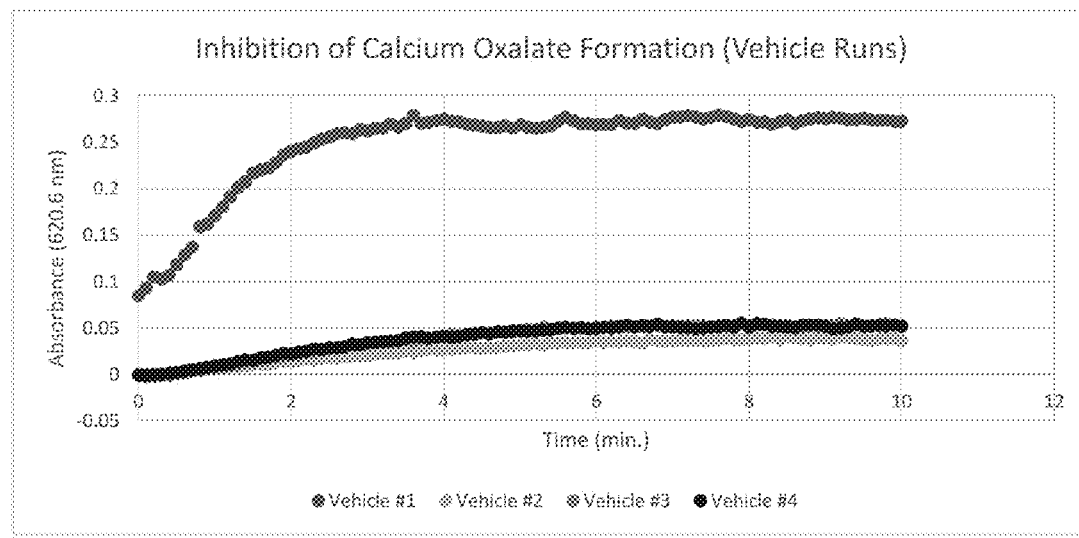
FIG. 9 is a graph showing absorbance at 620.6 nm as a function of time for Control Vehicle Runs Associated with Test Solution 3.
Figure 10:
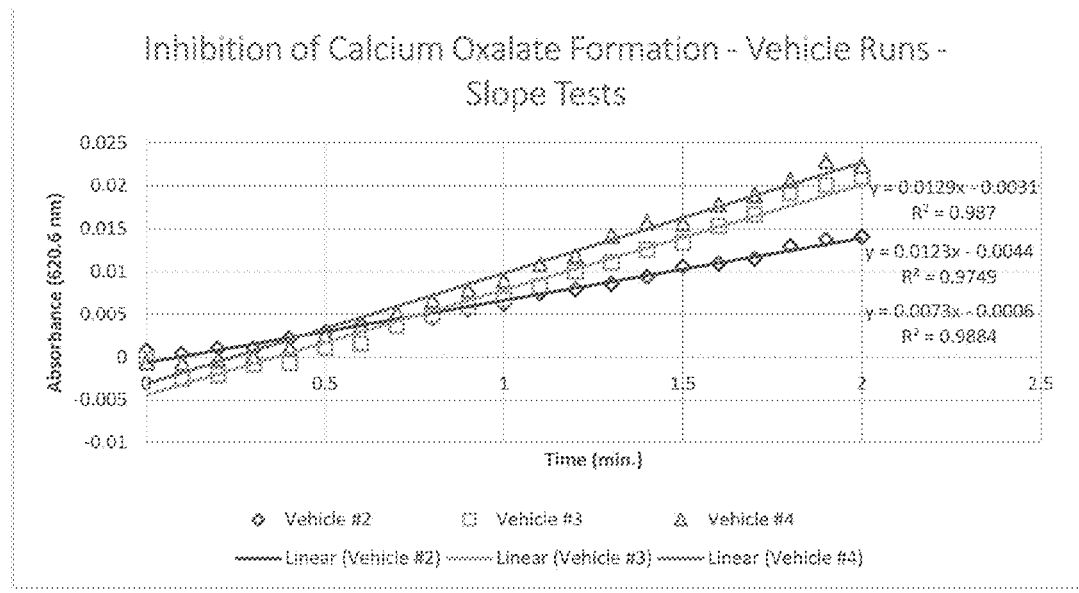
FIG. 10 is a graph showing absorbance at 620.6 nm as a function of time to determine the Slope for Control Vehicle Runs Associated with Test Solution 3.
Figure 11:
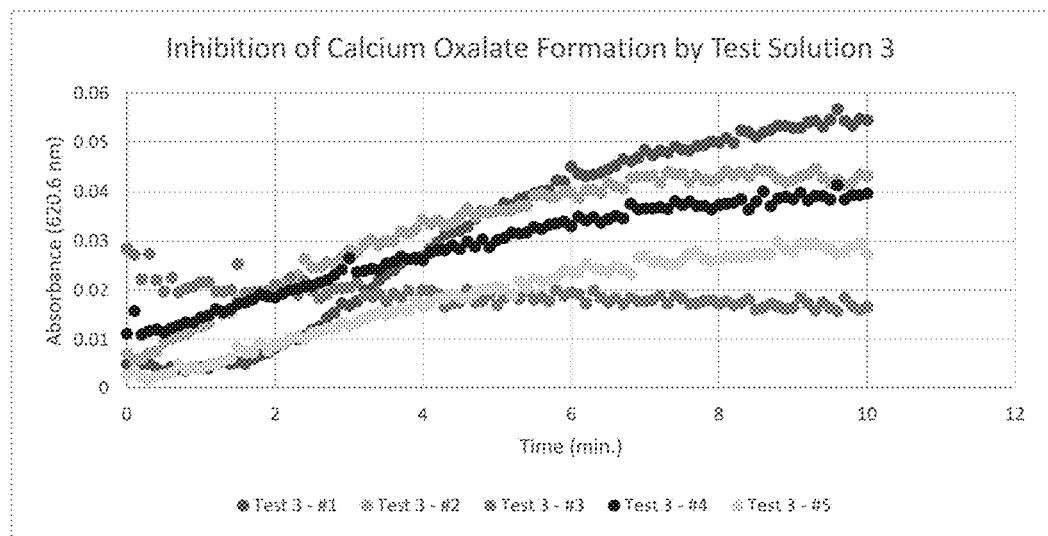
FIG. 11 is a graph showing absorbance at 620.6 nm as a function of time for Test Solution 3.
Figure 12:
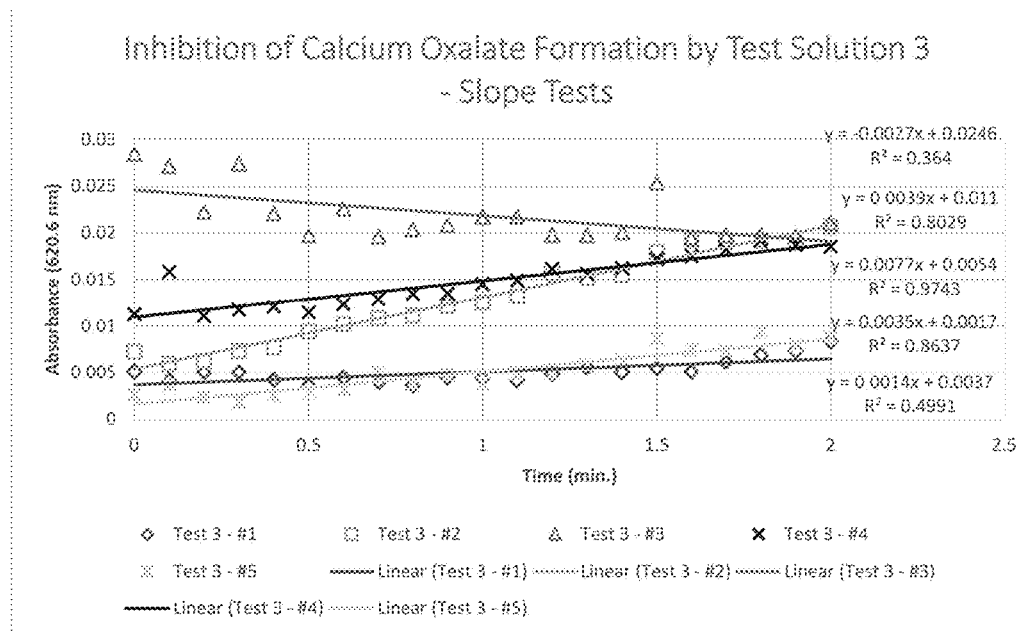
FIG. 12 is a graph showing absorbance at 620.6 nm as a function of time to determine the Slope for Test Solution 3.

FIG. 9 shows the absorbance as function of time for the first 10 minutes and measures the formation of calcium oxalate over time for the Control Vehicle runs used for Test Solution 3. From the figure it can be seen that calcium oxalate crystals are indeed forming during the ten minutes of the run. FIG. 10 shows the slopes of the curves for the initial two minutes of the runs for the Control Vehicle used for Test Solution 3. Since the data was linear ($R^2>0.95$) for the first two (2) minutes, this data was plotted for slope determination by linear regression analysis. FIG. 11 shows the absorbance as function of time for the first 10 minutes and measures the formation of calcium oxalate over time for the Control Vehicle runs used for Test Solution 3. FIG. 12 shows the slopes of the curves for the initial two minutes of the runs for Test Solution 3. Since the data was linear ($R^2>0.95$) for the first two (2) minutes, this data was plotted for slope determination by linear regression analysis. Table 4 shows the analysis of the slopes FIGS. 10 and 12. Each run is designated as a Replicate.

TABLE 2

Data Analysis for Slope Test, Control Vehicle & Test Solution 1

| | Replicate #1 | Replicate #2 | Replicate #3 | Replicate #4 | Replicate #5 | Replicate #6 | Median | Median % Inhibition |
|---|---|---|---|---|---|---|---|---|
| Control Vehicle | 0.0047 | 0.0172 | 0.0022 | 0.0042 | 0.0057 | 0.0036 | 0.00445 | |
| Test Solution 1 | −0.0002 | 0.0002 | 0.00003 | 0.00007 | −0.0003 | 0.001 | 0.00005 | 98.8764 |

TABLE 4

Data Analysis for Slope Test, Control Vehicle & Test Solution 3

| | Replicate #1 | Replicate #2 | Replicate #3 | Replicate #4 | Median | Median % Inhibition |
|---|---|---|---|---|---|---|
| Control Vehicle | 0.0073 | 0.0123 | 0.0129 | 0.0115 | 0.0119 | |
| Test Solution 3 | 0.0014 | 0.0077 | 0.0039 | 0.0035 | 0.0035 | 70.5882 |

Figure 13:
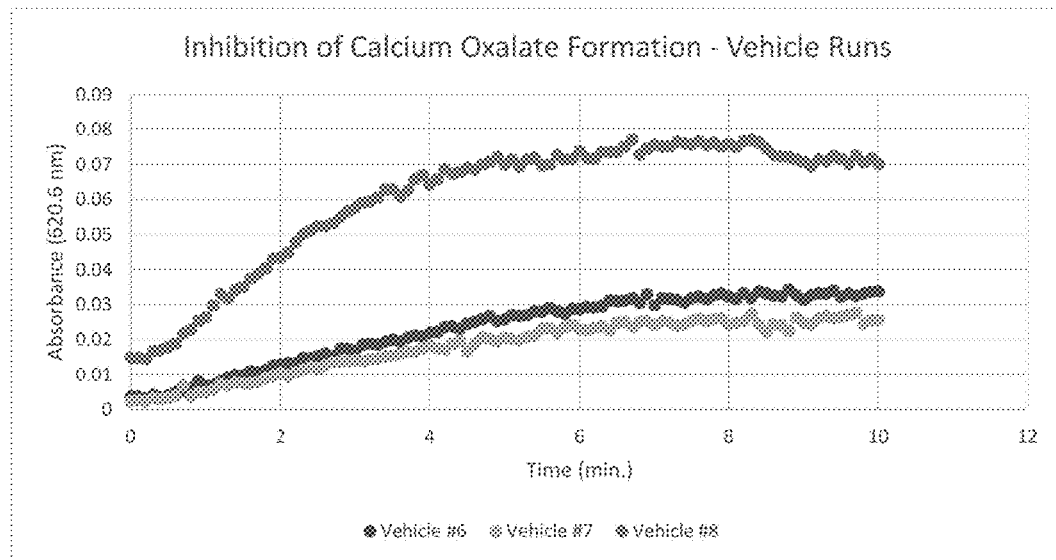
FIG. 13 is a graph showing absorbance at 620.6 nm as a function of time for Control Vehicle Runs Associated with Test Solution 4.
Figure 14:
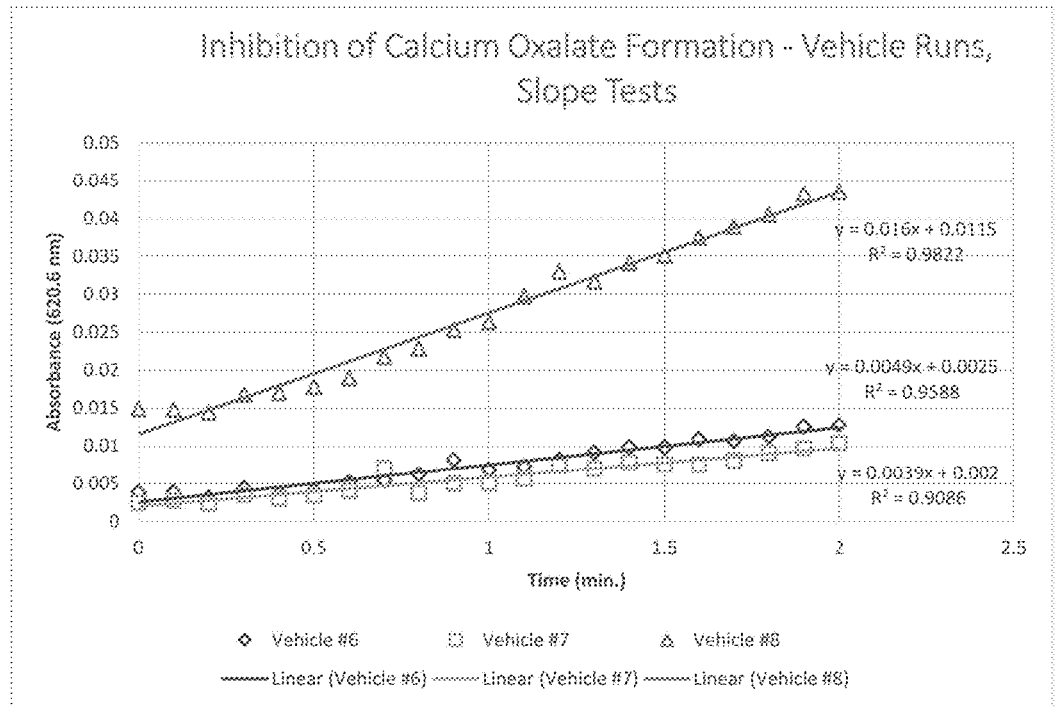
FIG. 14 is a graph showing absorbance at 620.6 nm as a function of time to determine the Slope for Control Vehicle Runs Associated with Test Solution 4.
Figure 15:
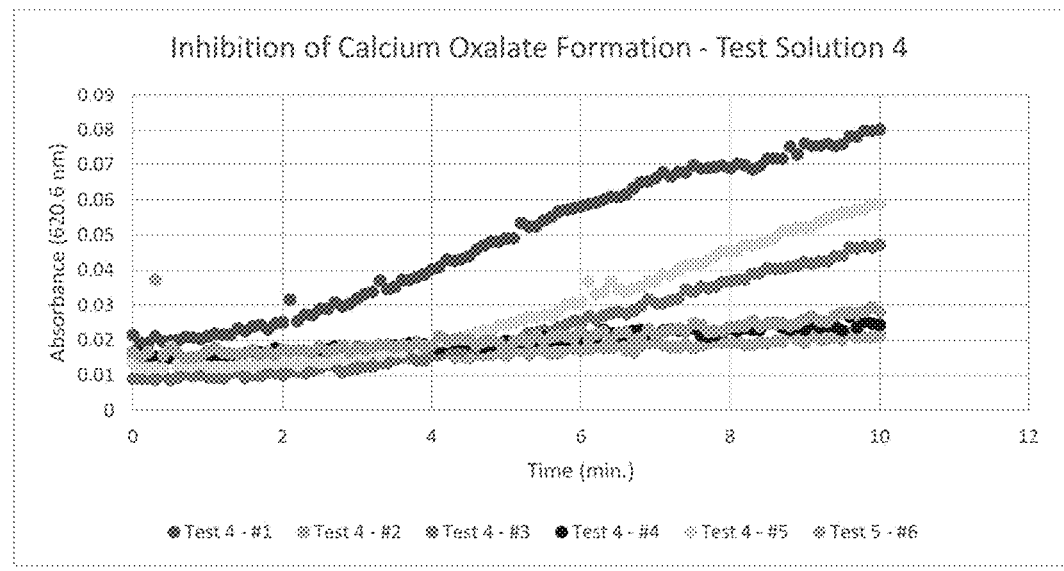
FIG. 15 is a graph showing absorbance at 620.6 nm as a function of time for Test Solution 4.
Figure 16:
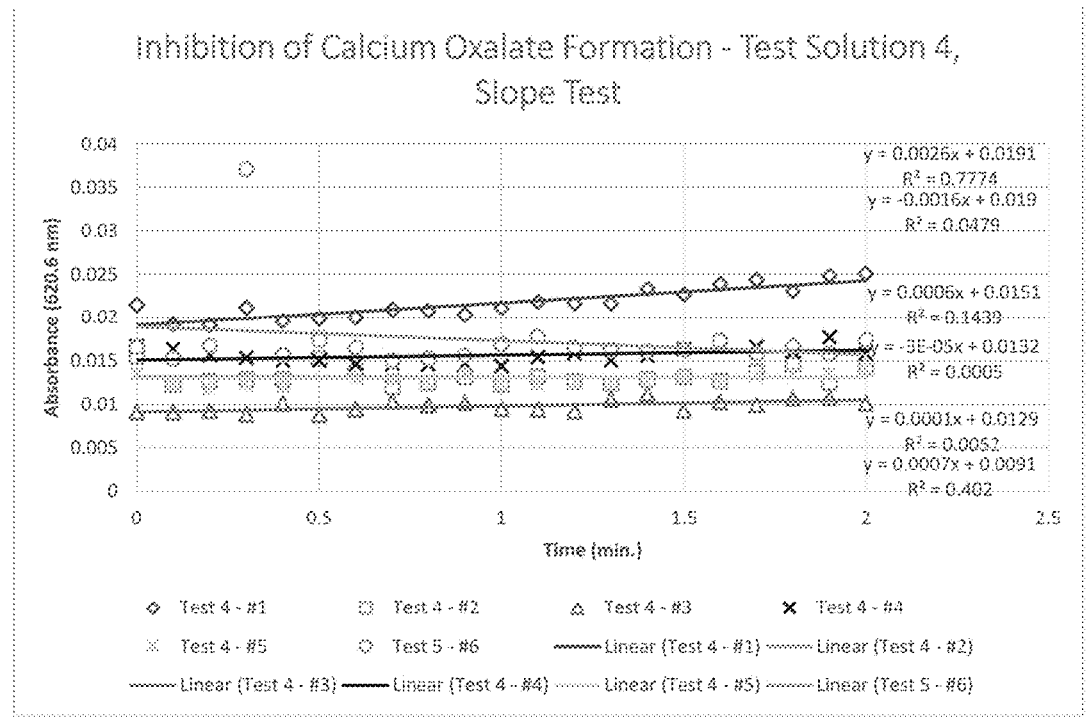
FIG. 16 is a graph showing absorbance at 620.6 nm as a function of time to determine the Slope for Test Solution 4.

FIG. 13 shows the absorbance as function of time for the first 10 minutes and measures the formation of calcium oxalate over time for the Control Vehicle runs used for Test Solution 4. From the figure it can be seen that calcium oxalate crystals are indeed forming during the ten minutes of the run. FIG. 14 shows the slopes of the curves for the initial two minutes of the runs for the Control Vehicle used for Test Solution 4. Since the data was linear ($R^2 > 0.95$) for the first two (2) minutes, this data was plotted for slope determination by linear regression analysis. FIG. 15 shows the absorbance as function of time for the first 10 minutes and measures the formation of calcium oxalate over time for the Control Vehicle runs used for Test Solution 4. FIG. 16 shows the slopes of the curves for the initial two minutes of the runs for Test Solution 4. Since the data was linear ($R^2 > 0.95$) for the first two (2) minutes, this data was plotted for slope determination by linear regression analysis. Table 5 shows the analysis of the slopes FIGS. 14 and 16. Each run is designated as a Replicate.

TABLE 5

Data Analysis for Slope Test, Control Vehicle & Test Solution 4

| | Replicate #1 | Replicate #2 | Replicate #3 | Median | Median % Inhibition |
|---|---|---|---|---|---|
| Control Vehicle | 0.0772 | 0.107 | 0.081 | 0.081 | |
| Test Solution 4 | 0.0026 | 0.0007 | 0.0006 | 0.0004 | 99.5679 |

Figure 17:
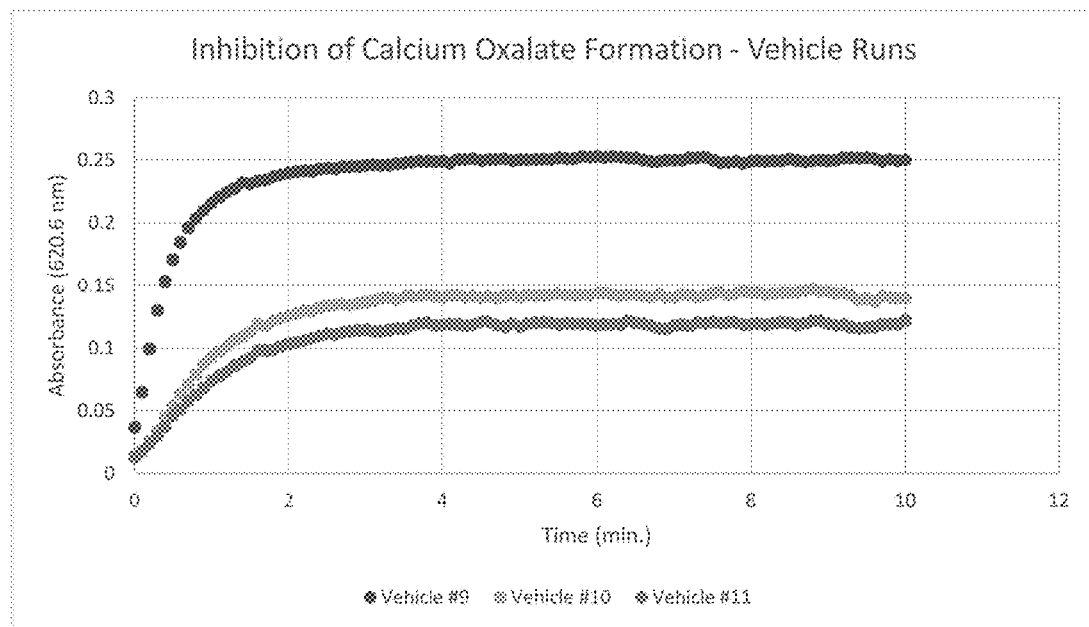
FIG. 17 is a graph showing absorbance at 620.6 nm as a function of times for Control Vehicle Runs Associated with Test Solution 5.
Figure 18:
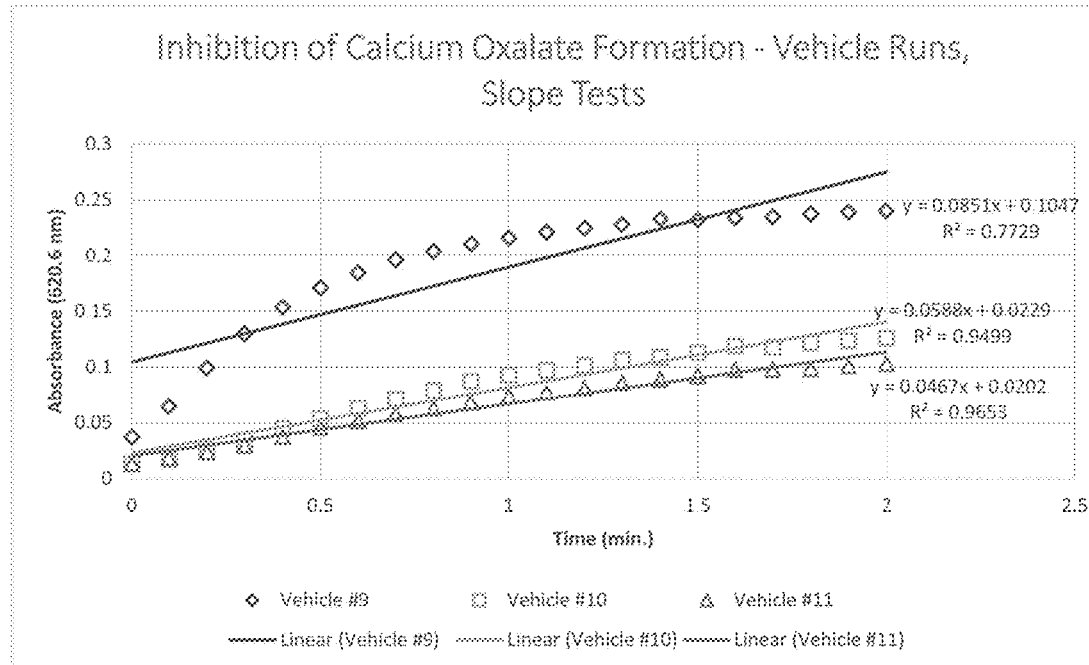
FIG. 18 is a graph showing absorbance at 620.6 nm as a function of time to determine the Slope for Vehicle Runs Associated with Test Solution 5.
Figure 19:
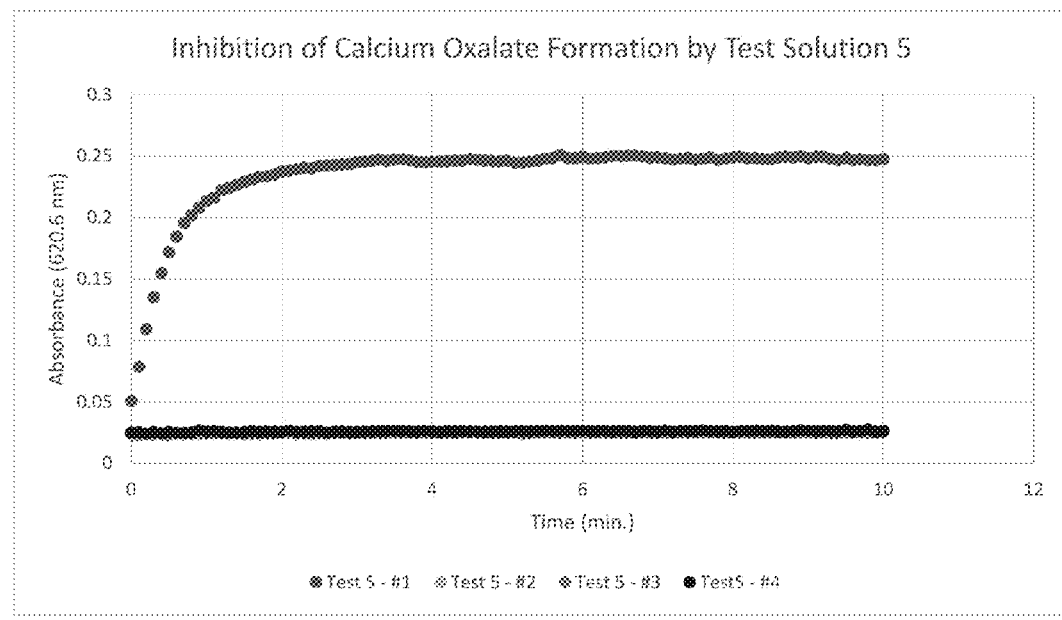
FIG. 19 is a graph showing absorbance at 620.6 nm as a function of time for Test Solution 5.
Figure 20:
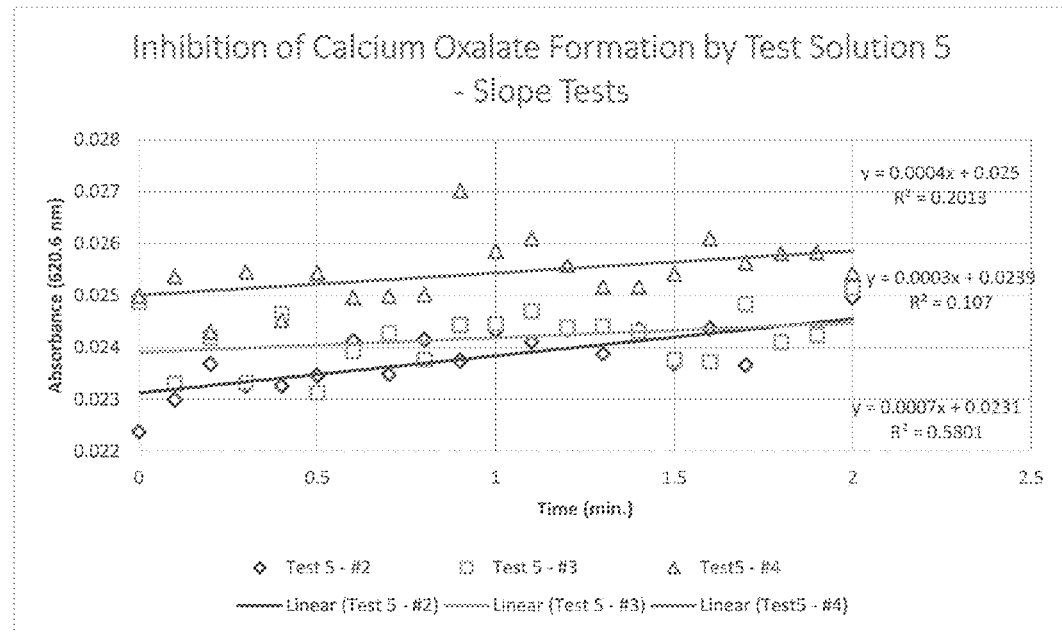
FIG. 20 is a graph showing absorbance at 620.6 nm as a function of time to determine the Slope for Test Solution 5.

FIG. 17 shows the absorbance as function of time for the first 10 minutes and measures the formation of calcium oxalate over time for the Control Vehicle runs used for Test Solution 5. From the figure it can be seen that calcium oxalate crystals are indeed forming during the ten minutes of the run. FIG. 18 shows the slopes of the curves for the initial two minutes of the runs for the Control Vehicle used for Test Solution 5. Since the data was linear ($R^2 > 0.95$) for the first two (2) minutes, this data was plotted for slope determination by linear regression analysis. FIG. 19 shows the absorbance as function of time for the first 10 minutes and measures the formation of calcium oxalate over time for the Control Vehicle runs used for Test Solution 5. FIG. 20 shows the slopes of the curves for the initial two minutes of the runs for Test Solution 5. Since the data was linear ($R^2 > 0.95$) for the first two (2) minutes, this data was plotted for slope determination by linear regression analysis. Table 6 shows the analysis of the slopes FIGS. 18 and 20. Each run is designated as a Replicate.

TABLE 6

Data Analysis for Slope Test, Control Vehicle & Test Solution 5

| | Replicate #1 | Replicate #2 | Replicate #3 | Median | Median % Inhibition |
|---|---|---|---|---|---|
| Control Vehicle | 0.0851 | 0.0508 | 0.0467 | 0.0588 | |
| Test Solution 5 | 0.0007 | 0.0003 | 0.0004 | 0.0004 | 99.3197 |

Figure 21:
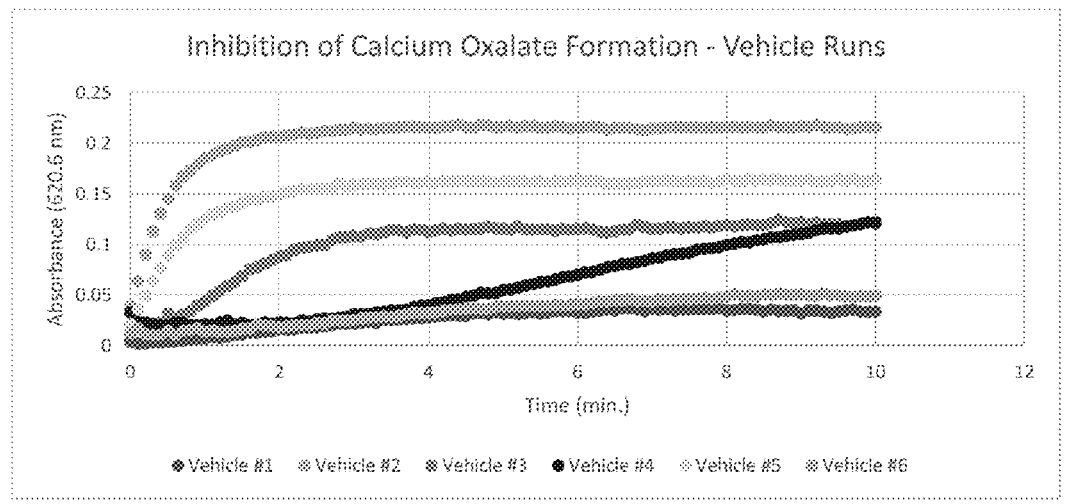
FIG. 21 is a graph showing absorbance at 620.6 nm as a function of time for Control Vehicle Runs Associated with Test Solution 6.
Figure 22:
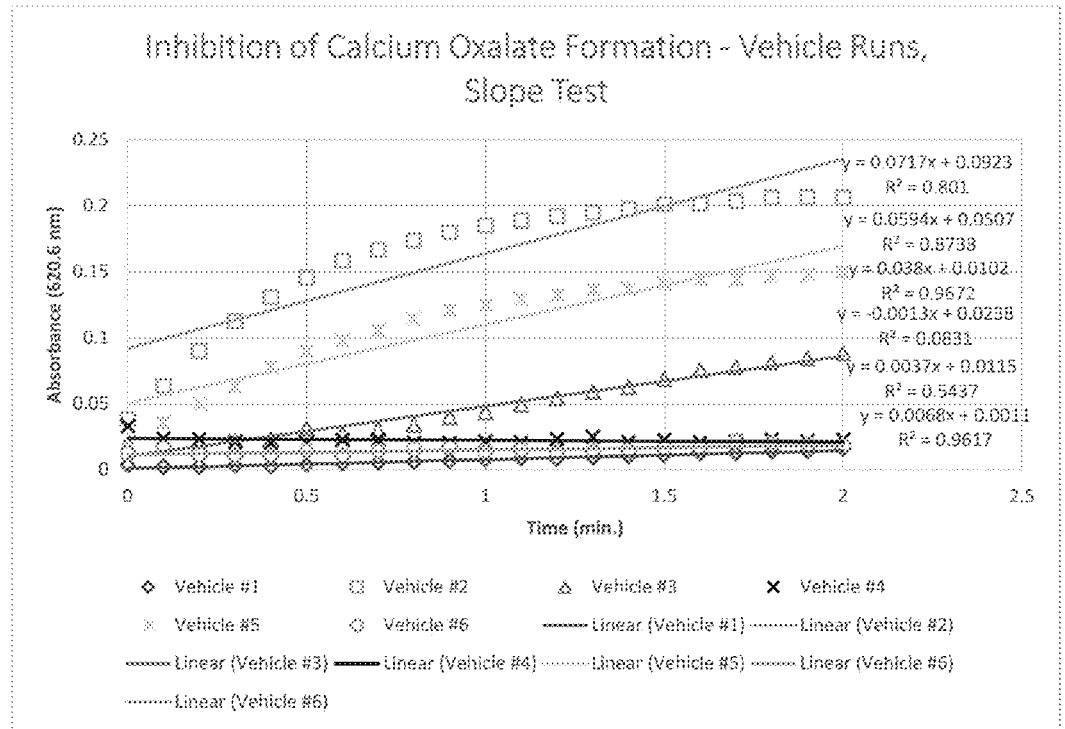
FIG. 22 is a graph showing absorbance at 620.6 nm as a function of time to determine the Slope for Control Vehicle Runs Associated with Test Solution 6.
Figure 23:
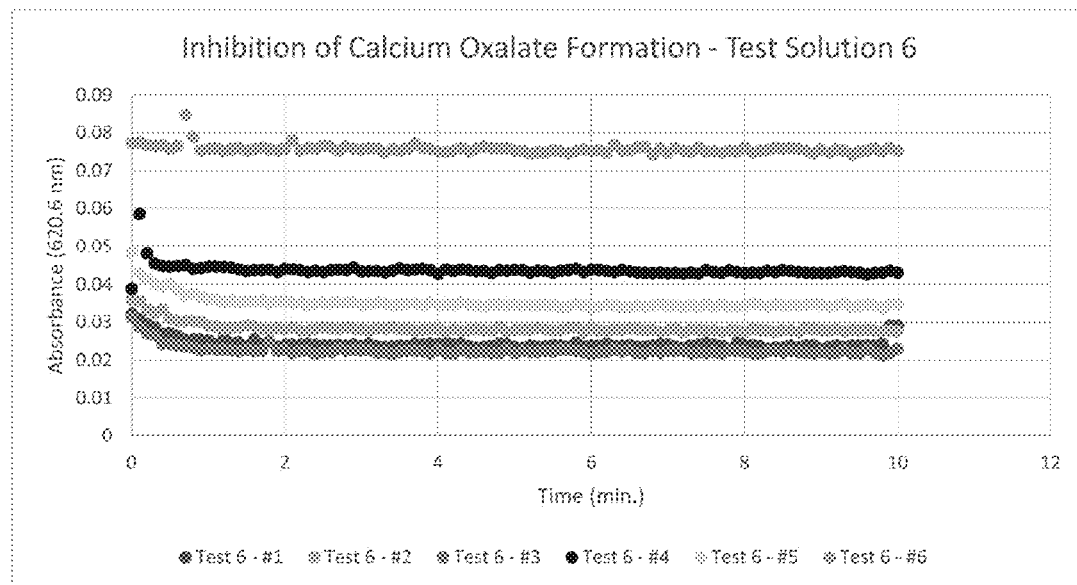
FIG. 23 is a graph showing absorbance at 620.6 nm as a function of time for Test Solution 6.
Figure 24:
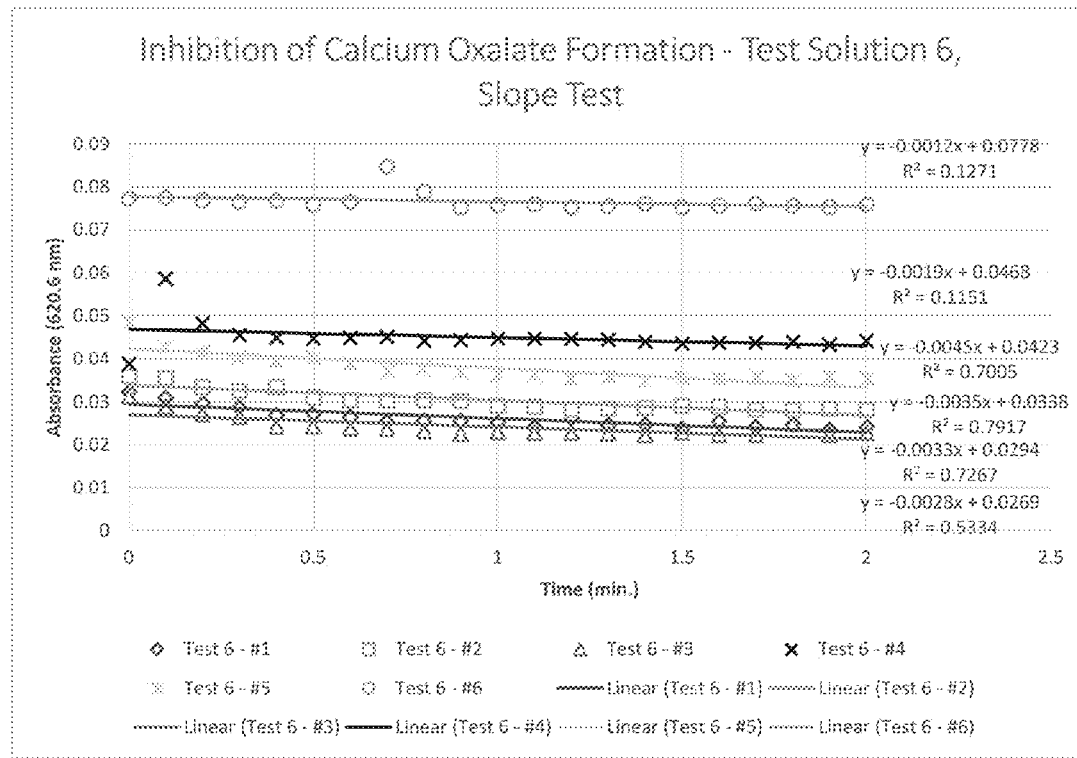
FIG. 24 is a graph showing absorbance at 620.6 nm as a function of time to determine the Slope for Test Solution 6.
Figure 25:
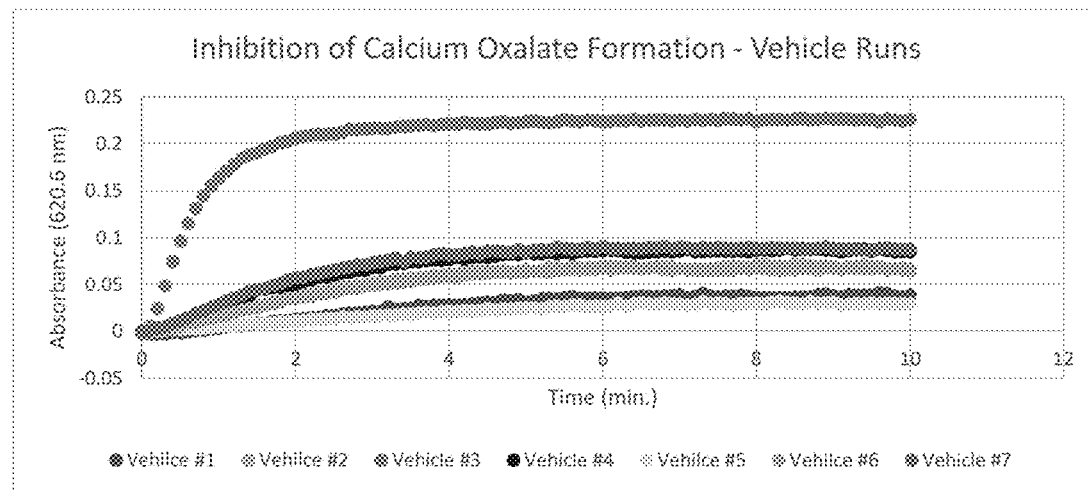
FIG. 25 is a graph showing absorbance at 620.6 nm as a function of time for Control Vehicle Runs Associated with Test Solution 7 (Repeat of Test Solution 1).
Figure 26:
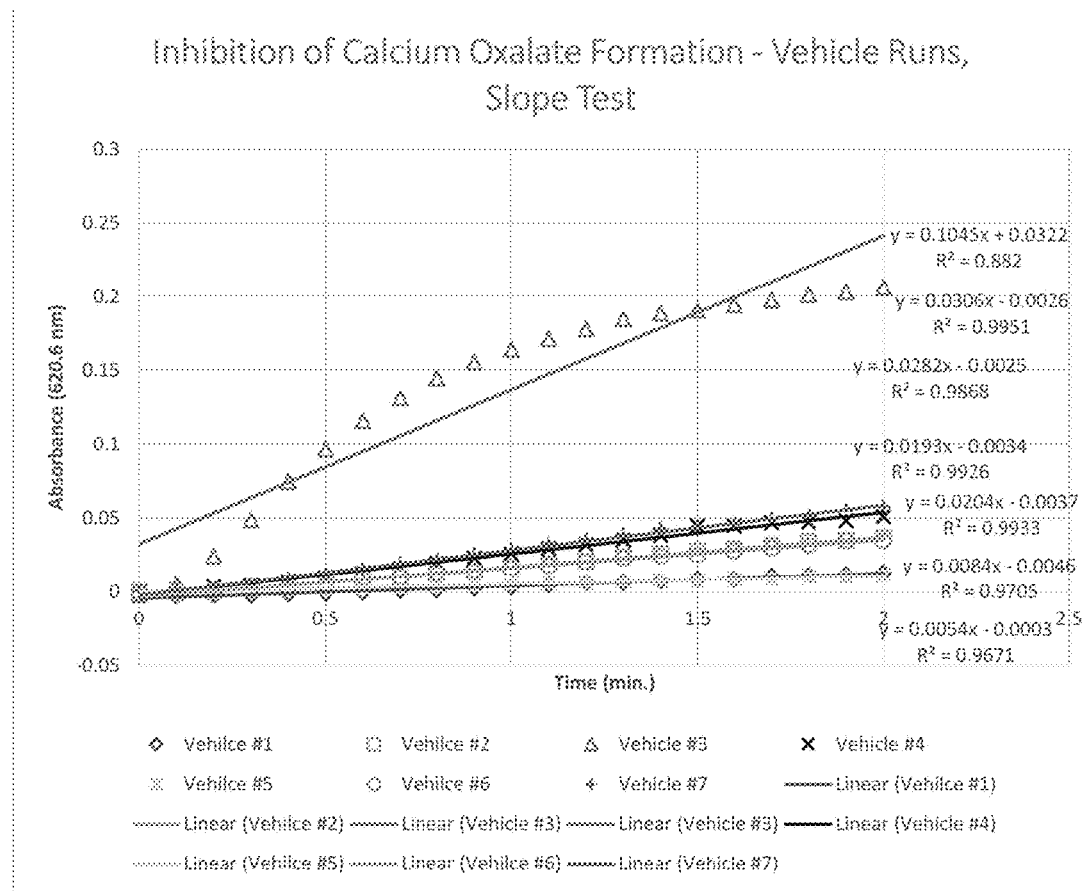
FIG. 26 is a graph showing absorbance at 620.6 nm as a function of time to determine the Slope for Control Vehicle Runs Associated with Test Solution 7 (Repeat of Test Solution 1).
Figure 27:
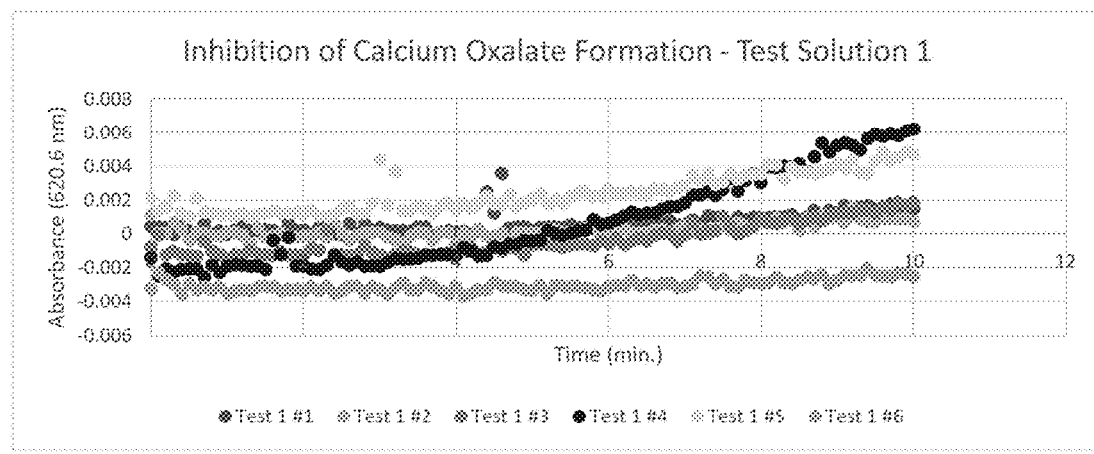
FIG. 27 is a graph showing absorbance at 620.6 nm as a function of time for Test Solution 7 (Repeat of Test Solution 1).
Figure 28:
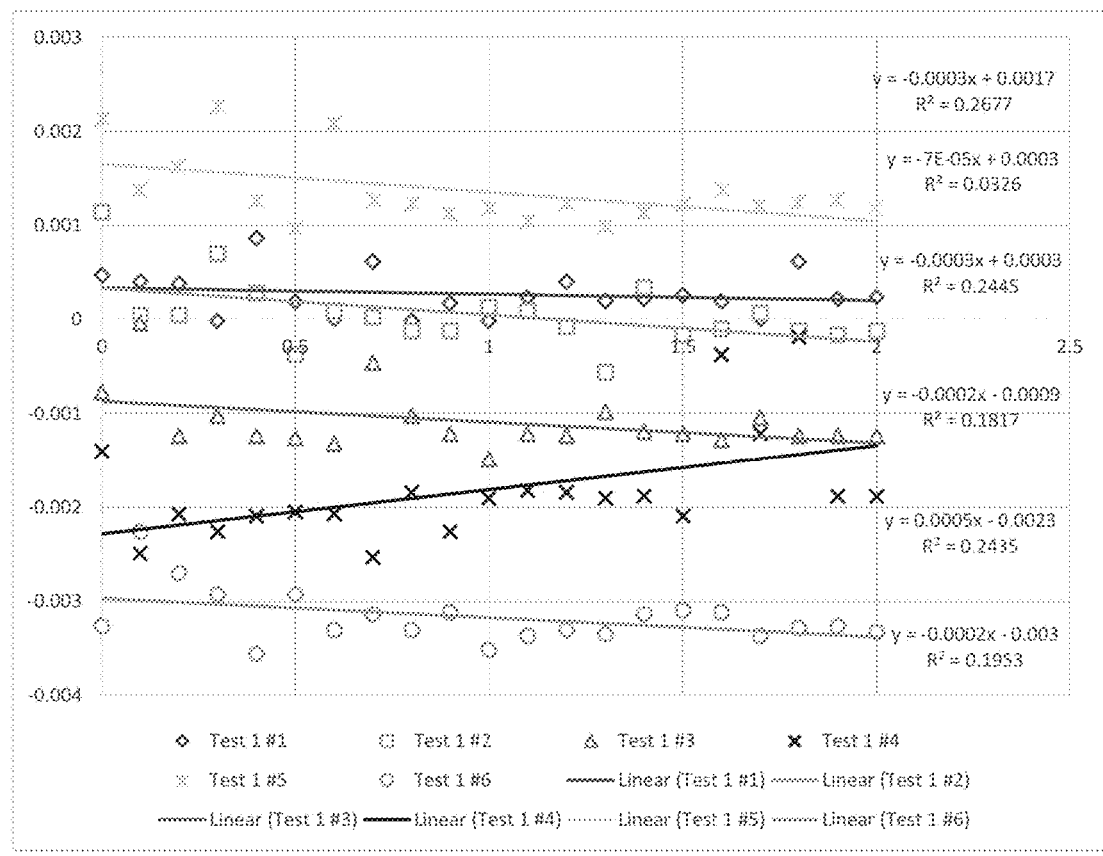
FIG. 28 is a graph showing absorbance at 620.6 nm as a function of time to determine the Slope for Test Solution 7 (Repeat of Test Solution 1).
Figure 29:
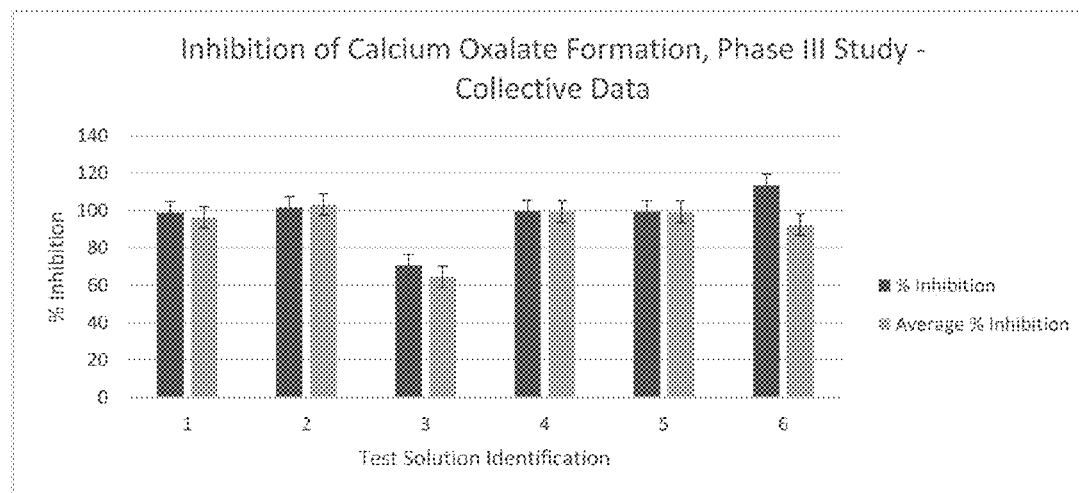
FIG. 29 is a histogram showing median and mean inhibition of calcium oxalate crystal formation by Test Solutions 1-6.
Figure 30:
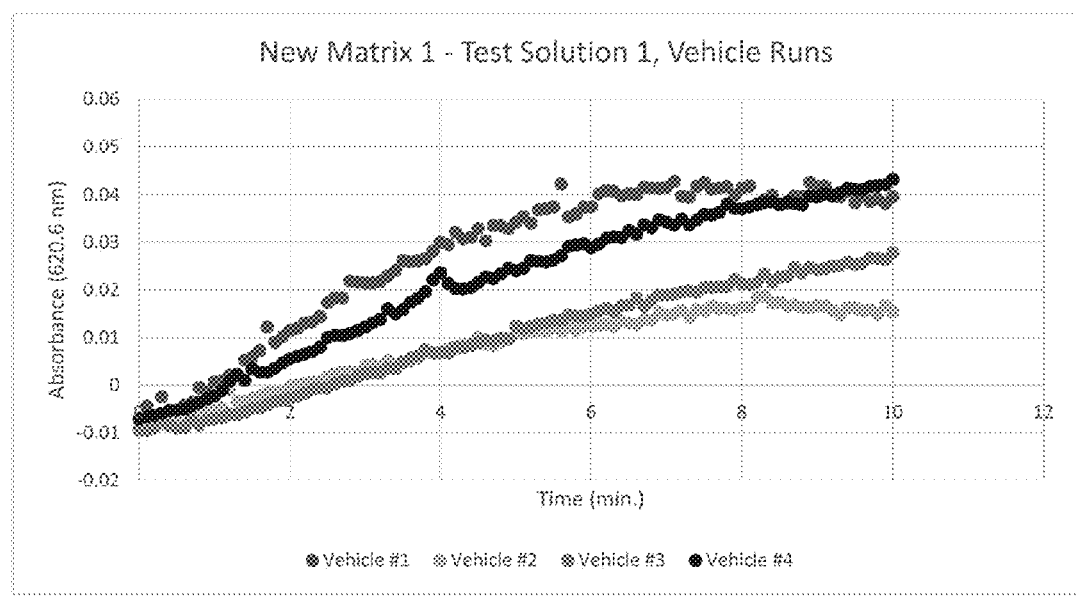
FIG. 30 is a graph showing absorbance at 620.6 nm as a function of time for Control Vehicle Runs Associated with Matrix 1 for Test Solution 1.
Figure 31:
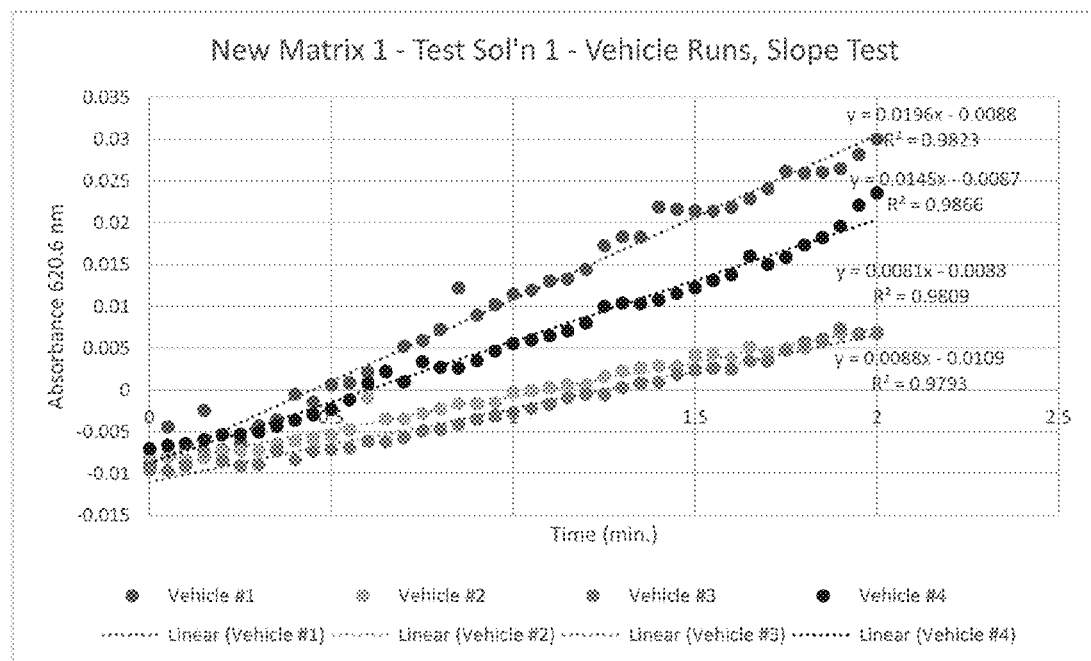
FIG. 31 is a graph showing absorbance at 620.6 nm as a function of time to determine the Slope for Control Vehicle Runs Associated with Matrix 1 for Test Solution 1.
Figure 32:
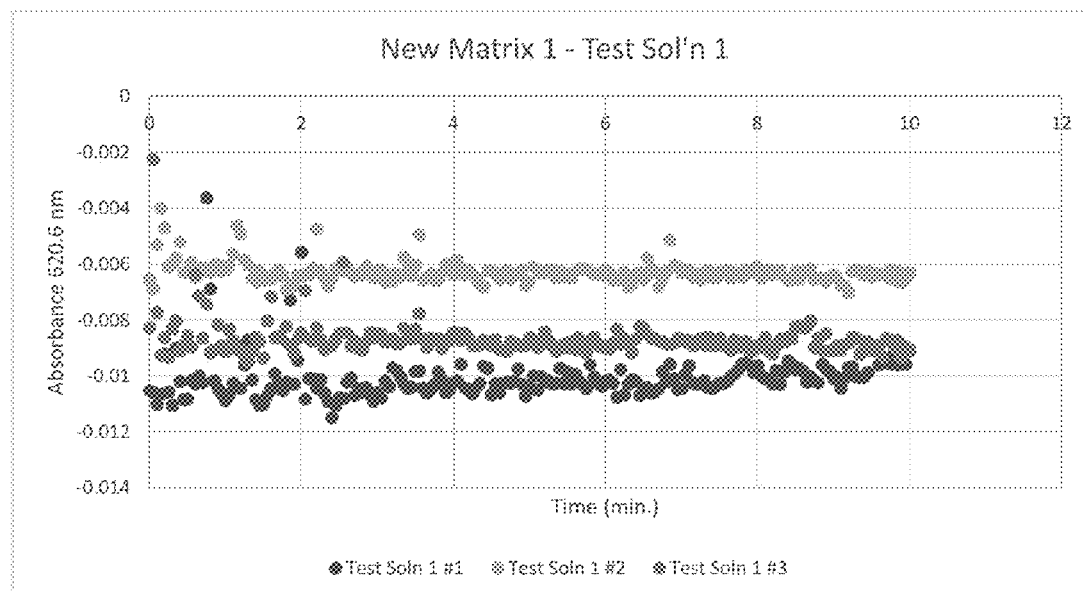
FIG. 32 is a graph showing absorbance at 620.6 nm as a function of time for Matrix 1 for Test Solution 1.
Figure 33:
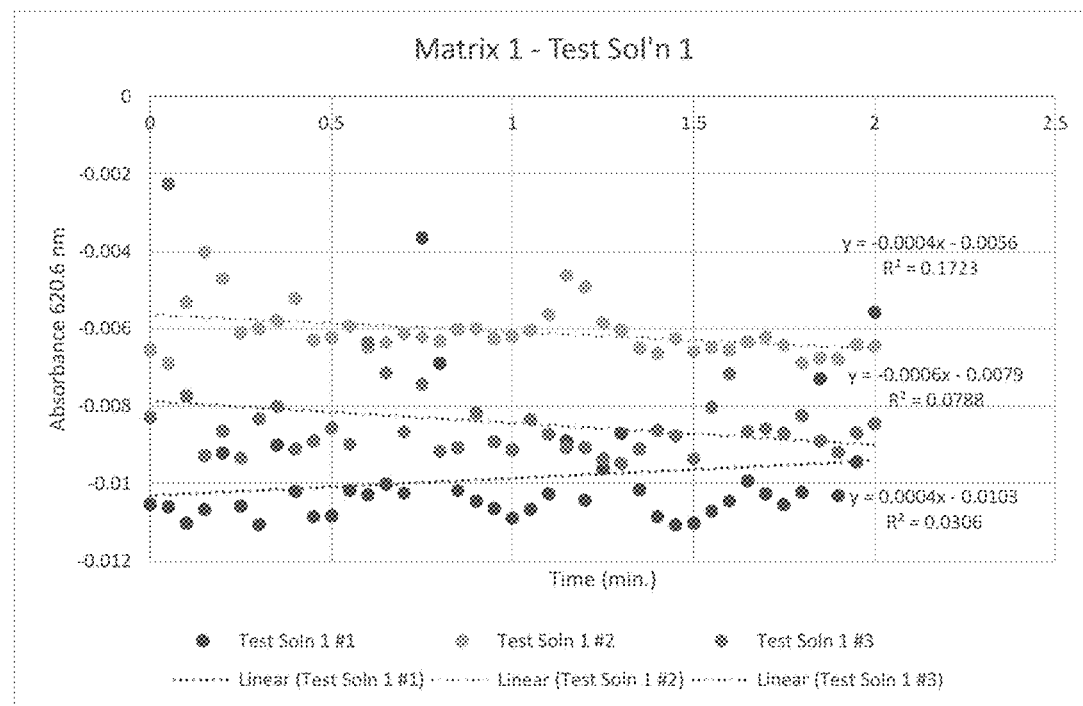
FIG. 33 is a graph showing absorbance at 620.6 nm as a function of time to determine the Slope for Matrix 1 for Test Solution 1.
Figure 34:
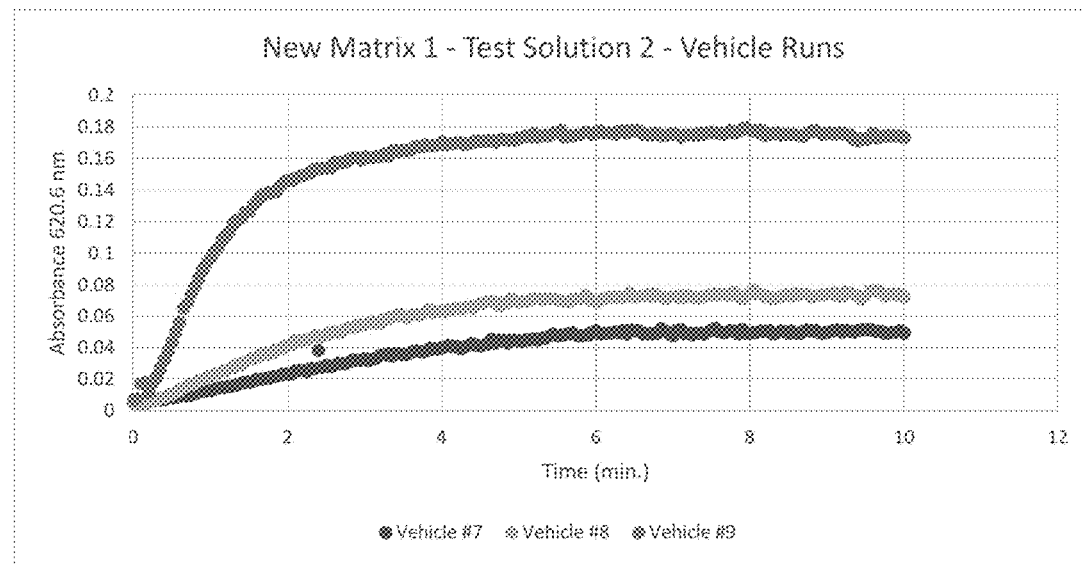
FIG. 34 is a graph showing absorbance at 620.6 nm as a function of time for Control Vehicle Runs Associated with Matrix 1 for Test Solution 2.
Figure 35:
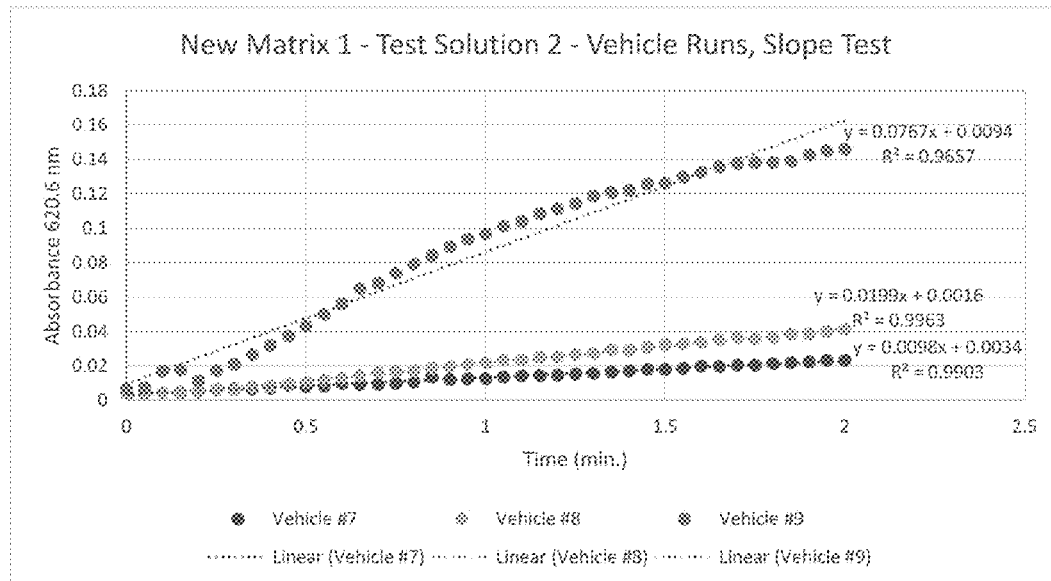
FIG. 35 is a graph showing absorbance at 620.6 nm as a function of time to determine the Slope for Control Vehicle Runs Associated with Matrix 1 for Test Solution 2.
Figure 36:
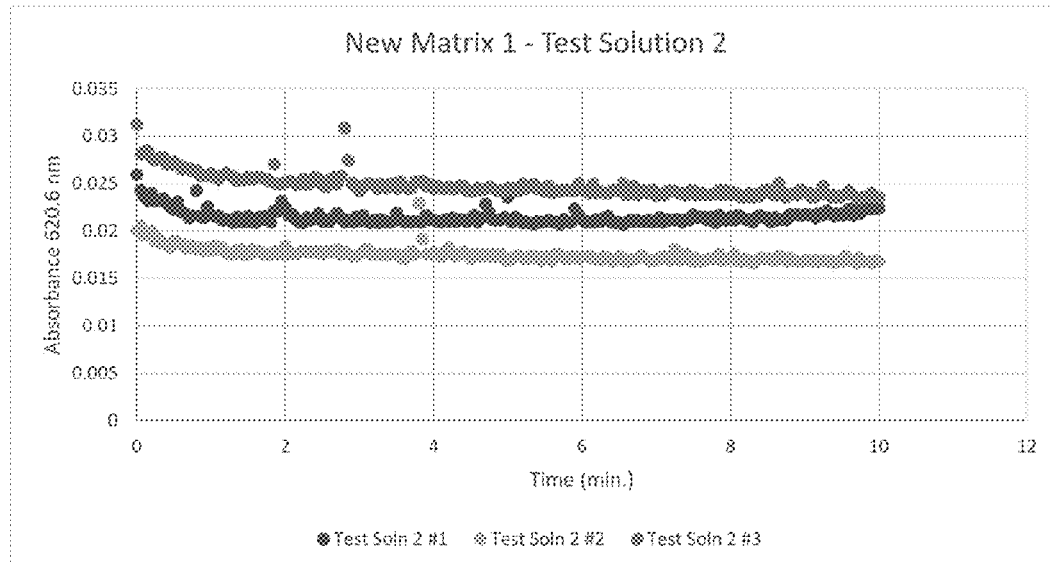
FIG. 36 is a graph showing absorbance at 620.6 nm as a function of time for Matrix 1 for Test Solution 2.
Figure 37:
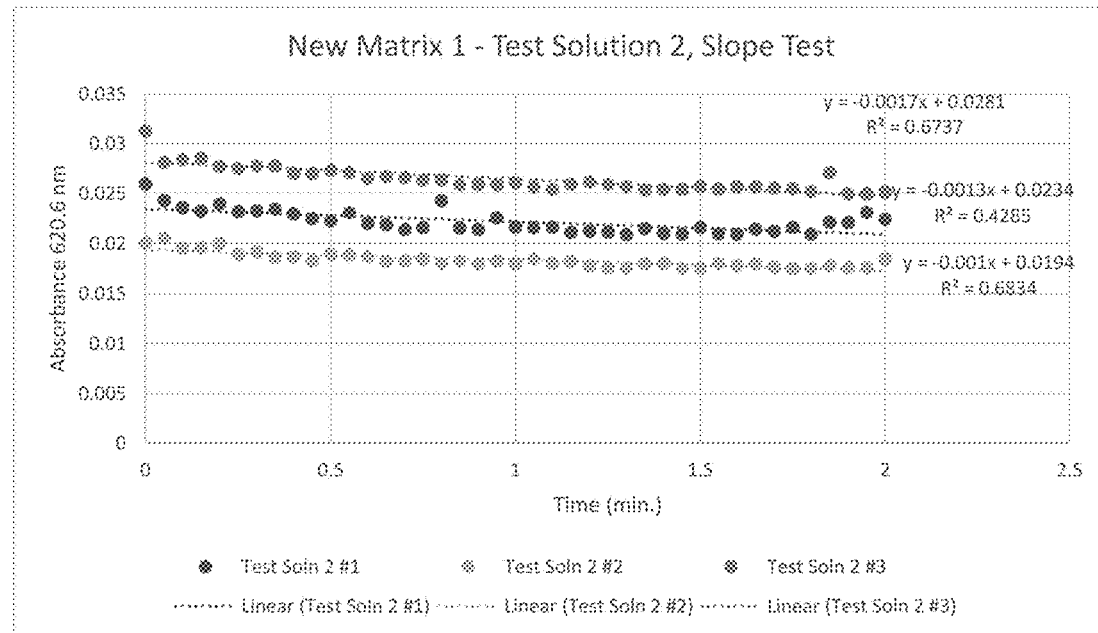
FIG. 37 is a graph showing absorbance at 620.6 nm as a function of time to determine the Slope for Matrix 1 for Test Solution 2.
Figure 38:
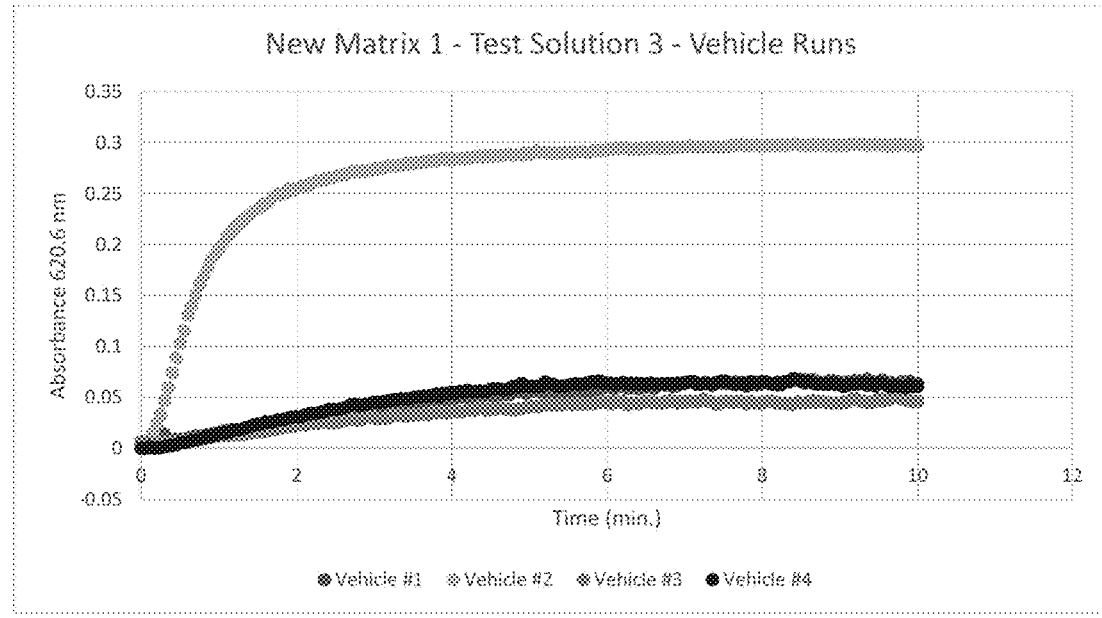
FIG. 38 is a graph showing absorbance at 620.6 nm as a function of time for Control Vehicle Runs Associated with Matrix 1 for Test Solution 3.
Figure 39:
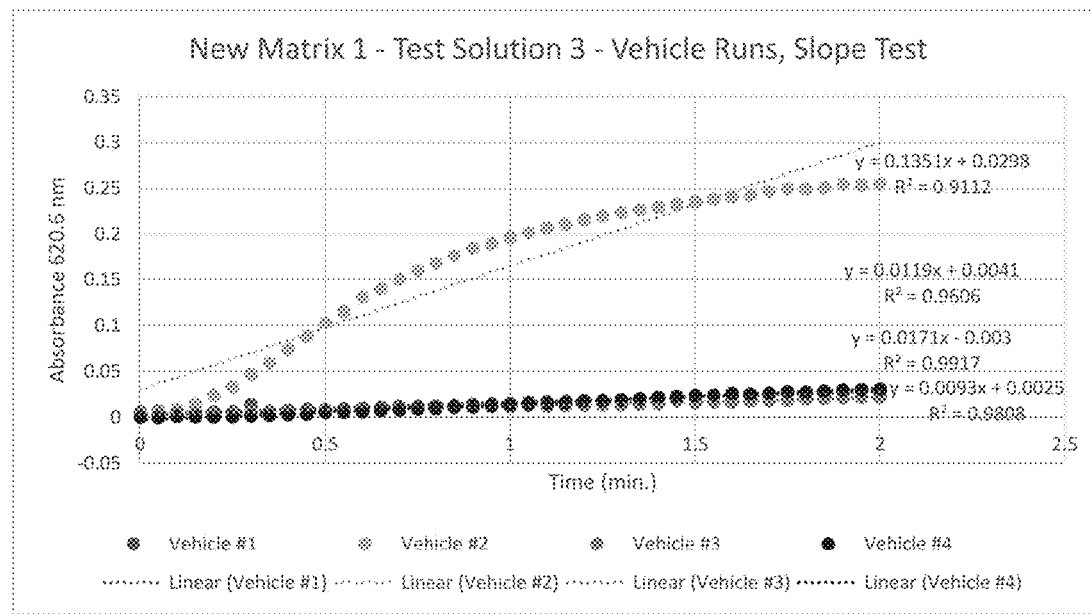
FIG. 39 is a graph showing absorbance at 620.6 nm as a function of time to determine the Slope for Control Vehicle Runs Associated with Matrix 1 for Test Solution 3.
Figure 40:
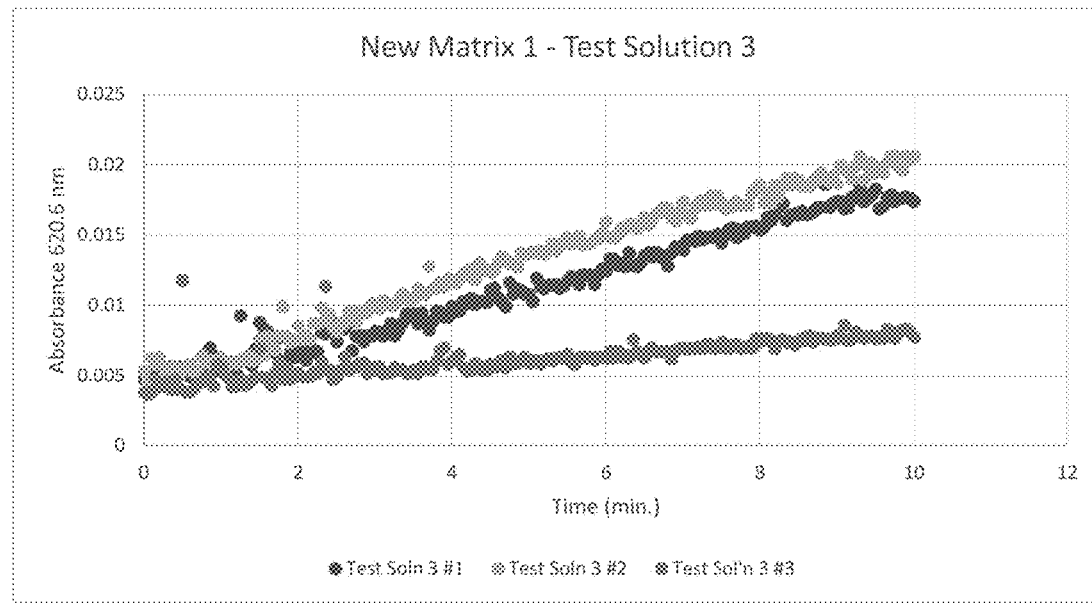
FIG. 40 is a graph showing absorbance at 620.6 nm as a function of time for Matrix 1 for Test Solution 3.
Figure 41:
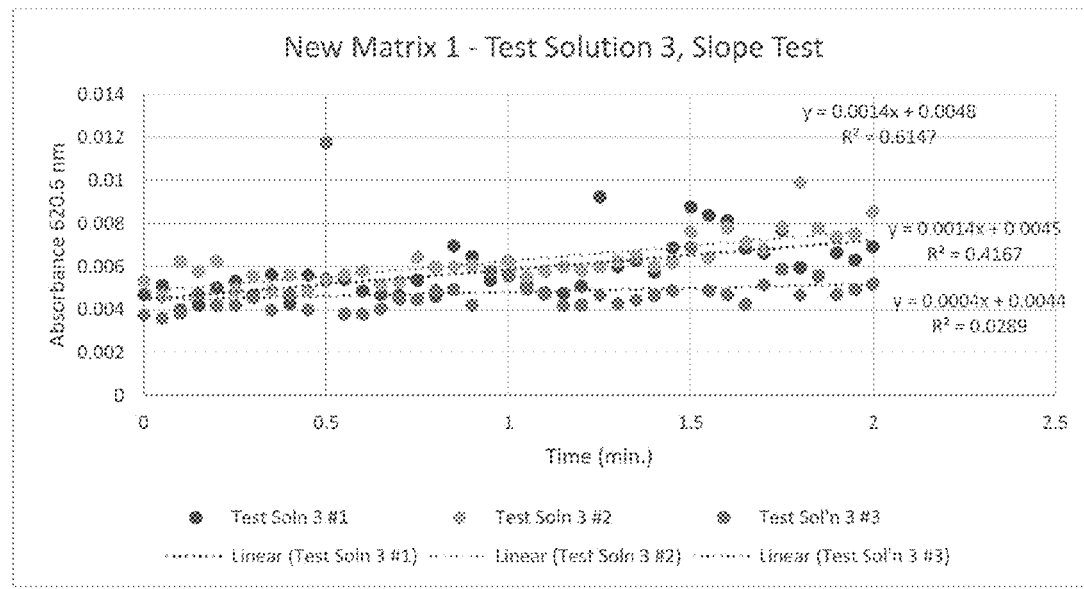
FIG. 41 is a graph showing absorbance at 620.6 nm as a function of time to determine the Slope for Matrix 1 for Test Solution 3.
Figure 42:
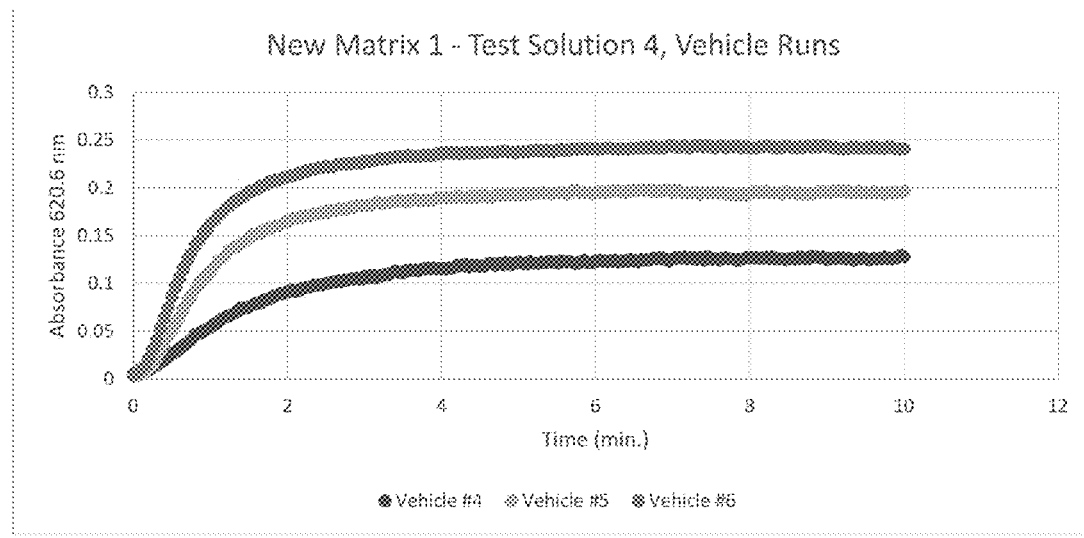
FIG. 42 is a graph showing absorbance at 620.6 nm as a function of time for Control Vehicle Runs Associated with Matrix 1 for Test Solution 4.
Figure 43:
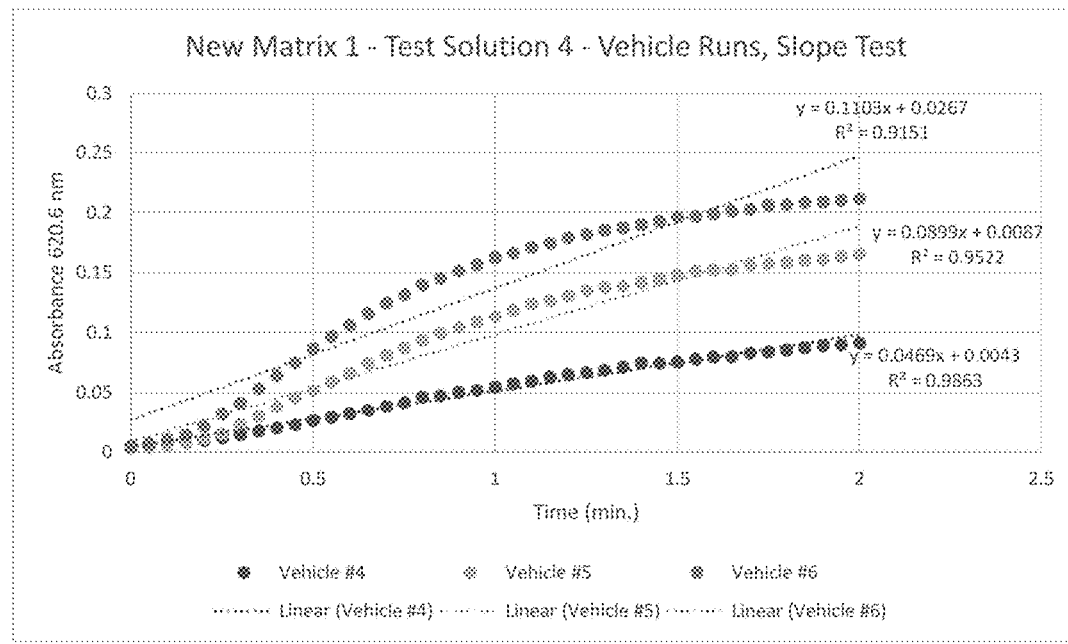
FIG. 43 is a graph showing absorbance at 620.6 nm as a function of time to determine the Slope for Control Vehicle Runs Associated with Matrix 1 for Test Solution 4.
Figure 44:
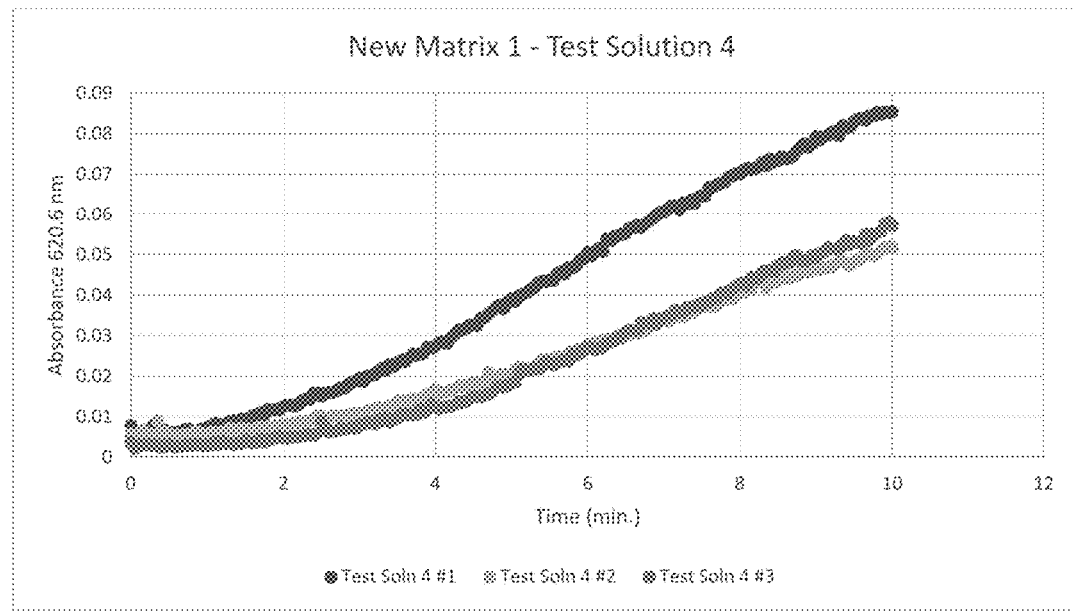
FIG. 44 is a graph showing absorbance at 620.6 nm as a function of time for Matrix 1 for Test Solution 4.
Figure 45:
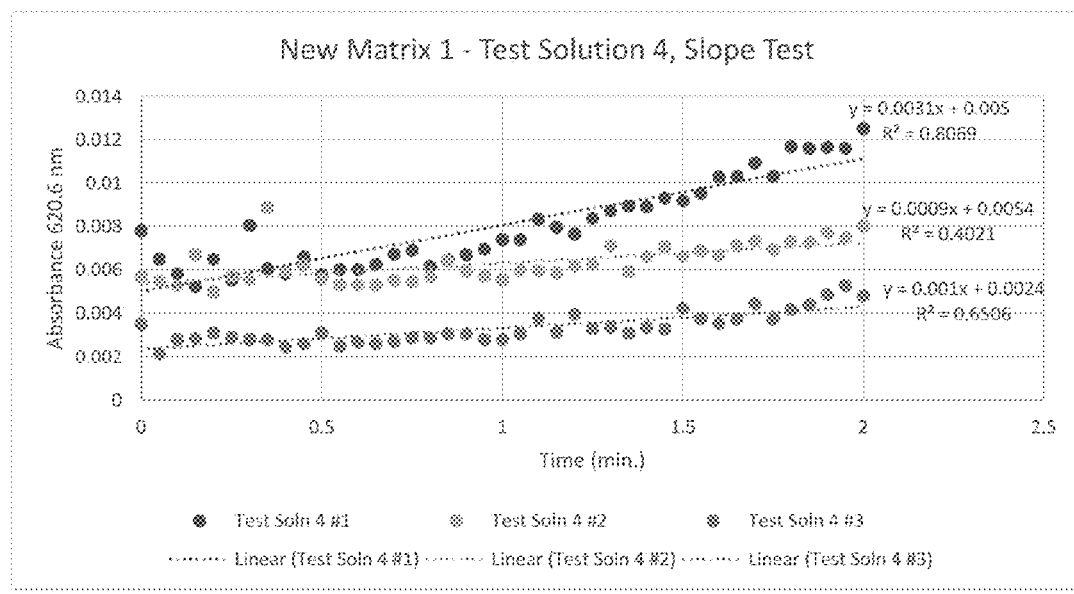
FIG. 45 is a graph showing absorbance at 620.6 nm as a function of time to determine the Slope for Matrix 1 for Test Solution 4.
Figure 46:
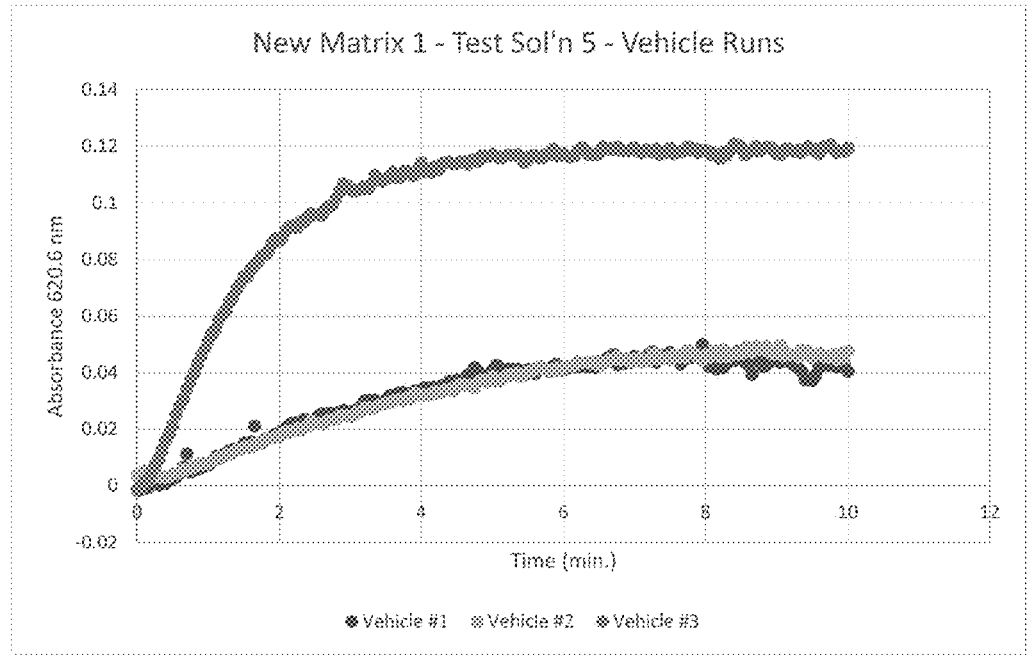
FIG. 46 is a graph showing absorbance at 620.6 nm as a function of times for Control Vehicle Runs Associated with Matrix 1 for Test Solution 5.
Figure 47:
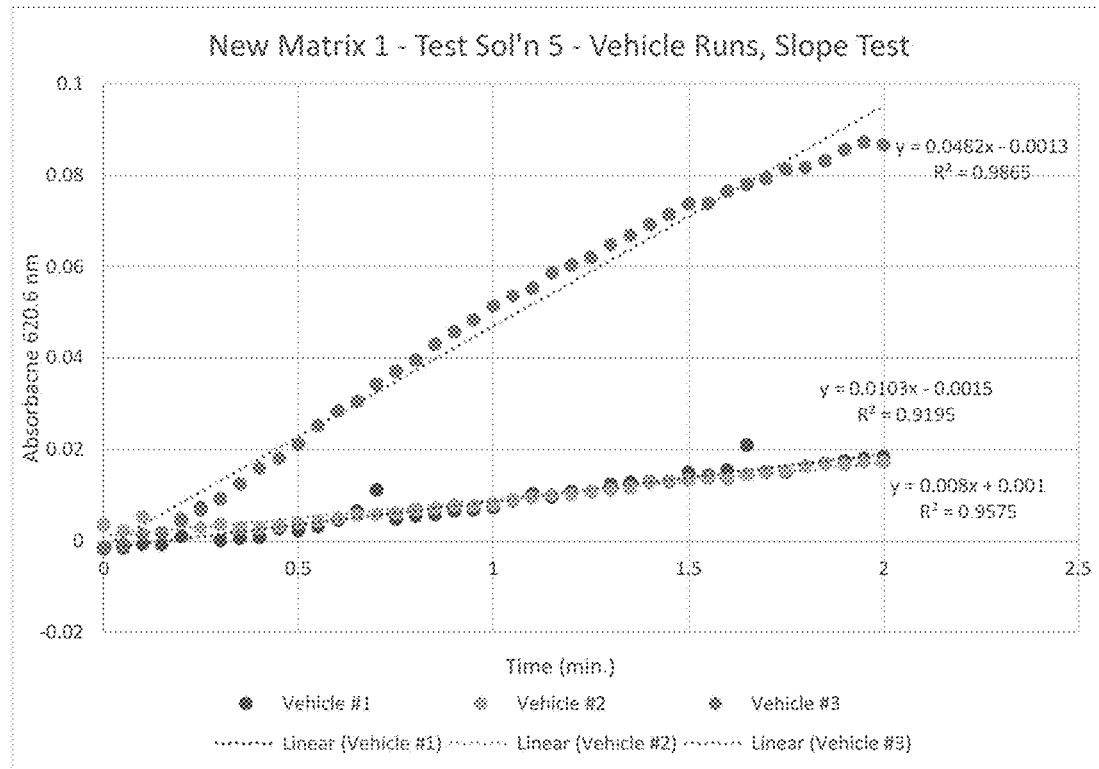
FIG. 47 is a graph showing absorbance at 620.6 nm as a function of time to determine the Slope for Vehicle Runs Associated with Matrix 1 for Test Solution 5.
Figure 48:
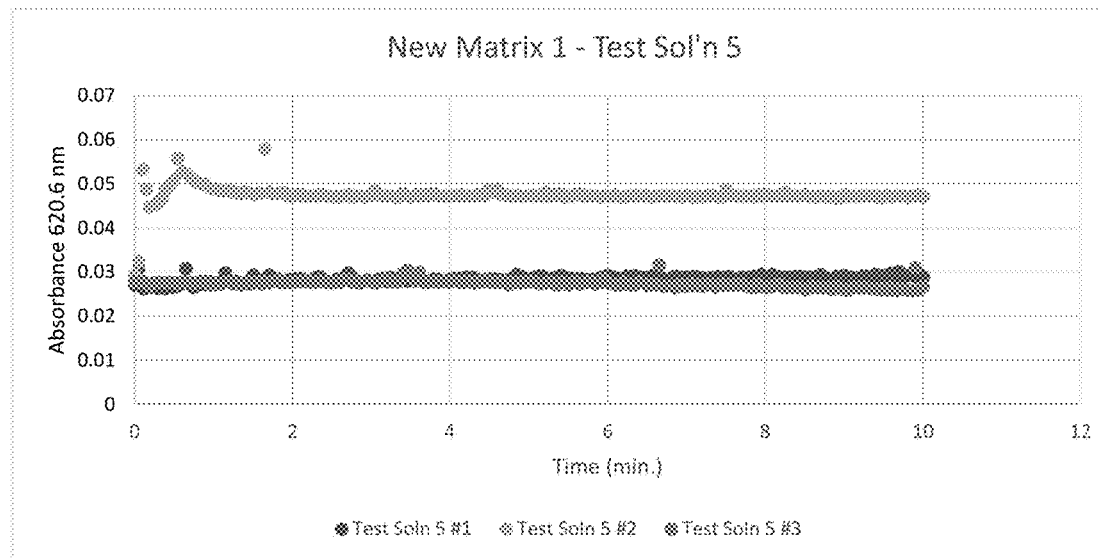
FIG. 48 is a graph showing absorbance at 620.6 nm as a function of time for Matrix 1 for Test Solution 5.
Figure 49:
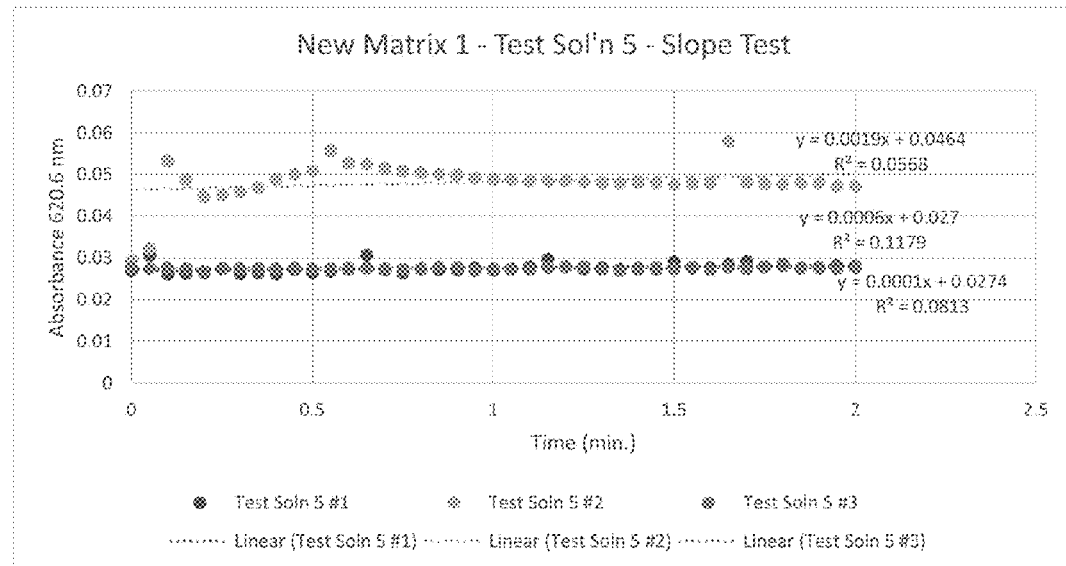
FIG. 49 is a graph showing absorbance at 620.6 nm as a function of time to determine the Slope for Matrix 1 for Test Solution 5.
Figure 50:
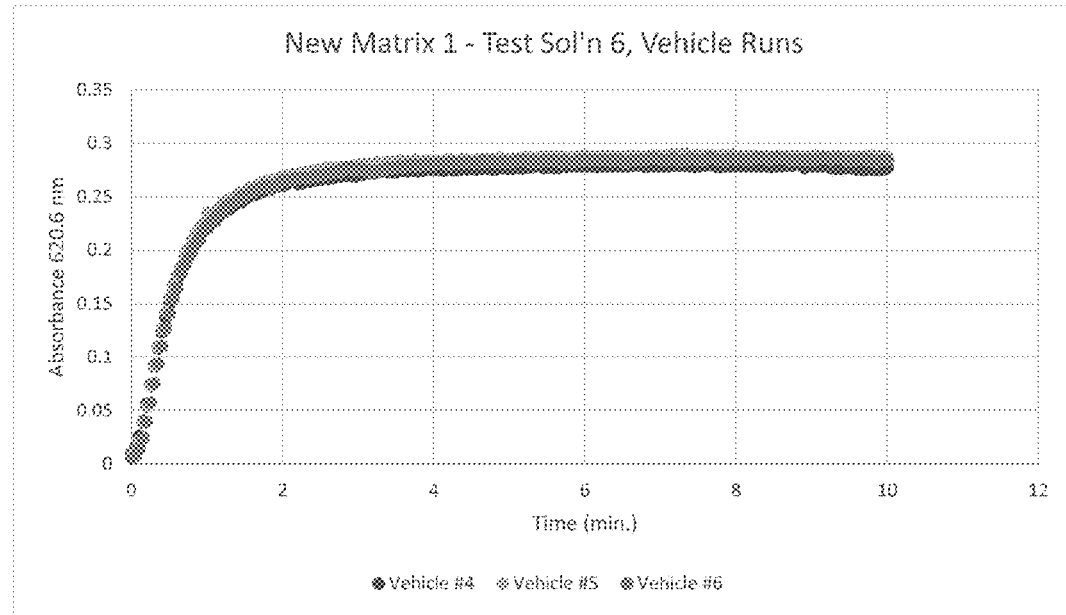
FIG. 50 is a graph showing absorbance at 620.6 nm as a function of time for Control Vehicle Runs Associated with Matrix 1 for Test Solution 6.
Figure 51:
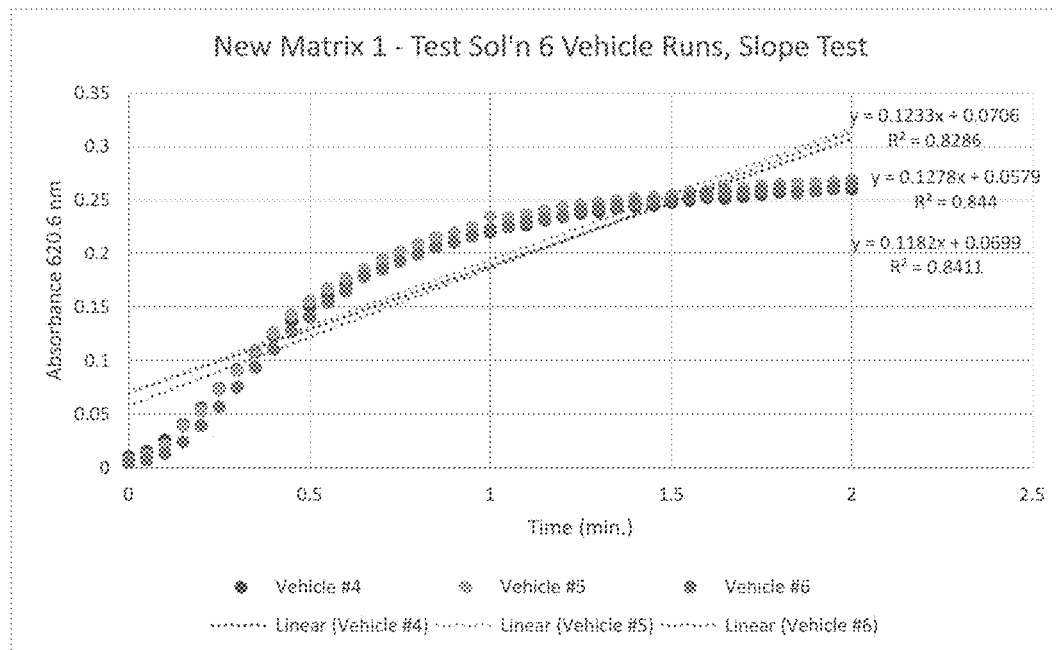
FIG. 51 is a graph showing absorbance at 620.6 nm as a function of time to determine the Slope for Control Vehicle Runs Associated with Matrix 1 for Test Solution 6.
Figure 52:
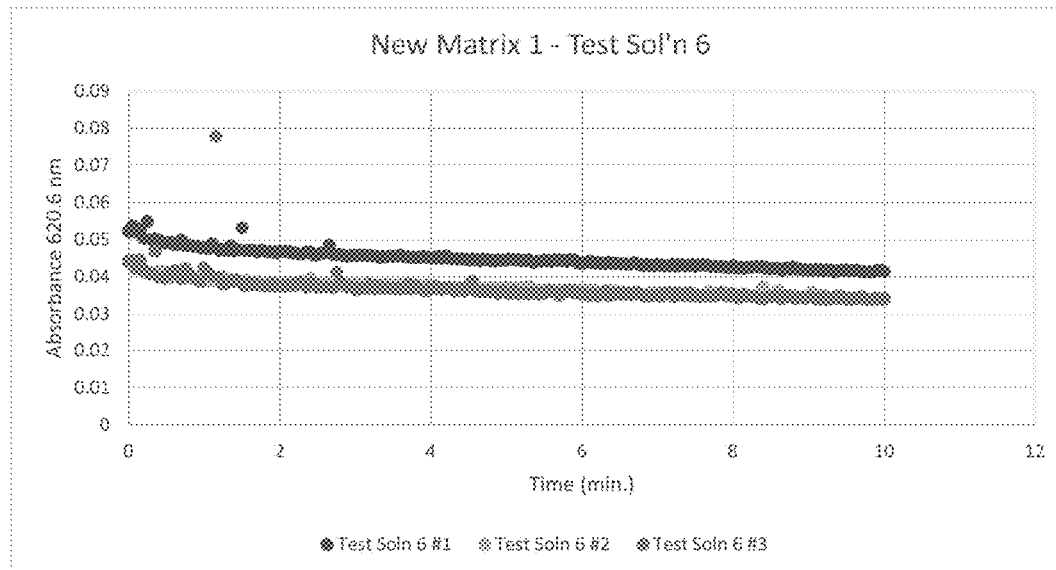
FIG. 52 is a graph showing absorbance at 620.6 nm as a function of time for Matrix 1 for Test Solution 6.
Figure 53:
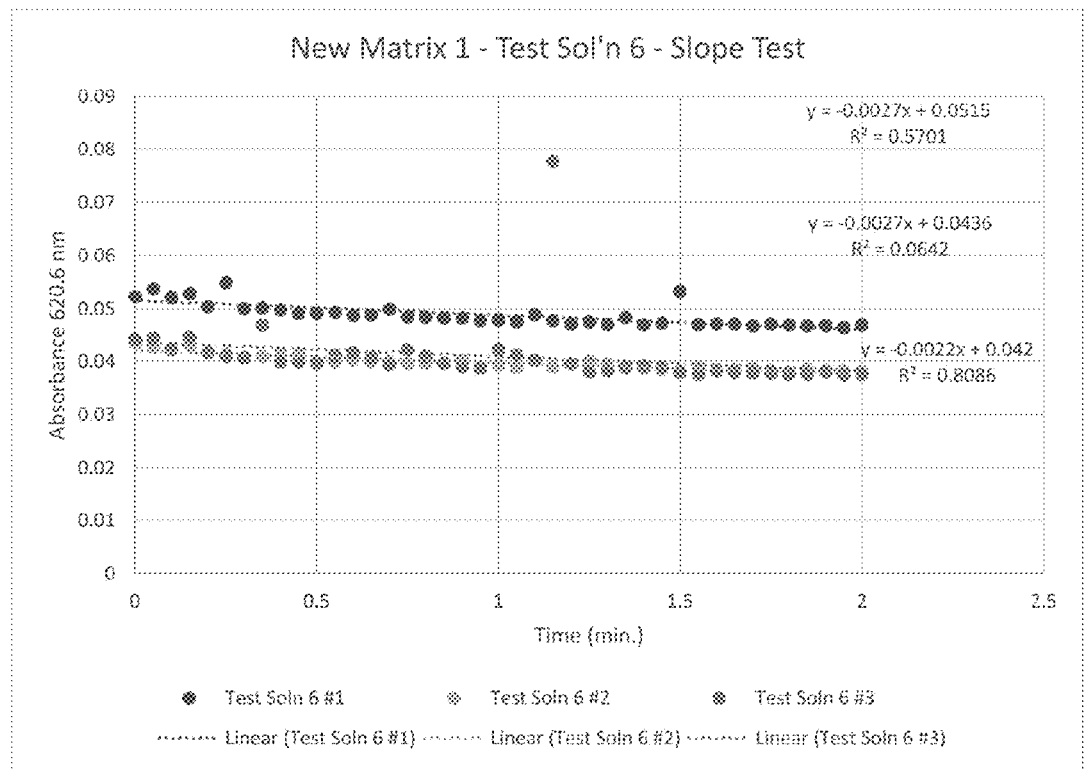
FIG. 53 is a graph showing absorbance at 620.6 nm as a function of time to determine the Slope for Matrix 1 for Test Solution 6.
Figure 54:
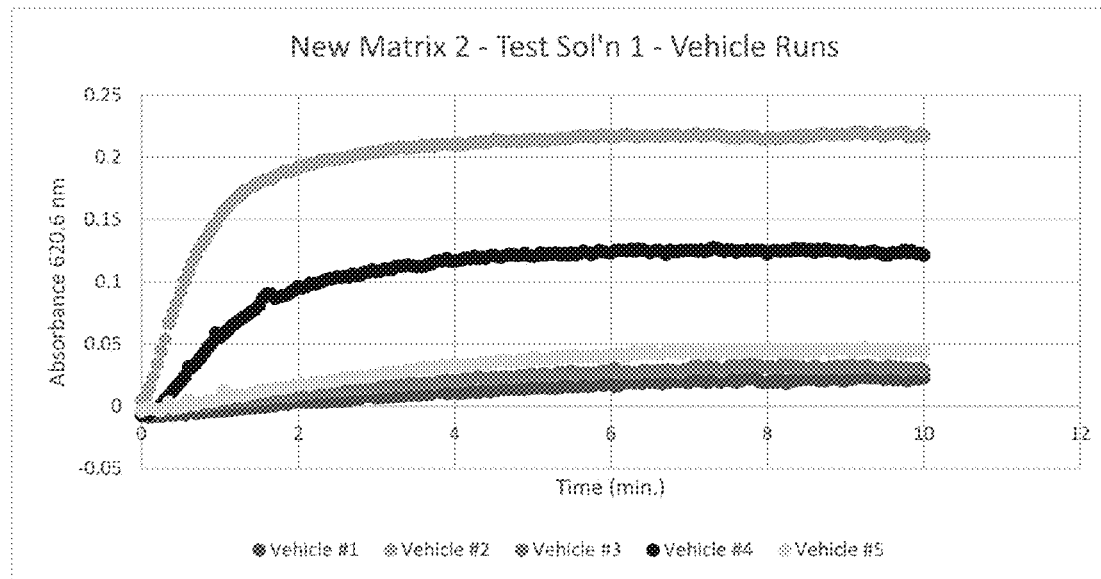
FIG. 54 is a graph showing absorbance at 620.6 nm as a function of time for Control Vehicle Runs Associated with Matrix 2 for Test Solution 1.
Figure 55:
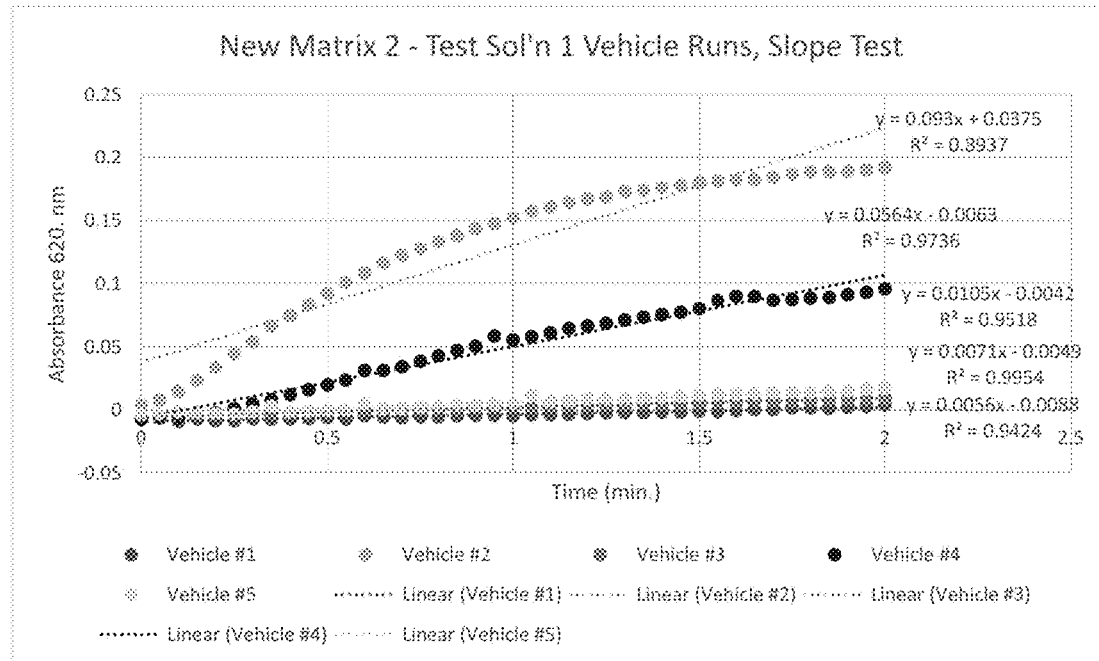
FIG. 55 is a graph showing absorbance at 620.6 nm as a function of time to determine the Slope for Control Vehicle Runs Associated with Matrix 2 for Test Solution 1.
Figure 56:
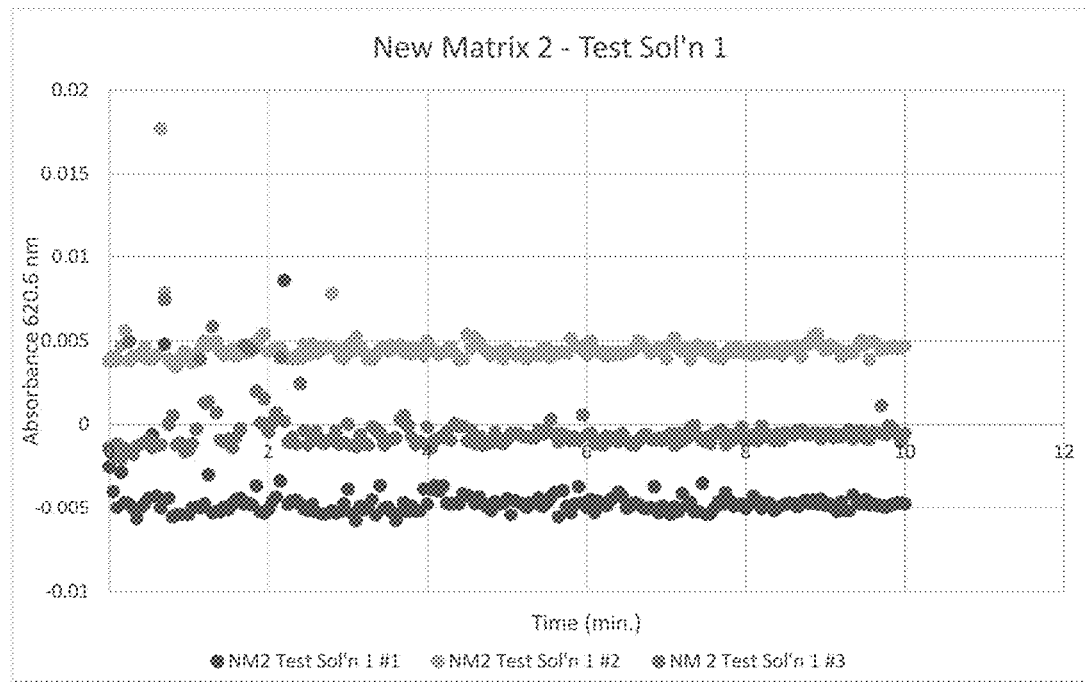
FIG. 56 is a graph showing absorbance at 620.6 nm as a function of time for Matrix 2 for Test Solution 1.
Figure 57:
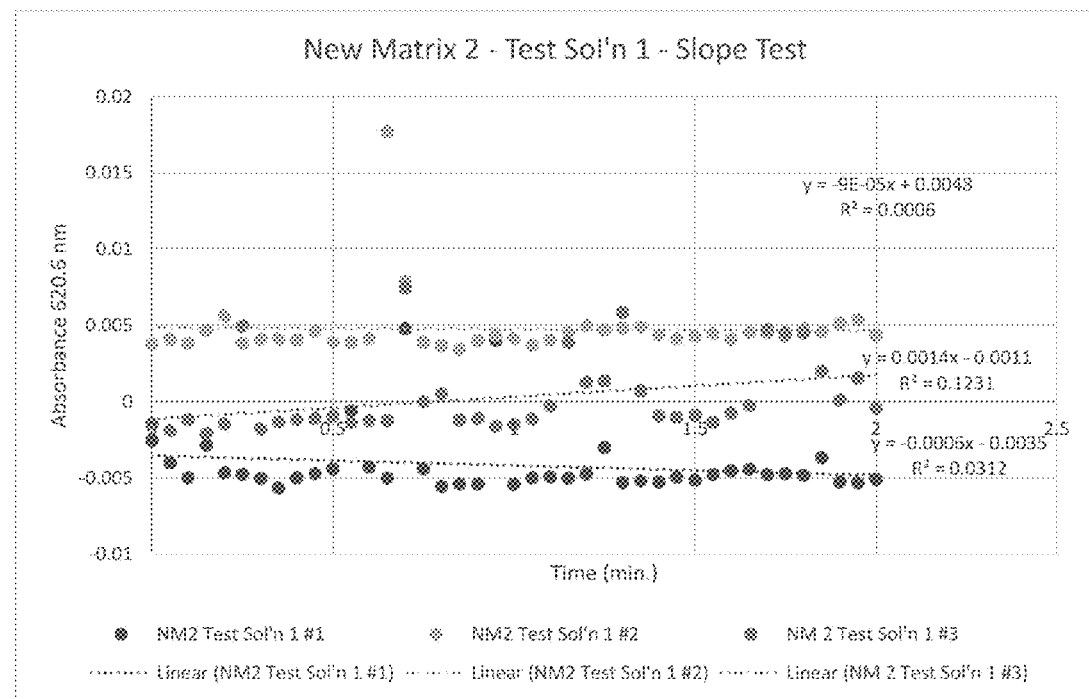
FIG. 57 is a graph showing absorbance at 620.6 nm as a function of time to determine the Slope for Matrix 2 for Test Solution 1.
Figure 58:
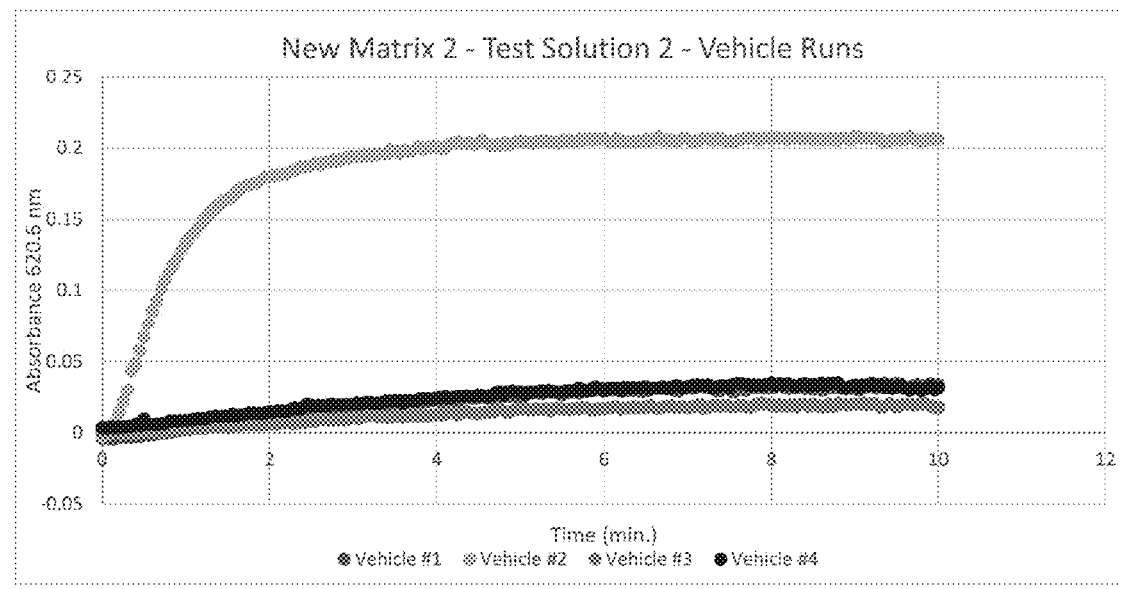
FIG. 58 is a graph showing absorbance at 620.6 nm as a function of time for Control Vehicle Runs Associated with Matrix 2 for Test Solution 2.
Figure 59:
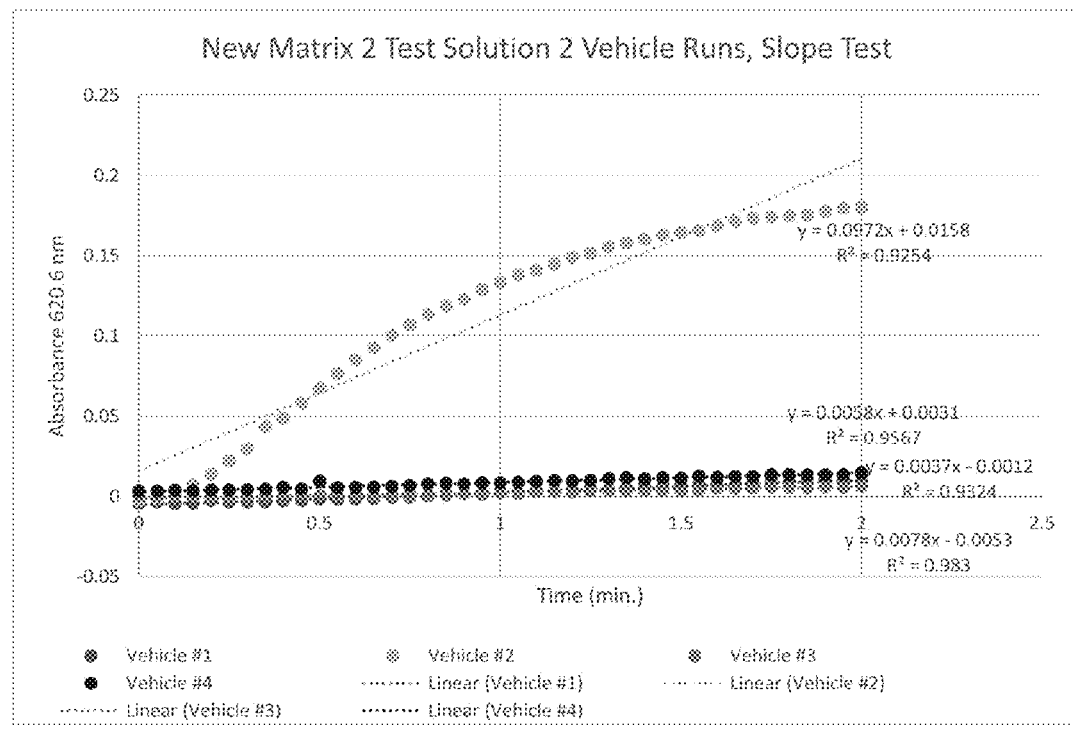
FIG. 59 is a graph showing absorbance at 620.6 nm as a function of time to determine the Slope for Control Vehicle Runs Associated with Matrix 2 for Test Solution 2.
Figure 60:
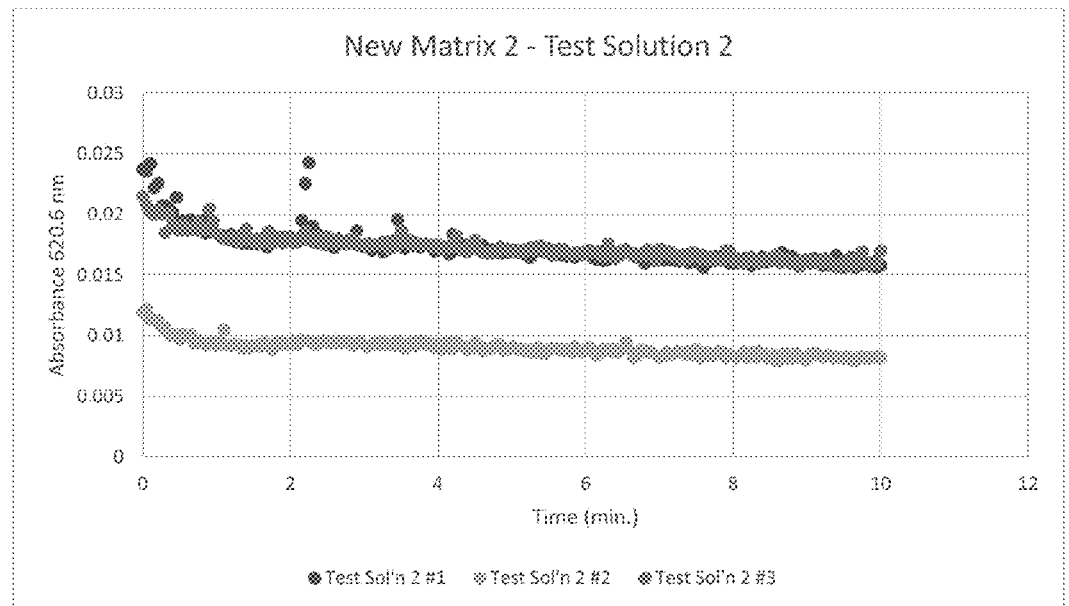
FIG. 60 is a graph showing absorbance at 620.6 nm as a function of time for Matrix 2 for Test Solution 2.
Figure 61:
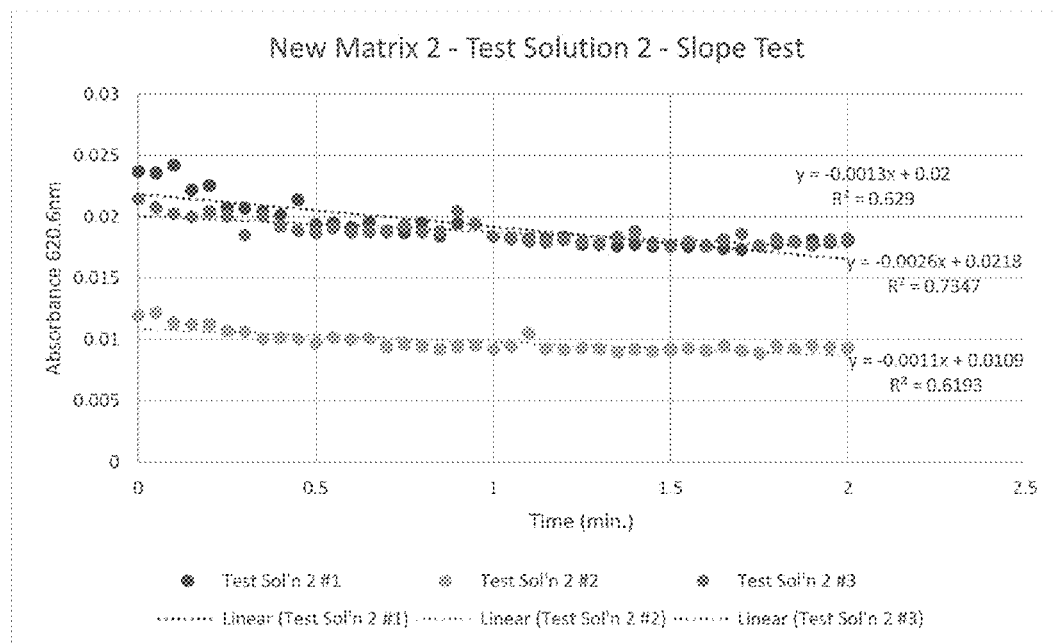
FIG. 61 is a graph showing absorbance at 620.6 nm as a function of time to determine the Slope for Matrix 2 for Test Solution 2.
Figure 62:
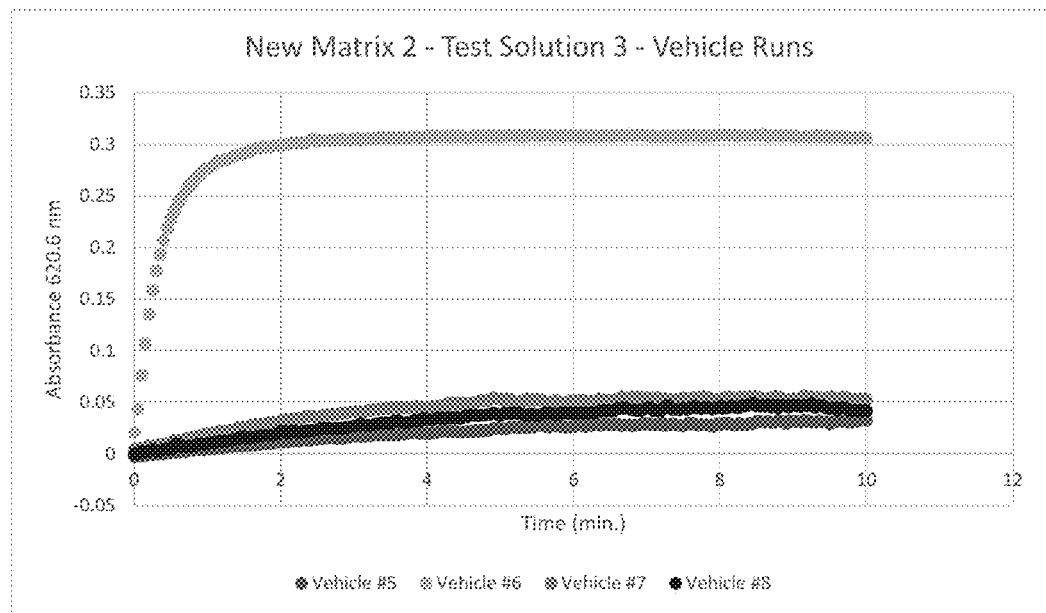
FIG. 62 is a graph showing absorbance at 620.6 nm as a function of time for Control Vehicle Runs Associated with Matrix 2 for Test Solution 3.
Figure 63:
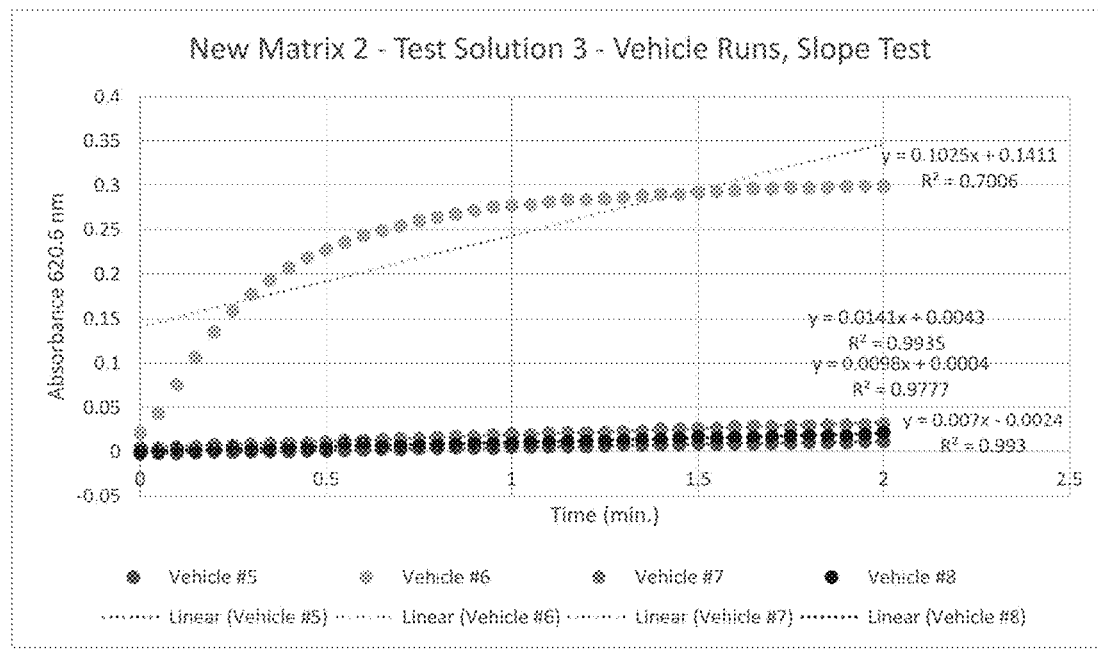
FIG. 63 is a graph showing absorbance at 620.6 nm as a function of time to determine the Slope for Control Vehicle Runs Associated with Matrix 2 for Test Solution 3.
Figure 64:
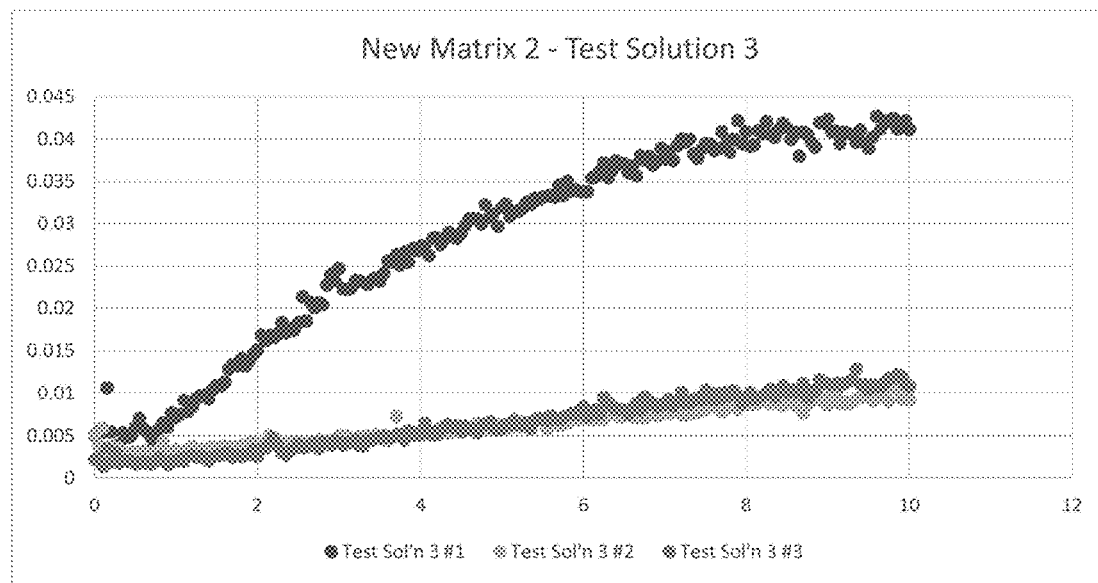
FIG. 64 is a graph showing absorbance at 620.6 nm as a function of time for Matrix 2 for Test Solution 3.
Figure 65:
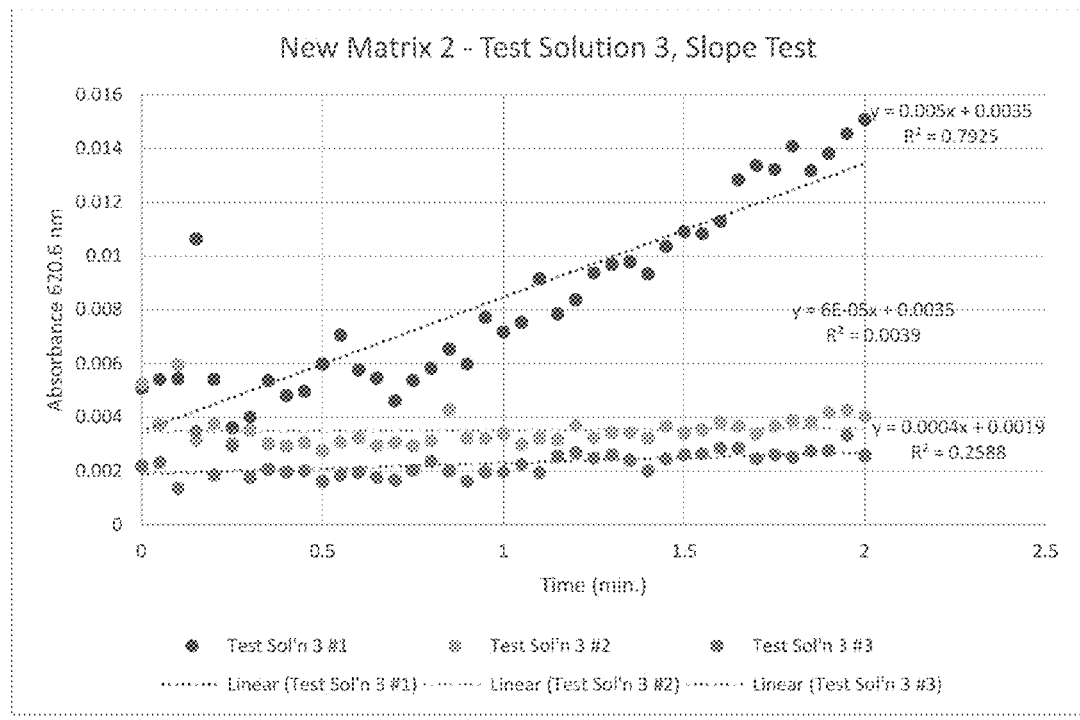
FIG. 65 is a graph showing absorbance at 620.6 nm as a function of time to determine the Slope for Matrix 2 for Test Solution 3.
Figure 66:
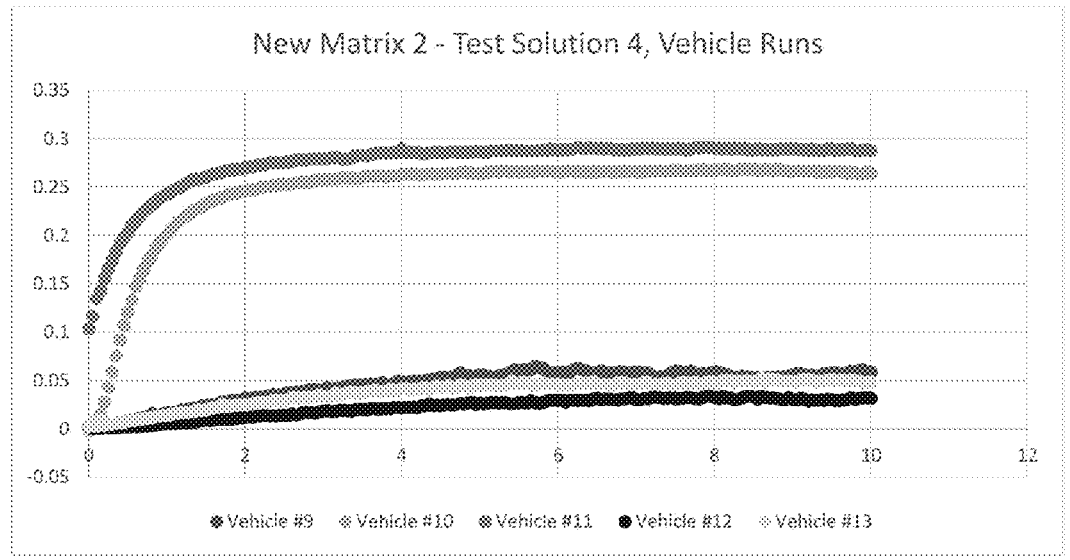
FIG. 66 is a graph showing absorbance at 620.6 nm as a function of time for Control Vehicle Runs Associated with Matrix 2 for Test Solution 4.
Figure 67:
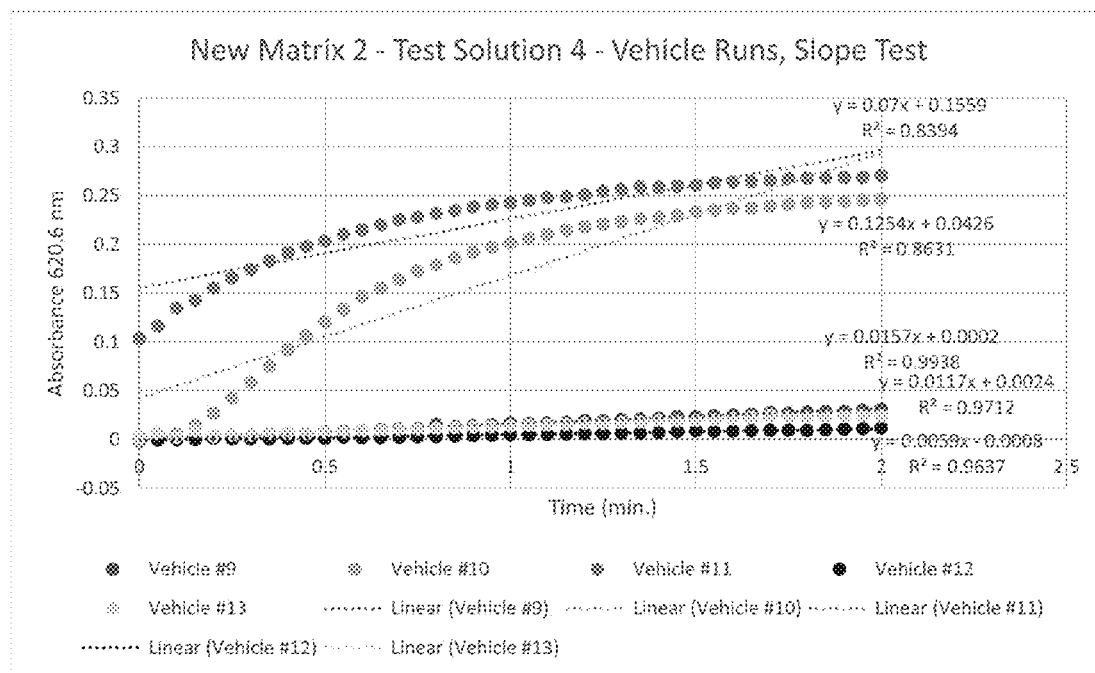
FIG. 67 is a graph showing absorbance at 620.6 nm as a function of time to determine the Slope for Control Vehicle Runs Associated with Matrix 2 for Test Solution 4.
Figure 68:
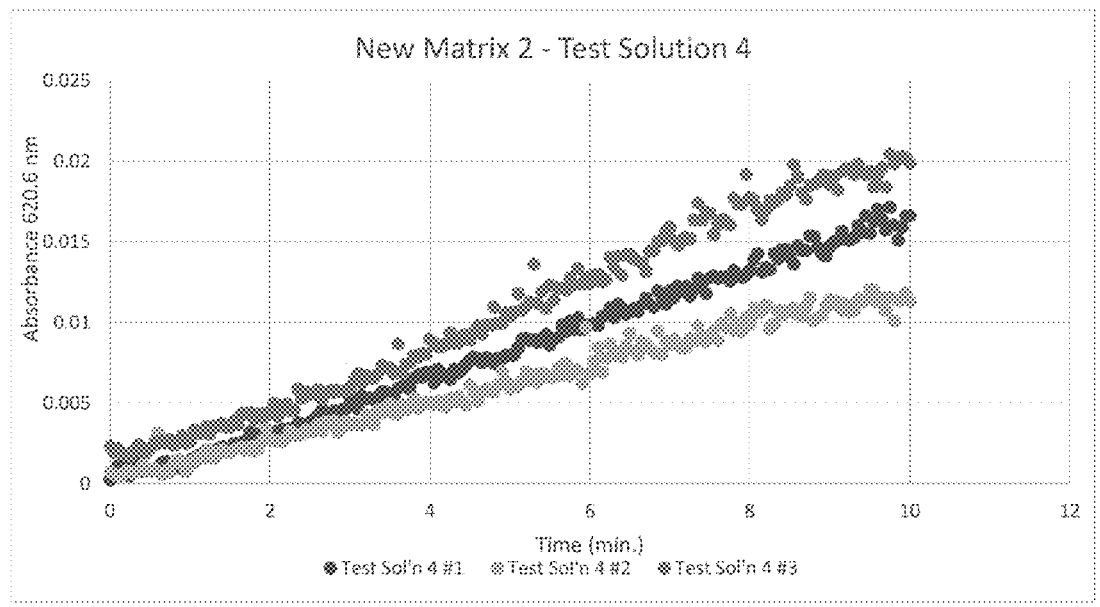
FIG. 68 is a graph showing absorbance at 620.6 nm as a function of time for Matrix 2 for Test Solution 4.
Figure 69:
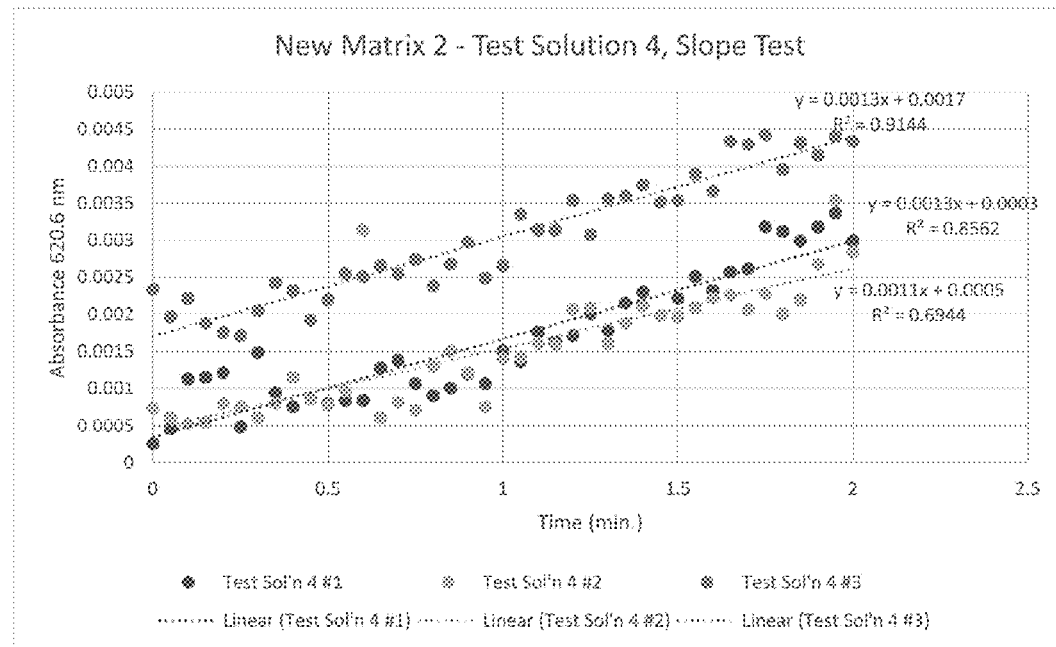
FIG. 69 is a graph showing absorbance at 620.6 nm as a function of time to determine the Slope for Matrix 2 for Test Solution 4.
Figure 70:
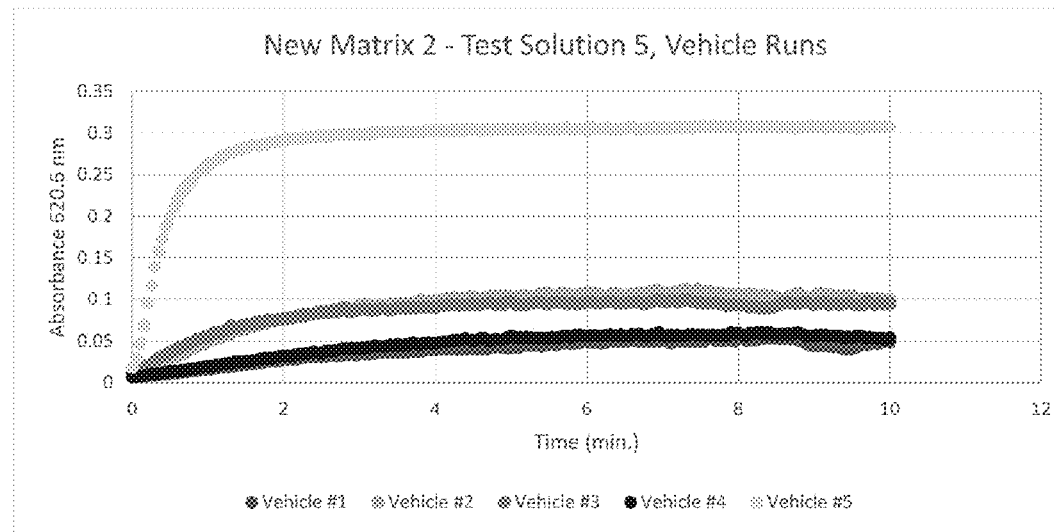
FIG. 70 is a graph showing absorbance at 620.6 nm as a function of times for Control Vehicle Runs Associated with Matrix 2 for Test Solution 5.
Figure 71:
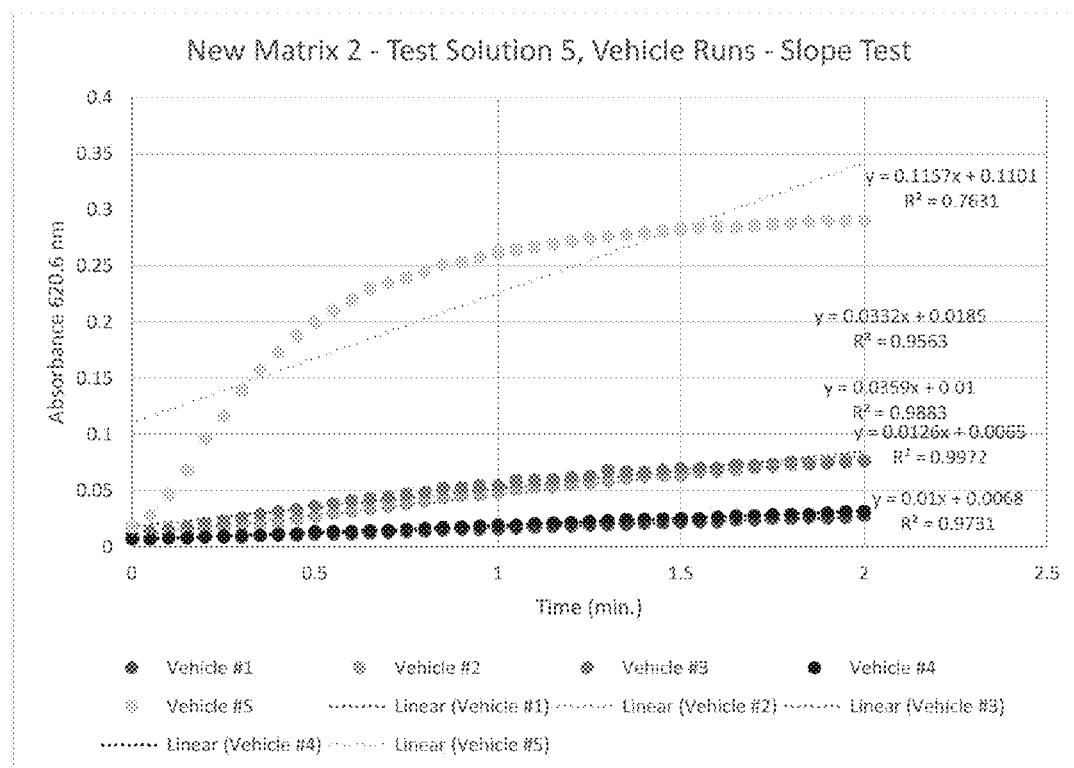
FIG. 71 is a graph showing absorbance at 620.6 nm as a function of time to determine the Slope for Vehicle Runs Associated with Matrix 2 for Test Solution 5.
Figure 72:
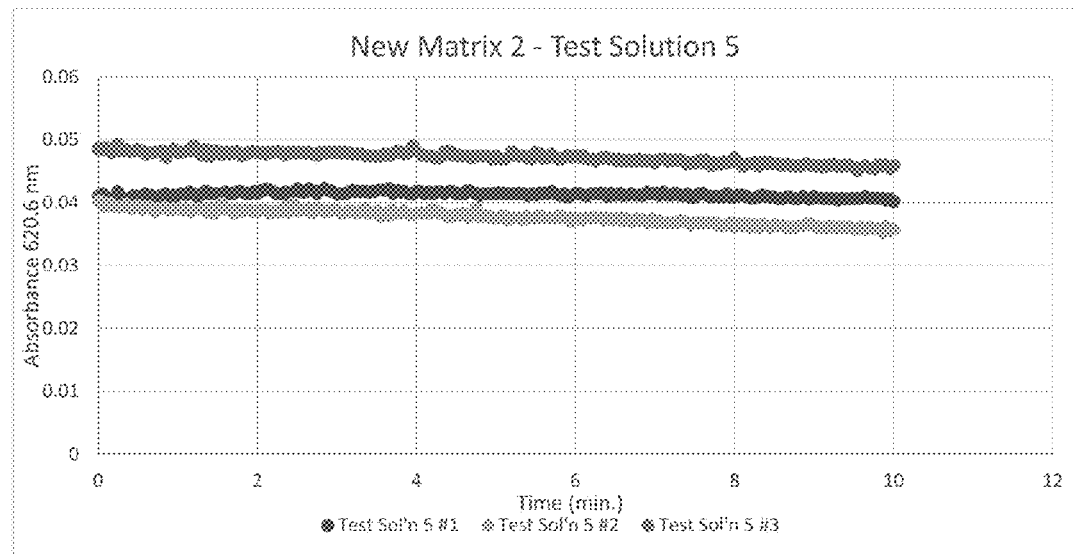
FIG. 72 is a graph showing absorbance at 620.6 nm as a function of time for Matrix 2 for Test Solution 5.
Figure 73:
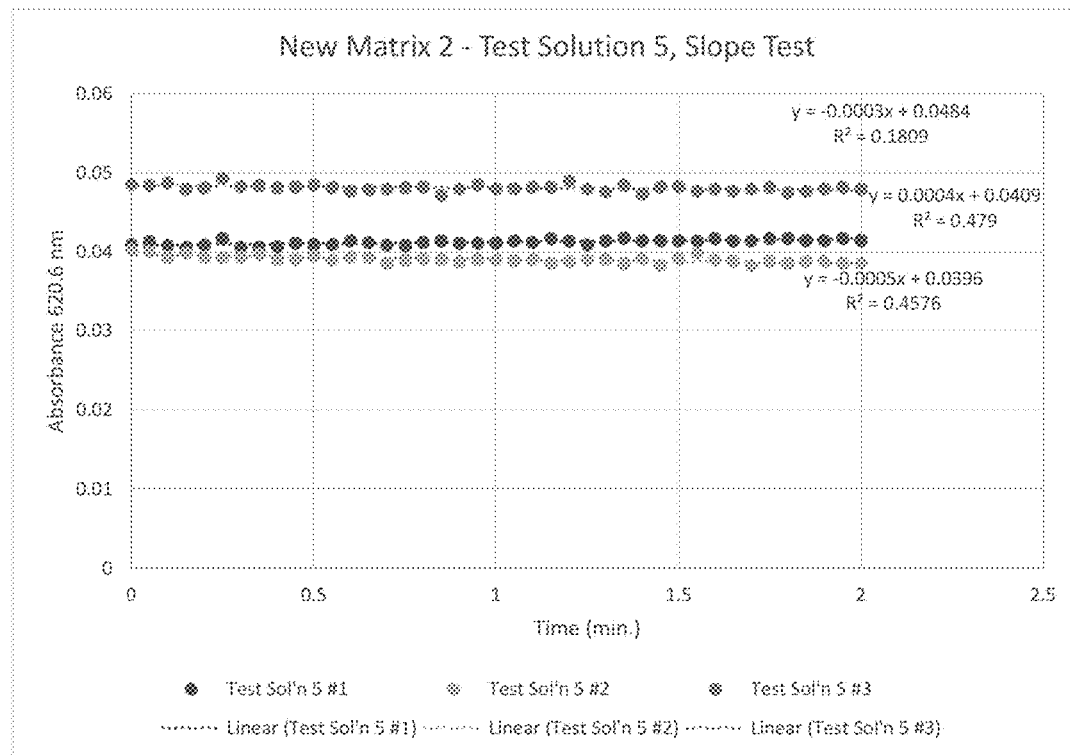
FIG. 73 is a graph showing absorbance at 620.6 nm as a function of time to determine the Slope for Matrix 2 for Test Solution 5.
Figure 74:
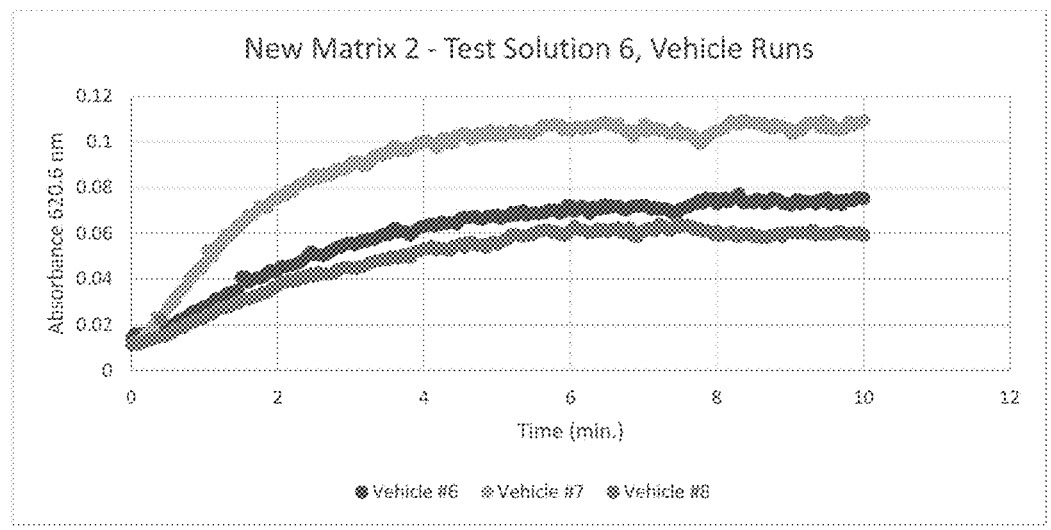
FIG. 74 is a graph showing absorbance at 620.6 nm as a function of time for Control Vehicle Runs Associated with Matrix 2 for Test Solution 6.
Figure 75:
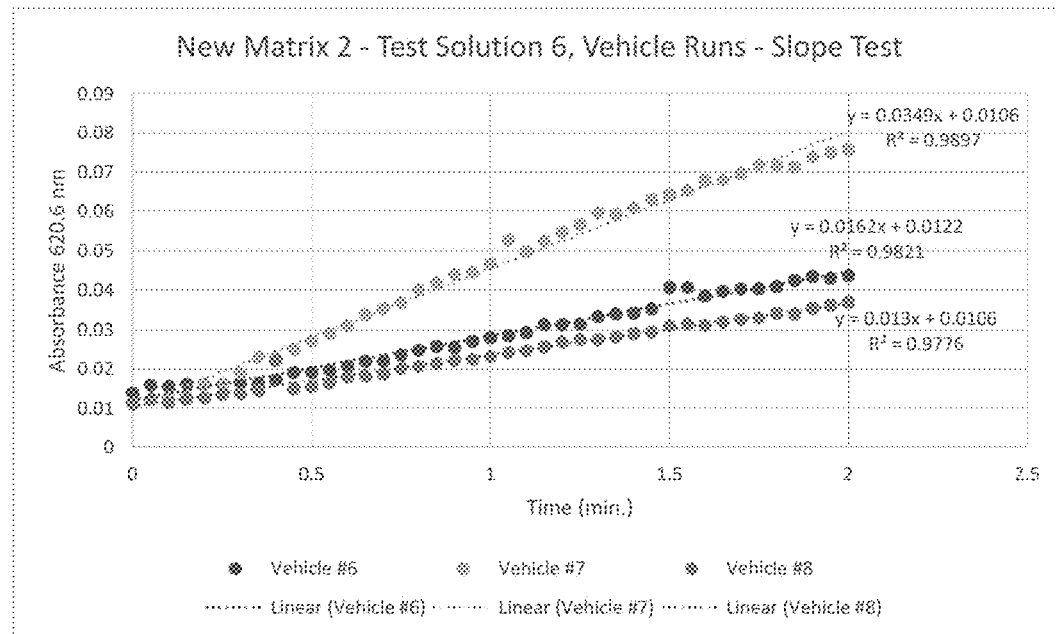
FIG. 75 is a graph showing absorbance at 620.6 nm as a function of time to determine the Slope for Control Vehicle Runs Associated with Matrix 2 for Test Solution 6.
Figure 76:
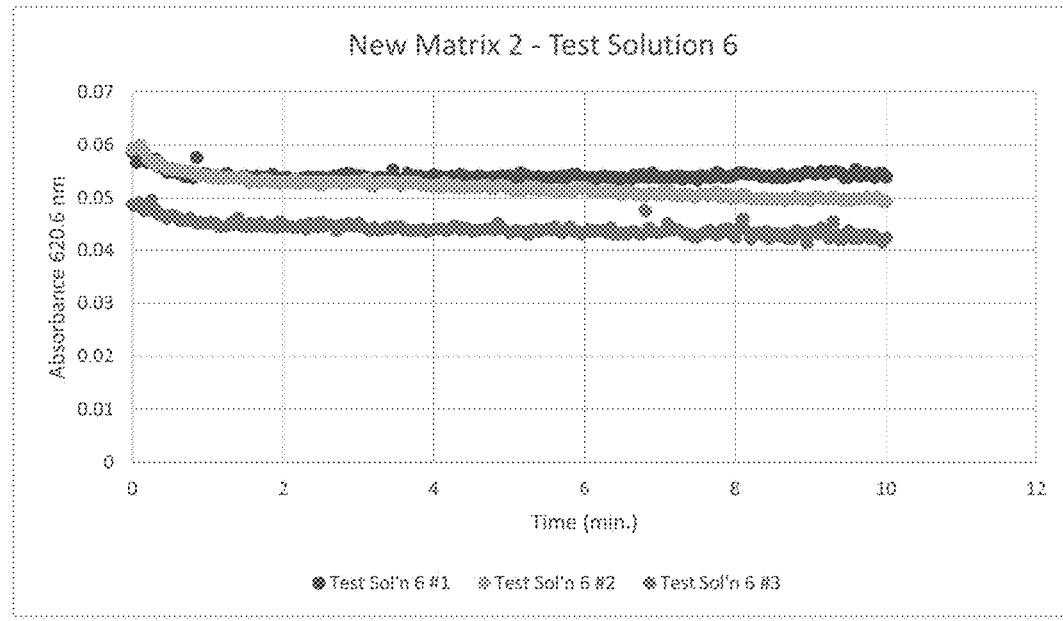
FIG. 76 is a graph showing absorbance at 620.6 nm as a function of time for Matrix 2 for Test Solution 6.
Figure 77:
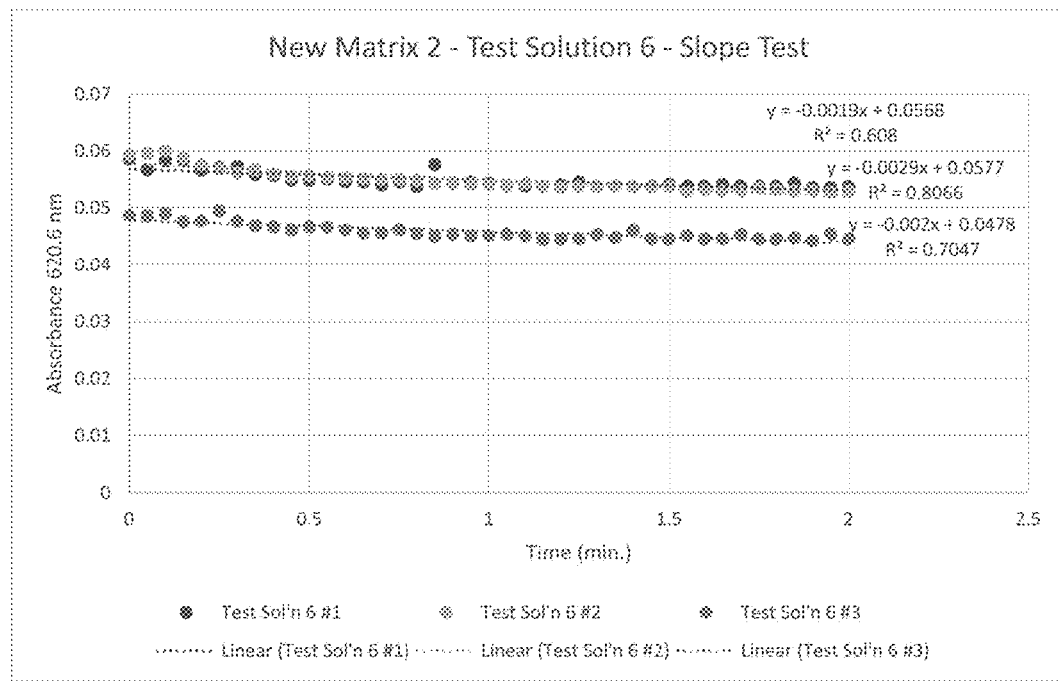
FIG. 77 is a graph showing absorbance at 620.6 nm as a function of time to determine the Slope for Matrix 2 for Test Solution 6.
Figure 78:
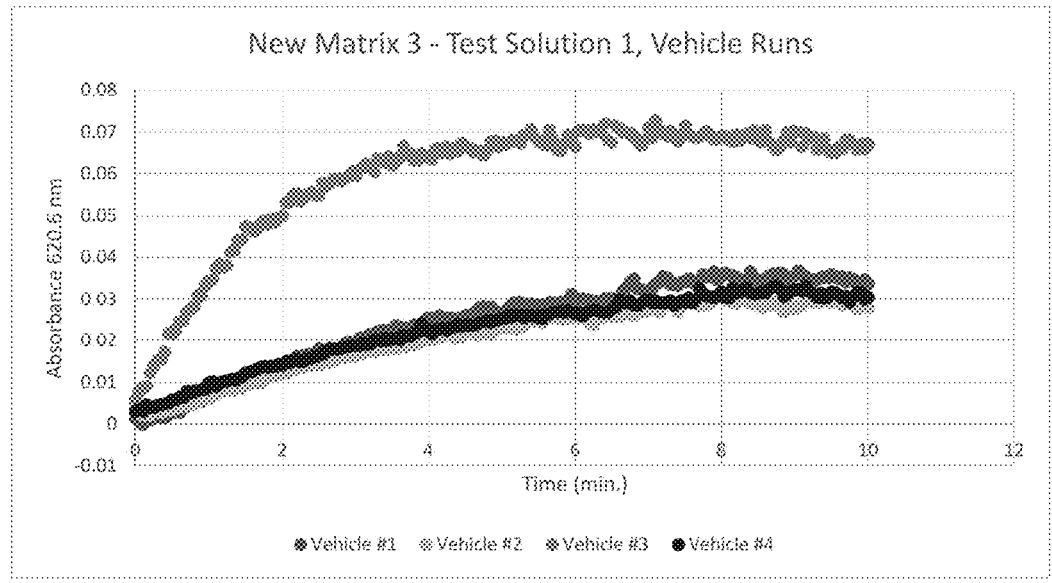
FIG. 78 is a graph showing absorbance at 620.6 nm as a function of time for Control Vehicle Runs Associated with Matrix 3 for Test Solution 1.
Figure 79:
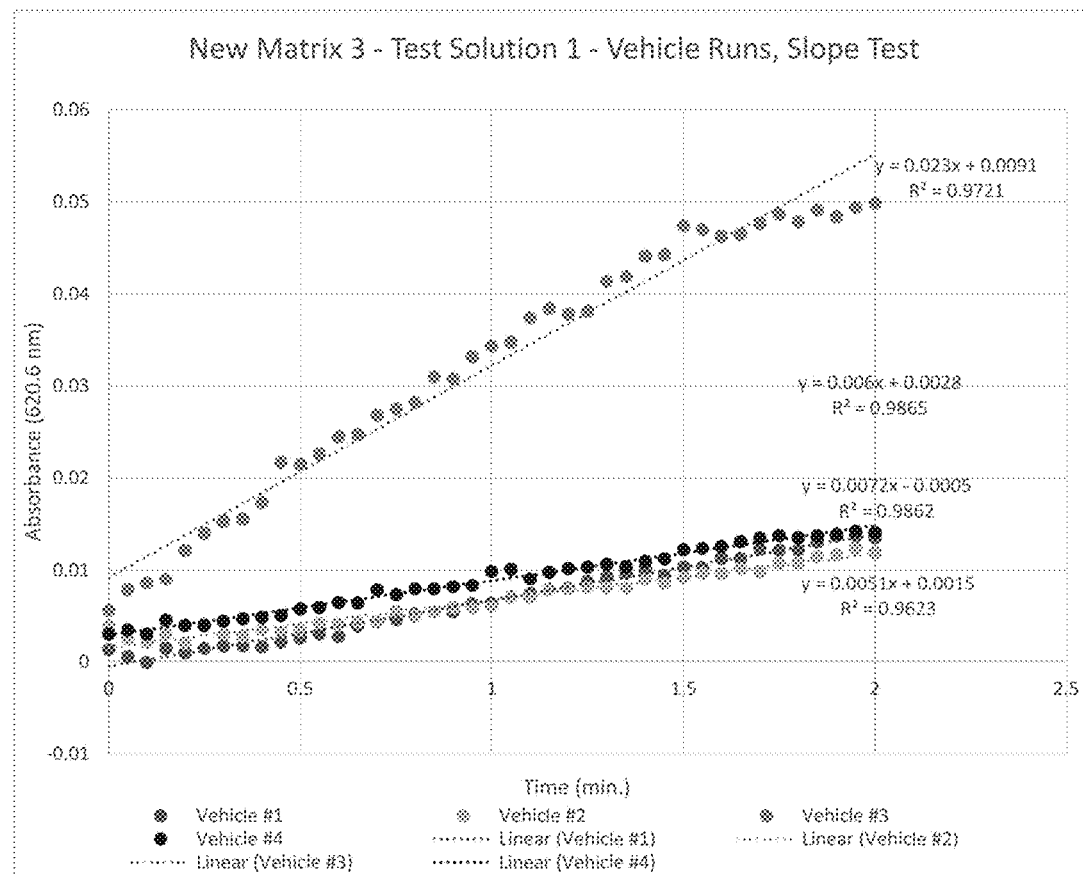
FIG. 79 is a graph showing absorbance at 620.6 nm as a function of time to determine the Slope for Control Vehicle Runs Associated with Matrix 3 for Test Solution 1.
Figure 80:
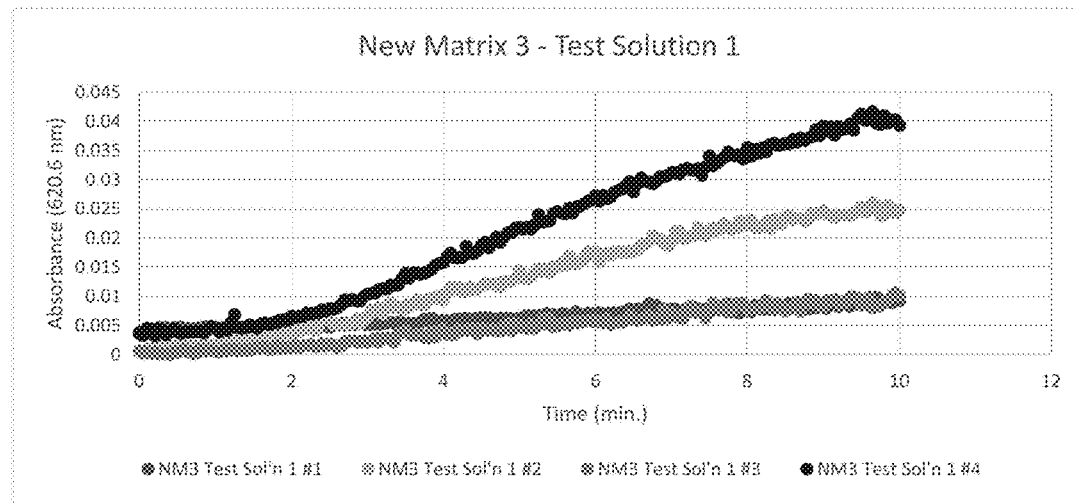
FIG. 80 is a graph showing absorbance at 620.6 nm as a function of time for Matrix 3 for Test Solution 1.
Figure 81:
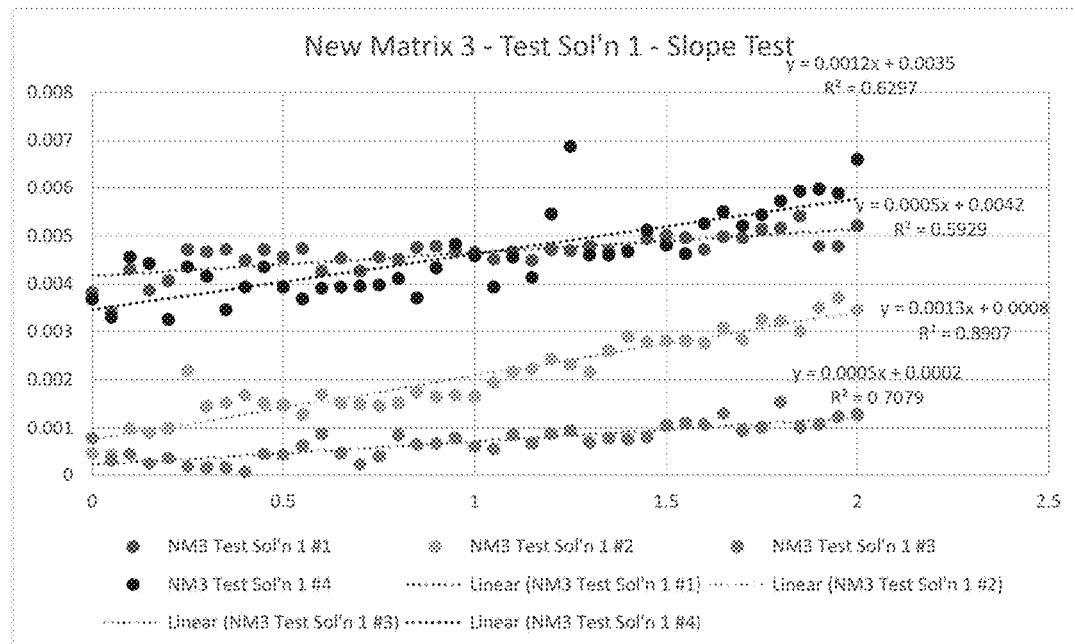
FIG. 81 is a graph showing absorbance at 620.6 nm as a function of time to determine the Slope for Matrix 3 for Test Solution 1.
Figure 82:
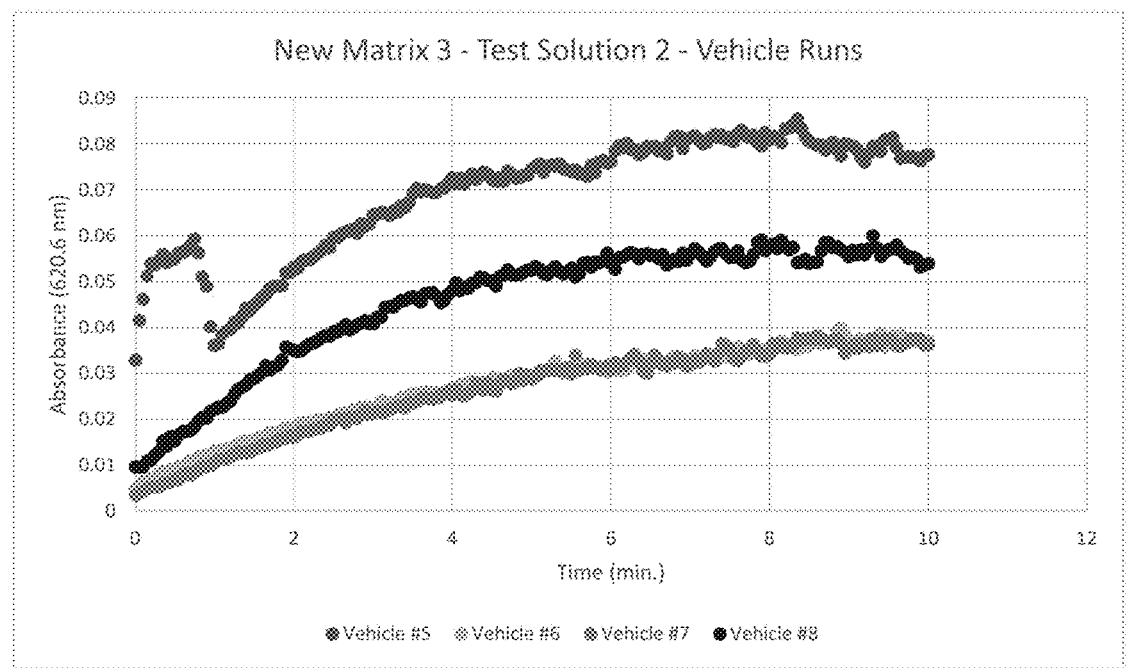
FIG. 82 is a graph showing absorbance at 620.6 nm as a function of time for Control Vehicle Runs Associated with Matrix 3 for Test Solution 2.
Figure 83:
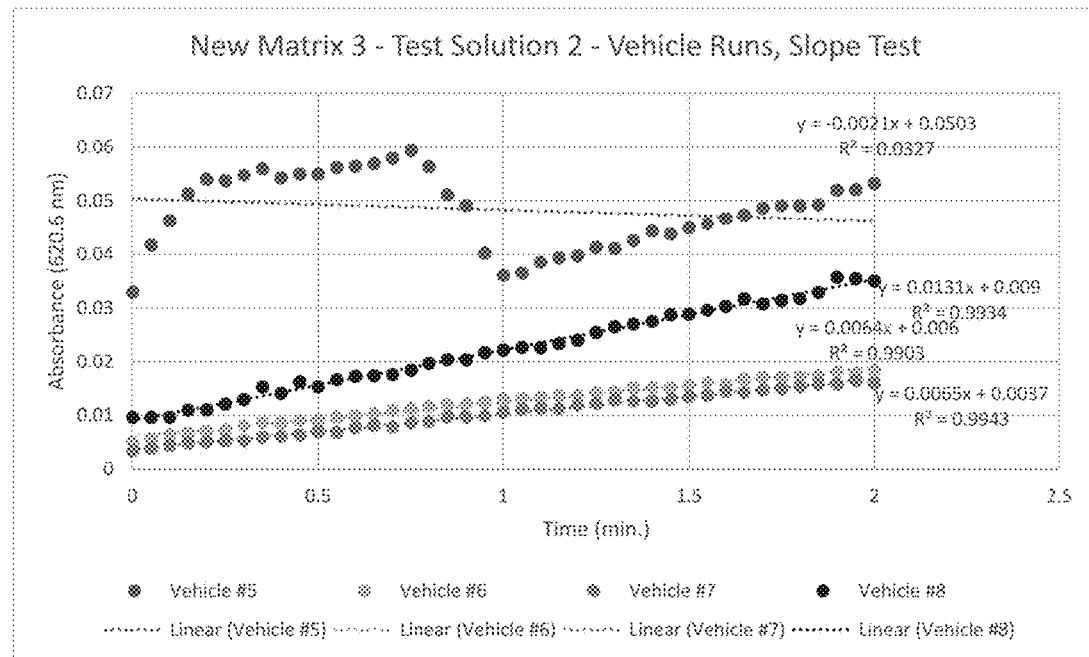
FIG. 83 is a graph showing absorbance at 620.6 nm as a function of time to determine the Slope for Control Vehicle Runs Associated with Matrix 3 for Test Solution 2.
Figure 84:
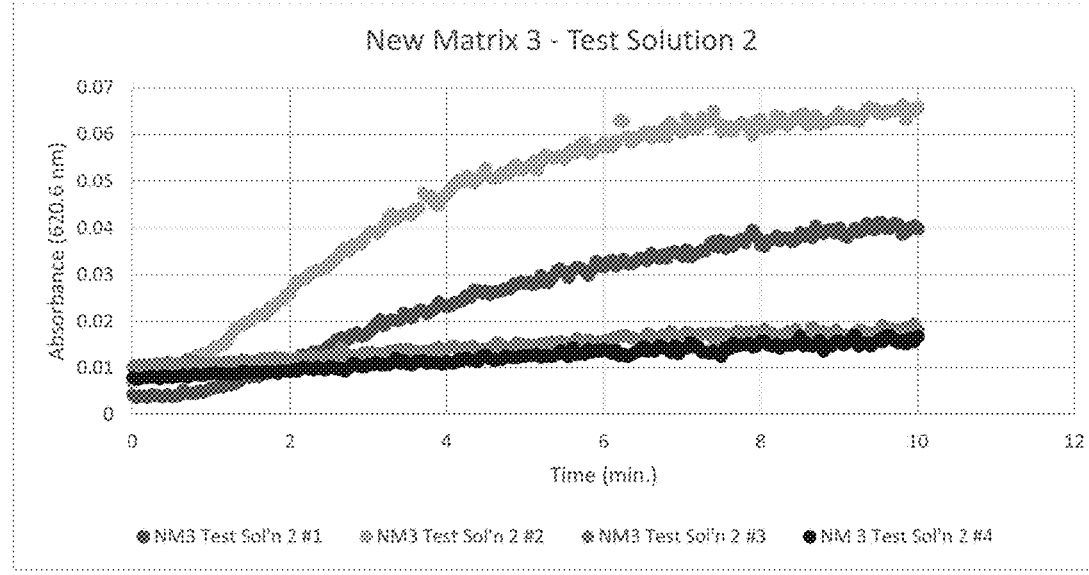
FIG. 84 is a graph showing absorbance at 620.6 nm as a function of time for Matrix 3 for Test Solution 2.
Figure 85:
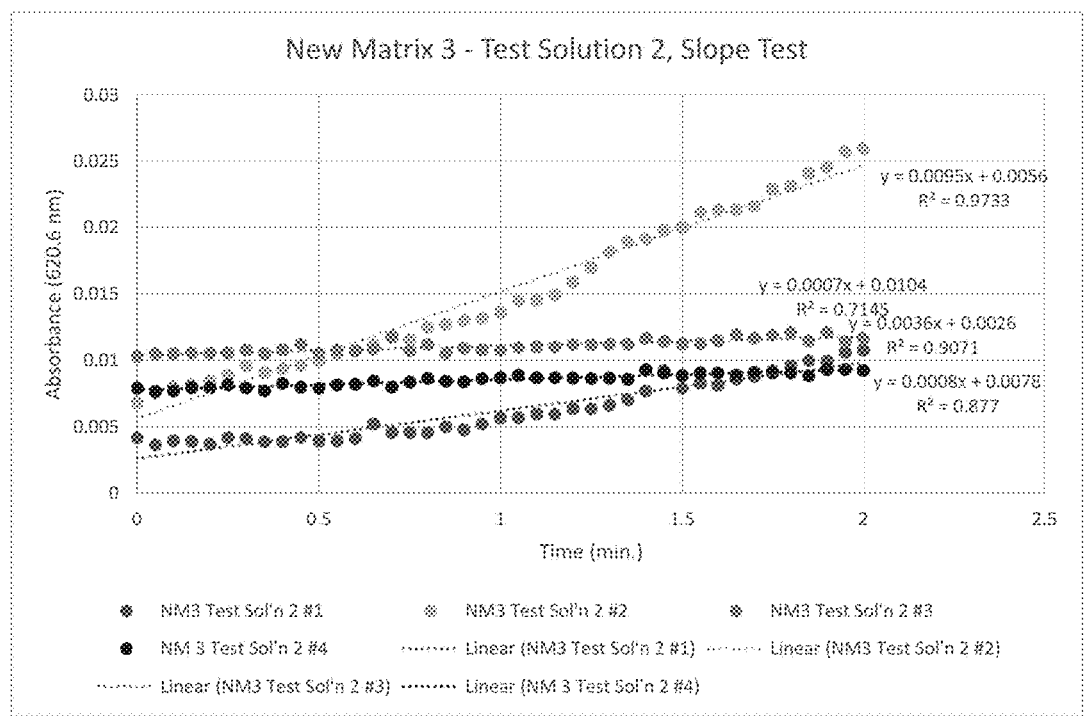
FIG. 85 is a graph showing absorbance at 620.6 nm as a function of time to determine the Slope for Matrix 3 for Test Solution 2.
Figure 86:
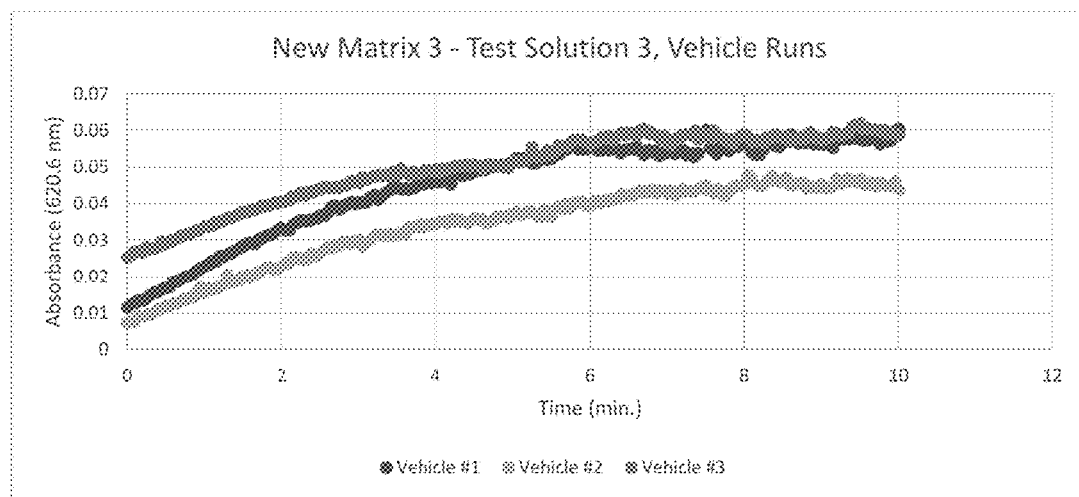
FIG. 86 is a graph showing absorbance at 620.6 nm as a function of time for Control Vehicle Runs Associated with Matrix 3 for Test Solution 3.
Figure 87:
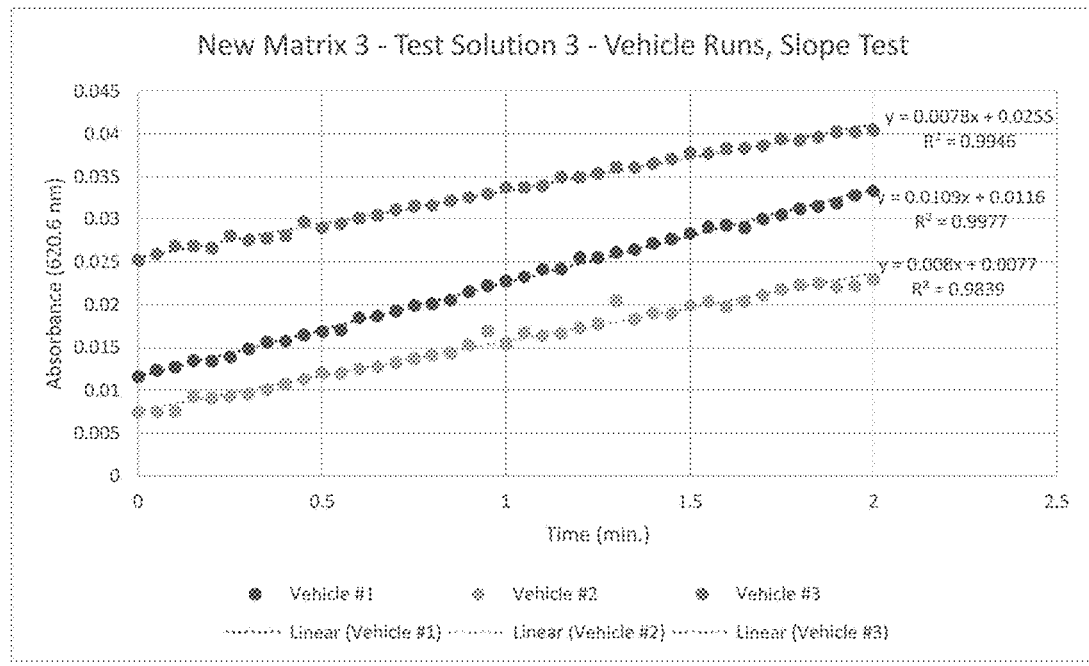
FIG. 87 is a graph showing absorbance at 620.6 nm as a function of time to determine the Slope for Control Vehicle Runs Associated with Matrix 3 for Test Solution 3.
Figure 88:
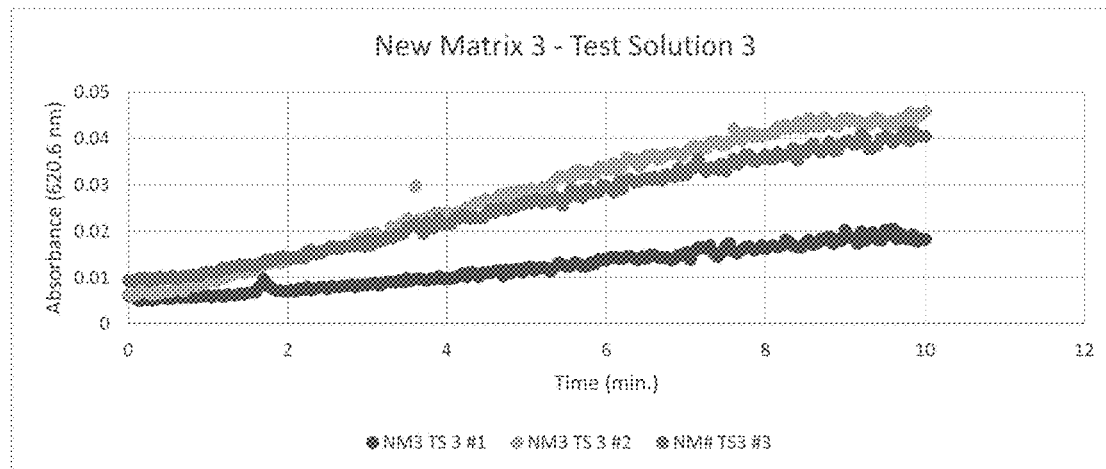
FIG. 88 is a graph showing absorbance at 620.6 nm as a function of time for Matrix 3 for Test Solution 3.
Figure 89:
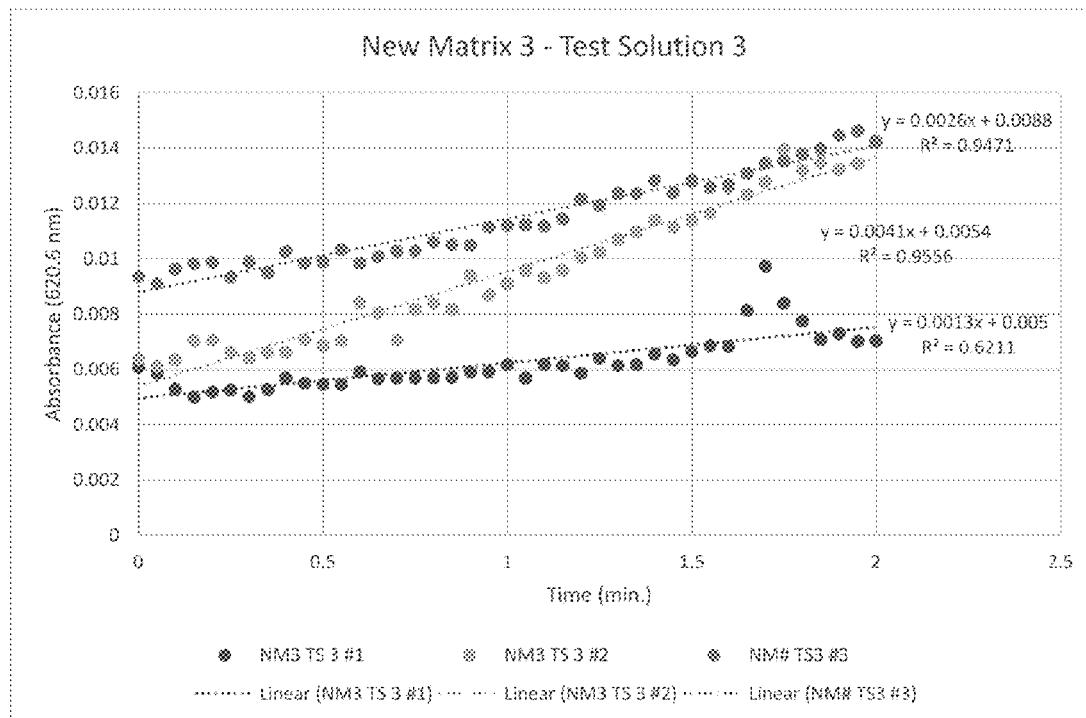
FIG. 89 is a graph showing absorbance at 620.6 nm as a function of time to determine the Slope for Matrix 3 for Test Solution 3.
Figure 90:
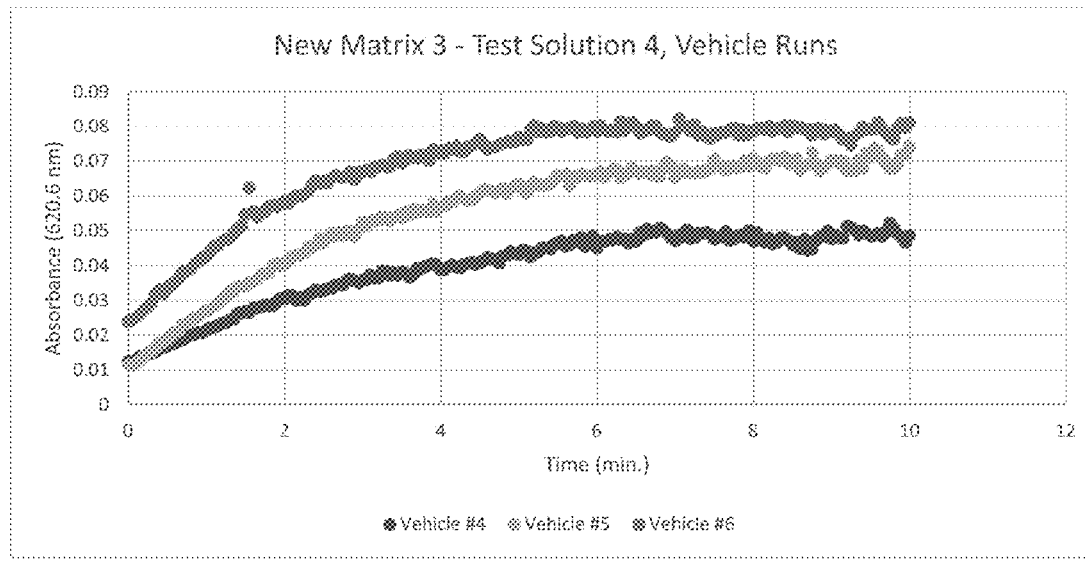
FIG. 90 is a graph showing absorbance at 620.6 nm as a function of time for Control Vehicle Runs Associated with Matrix 3 for Test Solution 4.
Figure 91:
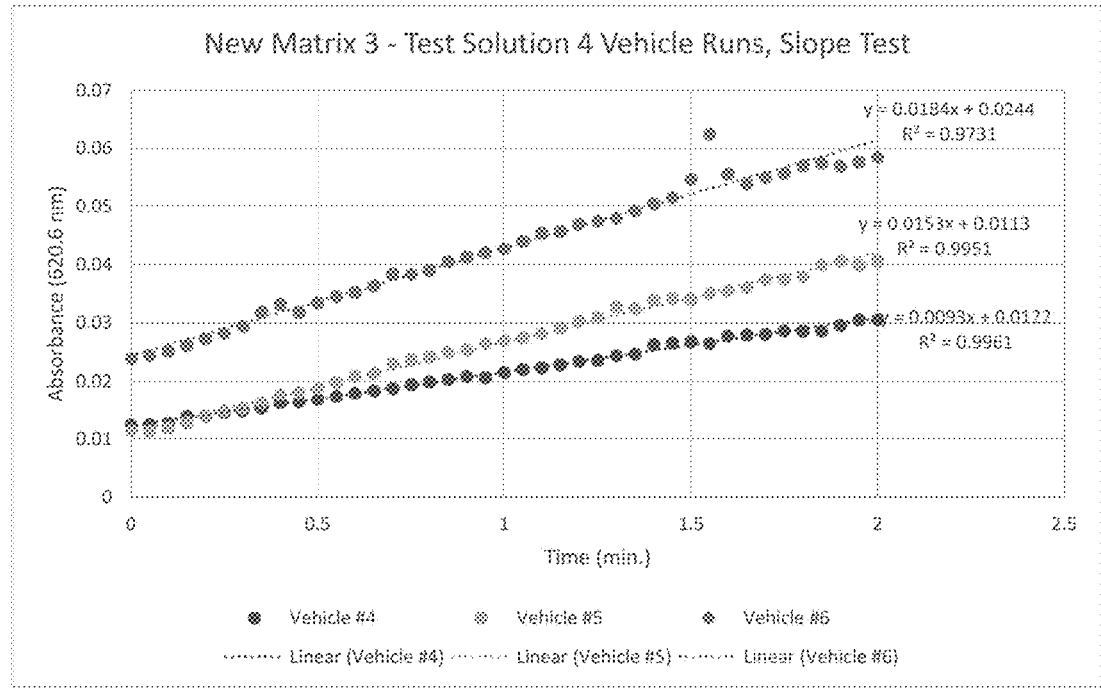
FIG. 91 is a graph showing absorbance at 620.6 nm as a function of time to determine the Slope for Control Vehicle Runs Associated with Matrix 3 for Test Solution 4.
Figure 92:
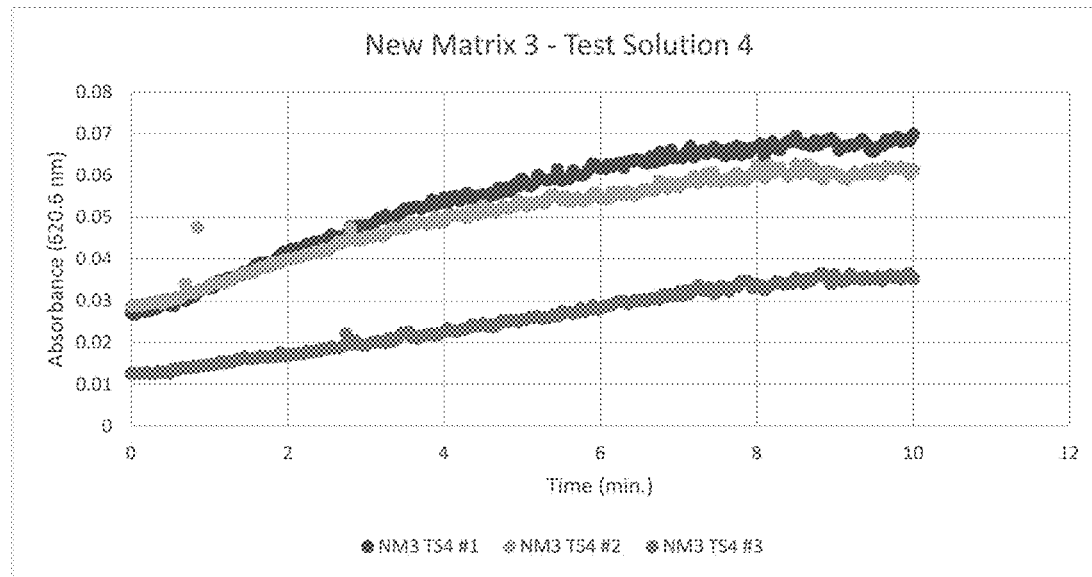
FIG. 92 is a graph showing absorbance at 620.6 nm as a function of time for Matrix 3 for Test Solution 4.
Figure 93:
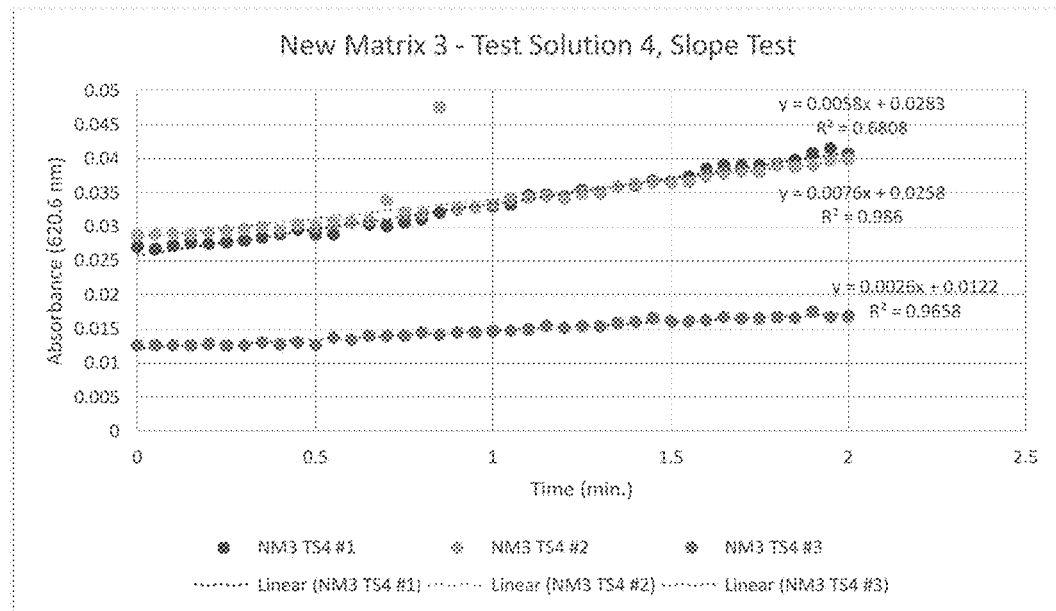
FIG. 93 is a graph showing absorbance at 620.6 nm as a function of time to determine the Slope for Matrix 3 for Test Solution 4.
Figure 94:
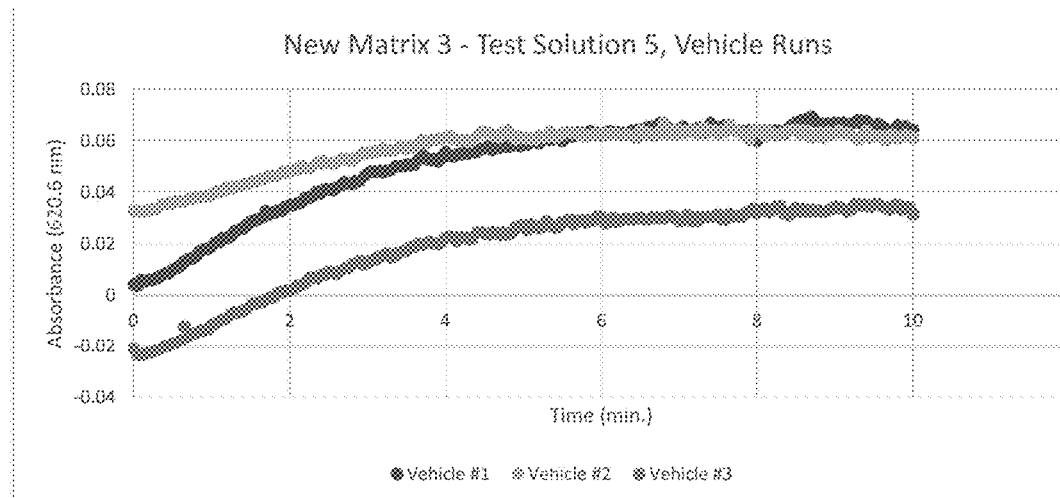
FIG. 94 is a graph showing absorbance at 620.6 nm as a function of times for Control Vehicle Runs Associated with Matrix 3 for Test Solution 5.
Figure 95:
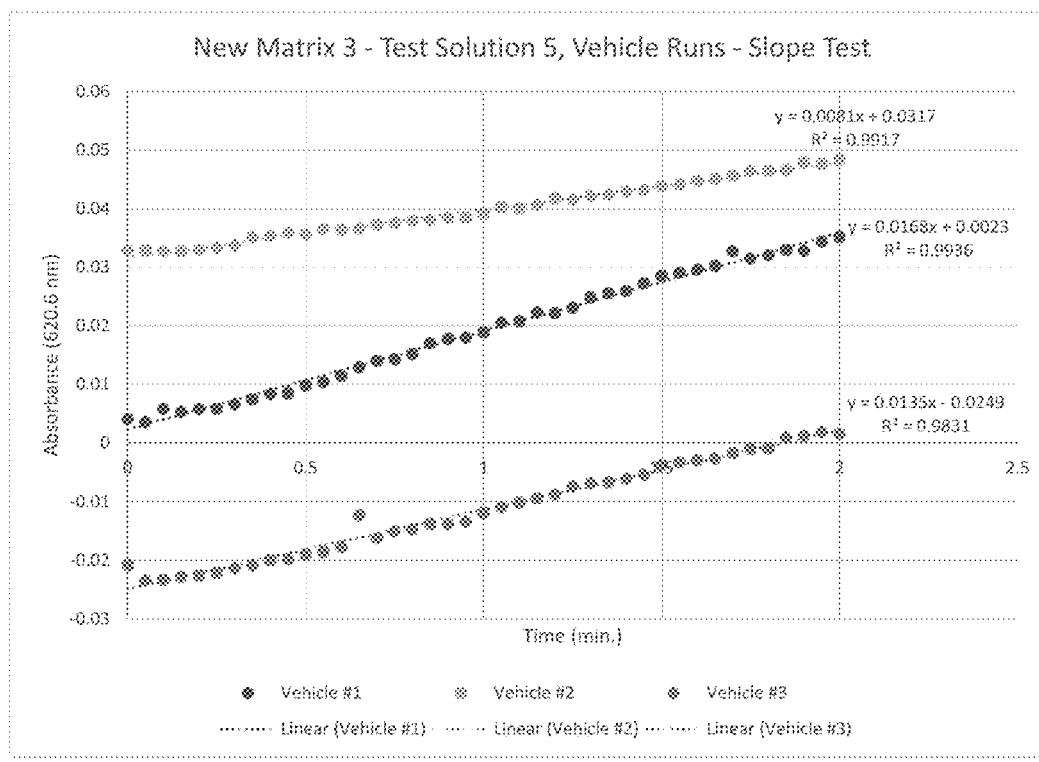
FIG. 95 is a graph showing absorbance at 620.6 nm as a function of time to determine the Slope for Vehicle Runs Associated with Matrix 3 for Test Solution 5.
Figure 96:
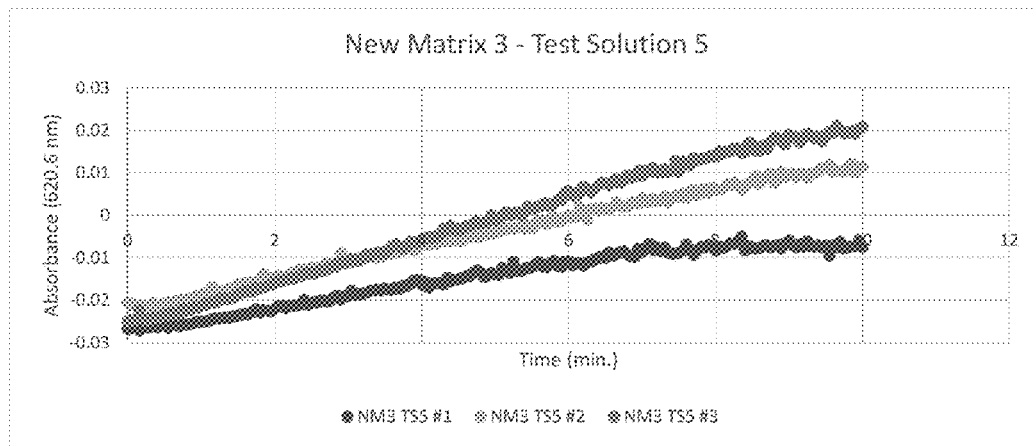
FIG. 96 is a graph showing absorbance at 620.6 nm as a function of time for Matrix 3 for Test Solution 5.
Figure 97:
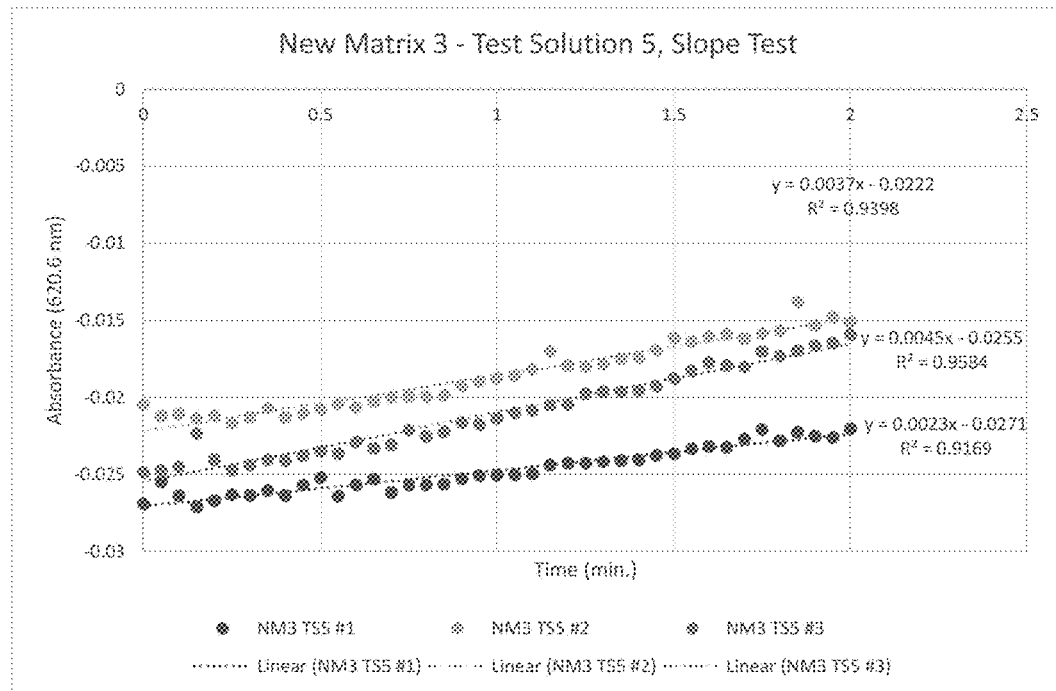
FIG. 97 is a graph showing absorbance at 620.6 nm as a function of time to determine the Slope for Matrix 3 for Test Solution 5.
Figure 98:
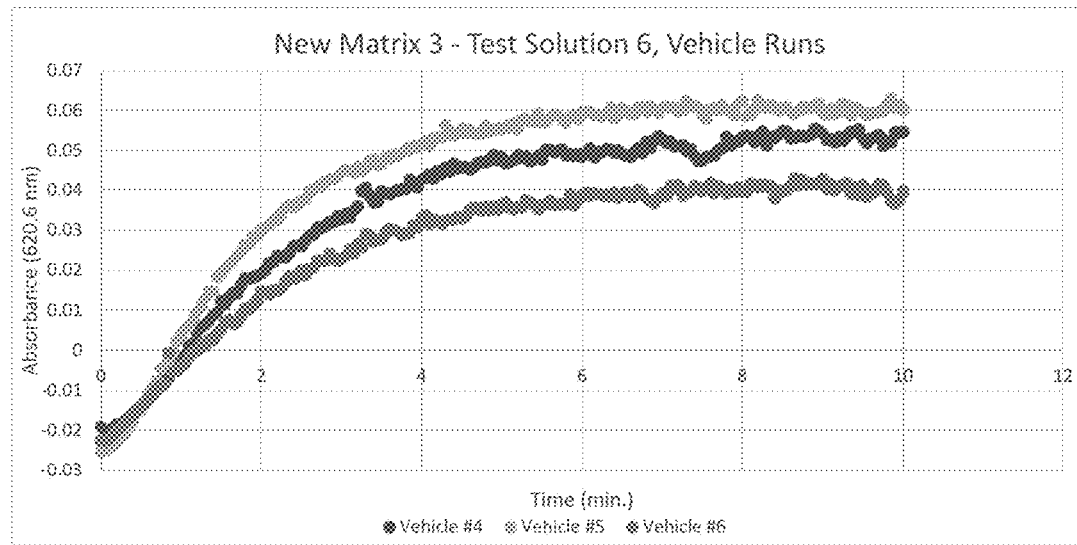
FIG. 98 is a graph showing absorbance at 620.6 nm as a function of time for Control Vehicle Runs Associated with Matrix 3 for Test Solution 6.
Figure 99:
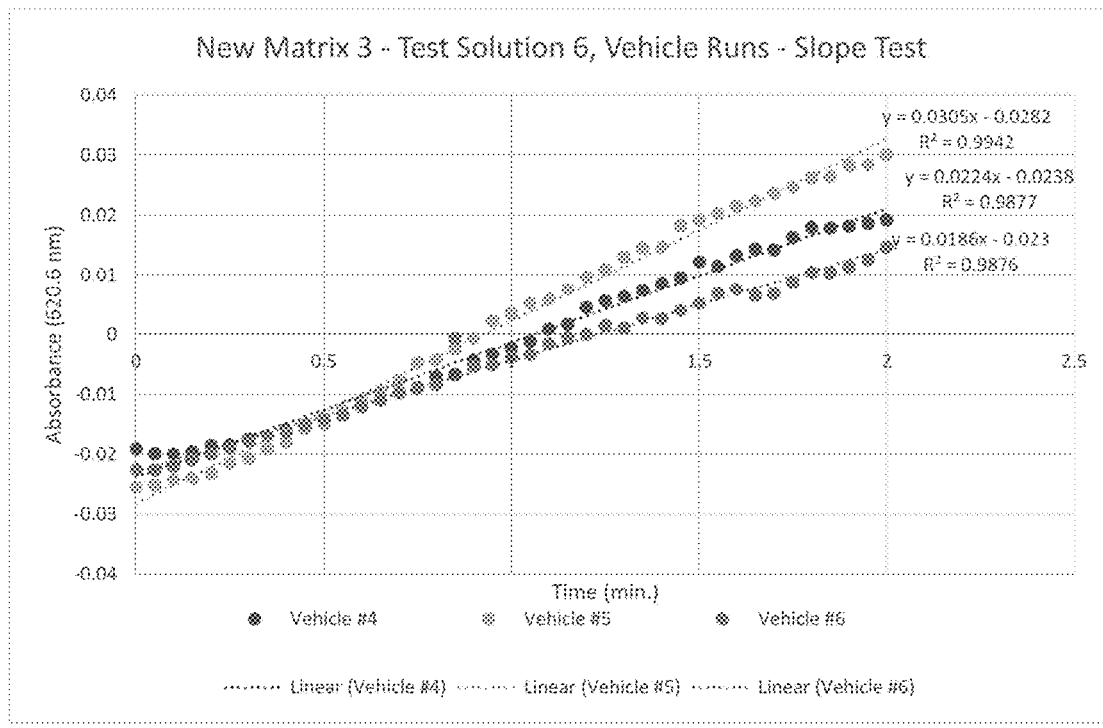
FIG. 99 is a graph showing absorbance at 620.6 nm as a function of time to determine the Slope for Control Vehicle Runs Associated with Matrix 3 for Test Solution 6.
Figure 100:
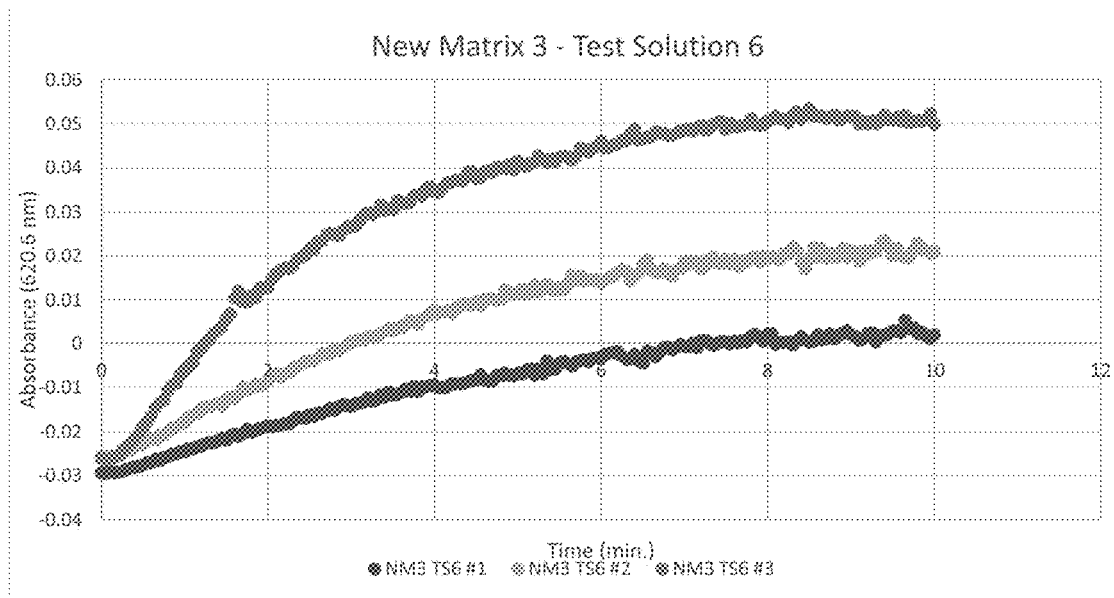
FIG. 100 is a graph showing absorbance at 620.6 nm as a function of time for Matrix 3 for Test Solution 6.
Figure 101:
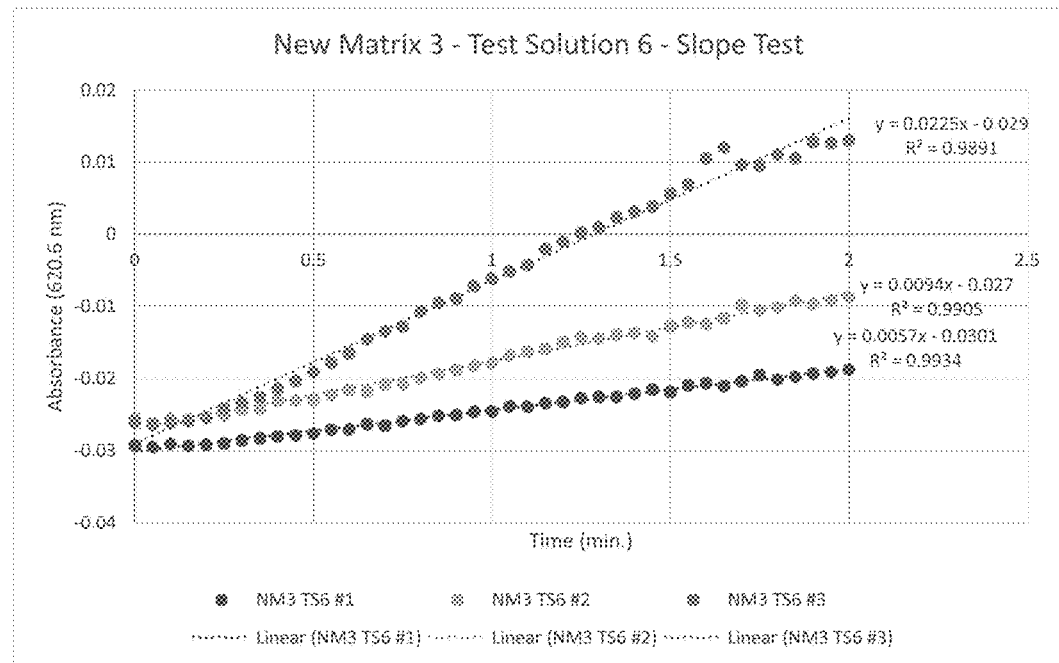
FIG. 101 is a graph showing absorbance at 620.6 nm as a function of time to determine the Slope for Matrix 3 for Test Solution 6.
Figure 102:
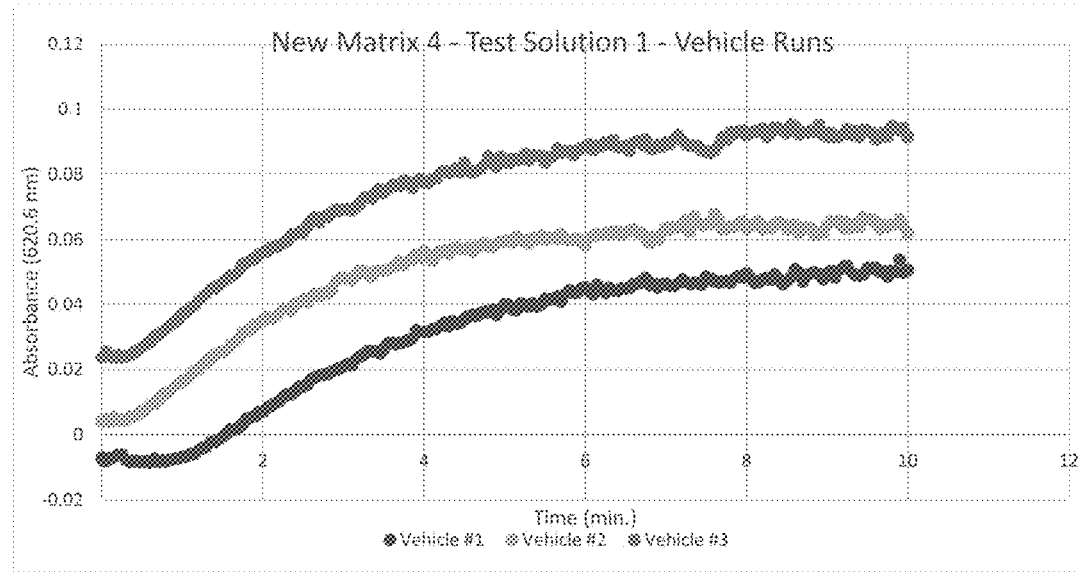
FIG. 102 is a graph showing absorbance at 620.6 nm as a function of time for Control Vehicle Runs Associated with Matrix 4 for Test Solution 1.
Figure 103:
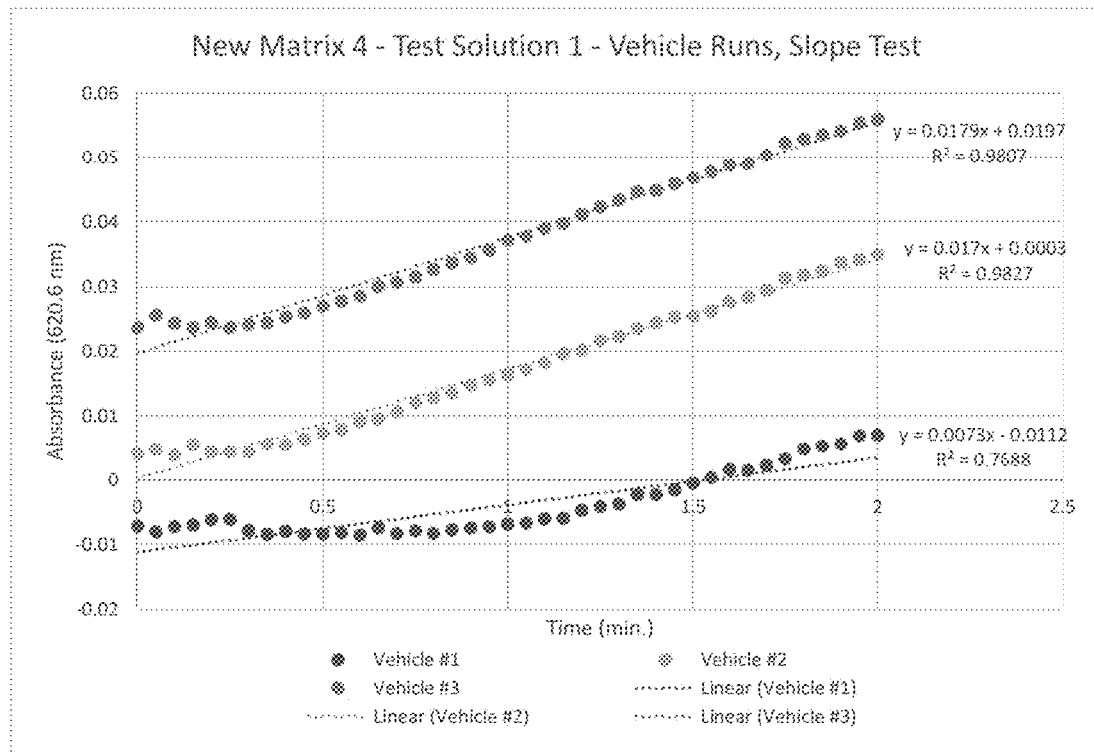
FIG. 103 is a graph showing absorbance at 620.6 nm as a function of time to determine the Slope for Control Vehicle Runs Associated with Matrix 4 for Test Solution 1.
Figure 104:
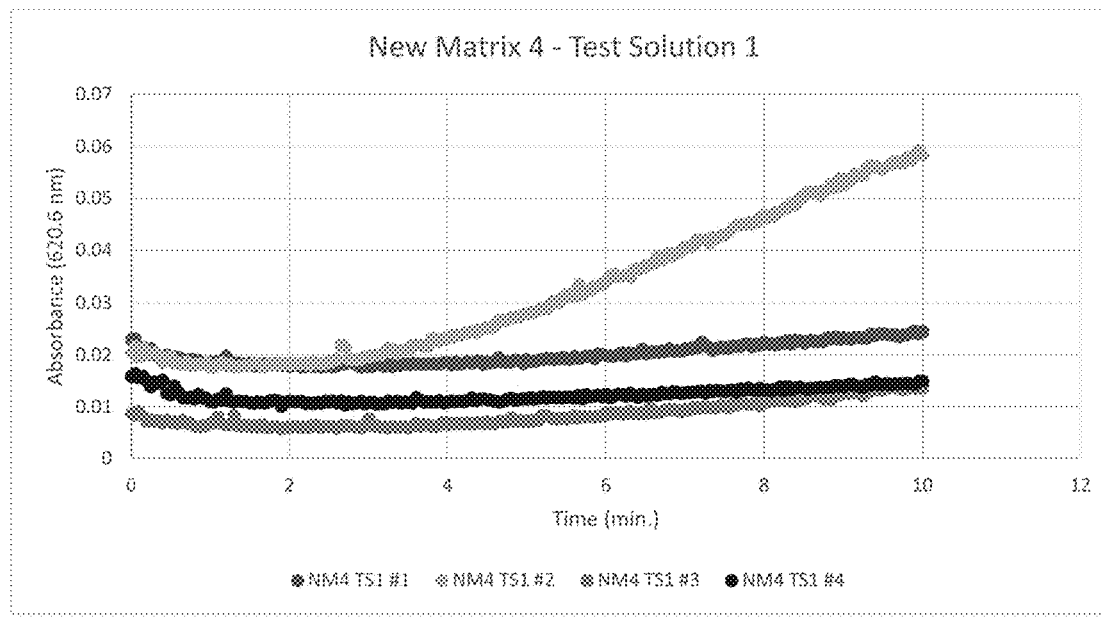
FIG. 104 is a graph showing absorbance at 620.6 nm as a function of time for Matrix 4 for Test Solution 1.
Figure 105:
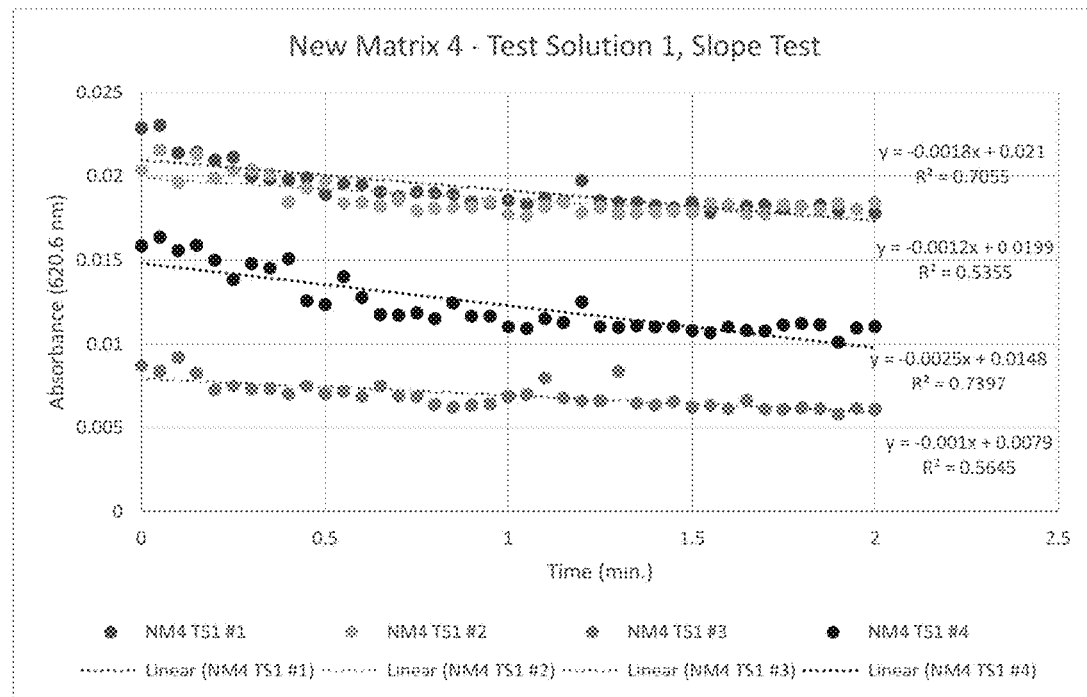
FIG. 105 is a graph showing absorbance at 620.6 nm as a function of time to determine the Slope for Matrix 4 for Test Solution 1.
Figure 106:
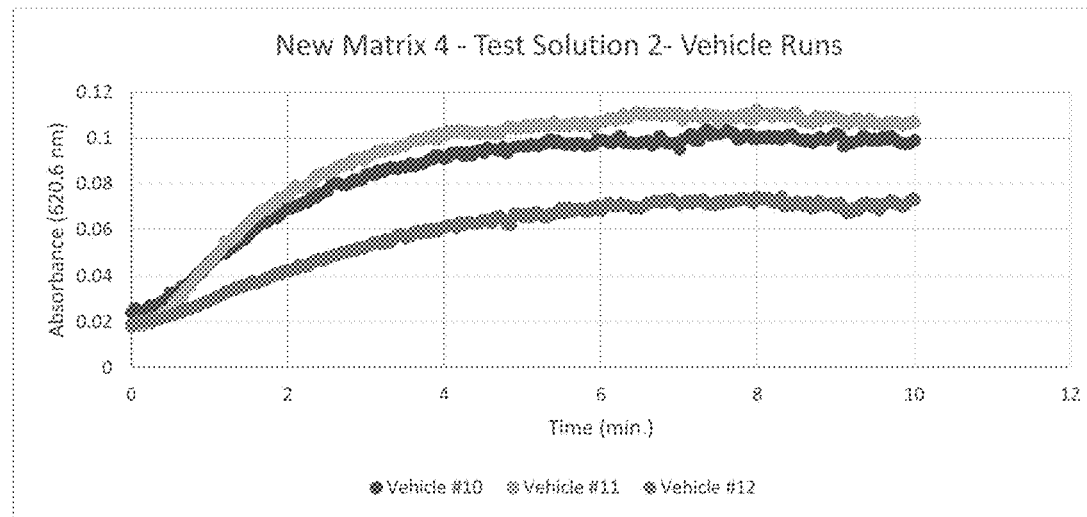
FIG. 106 is a graph showing absorbance at 620.6 nm as a function of time for Control Vehicle Runs Associated with Matrix 4 for Test Solution 2.
Figure 107:
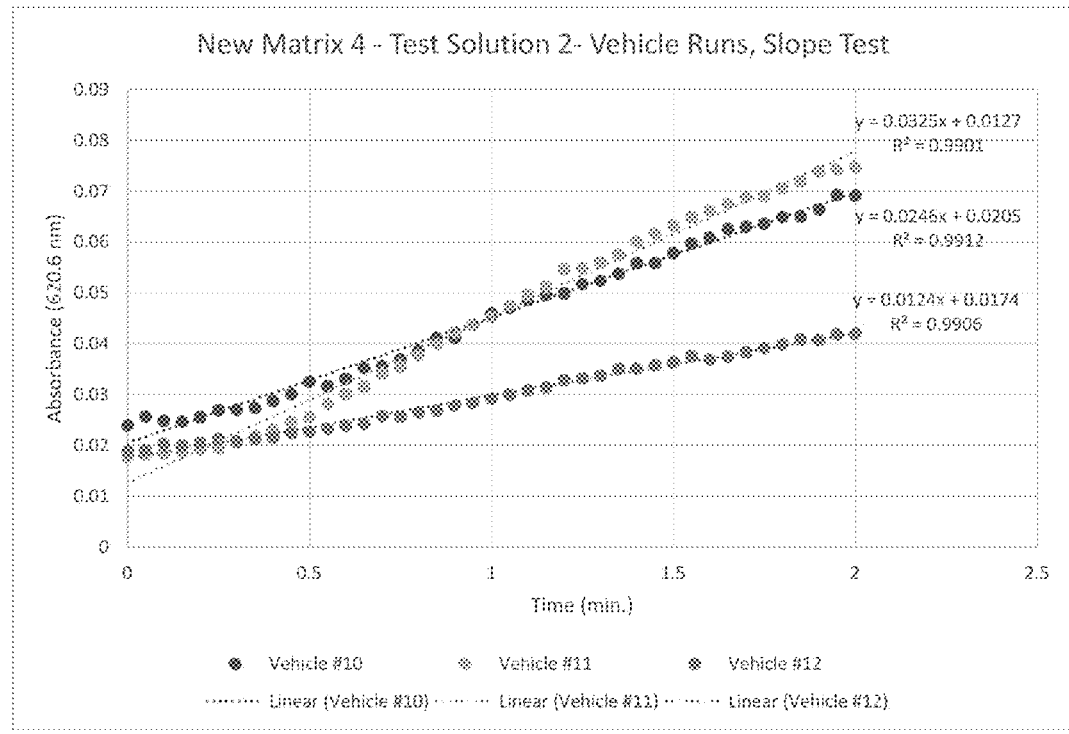
FIG. 107 is a graph showing absorbance at 620.6 nm as a function of time to determine the Slope for Control Vehicle Runs Associated with Matrix 4 for Test Solution 2.
Figure 108:
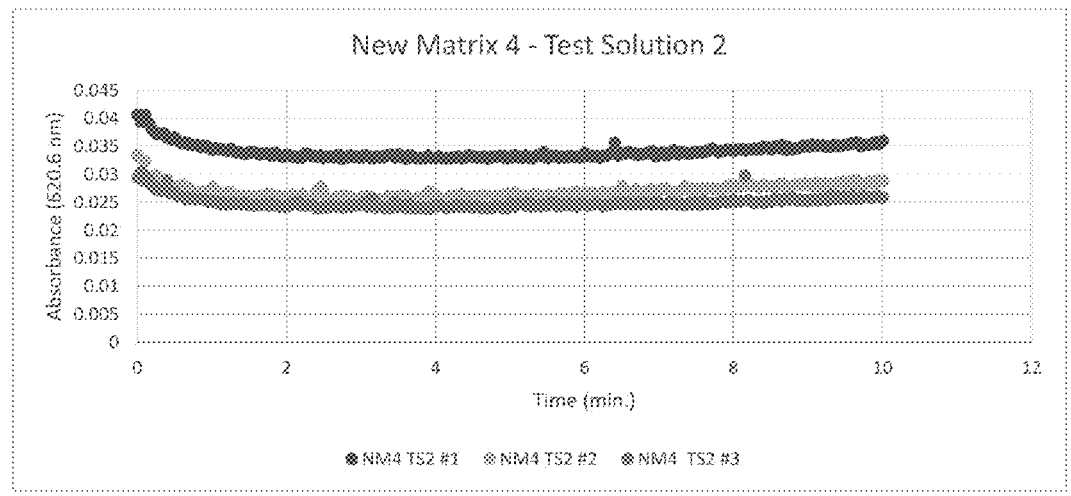
FIG. 108 is a graph showing absorbance at 620.6 nm as a function of time for Matrix 4 for Test Solution 2.
Figure 109:
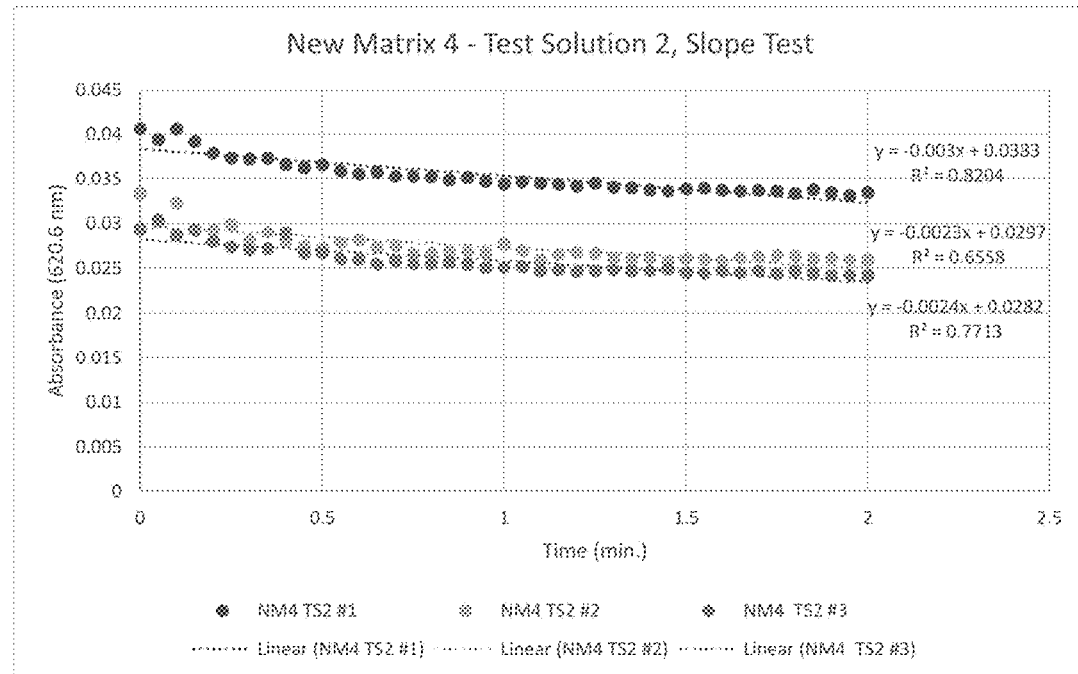
FIG. 109 is a graph showing absorbance at 620.6 nm as a function of time to determine the Slope for Matrix 4 for Test Solution 2.
Figure 110:
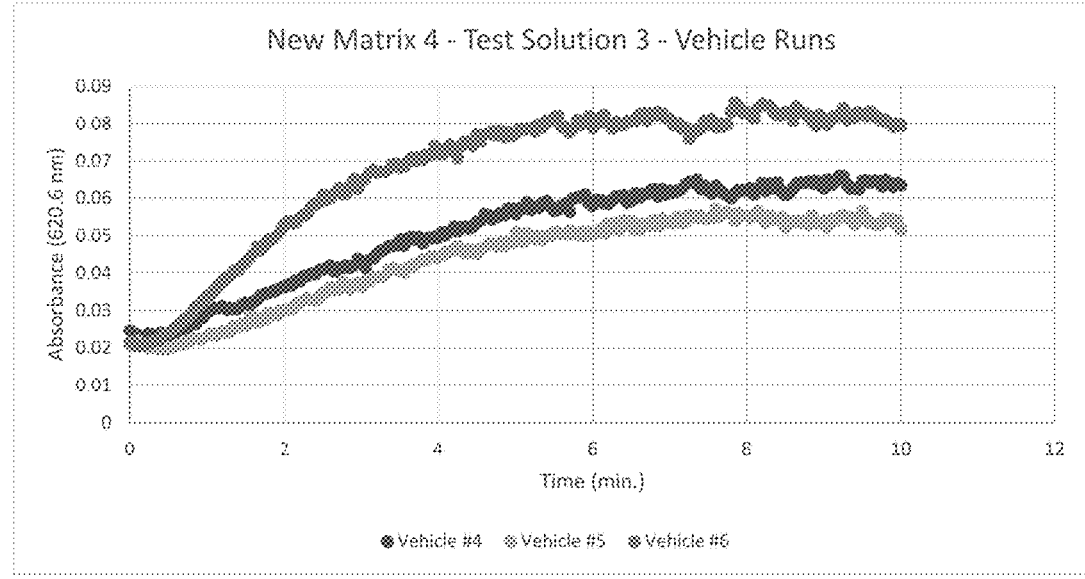
FIG. 110 is a graph showing absorbance at 620.6 nm as a function of time for Control Vehicle Runs Associated with Matrix 4 for Test Solution 3.
Figure 111:
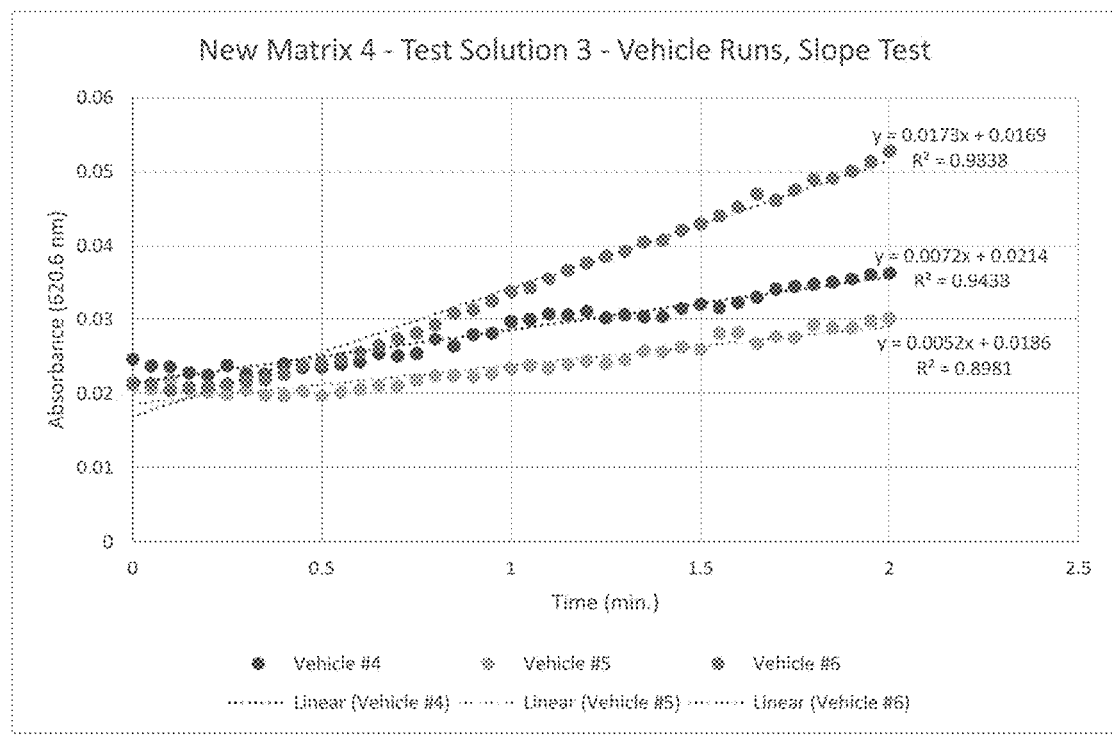
FIG. 111 is a graph showing absorbance at 620.6 nm as a function of time to determine the Slope for Control Vehicle Runs Associated with Matrix 4 for Test Solution 3.
Figure 112:
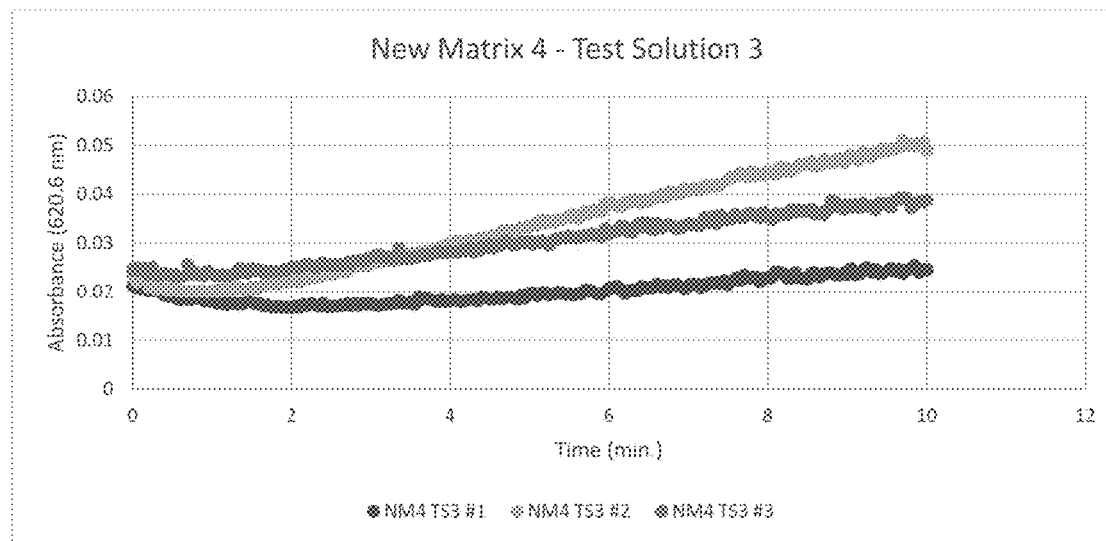
FIG. 112 is a graph showing absorbance at 620.6 nm as a function of time for Matrix 4 for Test Solution 3.
Figure 113:
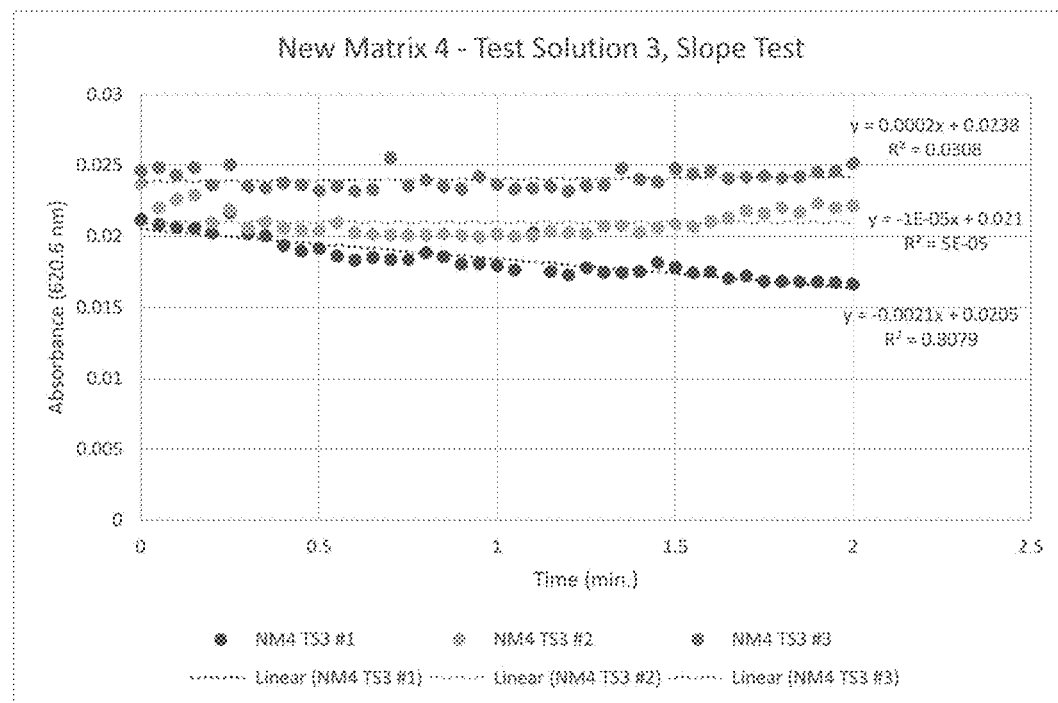
FIG. 113 is a graph showing absorbance at 620.6 nm as a function of time to determine the Slope for Matrix 4 for Test Solution 3.
Figure 114:
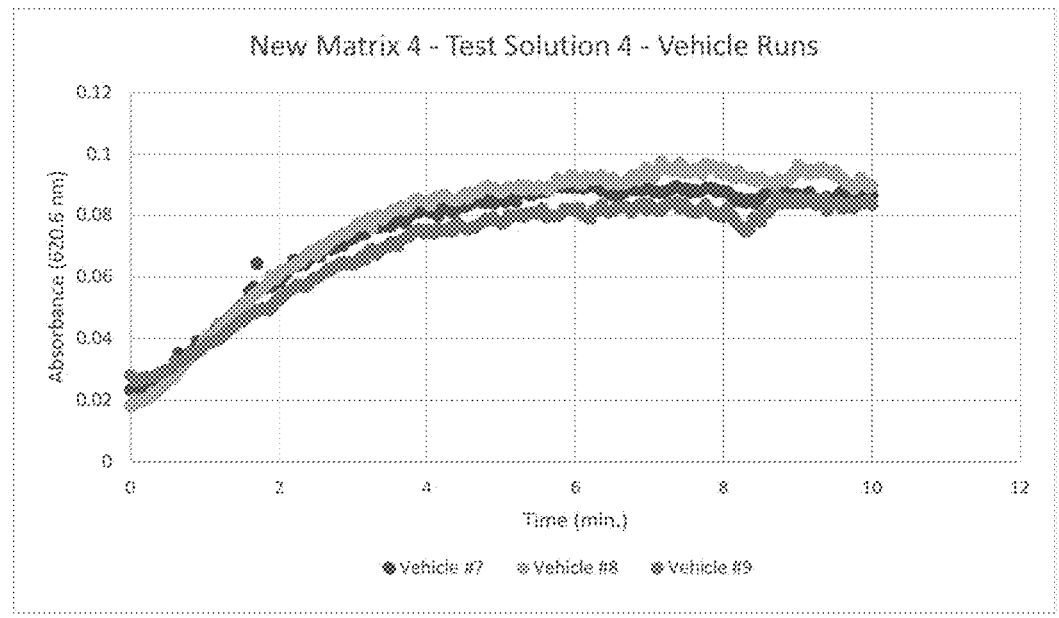
FIG. 114 is a graph showing absorbance at 620.6 nm as a function of time for Control Vehicle Runs Associated with Matrix 4 for Test Solution 4.
Figure 115:
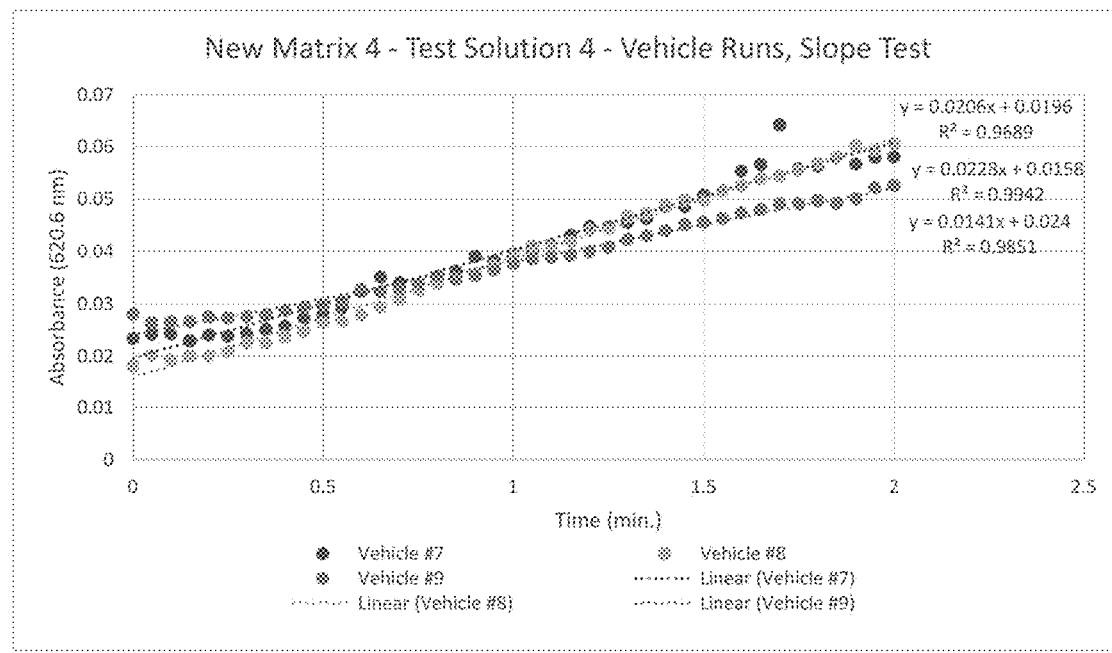
FIG. 115 is a graph showing absorbance at 620.6 nm as a function of time to determine the Slope for Control Vehicle Runs Associated with Matrix 4 for Test Solution 4.
Figure 116:
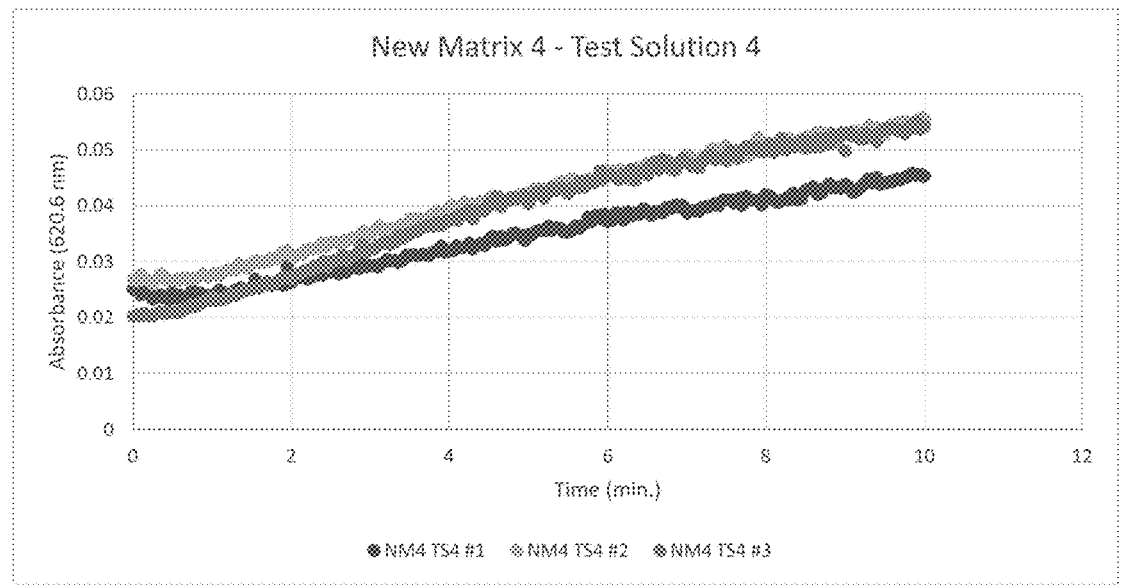
FIG. 116 is a graph showing absorbance at 620.6 nm as a function of time for Matrix 4 for Test Solution 4.
Figure 117:
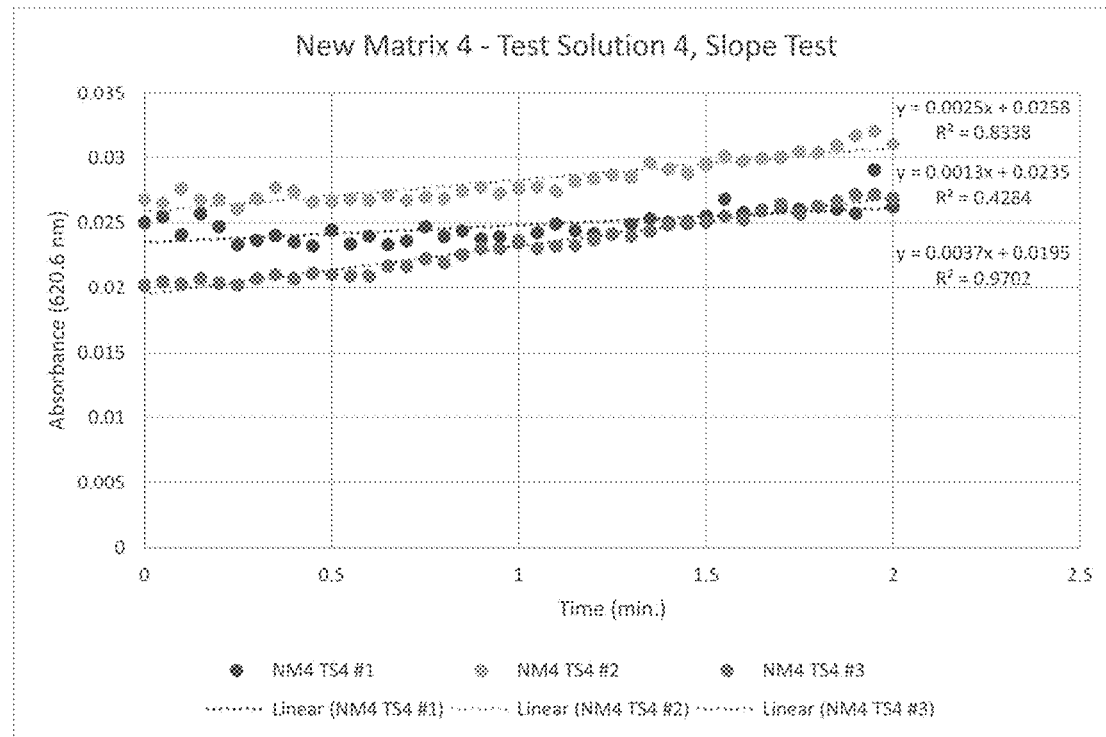
FIG. 117 is a graph showing absorbance at 620.6 nm as a function of time to determine the Slope for Matrix 4 for Test Solution 4.
Figure 118:
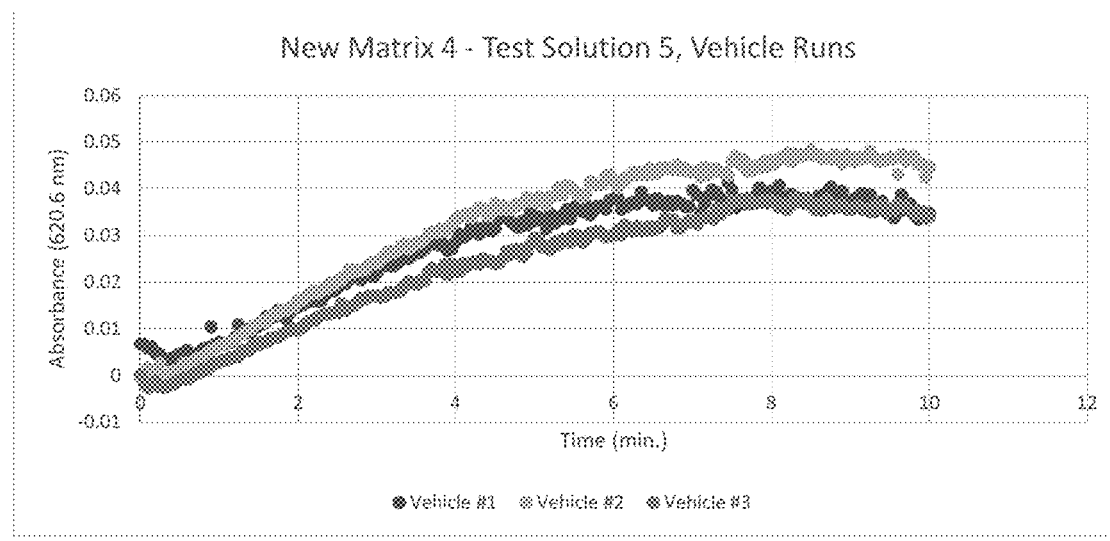
FIG. 118 is a graph showing absorbance at 620.6 nm as a function of times for Control Vehicle Runs Associated with Matrix 4 for Test Solution 5.
Figure 119:
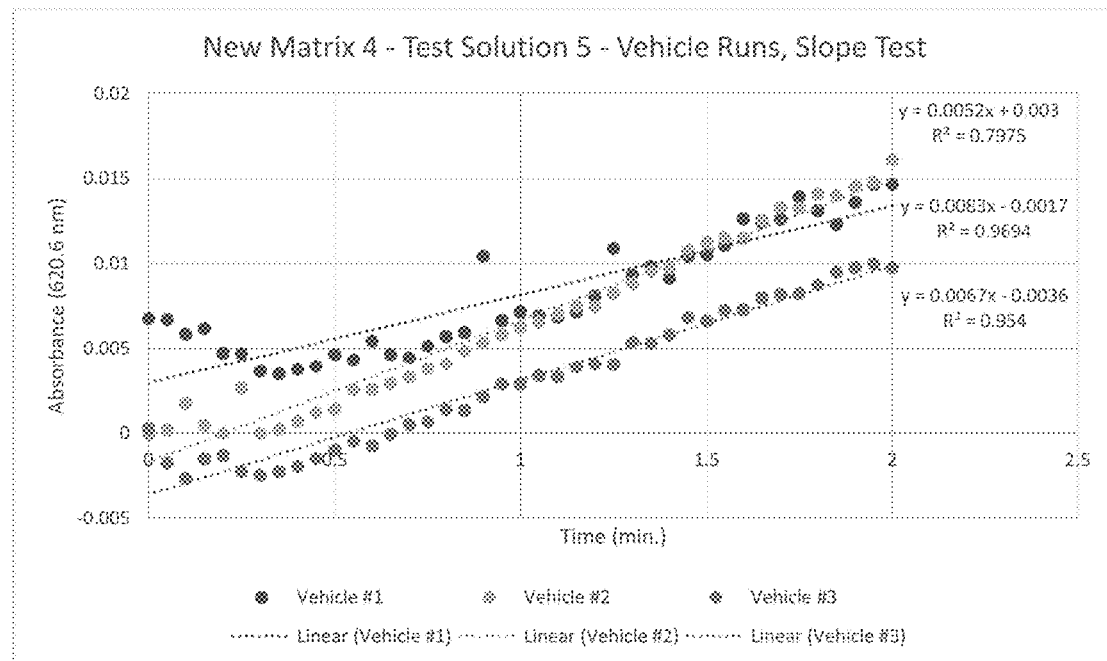
Figure 120:
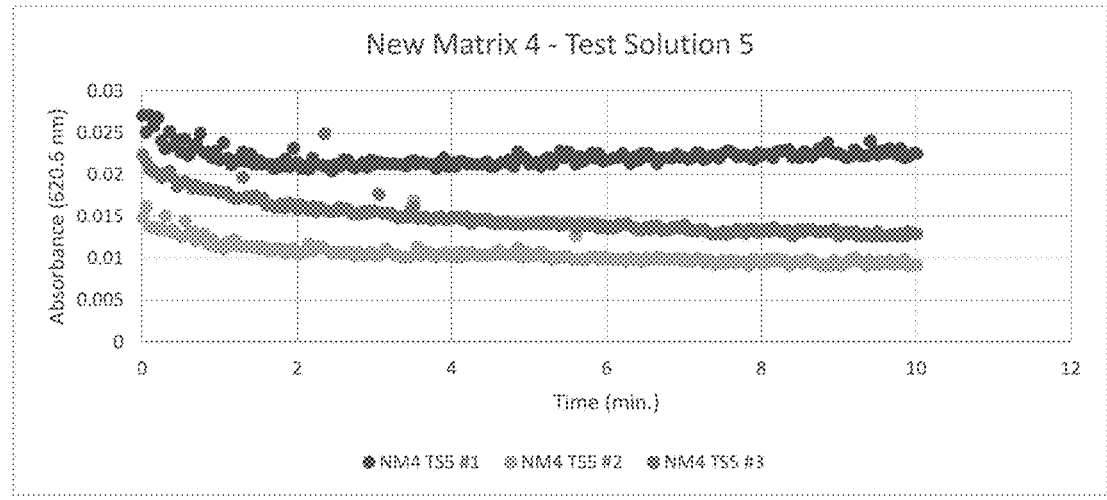
Figure 121:
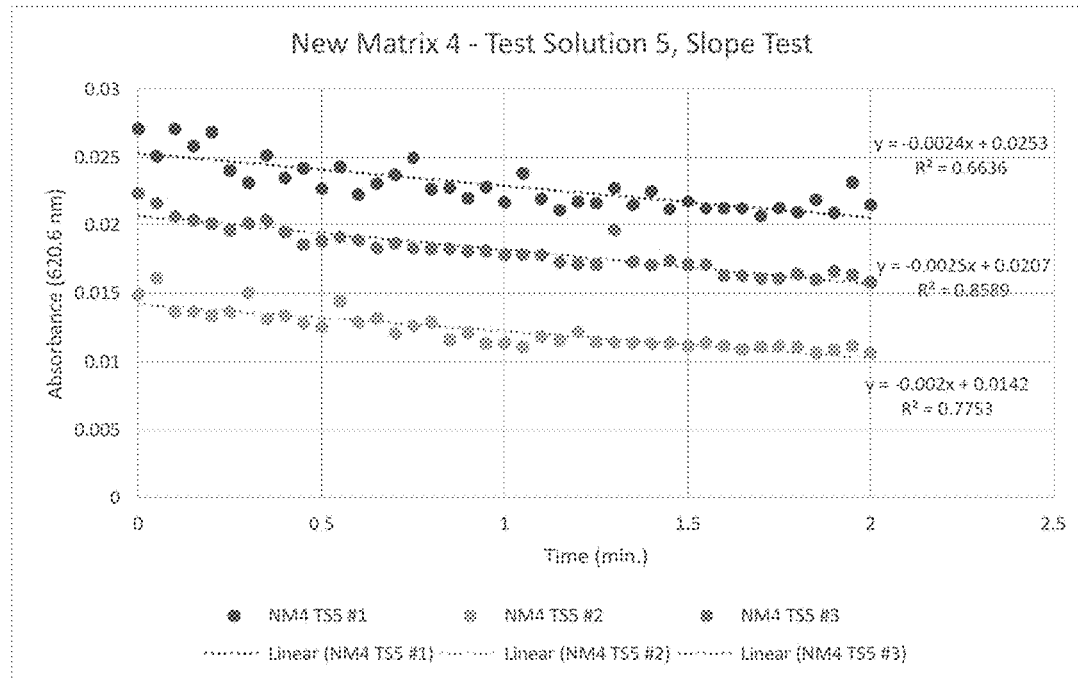
Figure 122:
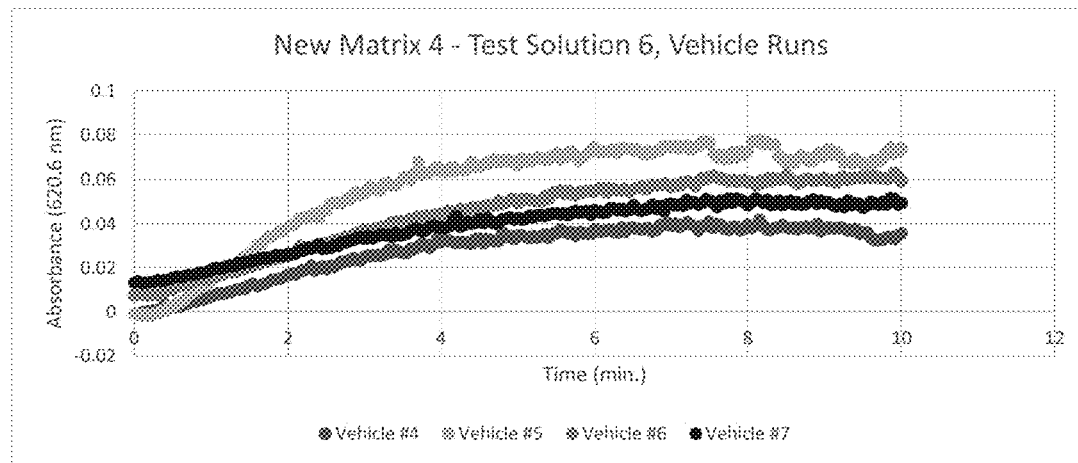
Figure 123:
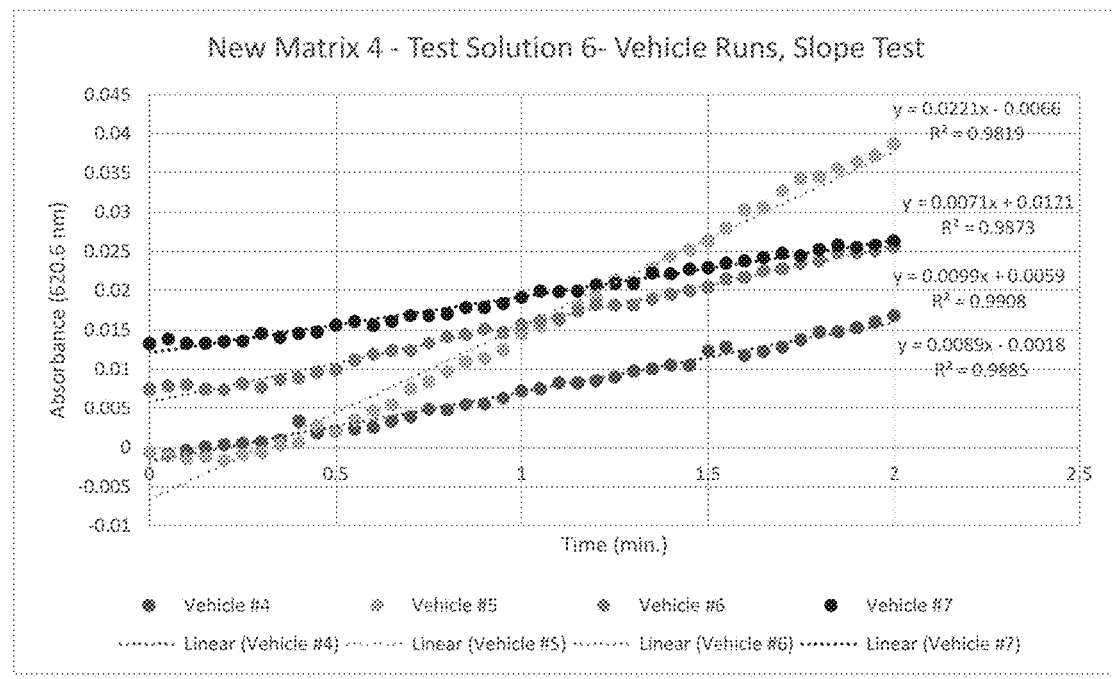
Figure 124:
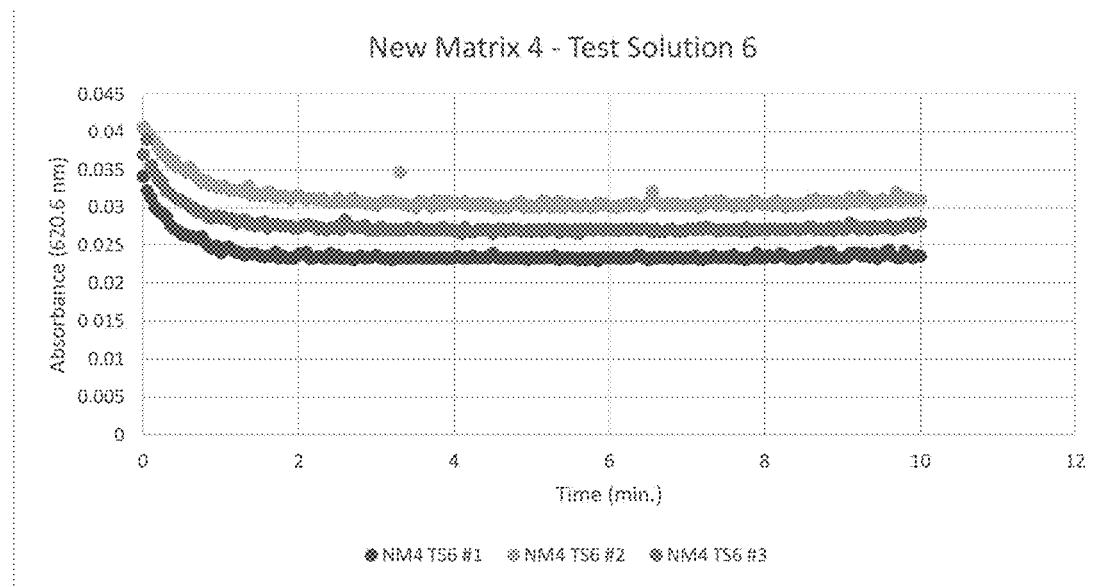
Figure 125:
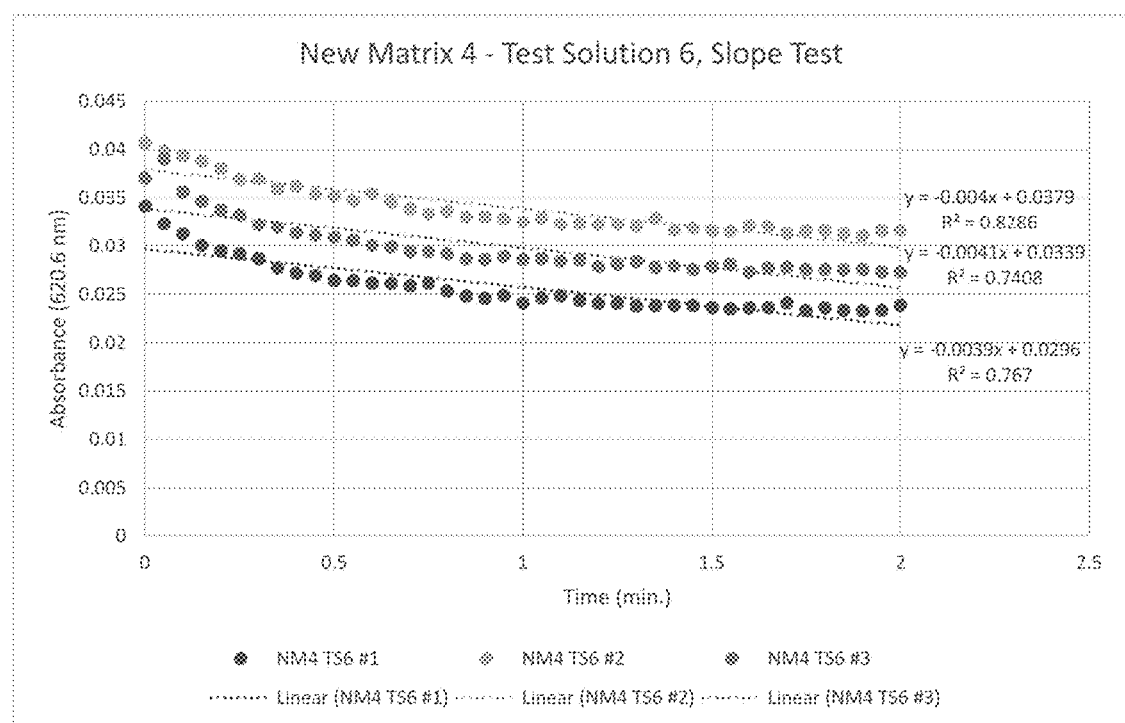
Figure 126:
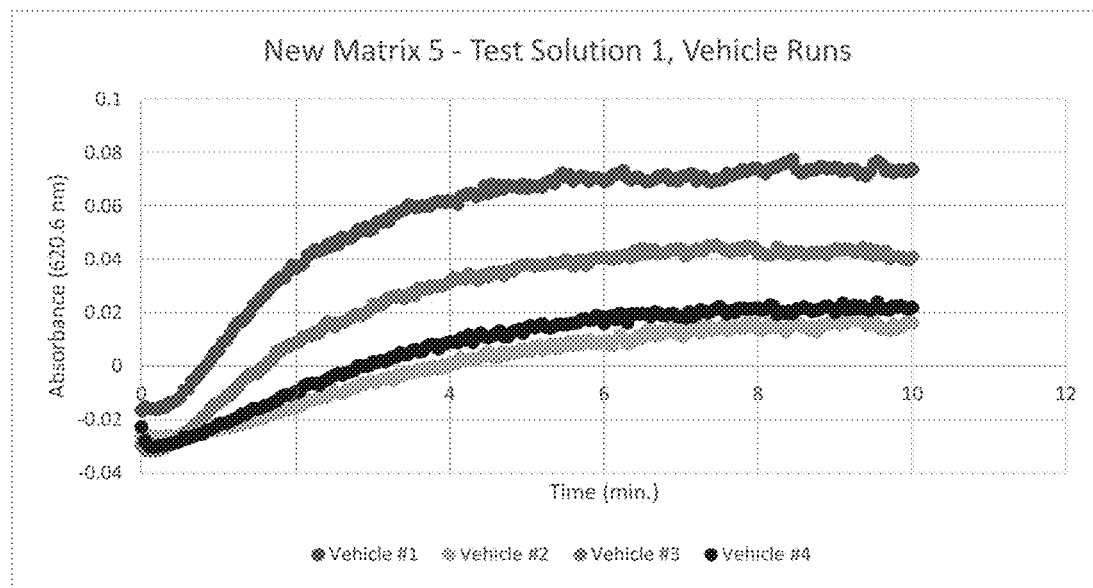
Figure 127:
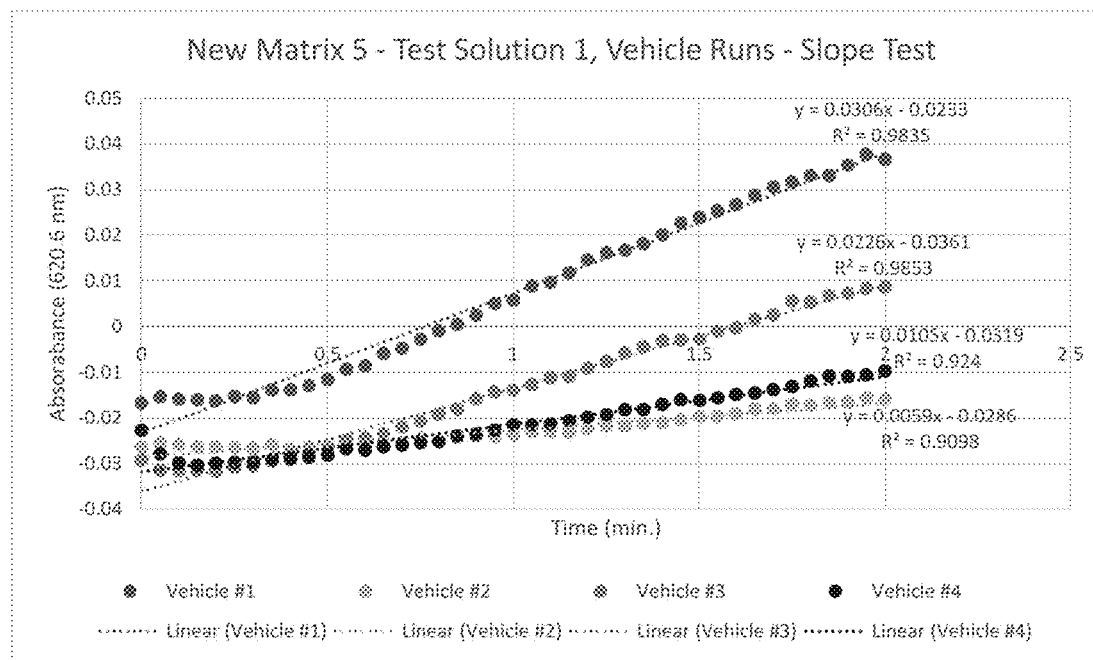
Figure 128:
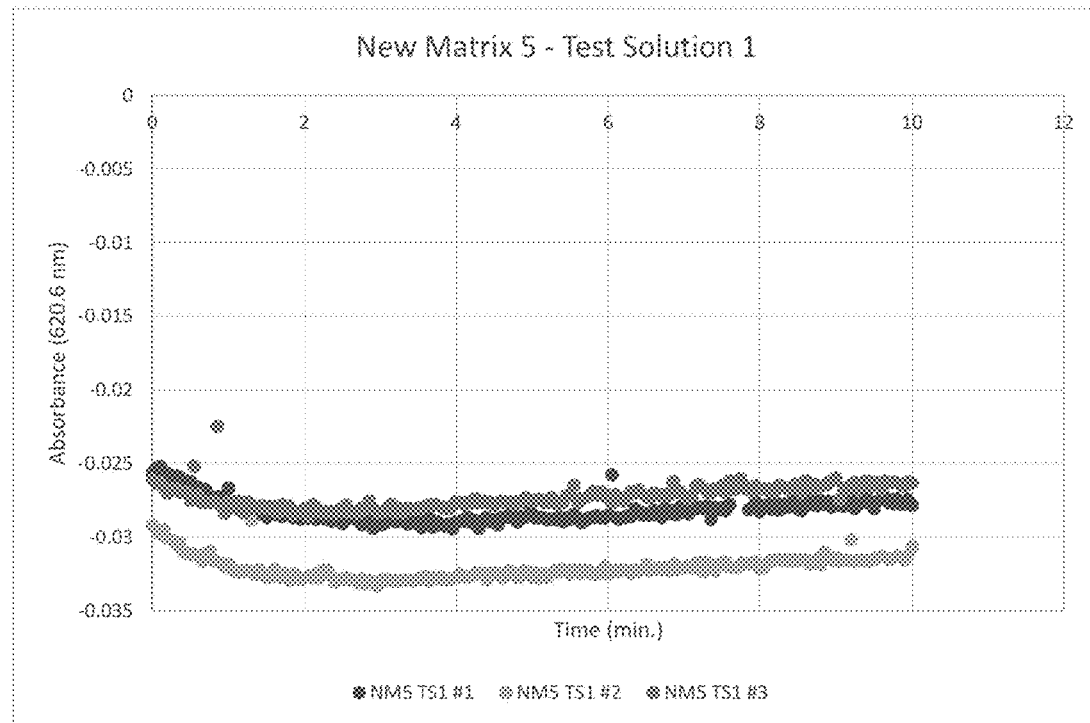
Figure 129:
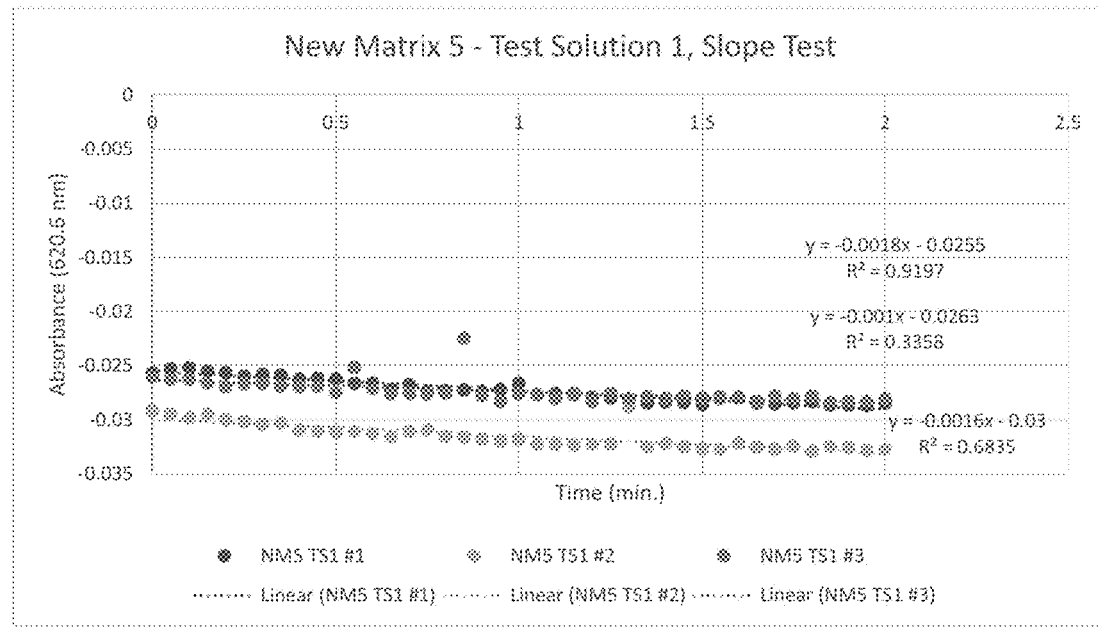
Figure 130:
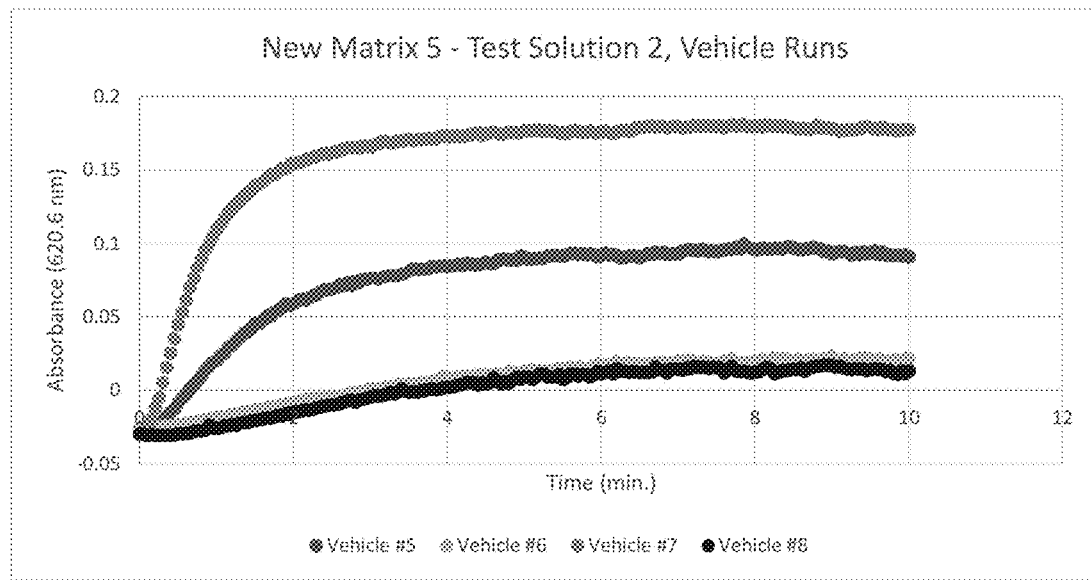

FIG. 21 shows the absorbance as function of time for the first 10 minutes and measures the formation of calcium oxalate over time for the Control Vehicle runs used for Test Solution 6. From the figure it can be seen that calcium oxalate crystals are indeed forming during the ten minutes of the run. FIG. 22 shows the slopes of the curves for the initial two minutes of the runs for the Control Vehicle used for Test Solution 6. Since the data was linear ($R^2 > 0.95$) for the first two (2) minutes, this data was plotted for slope determination by linear regression analysis. FIG. 23 shows the absorbance as function of time for the first 10 minutes and measures the formation of calcium oxalate over time for the Control Vehicle runs used for Test Solution 6. FIG. 24 shows the slopes of the curves for the initial two minutes of the runs for Test Solution 6. Since the data was linear ($R^2 > 0.95$) for the first two (2) minutes, this data was plotted for slope determination by linear regression analysis. Table 7 shows the analysis of the slopes FIGS. 22 and 24. Each run is designated as a Replicate.

TABLE 7

Data Analysis for Slope Test, Control Vehicle & Test Solution 6

| | Replicate #1 | Replicate #2 | Replicate #3 | Replicate #4 | Replicate #5 | Median | Median % Inhibition |
|---|---|---|---|---|---|---|---|
| Control Vehicle | 0.0068 | 0.0717 | 0.038 | 0.0594 | 0.0037 | 0.0224 | |
| Test Solution 6 | −0.0033 | −0.0035 | −0.0028 | −0.0045 | −0.0012 | −0.0031 | 113.6161 |

Table 8 shows the analysis of the slopes of solution 7, a duplicate of test solution 1, which was calculated similarly to Test Solution 1. Each run is designated as a Replicate. The data from these experiments are shown FIGS. 25-28.

TABLE 8

Data Analysis for Slope Test, Control Vehicle & Test Solution 7

| | Replicate #1 | Replicate #2 | Replicate #3 | Replicate #4 | Replicate #5 | Replicate #6 | Median | % Inhibition |
|---|---|---|---|---|---|---|---|---|
| Vehicle | 0.0084 | 0.0204 | 0.0282 | 0.0054 | 0.0193 | 0.0306 | 0.01985 | |
| Test Solution 1 | −0.0000005 | −0.0003 | −0.0002 | 0.0005 | −0.0003 | −0.0002 | −0.0002 | 101.0076 |

Table 9 shows the percent inhibition results (calculated as median and average) and the ingredient weights for Test Solutions 1 through Test Solution 7.

TABLE 9

Median and Mean Inhibition of Calcium Oxalate Crystal Growth by 5 ingredient Test Solutions

| | Test Solution 1 | Test Solution 2 | Test Solution 3 | Test Solution 4 | Test Solution 5 | Test Solution 6 | Test Solution 7 |
|---|---|---|---|---|---|---|---|
| Median % Inhibition | 98.88 | 101.58 | 70.59 | 99.57 | 99.32 | 113.62 | 101.00 |
| Average % Inhibition | 96.26 | 103.11 | 64.39 | 99.48 | 99.27 | 92.44 | 99.19 |
| Citric Acid | 352 mg | 101 mg | 1050 mg | 700 mg | 352 mg | 176 mg | 351 mg |
| Mg Citrate | 151 mg | 75 mg | 2.02 mg | 226 mg | 201 mg | 150 mg | 152 mg |
| Phytin | 202 mg | 201 mg | 100 mg | 3.03 mg | 600 mg | 400 mg | 200 mg |
| Pyridoxine | 5.4 mg | 10.2 mg | 5.99 mg | 2.67 mg | 0.2 mg | 15.1 mg | 5.3 mg |
| Musa | 251 mg | 251 mg | 167 mg | 85 mg | 41 mg | 1.4 mg | 251 mg |

The results in Table 9 show that compositions having about 101 mg to about 700 mg citric acid; about 76 mg to about 226 mg magnesium citrate; about 3 mg to about 600 mg phytin; about 0.1 mg to about 15 mg pyridoxine; and about 1 mg to about 251 mg musa. result in a mean percent inhibition of calcium oxalate crystal growth of at least about 92%, while compositions having citric acid, magnesium citrate, phytin, pyridoxine, and musa concentrations outside these ranges are unexpectedly much less effective, resulting in mean percent inhibition of calcium oxalate crystal growth of only about 64%.

Inhibition of the kinetics of calcium oxalate crystal formation was also determined, using the method described above, for the four combinations of four out of the five ingredients in Table 1 each including citric acid. Herein, each of these four-ingredient combinations is referred to as a "Matrix". "Matrix 1" refers to a combination of citric acid, magnesium citrate, phytin, and pyridoxine. "Matrix 2" refers to a combination of citric acid, magnesium citrate, phytin, and musa. "Matrix 3" refers to a combination of citric acid, magnesium citrate, pyridoxine, and musa. "Matrix 4" refers to a combination of citric acid, phytin, pyridoxine, and musa. Matrix 5 refers to a combination of magnesium citrate, phytin, pyridoxine, and musa. The amounts of the ingredients in the Test Solutions for each of the five Matrices are set forth below in Tables 11-15, respectively, along with median and mean percent inhibition values determined for each Test Solution.

FIGS. 30 to 53 are graphs showing absorbance as function of time and slope determinations for the Control Vehicle and Test Solution replicates for the six Matrix 1 Test Solutions.

FIGS. 54 to 77 are graphs showing absorbance as a function of time and slope determinations for the Control Vehicle and Test Solution replicates for the six Matrix 2 Test Solutions.

FIGS. 78 to 101 are graphs showing absorbance as a function of time and slope determinations for the Control Vehicle and Test Solution replicates for the six Matrix 3 Test Solutions.

FIGS. 102 to 125 are graphs showing absorbance as a function of time and slope determinations for the Control Vehicle and Test Solution replicates for the six Matrix 4 Test Solutions.

FIGS. 126 to 153 are graphs showing absorbance as a function of time and slope determinations for the Control Vehicle and Test Solutions replicates for the seven Matrix 5 Test Solutions.

Since the data was linear ($R^2 > 0.95$) for the first two (2) minutes of the runs, that data was plotted for slope determination by linear regression analysis. The slopes determined for the Control Vehicle and Test Solutions 1-6 runs for each of Matrix 1, 2, 3, 4 and 5 are tabulated in Table 10. Table 10 further shows the results of analysis of the slopes to provide the median percent inhibition by each Test Solution. Each run is designated as a Replicate.

TABLE 10

Data Analysis for Slope Test for Control Vehicles and Test Solutions for Matrix 1,
Matrix 2, Matrix 3, Matrix 4 and Matrix 5
Matrix 1 through 5 - Four Ingredient
Data Analysis for Slope Tests, Control Vehicles & Test Solutions

|  | Replicate 1 | Replicate 2 | Replicate 3 | Median | % Inhibition Median |
|---|---|---|---|---|---|
| Matrix 1 - Citric Acid, Mg Citrate, Phytin, Pyridoxine ||||||
| Matrix 1 | | | | | |
| Control Vehicle | 0.0081 | 0.0088 | 0.0145 | 0.0088 | |
| Test Solution 1 | 0.0004 | −0.0004 | −0.0006 | −0.0004 | 104.5% |
| Control Vehicle | 0.0098 | 0.0199 | 0.0767 | 0.0199 | |
| Test Solution 2 | −0.0013 | −0.001 | −0.0017 | −0.0013 | 106.5% |
| Control Vehicle | 0.0119 | 0.0093 | 0.0171 | 0.0119 | |
| Test Solution 3 | 0.0014 | 0.0014 | 0.0004 | 0.0014 | 88.2% |
| Control Vehicle | 0.0469 | 0.0899 | 0.1103 | 0.0899 | |
| Test Solution 4 | 0.0031 | 0.0009 | 0.001 | 0.001 | 98.9% |
| Control Vehicle | 0.0103 | 0.008 | 0.0482 | 0.0103 | |
| Test Solution 5 | 0.0006 | 0.0019 | 0.0001 | 0.0006 | 94.2% |
| Control Vehicle | 0.1182 | 0.1233 | 0.1278 | 0.1233 | |
| Test Solution 6 | −0.0027 | −0.0022 | −0.0027 | −0.0027 | 102.2% |
| Matrix 2 - Citric Acid, Mg Citrate, Phytin, Musa ||||||
| Matrix 2 | | | | | |
| Control Vehicle | 0.0056 | 0.0071 | 0.0105 | 0.0105 | |
| Test Solution 1 | −0.00009 | −0.0006 | 0.0014 | −0.00009 | 100.9% |
| Control Vehicle | 0.0078 | 0.0037 | 0.0058 | 0.0068 | |
| Test Solution 2 | −0.0026 | −0.0011 | −0.0013 | −0.0013 | 119.1% |
| Control Vehicle | 0.007 | 0.0141 | 0.0098 | 0.01195 | |
| Test Solution 3 | 0.005 | 0.00006 | 0.0004 | 0.0004 | 96.7% |
| Control Vehicle | 0.0157 | 0.0059 | 0.0117 | 0.0157 | |
| Test Solution 4 | 0.0013 | 0.0011 | 0.0013 | 0.0013 | 91.7% |
| Control Vehicle | 0.01 | 0.0359 | 0.0332 | 0.0332 | |
| Test Solution 5 | 0.0004 | −0.0005 | −0.0003 | −0.0003 | 100.9% |
| Control Vehicle | 0.0162 | 0.0349 | 0.013 | 0.0162 | |
| Test Solution 6 | −0.0019 | −0.0029 | −0.002 | −0.002 | 112.3% |
| Matrix 3 - Citric Acid, Mg Citrate, Pyridoxine, Musa ||||||
| Matrix 3 | | | | | |
| Control Vehicle | 0.0072 | 0.0051 | 0.006 | 0.006 | |
| Test Solution 1 | 0.0005 | 0.0013 | 0.0012 | 0.00085 | 87.1% |
| Control Vehicle | 0.0064 | 0.0065 | 0.0131 | 0.0065 | |
| Test Solution 2 | 0.0036 | 0.0007 | 0.0008 | 0.0022 | 66.2% |
| Control Vehicle | 0.0109 | 0.008 | 0.0078 | 0.008 | |
| Test Solution 3 | 0.0013 | 0.0041 | 0.0026 | 0.0026 | 67.5% |
| Control Vehicle | 0.0093 | 0.0153 | 0.0184 | 0.0153 | |
| Test Solution 4 | 0.0076 | 0.0058 | 0.0026 | 0.0058 | 62.1% |
| Control Vehicle | 0.0168 | 0.0081 | 0.0135 | 0.0135 | |
| Test Solution 5 | 0.0023 | 0.0037 | 0.0045 | 0.0037 | 72.6% |
| Control Vehicle | 0.0224 | 0.0305 | 0.0186 | 0.0224 | |
| Test Solution 6 | 0.0057 | 0.0094 | 0.0225 | 0.0094 | 58.0% |
| Matrix 4 - Citric Acid, Phytin, Pyridoxine, Musa ||||||
| Matrix 4 | | | | | |
| Control Vehicle | 0.0073 | 0.017 | 0.0179 | 0.017 | |
| Test Solution 1 | −0.0018 | −0.001 | −0.0025 | −0.0015 | 108.8% |
| Control Vehicle | 0.0246 | 0.0325 | 0.0124 | 0.0246 | |
| Test Solution 2 | −0.003 | −0.0023 | −0.0024 | −0.0024 | 109.8% |
| Control Vehicle | 0.0072 | 0.0052 | 0.0173 | 0.0072 | |
| Test Solution 3 | −0.0021 | −0.00001 | 0.0002 | −0.00001 | 100.1% |
| Control Vehicle | 0.0206 | 0.0228 | 0.0141 | 0.0206 | |
| Test Solution 4 | 0.0013 | 0.0025 | 0.0037 | 0.0025 | 87.9% |
| Control Vehicle | 0.0052 | 0.0083 | 0.0067 | 0.0067 | |
| Test Solution 5 | −0.0024 | −0.002 | −0.0025 | −0.0024 | 135.8% |
| Control Vehicle | 0.0089 | 0.0099 | 0.0071 | 0.0094 | |
| Test Solution 6 | −0.0039 | −0.004 | −0.0041 | −0.004 | 142.6% |
| Matrix 5 - Mg Citrate, Phytin, Pyridoxine and Musa ||||||
| Matrix 5 | | | | | |
| Control Vehicle | 0.0306 | 0.0226 | 0.0105 | 0.01655 | |
| Test Solution 1 | −0.0018 | −0.0016 | −0.001 | −0.0016 | 109.7% |
| Control Vehicle | 0.0486 | 0.009 | 0.0082 | 0.0288 | |
| Test Solution 2 | −0.0019 | −0.0023 | −0.0016 | −0.0019 | 106.6% |
| Control Vehicle | 0.0062 | 0.0115 | 0.0111 | 0.0111 | |

TABLE 10-continued

Data Analysis for Slope Test for Control Vehicles and Test Solutions for Matrix 1,
Matrix 2, Matrix 3, Matrix 4 and Matrix 5
Matrix 1 through 5 - Four Ingredient
Data Analysis for Slope Tests, Control Vehicles & Test Solutions

|  | Replicate 1 | Replicate 2 | Replicate 3 | Median | % Inhibition Median |
|---|---|---|---|---|---|
| Test Solution 3 | −0.001 | −0.0012 | −0.001 | −0.001 | 109.0% |
| Control Vehicle | 0.0091 | 0.0518 | 0.0139 | 0.0139 |  |
| Test Solution 4 | −0.0004 | 0.0018 | 0.0002 | 0.0002 | 98.6% |
| Control Vehicle | 0.0244 | 0.0089 | 0.0082 | 0.0089 |  |
| Test Solution 5 | −0.0028 | −0.0054 | −0.0062 | −0.0054 | 160.7% |
| Control Vehicle | 0.0185 | 0.0348 | 0.012 | 0.0185 |  |
| Test Solution 6 | −0.0068 | −0.0056 | −0.0078 | −0.0068 | 136.8% |
| Control Vehicle | 0.0217 | 0.0133 | 0.0214 | 0.0214 |  |
| Test Solution 7 | −0.0009 | −0.0025 | 0.0003 | −0.0009 | 104.2% |

Table 11 shows the percent inhibition results (calculated as median and average) and the ingredient weights for Matrix 1 (citric acid, magnesium citrate, phytin, and pyridoxine) Test Solutions 1 through Test Solution 6.

TABLE 11

Matrix 1 Test Solution Ingredient Amounts and Median and Mean Percent
Inhibition of Calcium Oxalate Crystal Growth

| Matrix 1 Ingredient | Test Solution 1 mg | Test Solution 2 mg | Test Solution 3 mg | Test Solution 4 mg | Test Solution 5 mg | Test Solution 6 mg |
|---|---|---|---|---|---|---|
| Citric Acid | 354 | 101 | 1051 | 699 | 352 | 178 |
| Mg Citrate | 151 | 77 | 2.31 | 227 | 202 | 151 |
| Phytin | 201 | 201 | 100 | 3.06 | 600 | 400 |
| Pyridoxine | 5.45 | 10.67 | 5.95 | 2.68 | 0.23 | 15.13 |
| Median % inhibition | 104.55 | 106.53 | 88.24 | 98.89 | 94.17 | 102.19 |
| Average % inhibition | 101.25 | 106.84 | 90.28 | 97.16 | 90.07 | 102.06 |

The results in Table 11 show that compositions where citric acid is present in an amount of about 101 mg to about 699 mg, magnesium citrate is present in an amount of about 77 mg to about 227 mg, phytin is present in an amount of about 3.06 mg to about 600 mg, and pyridoxine is present in an amount of about 0.23 mg to about 15.13 mg result in a median percent inhibition of calcium oxalate crystal growth of at least about 94%, while compositions having citric acid, magnesium citrate, phytin, and pyridoxine concentrations outside these ranges are unexpectedly much less effective, resulting in median percent inhibition of calcium oxalate crystal growth of only about 88%.

Table 12 shows the percent inhibition results (calculated as median and average) and the ingredient weights for Matrix 2 (citric acid, magnesium citrate, phytin, and musa) Test Solutions 1 through Test Solution 6.

The results in Table 12 show that compositions where citric acid is present in an amount of about 102 mg to about 1052 mg, magnesium citrate is present in an amount of about 2.32 mg to about 201 mg, phytin is present in an amount of about 100 mg to about 600 mg, and musa is present in an amount of about 1.51 mg to about 251 mg result in a median percent inhibition of calcium oxalate crystal growth of at least about 96%, while compositions citric acid, magnesium citrate, phytin, and musa concentrations outside these ranges are unexpectedly much less effective, resulting in median percent inhibition of calcium oxalate crystal growth of only about 92%.

Table 13 shows the percent inhibition results (calculated as median and average) and the ingredient weights for Matrix 3 (citric acid, magnesium citrate, pyridoxine, and musa) Test Solutions 1 through Test Solution 6.

TABLE 12

Matrix 2 Test Solution Ingredient Amounts and Median and Mean Percent
Inhibition of Calcium Oxalate Crystal Growth

| Matrix 2 Ingredient | Test Solution 1 mg | Test Solution 2 mg | Test Solution 3 mg | Test Solution 4 mg | Test Solution 5 mg | Test Solution 6 mg |
|---|---|---|---|---|---|---|
| Citric Acid | 352 | 102 | 1052 | 700 | 351 | 177 |
| Mg Citrate | 151 | 77 | 2.32 | 226 | 201 | 150 |
| Phytin | 202 | 201 | 100 | 3.28 | 600 | 401 |
| Musa | 251 | 251 | 167 | 86 | 41 | 1.51 |
| Median % inhibition | 100.86 | 119.12 | 96.65 | 91.72 | 100.90 | 112.35 |
| Average % inhibition | 98.91 | 128.49 | 74.69 | 87.32 | 99.43 | 111.81 |

TABLE 13

Matrix 3 Test Solution Ingredient Amounts and Median and Mean Percent Inhibition of Calcium Oxalate Crystal Growth

| Matrix 3 Ingredient | Test Solution 1 mg | Test Solution 2 mg | Test Solution 3 mg | Test Solution 4 mg | Test Solution 5 mg | Test Solution 6 mg |
|---|---|---|---|---|---|---|
| Citric Acid | 352 | 101 | 1051 | 700 | 353 | 176 |
| Mg Citrate | 153 | 77 | 2.14 | 226 | 202 | 151 |
| Pyridoxine | 5.41 | 10.23 | 5.95 | 2.63 | 0.25 | 15.14 |
| Musa | 251 | 252 | 167 | 85 | 41.02 | 1.41 |
| Median % inhibition | 87.12 | 66.15 | 67.50 | 62.09 | 72.59 | 58.04 |
| Average % inhibition | 82.52 | 75.62 | 67.83 | 55.41 | 69.10 | 40.92 |

The results in Table 13 show that compositions where citric acid is present in an amount of about 101 mg to about 1051 mg, magnesium citrate is present in an amount of about 2.14 mg to about 226 mg, pyridoxine is present in an amount of about 0.25 mg to about 10.23 mg, and musa is present in an amount of about 41.02 mg to about 252 mg result in a median percent inhibition of calcium oxalate crystal growth of at least about 62%, while compositions citric acid, magnesium citrate, pyridoxine, and musa concentrations outside these ranges are unexpectedly much less effective, resulting in median percent inhibition of calcium oxalate crystal growth of only about 58%.

Table 14 shows the percent inhibition results (calculated as median and average) and the ingredient weights for Matrix 4 (citric acid, phytin, pyridoxine, and musa) Test Solutions 1 through Test Solution 6.

TABLE 14

Matrix 4 Test Solution Ingredient Amounts and Median and Mean Percent Inhibition of Calcium Oxalate Crystal Growth

| Matrix 4 Ingredient | Test Solution 1 mg | Test Solution 2 mg | Test Solution 3 mg | Test Solution 4 mg | Test Solution 5 mg | Test Solution 6 mg |
|---|---|---|---|---|---|---|
| Citric Acid | 353 | 101 | 1050 | 700 | 352 | 177 |
| Phytin | 203 | 202 | 101 | 3.01 | 600 | 400 |
| Pyridoxine | 5.45 | 10.20 | 6 | 2.69 | 0.23 | 15.12 |
| Musa | 252 | 252 | 167 | 86 | 41 | 1.46 |
| Median % inhibition | 108.82 | 109.76 | 100.14 | 87.86 | 135.82 | 142.55 |
| Average % inhibition | 114.84 | 112.88 | 109.40 | 85.49 | 135.85 | 147.32 |

The results in Table 14 show that compositions wherein citric acid is present in an amount of about 101 mg to less than about 700 mg, phytin is present in an amount of about 101 mg to about 600 mg, pyridoxine is present in an amount of about 0.23 mg to about 15.12 mg, and musa is present in an amount of about 1.46 mg to about 252 mg result in a median percent inhibition of calcium oxalate crystal growth of at least about 100%, while compositions citric acid, phytin, pyridoxine, and musa concentrations outside these ranges are unexpectedly much less effective, resulting in median percent inhibition of calcium oxalate crystal growth of only about 88%.

Table 15 shows the percent inhibition results (calculated as median and average) and the ingredient weights for Matrix 5 (magnesium citrate, phytin, pyridoxine and musa) Test Solutions 1 through Test Solution 6.

TABLE 15

Matrix 5 Test Solution Ingredient Amounts and Median and Mean Percent Inhibition of Calcium Oxalate Crystal Growth

| Matrix 5 Ingredient | Test Solution 1 mg | Test Solution 2 mg | Test Solution 3 mg | Test Solution 4 mg | Test Solution 5 mg | Test Solution 6 mg | Test Solution 7 mg |
|---|---|---|---|---|---|---|---|
| Magnesium Citrate | 151 | 77 | 2.03 | 226 | 201 | 151 | 203 |
| Phytin | 202 | 201 | 100 | 3.02 | 475 | 400 | 600 |
| Pyridoxine | 5.4 | 10.11 | 6.01 | 2.69 | 0.25 | 15.1 | 0.22 |
| Musa | 252 | 252 | 168 | 85 | 42 | 1.46 | 41 |
| Median % Inhibition | 109.67 | 106.60 | 109.01 | 98.56 | 160.67 | 136.76 | 104.21 |
| Average % Inhibition | 107.50 | 116.33 | 111.86 | 99.83 | 149.25 | 139.28 | 107.18 |

The results in Table 15 show that compositions wherein magnesium citrate is present in an amount of about 2.03 mg to 203 mg, phytin is present in an amount of about 100 mg to about 600 mg, pyridoxine is present in an amount of about 0.22 mg to about 15.1 mg, and musa is present in an amount of about 1.46 mg to about 252 mg result in a median percent inhibition of calcium oxalate crystal growth of at least about 104%, while compositions magnesium citrate, phytin, pyridoxine, and musa concentrations outside these ranges are unexpectedly much less effective, resulting in median percent inhibition of calcium oxalate crystal growth of only about 98%.

Example 2

Oral Dosage Forms

TABLE 16

Five Ingredient Oral Capsule

| Ingredient | Amount |
|---|---|
| Citric Acid | about 101 mg to about 700 mg |
| Mg Citrate | about 76 mg to about 226 mg |
| Phytin | about 3 mg to about 600 mg |
| Pyridoxine | about 0.1 mg to about 15 mg |
| Musa | about 1 mg to about 251 mg |

The five active ingredients are blended in the above amounts and deposited into a hard shell capsule, e.g., a hydroxypropyl methylcellulose (HPMC) capsule, such as a DRcap™ (Capsugel®, Morristown, N.J.).

Tables 17-21 below provide additional oral capsule formulations. In each formulation, the four active ingredients are blended in the indicated amounts and deposited into a hard shell capsule, e.g., a hydroxypropyl methylcellulose (HPMC) capsule, such as a DRcap™ (Capsugel®, Morristown, N.J.).

TABLE 17

Matrix 1 Oral Capsule

| Ingredient | Amount |
|---|---|
| Citric Acid | about 101 mg to about 699 mg |
| Mg Citrate | about 77 mg to about 227 mg |
| Phytin | about 3.06 mg to about 600 mg |
| Pyridoxine | about 0.23 mg to about 15.13 mg |

TABLE 18

Matrix 2 Oral Capsule

| Ingredient | Amount |
|---|---|
| Citric Acid | about 102 mg to about 1052 mg |
| Mg Citrate | about 2.32 mg to about 201 mg |
| Phytin | about 100 mg to about 600 mg |
| Musa | about 1.51 mg to about 251 mg |

TABLE 19

Matrix 3 Oral Capsule

| Ingredient | Amount |
|---|---|
| Citric Acid | about 101 mg to about 1051 mg |
| Mg Citrate | about 2.14 mg to about 226 mg |
| Pyridoxine | about 0.25 mg to about 10.23 mg |
| Musa | about 41.02 mg to about 252 mg |

TABLE 20

Matrix 4 Oral Capsule

| Ingredient | Amount |
|---|---|
| Citric Acid | about 101 mg to less than about 700 |
| Phytin | about 101 mg to about 600 mg |
| Pyridoxine | about 0.23 mg to about 15.12 mg |
| Musa | about 1.46 mg to about 252 mg |

TABLE 21

Matrix 5 Oral Capsule

| Ingredient | Amount |
|---|---|
| Magnesium Citrate | about 2.03 mg to 203 mg |
| Phytin | about 100 mg to about 600 mg |
| Pyridoxine | about 0.22 mg to about 15.1 mg |
| Musa | about 1.46 mg to about 252 mg |

Set forth below are some embodiments of the oral dosage forms and methods for disclosed herein.

Embodiment 1

An oral dosage form or a plurality of dosage forms comprising as active ingredients citric acid, magnesium citrate, phytin, pyridoxine, and musa.

Embodiment 2

The oral dosage form or plurality of dosage forms of embodiment 1, wherein citric acid is present in an amount of about 101 mg to about 700 mg.

Embodiment 3

The oral dosage form or plurality of dosage forms according to embodiment 2 wherein citric acid is present in an amount selected from: about 101 mg to about 352 mg, about 101 mg to about 176 mg, about 176 mg to about 700 mg, and about 352 mg to about 700 mg.

Embodiment 4

The oral dosage form or plurality of dosage forms of embodiment 1, wherein magnesium citrate is present in an amount of about 76 mg to about 226 mg.

Embodiment 5

The oral dosage form or plurality of dosage forms according to embodiment 4 wherein magnesium citrate is present in an amount selected from: about 76 mg to about 201 mg, about 76 mg to about 150 mg, about 150 to about 226 mg, and about 201 mg to about 225 mg.

Embodiment 6

The oral dosage form or plurality of dosage forms of embodiment 1, wherein phytin is present in an amount of about 3 mg to about 600 mg.

Embodiment 7

The oral dosage form or plurality of dosage forms according to embodiment 6 wherein phytin is present in an amount selected from: about 3 mg to about 400 mg, about 3 mg to about 202 mg, about 3 mg to about 100 mg, about 100 mg to about 600 mg, about 200 mg to about 600 mg, and about 400 mg to about 600 mg.

Embodiment 8

The oral dosage form or plurality of dosage forms of embodiment 1, wherein pyridoxine is present in an amount of about 0.2 mg to about 15 mg.

Embodiment 9

The oral dosage form or plurality of dosage forms according to embodiment 8 wherein pyridoxine is present in an amount selected from: about 0.2 mg to about 10 mg, about 0.2 mg to about 6 mg, about 0.2 mg to about 2.7 mg, about 2.7 mg to about 15 mg, about 6.0 mg to about 15 mg, and about 10 mg to about 15 mg.

Embodiment 10

The oral dosage form or plurality of dosage forms of embodiment 1, wherein musa is present in amount of about 1 mg to about 251 mg.

Embodiment 11

The oral dosage form or plurality of dosage forms according to embodiment 10 wherein musa is present in an amount selected from: about 1 mg to about 167 mg, about 1 mg to about 85 mg, about 1 mg to about 41 mg, about 41 mg to about 251 mg, about 85 mg to about 251 mg, and about 167 mg to about 251 mg.

Embodiment 12

The oral dosage form or plurality of dosage forms of embodiment 1 wherein citric acid is present in an amount of about 101 mg to about 700 mg; magnesium citrate is present in an amount of about 76 mg to about 226 mg; phytin is present in an amount of about 3 mg to about 600 mg; pyridoxine is present in an amount of about 0.1 mg to about 15 mg; and musa is present in amount of about 1 mg to about 251 mg.

Embodiment 13

The oral dosage form or plurality of dosage forms according to embodiment 12 wherein citric acid is present in an amount selected from: about 51 mg to about 352 mg, about 101 mg to about 176 mg, about 176 mg to about 700 mg, and about 352 mg to about 700 mg; magnesium citrate is present in an amount selected from: about 76 mg to about 201 mg, about 76 mg to about 150 mg, about 150 to about 226 mg, and about 201 mg to about 225 mg; phytin is present in an amount selected from: about 3 mg to about 400 mg, about 3 mg to about 202 mg, about 3 mg to about 100 mg, about 100 mg to about 600 mg, about 200 mg to about 600 mg, and about 400 mg to about 600 mg; pyridoxine is present in an amount selected from: about 0.2 mg to about 10 mg, about 0.2 mg to about 6 mg, about 0.2 mg to about 2.7 mg, about 2.7 mg to about 15 mg, about 6.0 mg to about 15 mg, and about 10 mg to about 15 mg; and musa is present in an amount selected from: about 1 mg to about 167 mg, about 1 mg to about 85 mg, about 1 mg to about 41 mg, about 41 mg to about 251 mg, about 85 mg to about 251 mg, and about 167 mg to about 251 mg.

Embodiment 14

The oral dosage form or plurality of dosage forms of embodiment 1, wherein the amount of one of the active ingredients is selected from: citric acid is present in an amount of about 101 mg to about 700 mg; magnesium citrate is present in an amount of about 76 mg to about 226 mg; phytin is present in an amount of about 3 mg to about 600 mg; pyridoxine is present in an amount of about 0.1 mg to about 15 mg; and musa is present in amount of about 1 mg to about 251 mg.

Embodiment 15

The oral dosage form or plurality of dosage forms of embodiment 1, wherein the amounts of two of the active ingredients are selected from: citric acid is present in an amount of about 101 mg to about 700 mg; magnesium citrate is present in an amount of about 76 mg to about 226 mg; phytin is present in an amount of about 3 mg to about 600 mg; pyridoxine is present in an amount of about 0.1 mg to about 15 mg; and musa is present in amount of about 1 mg to about 251 mg.

Embodiment 16

The oral dosage form or plurality of dosage forms of embodiment 1, wherein the amounts of 3 of the ingredients are selected from: citric acid is present in an amount of about 101 mg to about 700 mg; magnesium citrate is present in an amount of about 76 mg to about 226 mg; phytin is present in an amount of about 3 mg to about 600 mg; pyridoxine is present in an amount of about 0.1 mg to about 15 mg; and musa is present in amount of about 1 mg to about 251 mg.

Embodiment 17

The oral dosage form or plurality of dosage forms of embodiment 1, wherein the amounts of 4 of the ingredients are selected from: citric acid is present in an amount of about 101 mg to about 700 mg; magnesium citrate is present in an amount of about 76 mg to about 226 mg; phytin is present in an amount of about 3 mg to about 600 mg; pyridoxine is present in an amount of about 0.1 mg to about 15 mg; and musa is present in amount of about 1 mg to about 251 mg.

Embodiment 18

The oral dosage form or plurality of dosage forms of embodiment 1, wherein citric acid is present in an amount of about 350 mg; magnesium citrate is present in an amount of about 150 mg; phytin is present in an amount of about 200 mg; pyridoxine is present in an amount of about 5 mg; and musa is present in amount of about 250 mg.

Embodiment 19

The oral dosage form or a plurality of dosage forms according to any one of embodiments 1 to 18, wherein the percent inhibition of calcium oxalate crystal formation by the combination of active ingredients is greater than about 92%.

Embodiment 20

The oral dosage form or plurality of dosage forms according to embodiment 19, where the percent inhibition is greater than about 96%.

Embodiment 21

The oral dosage form or plurality of dosage forms according to embodiment 20 where the percent inhibition is greater than about 99%.

Embodiment 22

An oral dosage form or a plurality of dosage forms comprising as active ingredients citric acid, magnesium citrate, phytin, and pyridoxine.

Embodiment 23

The oral dosage form or plurality of dosage forms of embodiment 22, wherein citric acid is present in an amount of about 101 mg to about 699 mg.

Embodiment 24

The oral dosage form or plurality of dosage forms according to embodiment 23, wherein citric acid is present in an amount selected from: about 101 mg to about 354 mg, about 101 mg to about 178 mg, about 178 mg to about 699 mg, about 178 mg to about 354 mg, and about 352 mg to about 699 mg.

Embodiment 25

The oral dosage form or plurality of dosage forms of embodiment 22, wherein magnesium citrate is present in an amount of about 77 mg to about 227 mg.

Embodiment 26

The oral dosage form or plurality of dosage forms according to embodiment 25 wherein magnesium citrate is present in an amount selected from: about 77 mg to about 202 mg, about 77 mg to about 151 mg, about 151 to about 227 mg, about 151 to about 202 mg, and about 202 mg to about 227 mg.

Embodiment 27

The oral dosage form or plurality of dosage forms of embodiment 22, wherein phytin is present in an amount of about 3.06 mg to about 600 mg.

Embodiment 28

The oral dosage form or plurality of dosage forms according to embodiment 27 wherein phytin is present in an amount selected from: about 3.06 mg to about 400 mg, about 3.06 mg to about 201 mg, about 3.06 mg to about 100 mg, about 100 mg to about 600 mg, about 100 mg to about 400 mg, about 100 mg to about 201 mg, about 201 mg to about 600 mg, about 201 mg to about 400 mg, and about 400 mg to about 600 mg.

Embodiment 29

The oral dosage form or plurality of dosage forms of embodiment 22, wherein pyridoxine is present in an amount of about 0.23 mg to about 15.13 mg.

Embodiment 30

The oral dosage form or plurality of dosage forms according to embodiment 29 wherein pyridoxine is present in an amount selected from: about 0.23 mg to about 10.67 mg, about 0.23 mg to about 5.95 mg, about 0.23 mg to about 2.68 mg, about 2.68 mg to about 15.13 mg, about 2.68 mg to about 10.67 mg, about 2.68 mg to about 5.95 mg, about 5.45 mg to about 15.13 mg, about 5.45 mg to about 10.67 mg, and about 10.67 mg to about 15.13 mg.

Embodiment 31

The oral dosage form or plurality of dosage forms of embodiment 22, wherein citric acid is present in an amount of about 101 mg to about 699 mg, magnesium citrate is present in an amount of about 77 mg to about 227 mg, phytin is present in an amount of about 3.06 mg to about 600 mg, and pyridoxine is present in an amount of about 0.23 mg to about 15.13 mg.

Embodiment 32

The oral dosage form or plurality of dosage forms according to embodiment 31 wherein citric acid is present in an amount selected from: about 101 mg to about 354 mg, about 101 mg to about 178 mg, about 178 mg to about 699 mg, about 178 mg to about 354 mg, and about 352 mg to about 699 mg; magnesium citrate is present in an amount selected from: about 77 mg to about 202 mg, about 77 mg to about 151 mg, about 151 to about 227 mg, about 151 to about 202 mg, and about 202 mg to about 227 mg; phytin is present in an amount selected from: about 3.06 mg to about 400 mg, about 3.06 mg to about 201 mg, about 3.06 mg to about 100 mg, about 100 mg to about 600 mg, about 100 mg to about 400 mg, about 100 mg to about 201 mg, about 201 mg to about 600 mg, about 201 mg to about 400 mg, and about 400 mg to about 600 mg; and pyridoxine is present in an amount selected from: about 0.23 mg to about 10.67 mg, about 0.23 mg to about 5.95 mg, about 0.23 mg to about 2.68 mg, about 2.68 mg to about 15.13 mg, about 2.68 mg to about 10.67 mg, about 2.68 mg to about 5.95 mg, about 5.45 mg to about 15.13 mg, about 5.45 mg to about 10.67 mg, and about 10.67 mg to about 15.13 mg.

Embodiment 33

The oral dosage form or plurality of dosage forms of embodiment 22, wherein the amount of one of the active ingredients is selected from: citric acid is present in an amount selected from: about 101 mg to about 354 mg, about 101 mg to about 178 mg, about 178 mg to about 699 mg, about 178 mg to about 354 mg, and about 352 mg to about 699 mg; magnesium citrate is present in an amount selected from: about 77 mg to about 202 mg, about 77 mg to about 151 mg, about 151 to about 227 mg, about 151 to about 202 mg, and about 202 mg to about 227 mg; phytin is present in an amount selected from: about 3.06 mg to about 400 mg, about 3.06 mg to about 201 mg, about 3.06 mg to about 100 mg, about 100 mg to about 600 mg, about 100 mg to about 400 mg, about 100 mg to about 201 mg, about 201 mg to about 600 mg, about 201 mg to about 400 mg, and about 400 mg to about 600 mg; and pyridoxine is present in an amount selected from: about 0.23 mg to about 10.67 mg, about 0.23 mg to about 5.95 mg, about 0.23 mg to about 2.68 mg, about 2.68 mg to about 15.13 mg, about 2.68 mg to about 10.67 mg, about 2.68 mg to about 5.95 mg, about 5.45 mg to about 15.13 mg, about 5.45 mg to about 10.67 mg, and about 10.67 mg to about 15.13 mg.

Embodiment 34

The oral dosage form or plurality of dosage forms of embodiment 22, wherein the amounts of two of the active ingredients are selected from: citric acid is present in an amount selected from: about 101 mg to about 354 mg, about 101 mg to about 178 mg, about 178 mg to about 699 mg, about 178 mg to about 354 mg, and about 352 mg to about 699 mg; magnesium citrate is present in an amount selected from: about 77 mg to about 202 mg, about 77 mg to about 151 mg, about 151 to about 227 mg, about 151 to about 202 mg, and about 202 mg to about 227 mg; phytin is present in an amount selected from: about 3.06 mg to about 400 mg, about 3.06 mg to about 201 mg, about 3.06 mg to about 100 mg, about 100 mg to about 600 mg, about 100 mg to about 400 mg, about 100 mg to about 201 mg, about 201 mg to about 600 mg, about 201 mg to about 400 mg, and about 400 mg to about 600 mg; and pyridoxine is present in an amount selected from: about 0.23 mg to about 10.67 mg, about 0.23 mg to about 5.95 mg, about 0.23 mg to about 2.68 mg, about 2.68 mg to about 15.13 mg, about 2.68 mg to about 10.67 mg, about 2.68 mg to about 5.95 mg, about 5.45 mg to about 15.13 mg, about 5.45 mg to about 10.67 mg, and about 10.67 mg to about 15.13 mg.

Embodiment 35

The oral dosage form or plurality of dosage forms of embodiment 22, wherein the amounts of 3 of the ingredients are selected from: citric acid is present in an amount selected from: about 101 mg to about 354 mg, about 101 mg to about 178 mg, about 178 mg to about 699 mg, about 178 mg to about 354 mg, and about 352 mg to about 699 mg; magnesium citrate is present in an amount selected from: about 77 mg to about 202 mg, about 77 mg to about 151 mg, about 151 to about 227 mg, about 151 to about 202 mg, and about 202 mg to about 227 mg; phytin is present in an amount selected from: about 3.06 mg to about 400 mg, about 3.06 mg to about 201 mg, about 3.06 mg to about 100 mg, about 100 mg to about 600 mg, about 100 mg to about 400 mg, about 100 mg to about 201 mg, about 201 mg to about 600 mg, about 201 mg to about 400 mg, and about 400 mg to about 600 mg; and pyridoxine is present in an amount selected from: about 0.23 mg to about 10.67 mg, about 0.23 mg to about 5.95 mg, about 0.23 mg to about 2.68 mg, about 2.68 mg to about 15.13 mg, about 2.68 mg to about 10.67 mg, about 2.68 mg to about 5.95 mg, about 5.45 mg to about 15.13 mg, about 5.45 mg to about 10.67 mg, and about 10.67 mg to about 15.13 mg.

Embodiment 36

The oral dosage form or plurality of dosage forms of embodiment 22, wherein citric acid is present in an amount of about 350 mg; magnesium citrate is present in an amount of about 150 mg; phytin is present in an amount of about 200 mg; and pyridoxine is present in an amount of about 5 mg.

Embodiment 37

The oral dosage form or a plurality of dosage forms according to any one of embodiments 22 to 36, wherein the percent inhibition of calcium oxalate crystal formation by the combination of active ingredients is greater than about 89%.

Embodiment 38

The oral dosage form or plurality of dosage forms according to embodiment 37, where the percent inhibition is greater than about 94%.

Embodiment 39

The oral dosage form or plurality of dosage forms according to embodiment 38 where the percent inhibition is greater than about 98%.

Embodiment 40

An oral dosage form or a plurality of dosage forms comprising as active ingredients citric acid, magnesium citrate, phytin, and musa.

Embodiment 41

The oral dosage form or plurality of dosage forms of embodiment 40, wherein citric acid is present in an amount of about 102 mg to about 1052 mg.

Embodiment 42

The oral dosage form or plurality of dosage forms according to embodiment 41 wherein citric acid is present in an amount selected from: about 102 mg to about 700 mg, about 102 mg to about 352 mg, about 102 mg to about 177 mg, about 177 mg to about 1052 mg, about 177 mg to about 700 mg, about 177 mg to about 352 mg, about 351 mg to about 1052 mg, about 351 mg to about 700 mg, and about 700 mg to about 1052 mg.

Embodiment 43

The oral dosage form or plurality of dosage forms of embodiment 40, wherein magnesium citrate is present in an amount of about 2.32 mg to about 201 mg.

Embodiment 44

The oral dosage form or plurality of dosage forms according to embodiment 43 wherein magnesium citrate is present in an amount selected from: about 2.32 mg to about 201 mg, about 2.32 mg to about 151 mg, about 2.32 to about 77 mg, about 77 to about 201 mg, about 77 to about 151 mg, and about 150 mg to about 201 mg.

Embodiment 45

The oral dosage form or plurality of dosage forms of embodiment 40, wherein phytin is present in an amount of about 100 mg to about 600 mg.

Embodiment 46

The oral dosage form or plurality of dosage forms according to embodiment 45 wherein phytin is present in an amount selected from: about 100 mg to about 401 mg, about 100 mg to about 202 mg, about 201 mg to about 600 mg, about 201 mg to about 401 mg, and about 401 mg to about 600 mg.

Embodiment 47

The oral dosage form or plurality of dosage forms of embodiment 40, wherein musa is present in an amount of about 1.51 mg to about 251 mg.

Embodiment 48

The oral dosage form or plurality of dosage forms according to embodiment 47 wherein musa is present in an amount selected from: about 1.51 mg to about 167 mg, about 1.51 mg to about 86 mg, about 1.51 mg to about 41 mg, about 41 mg to about 251 mg, about 41 mg to about 167 mg, about 41 mg to about 86 mg, about 86 mg to about 251 mg, about 86 mg to about 167, and about 167 mg to about 251 mg.

Embodiment 49

The oral dosage form or plurality of dosage forms of embodiment 40, wherein citric acid is present in an amount of about 102 mg to about 1052 mg, magnesium citrate is present in an amount of about 2.32 mg to about 201 mg, phytin is present in an amount of about 100 mg to about 600 mg, and musa is present in an amount of about 1.51 mg to about 251 mg.

Embodiment 50

The oral dosage form or plurality of dosage forms according to embodiment 49 wherein citric acid is present in an amount selected from: about 102 mg to about 700 mg, about 102 mg to about 352 mg, about 102 mg to about 177 mg, about 177 mg to about 1052 mg, about 177 mg to about 700 mg, about 177 mg to about 352 mg, about 351 mg to about 1052 mg, about 351 mg to about 700 mg, and about 700 mg to about 1052 mg; magnesium citrate is present in an amount selected from: about 2.32 mg to about 201 mg, about 2.32 mg to about 151 mg, about 2.32 to about 77 mg, about 77 to about 201 mg, about 77 to about 151 mg, and about 150 mg to about 201 mg; phytin is present in an amount selected from: about 100 mg to about 401 mg, about 100 mg to about 202 mg, about 201 mg to about 600 mg, about 201 mg to about 401 mg, and about 401 mg to about 600 mg; and musa is present in an amount selected from: about 1.51 mg to about 167 mg, about 1.51 mg to about 86 mg, about 1.51 mg to about 41 mg, about 41 mg to about 251 mg, about 41 mg to about 167 mg, about 41 mg to about 86 mg, about 86 mg to about 251 mg, about 86 mg to about 167, and about 167 mg to about 251 mg.

Embodiment 51

The oral dosage form or plurality of dosage forms of embodiment 40, wherein the amount of one of the active ingredients is selected from: citric acid is present in an amount selected from: about 102 mg to about 700 mg, about 102 mg to about 352 mg, about 102 mg to about 177 mg, about 177 mg to about 1052 mg, about 177 mg to about 700 mg, about 177 mg to about 352 mg, about 351 mg to about 1052 mg, about 351 mg to about 700 mg, and about 700 mg to about 1052 mg; magnesium citrate is present in an amount selected from: about 2.32 mg to about 201 mg, about 2.32 mg to about 151 mg, about 2.32 to about 77 mg, about 77 to about 201 mg, about 77 to about 151 mg, and about 150 mg to about 201 mg; phytin is present in an amount selected from: about 100 mg to about 401 mg, about 100 mg to about 202 mg, about 201 mg to about 600 mg, about 201 mg to about 401 mg, and about 401 mg to about 600 mg; and musa is present in an amount selected from: about 1.51 mg to about 167 mg, about 1.51 mg to about 86 mg, about 1.51 mg to about 41 mg, about 41 mg to about 251 mg, about 41 mg to about 167 mg, about 41 mg to about 86 mg, about 86 mg to about 251 mg, about 86 mg to about 167, and about 167 mg to about 251 mg.

Embodiment 52

The oral dosage form or plurality of dosage forms of embodiment 40, wherein the amounts of two of the active ingredients are selected from: citric acid is present in an amount selected from: about 102 mg to about 700 mg, about 102 mg to about 352 mg, about 102 mg to about 177 mg, about 177 mg to about 1052 mg, about 177 mg to about 700 mg, about 177 mg to about 352 mg, about 351 mg to about 1052 mg, about 351 mg to about 700 mg, and about 700 mg to about 1052 mg; magnesium citrate is present in an amount selected from: about 2.32 mg to about 201 mg, about 2.32 mg to about 151 mg, about 2.32 to about 77 mg, about 77 to about 201 mg, about 77 to about 151 mg, and about 150 mg to about 201 mg; phytin is present in an amount selected from: about 100 mg to about 401 mg, about 100 mg to about 202 mg, about 201 mg to about 600 mg, about 201 mg to about 401 mg, and about 401 mg to about 600 mg; and musa is present in an amount selected from: about 1.51 mg to about 167 mg, about 1.51 mg to about 86 mg, about 1.51 mg to about 41 mg, about 41 mg to about 251 mg, about 41 mg to about 167 mg, about 41 mg to about 86 mg, about 86 mg to about 251 mg, about 86 mg to about 167, and about 167 mg to about 251 mg.

Embodiment 53

The oral dosage form or plurality of dosage forms of embodiment 40, wherein the amounts of 3 of the ingredients are selected from: citric acid is present in an amount selected from: about 102 mg to about 700 mg, about 102 mg to about 352 mg, about 102 mg to about 177 mg, about 177 mg to about 1052 mg, about 177 mg to about 700 mg, about 177 mg to about 352 mg, about 351 mg to about 1052 mg, about 351 mg to about 700 mg, and about 700 mg to about 1052 mg; magnesium citrate is present in an amount selected from: about 2.32 mg to about 201 mg, about 2.32 mg to about 151 mg, about 2.32 to about 77 mg, about 77 to about 201 mg, about 77 to about 151 mg, and about 150 mg to about 201 mg; phytin is present in an amount selected from: about 100 mg to about 401 mg, about 100 mg to about 202 mg, about 201 mg to about 600 mg, about 201 mg to about 401 mg, and about 401 mg to about 600 mg; and musa is present in an amount selected from: about 1.51 mg to about 167 mg, about 1.51 mg to about 86 mg, about 1.51 mg to about 41 mg, about 41 mg to about 251 mg, about 41 mg to about 167 mg, about 41 mg to about 86 mg, about 86 mg to about 251 mg, about 86 mg to about 167, and about 167 mg to about 251 mg.

Embodiment 54

The oral dosage form or plurality of dosage forms of embodiment 40, wherein citric acid is present in an amount of about 350 mg; magnesium citrate is present in an amount of about 150 mg; phytin is present in an amount of about 200 mg; and musa is present in an amount of about 250 mg.

Embodiment 55

The oral dosage form or a plurality of dosage forms according to any one of embodiments 40 to 54, wherein the percent inhibition of calcium oxalate crystal formation by the combination of active ingredients is greater than about 92%.

Embodiment 56

The oral dosage form or plurality of dosage forms according to embodiment 55, where the percent inhibition is greater than about 96%.

Embodiment 57

The oral dosage form or plurality of dosage forms according to embodiment 56 where the percent inhibition is greater than about 100%.

Embodiment 58

An oral dosage form or a plurality of dosage forms comprising as active ingredients citric acid, magnesium citrate, pyridoxine, and musa.

Embodiment 59

The oral dosage form or plurality of dosage forms of embodiment 58, wherein citric acid is present in an amount of about 101 mg to about 1051 mg.

Embodiment 60

The oral dosage form or plurality of dosage forms according to embodiment 59 wherein citric acid is present in an amount selected from: about 101 mg to about 700 mg, about 101 mg to about 353 mg, about 101 mg to about 176 mg, about 176 mg to about 1051 mg, about 176 mg to about 700 mg, about 176 mg to about 353 mg, about 352 mg to about 1051 mg, about 352 mg to about 700 mg, and about 700 mg to about 1051 mg.

Embodiment 61

The oral dosage form or plurality of dosage forms of embodiment 58, wherein magnesium citrate is present in an amount of about 2.14 mg to about 226 mg.

Embodiment 62

The oral dosage form or plurality of dosage forms according to embodiment 61 wherein magnesium citrate is present in an amount selected from: about 2.14 mg to about 202 mg, about 2.14 mg to about 153 mg, about 2.14 mg to about 77 mg, about 77 to about 226 mg, about 77 to about 202 mg, about 77 to about 153 mg, about 151 mg to about 226 mg, about 151 mg to about 202 mg, and about 202 mg to about 226 mg.

Embodiment 63

The oral dosage form or plurality of dosage forms of embodiment 58, wherein pyridoxine is present in an amount of about 0.25 mg to about 10.23 mg.

Embodiment 64

The oral dosage form or plurality of dosage forms according to embodiment 63 wherein pyridoxine is present in an amount selected from: about 0.25 mg to about 5.95 mg, about 0.25 mg to about 2.63 mg, about 2.63 mg to about 10.23 mg, about 2.63 mg to about 5.95 mg, and about 5.41 mg to about 10.23 mg.

Embodiment 65

The oral dosage form or plurality of dosage forms of embodiment 58, wherein musa is present in an amount of about 41.02 mg to about 252 mg.

Embodiment 66

The oral dosage form or plurality of dosage forms according to embodiment 65 wherein musa is present in an amount selected from: about 41.02 mg to about 167 mg, about 41.02 mg to about 85 mg, about 85 mg to about 252 mg, about 85 mg to about 167 mg, and about 167 mg to about 252 mg.

Embodiment 67

The oral dosage form or plurality of dosage forms of embodiment 58, wherein citric acid is present in an amount of about 101 mg to about 1051 mg, magnesium citrate is present in an amount of about 2.14 mg to about 226 mg, pyridoxine is present in an amount of about 0.25 mg to about 10.23 mg, and musa is present in an amount of about 41.02 mg to about 252 mg.

Embodiment 68

The oral dosage form or plurality of dosage forms according to embodiment 67 wherein citric acid is present in an amount selected from: about 101 mg to about 700 mg, about 101 mg to about 353 mg, about 101 mg to about 176 mg, about 176 mg to about 1051 mg, about 176 mg to about 700 mg, about 176 mg to about 353 mg, about 352 mg to about 1051 mg, about 352 mg to about 700 mg, and about 700 mg to about 1051 mg; magnesium citrate is present in an amount selected from: about 2.14 mg to about 202 mg, about 2.14 mg to about 153 mg, about 2.14 mg to about 77 mg, about 77 to about 226 mg, about 77 to about 202 mg, about 77 to about 153 mg, about 151 mg to about 226 mg, about 151 mg to about 202 mg, and about 202 mg to about 226 mg; pyridoxine is present in an amount selected from: about 0.25 mg to about 5.95 mg, about 0.25 mg to about 2.63 mg, about 2.63 mg to about 10.23 mg, about 2.63 mg to about 5.95 mg, and about 5.41 mg to about 10.23 mg; and musa is present in an amount selected from: about 41.02 mg to about 167 mg, about 41.02 mg to about 85 mg, about 85 mg to about 252 mg, about 85 mg to about 167 mg, and about 167 mg to about 252 mg.

Embodiment 69

The oral dosage form or plurality of dosage forms of embodiment 58, wherein the amount of one of the active ingredients is selected from: citric acid is present in an amount selected from: about 101 mg to about 700 mg, about 101 mg to about 353 mg, about 101 mg to about 176 mg, about 176 mg to about 1051 mg, about 176 mg to about 700 mg, about 176 mg to about 353 mg, about 352 mg to about 1051 mg, about 352 mg to about 700 mg, and about 700 mg to about 1051 mg; magnesium citrate is present in an amount selected from: about 2.14 mg to about 202 mg, about 2.14 mg to about 153 mg, about 2.14 mg to about 77 mg, about 77 to about 226 mg, about 77 to about 202 mg, about 77 to about 153 mg, about 151 mg to about 226 mg, about 151 mg to about 202 mg, and about 202 mg to about 226 mg; pyridoxine is present in an amount selected from: about 0.25 mg to about 5.95 mg, about 0.25 mg to about 2.63 mg, about 2.63 mg to about 10.23 mg, about 2.63 mg to about 5.95 mg, and about 5.41 mg to about 10.23 mg; and musa is present in an amount selected from: about 41.02 mg to about 167 mg, about 41.02 mg to about 85 mg, about 85 mg to about 252 mg, about 85 mg to about 167 mg, and about 167 mg to about 252 mg.

Embodiment 70

The oral dosage form or plurality of dosage forms of embodiment 58, wherein the amounts of two of the active ingredients are selected from: citric acid is present in an amount selected from: about 101 mg to about 700 mg, about 101 mg to about 353 mg, about 101 mg to about 176 mg, about 176 mg to about 1051 mg, about 176 mg to about 700 mg, about 176 mg to about 353 mg, about 352 mg to about 1051 mg, about 352 mg to about 700 mg, and about 700 mg to about 1051 mg; magnesium citrate is present in an amount selected from: about 2.14 mg to about 202 mg, about 2.14 mg to about 153 mg, about 2.14 mg to about 77 mg, about 77 to about 226 mg, about 77 to about 202 mg, about 77 to about 153 mg, about 151 mg to about 226 mg, about 151 mg to about 202 mg, and about 202 mg to about 226 mg; pyridoxine is present in an amount selected from: about 0.25 mg to about 5.95 mg, about 0.25 mg to about 2.63 mg, about 2.63 mg to about 10.23 mg, about 2.63 mg to about 5.95 mg, and about 5.41 mg to about 10.23 mg; and musa is present in an amount selected from: about 41.02 mg to about 167 mg, about 41.02 mg to about 85 mg, about 85 mg to about 252 mg, about 85 mg to about 167 mg, and about 167 mg to about 252 mg.

Embodiment 71

The oral dosage form or plurality of dosage forms of embodiment 58, wherein the amounts of 3 of the ingredients are selected from: citric acid is present in an amount selected from: about 101 mg to about 700 mg, about 101 mg to about 353 mg, about 101 mg to about 176 mg, about 176 mg to about 1051 mg, about 176 mg to about 700 mg, about 176 mg to about 353 mg, about 352 mg to about 1051 mg, about 352 mg to about 700 mg, and about 700 mg to about 1051 mg; magnesium citrate is present in an amount selected from: about 2.14 mg to about 202 mg, about 2.14 mg to about 153 mg, about 2.14 mg to about 77 mg, about 77 to about 226 mg, about 77 to about 202 mg, about 77 to about 153 mg, about 151 mg to about 226 mg, about 151 mg to about 202 mg, and about 202 mg to about 226 mg; pyridoxine is present in an amount selected from: about 0.25 mg to about 5.95 mg, about 0.25 mg to about 2.63 mg, about 2.63 mg to about 10.23 mg, about 2.63 mg to about 5.95 mg, and about 5.41 mg to about 10.23 mg; and musa is present in an amount selected from: about 41.02 mg to about 167 mg, about 41.02 mg to about 85 mg, about 85 mg to about 252 mg, about 85 mg to about 167 mg, and about 167 mg to about 252 mg.

Embodiment 72

The oral dosage form or plurality of dosage forms of embodiment 58, wherein citric acid is present in an amount of about 350 mg; magnesium citrate is present in an amount of about 150 mg; pyridoxine is present in an amount of about 5 mg; and musa is present in an amount of about 250 mg.

Embodiment 73

The oral dosage form or a plurality of dosage forms according to any one of embodiments 58 to 72, wherein the percent inhibition of calcium oxalate crystal formation by the combination of active ingredients is greater than about 59%.

Embodiment 74

The oral dosage form or plurality of dosage forms according to embodiment 73, where the percent inhibition is greater than about 62%.

Embodiment 75

The oral dosage form or plurality of dosage forms according to embodiment 74 where the percent inhibition is greater than about 66%.

Embodiment 76

An oral dosage form or a plurality of dosage forms comprising as active ingredients citric acid, phytin, pyridoxine, and musa.

Embodiment 77

The oral dosage form or plurality of dosage forms of embodiment 76, wherein citric acid is present in an amount of about 101 mg to less than about 700 mg.

Embodiment 78

The oral dosage form or plurality of dosage forms according to embodiment 77 wherein citric acid is present in an amount selected from: about 101 mg to about 353 mg, about 101 mg to about 177 mg, about 177 mg to less than about 700 mg, about 177 mg to about 353 mg, and about 352 mg to less than about 700 mg.

Embodiment 79

The oral dosage form or plurality of dosage forms of embodiment 77, wherein citric acid is present in an amount of about 101 mg to about 353 mg.

Embodiment 80

The oral dosage form or plurality of dosage forms according to embodiment 79 wherein citric acid is present in an amount selected from: about 101 mg to about 353 mg, about 101 mg to about 177 mg, and about 177 mg to about 353 mg.

Embodiment 81

The oral dosage form or plurality of dosage forms of embodiment 76, wherein phytin is present in an amount of about 101 mg to about 600 mg.

Embodiment 82

The oral dosage form or plurality of dosage forms according to embodiment 81 wherein phytin is present in an amount selected from: about 101 mg to about 400 mg, about 101 mg to about 203 mg, about 202 mg to about 600 mg, about 202 to about 400 mg, and about 400 to about 600 mg.

Embodiment 83

The oral dosage form or plurality of dosage forms of embodiment 76, wherein pyridoxine is present in an amount of about 0.23 mg to about 15.12 mg.

Embodiment 84

The oral dosage form or plurality of dosage forms according to embodiment 83 wherein pyridoxine is present in an amount selected from: about 0.23 mg to about 10.20 mg, about 0.23 mg to about 6.00 mg, about 0.23 mg to about 2.69 mg, about 2.69 mg to about 15.12 mg, about 2.69 mg to about 10.20 mg, about 2.69 mg to about 6.00 mg, about 5.45 mg to about 15.12 mg, about 5.45 mg to about 10.20 mg, and about 10.20 mg to about 15.12 mg.

Embodiment 85

The oral dosage form or plurality of dosage forms of embodiment 76, wherein musa is present in an amount of about 1.46 mg to about 252 mg.

Embodiment 86

The oral dosage form or plurality of dosage forms according to embodiment 85 wherein musa is present in an amount selected from: about 1.46 mg to about 167 mg, about 1.46 mg to about 86 mg, about 1.46 mg to about 41 mg, about 41 mg to about 252 mg, about 41 mg to about 167 mg, about 41 mg to about 86 mg, about 86 mg to about 252 mg, about 86 mg to about 167 mg, and about 167 mg to about 252 mg.

Embodiment 87

The oral dosage form or plurality of dosage forms of embodiment 76, wherein citric acid is present in an amount of about 101 mg to less than about 700 mg, phytin is present in an amount of about 101 mg to about 600 mg, pyridoxine is present in an amount of about 0.23 mg to about 15.12 mg, and musa is present in an amount of about 1.46 mg to about 252 mg.

Embodiment 88

The oral dosage form or plurality of dosage forms of embodiment 87, wherein citric acid is present in an amount of about 101 mg to about 353 mg.

Embodiment 89

The oral dosage form or plurality of dosage forms according to embodiment 87 wherein citric acid is present in an amount selected from: about 101 mg to about 353 mg, about 101 mg to about 177 mg, about 177 mg to less than about 700 mg, about 177 mg to about 353 mg, and about 352 mg to less than about 700 mg; phytin is present in an amount selected from: about 101 mg to about 400 mg, about 101 mg to about 203 mg, about 202 mg to about 600 mg, about 202 to about 400 mg, and about 400 to about 600 mg; pyridoxine is present in an amount selected from: about 0.23 mg to about 10.20 mg, about 0.23 mg to about 6.00 mg, about 0.23 mg to about 2.69 mg, about 2.69 mg to about 15.12 mg, about 2.69 mg to about 10.20 mg, about 2.69 mg to about 6.00 mg, about 5.45 mg to about 15.12 mg, about 5.45 mg to about 10.20 mg, and about 10.20 mg to about 15.12 mg; and musa is present in an amount selected from: about 1.46 mg to about 167 mg, about 1.46 mg to about 86 mg, about 1.46 mg to about 41 mg, about 41 mg to about 252 mg, about 41 mg to about 167 mg, about 41 mg to about 86 mg, about 86 mg to about 252 mg, about 86 mg to about 167 mg, and about 167 mg to about 252 mg.

Embodiment 90

The oral dosage form or plurality of dosage forms according to embodiment 89 wherein citric acid is present in an amount selected from: about 101 mg to about 353 mg, about 101 mg to about 177 mg, and about 177 mg to about 353 mg Embodiment 91

The oral dosage form or plurality of dosage forms of embodiment 76, wherein the amount of one of the active ingredients is selected from: citric acid is present in an amount selected from: about 101 mg to about 353 mg, about 101 mg to about 177 mg, about 177 mg to less than about 700 mg, about 177 mg to about 353 mg, and about 352 mg to less than about 700 mg; phytin is present in an amount selected from: about 101 mg to about 400 mg, about 101 mg to about 203 mg, about 202 mg to about 600 mg, about 202 to about 400 mg, and about 400 to about 600 mg; pyridoxine is present in an amount selected from: about 0.23 mg to about 10.20 mg, about 0.23 mg to about 6.00 mg, about 0.23 mg to about 2.69 mg, about 2.69 mg to about 15.12 mg, about 2.69 mg to about 10.20 mg, about 2.69 mg to about 6.00 mg, about 5.45 mg to about 15.12 mg, about 5.45 mg to about 10.20 mg, and about 10.20 mg to about 15.12 mg; and musa is present in an amount selected from: about 1.46 mg to about 167 mg, about 1.46 mg to about 86 mg, about 1.46 mg to about 41 mg, about 41 mg to about 252 mg, about 41 mg to about 167 mg, about 41 mg to about 86 mg, about 86 mg to about 252 mg, about 86 mg to about 167 mg, and about 167 mg to about 252 mg.

Embodiment 92

The oral dosage form or plurality of dosage forms according to embodiment 91 wherein citric acid is present in an amount selected from: about 101 mg to about 353 mg, about 101 mg to about 177 mg, and about 177 mg to about 353 mg.

Embodiment 93

The oral dosage form or plurality of dosage forms of embodiment 76, wherein the amounts of two of the active ingredients are selected from: citric acid is present in an amount selected from: about 101 mg to about 353 mg, about 101 mg to about 177 mg, about 177 mg to less than about 700 mg, about 177 mg to about 353 mg, and about 352 mg to less than about 700 mg; phytin is present in an amount selected from: about 101 mg to about 400 mg, about 101 mg to about 203 mg, about 202 mg to about 600 mg, about 202 to about 400 mg, and about 400 to about 600 mg; pyridoxine is present in an amount selected from: about 0.23 mg to about 10.20 mg, about 0.23 mg to about 6.00 mg, about 0.23 mg to about 2.69 mg, about 2.69 mg to about 15.12 mg, about 2.69 mg to about 10.20 mg, about 2.69 mg to about 6.00 mg, about 5.45 mg to about 15.12 mg, about 5.45 mg to about 10.20 mg, and about 10.20 mg to about 15.12 mg; and musa is present in an amount selected from: about 1.46 mg to about 167 mg, about 1.46 mg to about 86 mg, about 1.46 mg to about 41 mg, about 41 mg to about 252 mg, about 41 mg to about 167 mg, about 41 mg to about 86 mg, about 86 mg to about 252 mg, about 86 mg to about 167 mg, and about 167 mg to about 252 mg Embodiment 94

The oral dosage form or plurality of dosage forms according to embodiment 93 wherein citric acid is present in an amount selected from: about 101 mg to about 353 mg, about 101 mg to about 177 mg, and about 177 mg to about 353 mg.

Embodiment 95

The oral dosage form or plurality of dosage forms of embodiment 76, wherein the amounts of 3 of the ingredients are selected from: citric acid is present in an amount selected from: about 101 mg to about 353 mg, about 101 mg to about 177 mg, about 177 mg to less than about 700 mg, about 177 mg to about 353 mg, and about 352 mg to less than about 700 mg; phytin is present in an amount selected from: about 101 mg to about 400 mg, about 101 mg to about 203 mg, about 202 mg to about 600 mg, about 202 to about 400 mg, and about 400 to about 600 mg; pyridoxine is present in an amount selected from: about 0.23 mg to about 10.20 mg, about 0.23 mg to about 6.00 mg, about 0.23 mg to about 2.69 mg, about 2.69 mg to about 15.12 mg, about 2.69 mg to about 10.20 mg, about 2.69 mg to about 6.00 mg, about 5.45 mg to about 15.12 mg, about 5.45 mg to about 10.20 mg, and about 10.20 mg to about 15.12 mg; and musa is present in an amount selected from: about 1.46 mg to about 167 mg, about 1.46 mg to about 86 mg, about 1.46 mg to about 41 mg, about 41 mg to about 252 mg, about 41 mg to about 167 mg, about 41 mg to about 86 mg, about 86 mg to about 252 mg, about 86 mg to about 167 mg, and about 167 mg to about 252 mg.

Embodiment 96

The oral dosage form or plurality of dosage forms according to embodiment 95 wherein citric acid is present in an amount selected from: about 101 mg to about 353 mg, about 101 mg to about 177 mg, and about 177 mg to about 353 mg.

Embodiment 97

The oral dosage form or plurality of dosage forms of embodiment 76, wherein citric acid is present in an amount of about 350 mg; phytin is present in an amount of about 200 mg; pyridoxine is present in an amount of about 5 mg; and musa is present in an amount of about 250 mg.

Embodiment 98

The oral dosage form or a plurality of dosage forms according to any one of embodiments 76 to 97, wherein the percent inhibition of calcium oxalate crystal formation by the combination of active ingredients is greater than about 88%.

Embodiment 99

The oral dosage form or plurality of dosage forms according to embodiment 98, where the percent inhibition is greater than about 100%.

Embodiment 100

The oral dosage form or plurality of dosage forms according to embodiment 99 where the percent inhibition is greater than about 108%.

Embodiment 101

An oral dosage form or a plurality of dosage forms comprising as active ingredients magnesium citrate, phytin, pyridoxine, and musa.

Embodiment 102

The oral dosage form or plurality of dosage forms of embodiment 101, wherein magnesium citrate is present in an amount of about 2.03 mg to about 203 mg.

Embodiment 103

The oral dosage form or plurality of dosage forms according to embodiment 102 wherein magnesium citrate is present in an amount selected from: about 2.03 mg to about 151 mg, about 2.03 mg to about 77 mg, about 77 mg to about 203 mg, about 77 mg to about 151 mg, and about 151 mg to about 203 mg.

Embodiment 104

The oral dosage form or plurality of dosage forms of embodiment 101, wherein phytin is present in an amount of about 100 mg to about 600 mg.

Embodiment 105

The oral dosage form or plurality of dosage forms according to embodiment 104 wherein phytin is present in an amount selected from: about 100 mg to about 475 mg, 100 mg to about 400 mg, about 100 mg to about 202 mg, about 201 mg to about 600 mg, about 201 mg to about 475 mg, about 201 to about 400 mg, about 400 mg to about 600 mg, about 400 to about 475 mg, and about 475 mg to about 600 mg.

Embodiment 106

The oral dosage form or plurality of dosage forms of embodiment 101, wherein pyridoxine is present in an amount of about 0.22 mg to about 15.1 mg.

Embodiment 107

The oral dosage form or plurality of dosage forms according to embodiment 106 wherein pyridoxine is present in an amount selected from: about 0.22 mg to about 10.11 mg, about 0.22 mg to about 6.01 mg, about 0.22 mg to about 2.69 mg, about 2.69 mg to about 15.1 mg, about 2.69 mg to about 10.11 mg, about 2.69 mg to about 6.01 mg, about 5.4 mg to about 15.1 mg, about 5.4 mg to about 10.11 mg, and about 10.11 mg to about 15.1 mg.

Embodiment 108

The oral dosage form or plurality of dosage forms of embodiment 101, wherein musa is present in an amount of about 1.46 mg to about 252 mg.

Embodiment 109

The oral dosage form or plurality of dosage forms according to embodiment 108 wherein musa is present in an amount selected from: about 1.46 mg to about 168 mg, about 1.46 mg to about 85 mg, about 1.46 mg to about 42 mg, about 42 mg to about 252 mg, about 42 mg to about 168 mg, about 42 mg to about 85 mg, about 85 mg to about 252 mg, about 85 mg to about 168 mg, and about 168 mg to about 252 mg.

Embodiment 110

The oral dosage form or plurality of dosage forms of embodiment 101, wherein magnesium citrate is present in an amount of about 2.03 mg to about 203 mg, phytin is present in an amount of about 100 mg to about 600 mg, pyridoxine is present in an amount of about 0.22 mg to about 15.1 mg, and musa is present in an amount of about 1.46 mg to about 252 mg.

Embodiment 111

The oral dosage form or plurality of dosage forms according to embodiment 110 wherein magnesium citrate is present in an amount selected from: about 2.03 mg to about 77 mg, about 2.03 mg to about 151 mg, about 77 mg to about 151 mg, about 77 mg to about 203 mg, and about 151 mg to about 203 mg; phytin is present in an amount selected from: 100 mg to about 475 mg, 100 mg to about 400 mg, about 100 mg to about 202 mg, about 201 mg to about 600 mg, about 201 mg to about 475 mg, about 201 to about 400 mg, about 400 mg to about 600 mg, about 400 to about 475 mg, and about 475 mg to about 600 mg; pyridoxine is present in an amount selected from: about 0.22 mg to about 10.11 mg, about 0.22 mg to about 6.01 mg, about 0.22 mg to about 2.69 mg, about 2.69 mg to about 15.1 mg, about 2.69 mg to about 10.11 mg, about 2.69 mg to about 6.01 mg, about 5.4 mg to about 15.1 mg, about 5.4 mg to about 10.1120 mg, and about 10.11 mg to about 15.1 mg; and musa is present in an amount selected from: about 1.46 mg to about 168 mg, about 1.46 mg to about 85 mg, about 1.46 mg to about 42 mg, about 41 mg to about 252 mg, about 41 mg to about 168 mg, about 41 mg to about 85 mg, about 85 mg to about 252 mg, about 85 mg to about 168 mg, and about 168 mg to about 252 mg.

Embodiment 112

The oral dosage form or plurality of dosage forms of embodiment 101, wherein the amount of one of the active ingredients is selected from: magnesium citrate is present in an amount selected from: about 2.03 mg to about 77 mg, about 2.03 mg to about 151 mg, about 77 mg to about 151 mg, about 77 mg to about 203 mg, and about 151 mg to about 203 mg; phytin is present in an amount selected from: 100 mg to about 475 mg, 100 mg to about 400 mg, about 100 mg to about 202 mg, about 201 mg to about 600 mg, about 201 mg to about 475 mg, about 201 to about 400 mg, about 400 mg to about 600 mg, about 400 to about 475 mg, and about 475 mg to about 600 mg; pyridoxine is present in an amount selected from: about 0.22 mg to about 10.11 mg, about 0.22 mg to about 6.01 mg, about 0.22 mg to about 2.69 mg, about 2.69 mg to about 15.1 mg, about 2.69 mg to about 10.11 mg, about 2.69 mg to about 6.01 mg, about 5.4 mg to about 15.1 mg, about 5.4 mg to about 10.1120 mg, and about 10.11 mg to about 15.1 mg; and musa is present in an amount selected from: about 1.46 mg to about 168 mg, about 1.46 mg to about 85 mg, about 1.46 mg to about 42 mg, about 41 mg to about 252 mg, about 41 mg to about 168 mg, about 41 mg to about 85 mg, about 85 mg to about 252 mg, about 85 mg to about 168 mg, and about 168 mg to about 252 mg.

Embodiment 113

The oral dosage form or plurality of dosage forms of embodiment 101, wherein the amounts of two of the active ingredients are selected from: magnesium citrate is present in an amount selected from: about 2.03 mg to about 77 mg, about 2.03 mg to about 151 mg, about 77 mg to about 151 mg, about 77 mg to about 203 mg, and about 151 mg to about 203 mg; phytin is present in an amount selected from: 100 mg to about 475 mg, 100 mg to about 400 mg, about 100 mg to about 202 mg, about 201 mg to about 600 mg, about 201 mg to about 475 mg, about 201 to about 400 mg, about 400 mg to about 600 mg, about 400 to about 475 mg, and about 475 mg to about 600 mg; pyridoxine is present in an amount selected from: about 0.22 mg to about 10.11 mg, about 0.22 mg to about 6.01 mg, about 0.22 mg to about 2.69 mg, about 2.69 mg to about 15.1 mg, about 2.69 mg to about 10.11 mg, about 2.69 mg to about 6.01 mg, about 5.4 mg to about 15.1 mg, about 5.4 mg to about 10.1120 mg, and about 10.11 mg to about 15.1 mg; and musa is present in an amount selected from: about 1.46 mg to about 168 mg, about 1.46 mg to about 85 mg, about 1.46 mg to about 42 mg, about 41 mg to about 252 mg, about 41 mg to about 168 mg, about 41 mg to about 85 mg, about 85 mg to about 252 mg, about 85 mg to about 168 mg, and about 168 mg to about 252 mg.

Embodiment 114

The oral dosage form or plurality of dosage forms of embodiment 101, wherein the amounts of 3 of the ingredients are selected from: magnesium citrate is present in an amount selected from: about 2.03 mg to about 77 mg, about 2.03 mg to about 151 mg, about 77 mg to about 151 mg, about 77 mg to about 203 mg, and about 151 mg to about 203 mg; phytin is present in an amount selected from: 100 mg to about 475 mg, 100 mg to about 400 mg, about 100 mg to about 202 mg, about 201 mg to about 600 mg, about 201 mg to about 475 mg, about 201 to about 400 mg, about 400 mg to about 600 mg, about 400 to about 475 mg, and about 475 mg to about 600 mg; pyridoxine is present in an amount selected from: about 0.22 mg to about 10.11 mg, about 0.22 mg to about 6.01 mg, about 0.22 mg to about 2.69 mg, about 2.69 mg to about 15.1 mg, about 2.69 mg to about 10.11 mg, about 2.69 mg to about 6.01 mg, about 5.4 mg to about 15.1 mg, about 5.4 mg to about 10.1120 mg, and about 10.11 mg to about 15.1 mg; and musa is present in an amount selected from: about 1.46 mg to about 168 mg, about 1.46 mg to about 85 mg, about 1.46 mg to about 42 mg, about 41 mg to about 252 mg, about 41 mg to about 168 mg, about 41 mg to about 85 mg, about 85 mg to about 252 mg, about 85 mg to about 168 mg, and about 168 mg to about 252 mg.

Embodiment 115

The oral dosage form or plurality of dosage forms of embodiment 101, wherein magnesium citrate is present in an amount of about 250 mg; phytin is present in an amount of about 200 mg; pyridoxine is present in an amount of about 5 mg; and musa is present in an amount of about 250 mg.

Embodiment 116

The oral dosage form or a plurality of dosage forms according to any one of embodiments 101 to 115, wherein the percent inhibition of calcium oxalate crystal formation by the combination of active ingredients is greater than about 99%.

Embodiment 117

The oral dosage form or plurality of dosage forms according to embodiment 116, where the percent inhibition is greater than about 104%.

Embodiment 118

The oral dosage form or plurality of dosage forms according to embodiment 117 where the percent inhibition is greater than about 106%.

Embodiment 119

An oral dosage form or a plurality of dosage forms comprising four ingredients selected from citric acid, magnesium citrate, phytin, pyridoxine, and musa.

Embodiment 120

The oral dosage form or plurality of dosage forms according to embodiment 119 selected from: (a) an oral dosage form or plurality of dosage forms wherein citric acid is present in an amount of about 101 mg to about 699 mg, magnesium citrate is present in an amount of about 77 mg to about 227 mg, phytin is present in an amount of about 3.06 mg to about 600 mg, and pyridoxine is present in an amount of about 0.23 mg to about 15.13 mg; (b) an oral dosage form or plurality of dosage forms wherein citric acid is present in an amount of about 102 mg to about 1052 mg, magnesium citrate is present in an amount of about 2.32 mg to about 201 mg, phytin is present in an amount of about 100 mg to about 600 mg, and musa is present in an amount of about 1.51 mg to about 251 mg; (c) an oral dosage form or plurality of dosage forms wherein citric acid is present in an amount of about 101 mg to about 1051 mg, magnesium citrate is present in an amount of about 2.14 mg to about 226 mg, pyridoxine is present in an amount of about 0.25 mg to about 10.23 mg, and musa is present in an amount of about 41 mg to about 252 mg; (d) an oral dosage form or plurality of dosage forms wherein citric acid is present in an amount of about 101 mg to less than about 700 mg, phytin is present in an amount of about 101 mg to about 600 mg, pyridoxine is present in an amount of about 0.23 mg to about 15.12 mg, and musa is present in an amount of about 1.46 mg to about 252 mg; and (e) an oral dosage form or plurality of dosage forms wherein magnesium citrate is present in an amount of about 2.03 mg to about 203 mg, phytin is present in an amount of about 100 mg to about 600 mg, pyridoxine is present in an amount of about 0.22 mg to about 15.1 mg, and musa is present in an amount of about 1.46 mg to about 252 mg.

Embodiment 121

The oral dosage form or plurality of dosage forms according to embodiment 119 or 120, wherein citric acid is present in an amount of about 101 mg to about 699 mg, magnesium citrate is present in an amount of about 77 mg to about 227 mg, phytin is present in an amount of about 3.06 mg to about 600 mg, and pyridoxine is present in an amount of about 0.23 mg to about 15.13 mg.

Embodiment 122

The oral dosage form or plurality of dosage forms of embodiment 121, wherein citric acid is present in an amount of about 350 mg; magnesium citrate is present in an amount of about 150 mg; phytin is present in an amount of about 200 mg; and pyridoxine is present in an amount of about 5 mg.

Embodiment 123

The oral dosage form or a plurality of dosage forms according to embodiment 121 or 122, wherein the percent inhibition of calcium oxalate crystal formation by the combination of active ingredients is greater than about 89%.

Embodiment 124

The oral dosage form or plurality of dosage forms according to embodiment 123, where the percent inhibition is greater than about 94%.

Embodiment 125

The oral dosage form or plurality of dosage forms according to embodiment 125 where the percent inhibition is greater than about 98%.

Embodiment 126

The oral dosage form or plurality of dosage forms according to embodiment 119 or 120 wherein citric acid is present in an amount of about 102 mg to about 1052 mg, magnesium citrate is present in an amount of about 2.32 mg to about 201 mg, phytin is present in an amount of about 100 mg to about 600 mg, and musa is present in an amount of about 1.51 mg to about 251 mg.

Embodiment 127

The oral dosage form or plurality of dosage forms of embodiment 126, wherein citric acid is present in an amount of about 350 mg; magnesium citrate is present in an amount of about 150 mg; phytin is present in an amount of about 200 mg; and musa is present in an amount of about 250 mg.

Embodiment 128

The oral dosage form or a plurality of dosage forms according to embodiments 126 or 127, wherein the percent inhibition of calcium oxalate crystal formation by the combination of active ingredients is greater than about 92%.

Embodiment 129

The oral dosage form or plurality of dosage forms according to embodiment 128, where the percent inhibition is greater than about 96%.

Embodiment 130

The oral dosage form or plurality of dosage forms according to embodiment 129 where the percent inhibition is greater than about 100%.

Embodiment 131

The oral dosage form or plurality of dosage forms according to embodiment 119 or 120 wherein citric acid is present in an amount of about 101 mg to about 1051 mg, magnesium citrate is present in an amount of about 2.14 mg to about 226 mg, pyridoxine is present in an amount of about 0.25 mg to about 10.23 mg, and musa is present in an amount of about 41 mg to about 252 mg.

Embodiment 132

The oral dosage form or plurality of dosage forms of embodiment 131, wherein citric acid is present in an amount of about 350 mg; magnesium citrate is present in an amount of about 150 mg; pyridoxine is present in an amount of about 5 mg; and musa is present in an amount of about 250 mg.

Embodiment 133

The oral dosage form or a plurality of dosage forms according to embodiment 131 or 132, wherein the percent inhibition of calcium oxalate crystal formation by the combination of active ingredients is greater than about 59%.

Embodiment 134

The oral dosage form or plurality of dosage forms according to embodiment 133, where the percent inhibition is greater than about 62%.

Embodiment 135

The oral dosage form or plurality of dosage forms according to embodiment 134 where the percent inhibition is greater than about 66%.

Embodiment 136

The oral dosage form or plurality of dosage forms according to embodiment 119 or 120 wherein citric acid is present in an amount of about 101 mg to less than about 700 mg, phytin is present in an amount of about 101 mg to about 600 mg, pyridoxine is present in an amount of about 0.23 mg to about 15.12 mg, and musa is present in an amount of about 1.46 mg to about 252 mg.

Embodiment 137

The oral dosage form or plurality of dosage forms of embodiment 136, wherein citric acid is present in an amount of about 101 mg to about 353 mg.

Embodiment 138

The oral dosage form or plurality of dosage forms of embodiment 136 or 137, wherein citric acid is present in an amount of about 350 mg; phytin is present in an amount of about 200 mg; pyridoxine is present in an amount of about 5 mg; and musa is present in an amount of about 250 mg.

Embodiment 139

The oral dosage form or a plurality of dosage forms according to any one of embodiments 136 to 138, wherein the percent inhibition of calcium oxalate crystal formation by the combination of active ingredients is greater than about 88%.

Embodiment 140

The oral dosage form or plurality of dosage forms according to embodiment 139, where the percent inhibition is greater than about 100%.

Embodiment 141

The oral dosage form or plurality of dosage forms according to embodiment 140 where the percent inhibition is greater than about 108%.

Embodiment 142

The oral dosage form or plurality of dosage forms according to embodiment 119 or 120 wherein magnesium citrate is present in an amount of about 2.03 mg to about 203 mg, phytin is present in an amount of about 100 mg to about 600 mg, pyridoxine is present in an amount of about 0.22 mg to about 15.1 mg, and musa is present in an amount of about 1.46 mg to about 252 mg.

Embodiment 143

The oral dosage form or plurality of dosage forms of embodiment 142, wherein magnesium citrate is present in an amount of about 250 mg; phytin is present in an amount of about 200 mg; pyridoxine is present in an amount of about 5 mg; and musa is present in an amount of about 250 mg.

Embodiment 144

The oral dosage form or a plurality of dosage forms according to any one of embodiments 142 or 143, wherein the percent inhibition of calcium oxalate crystal formation by the combination of active ingredients is greater than about 99%.

Embodiment 145

The oral dosage form or plurality of dosage forms according to embodiment 144, where the percent inhibition is greater than about 104%.

Embodiment 146

The oral dosage form or plurality of dosage forms according to embodiment 145, where the percent inhibition is greater than about 106%.

Embodiment 147

The oral dosage form or plurality of dosage forms according to embodiment 119 wherein one of the ingredients is selected from: citric acid is present in an amount of about 101 mg to about 699 mg, magnesium citrate is present in an amount of about 77 mg to about 227 mg, phytin is present in an amount of about 3.06 mg to about 600 mg, and pyridoxine is present in an amount of about 0.23 mg to about 15.13 mg.

Embodiment 148

The oral dosage form or plurality of dosage forms according to embodiment 119 wherein one of the ingredients is selected from: citric acid is present in an amount of about 102 mg to about 1052 mg, magnesium citrate is present in an amount of about 2.32 mg to about 201 mg, phytin is present in an amount of about 100 mg to about 600 mg, and musa is present in an amount of about 1.51 mg to about 251 mg.

Embodiment 149

The oral dosage form or plurality of dosage forms according to embodiment 119 wherein one of the ingredients is selected from: citric acid is present in an amount of about 101 mg to about 1051 mg, magnesium citrate is present in an amount of about 2.14 mg to about 226 mg, pyridoxine is present in an amount of about 0.25 mg to about 10.23 mg, and musa is present in an amount of about 41 mg to about 252 mg.

Embodiment 150

The oral dosage form or plurality of dosage forms according to embodiment 119 wherein one of the ingredients is selected from: citric acid is present in an amount of about 101 mg to less than about 700 mg, phytin is present in an amount of about 101 mg to about 600 mg, pyridoxine is present in an amount of about 0.23 mg to about 15.12 mg, and musa is present in an amount of about 1.46 mg to about 252 mg.

Embodiment 151

The oral dosage form or plurality of dosage forms according to embodiment 119 wherein one of the ingredients is selected from: magnesium citrate is present in an amount of about 2.03 mg to about 203 mg, phytin is present in an amount of about 100 mg to about 600 mg, pyridoxine is present in an amount of about 0.22 mg to about 15.1 mg, and musa is present in an amount of about 1.46 mg to about 252 mg.

Embodiment 152

The oral dosage form or plurality of dosage forms according to any one of embodiments 147 to 151, wherein two ingredients are selected.

Embodiment 153

The oral dosage form or plurality of dosage forms according to any one of embodiments 147 to 151, wherein three ingredients are selected.

Embodiment 154

The oral dosage form or plurality of dosage forms according to any one of embodiments 1 to 153, which is a single oral dosage form.

Embodiment 155

The oral dosage form or plurality of dosage forms according to any one of embodiments 1 to 154, comprising an oral dosage form in the form of a capsule.

Embodiment 156

The oral dosage form or plurality of dosage forms of embodiment 155, wherein the capsule is a hard capsule.

Embodiment 157

The oral dosage form or plurality of dosage forms according to any one of embodiments 1 to 153, which is two oral dosage forms.

Embodiment 158

A method of treating or inhibiting formation of kidney stones comprising administering to a patient in need thereof the oral dosage form or plurality of dosage forms according to any one of embodiments 1 to 157.

Embodiment 159

The method of embodiment 158, wherein the oral dosage form or plurality of dosage forms is administered once daily.

Embodiment 160

The method of embodiment 158, wherein the oral dosage form or plurality of dosage forms is administered twice daily.

Embodiment 161

The method of any one of embodiments 158 to 160, wherein the oral dosage form or plurality of dosage forms comprises about 101 mg to about 700 mg citric acid; about 76 mg to about 226 mg magnesium citrate; about 3 mg to about 600 mg phytin; about 0.1 mg to about 15 mg pyridoxine; and about 1 mg to about 251 mg musa.

Embodiment 162

The method of embodiment 161, wherein the oral dosage form or plurality of dosage forms comprises about 350 mg citric acid, about 150 magnesium citrate, about 200 mg phytin, about 5 mg pyridoxine, and about 250 mg musa.

Embodiment 163

The method of any one of embodiments 158 to 162, wherein the oral dosage form or plurality of dosage forms is an oral capsule or a plurality of oral capsules.

Embodiment 164

The method of any one of embodiments 158 to 163, wherein the administering is without regard to food.

Embodiment 165

The method of any one of embodiments 157 to 162, wherein the administering is with food.

Embodiment 166

The method of any one of embodiments 158 to 163, wherein the administering is without food.

Embodiment 167

A method of inhibiting growth of calcium oxalate crystals comprising contacting an aqueous solution comprising calcium oxalate with the oral dosage form or plurality of dosage forms according to any one of embodiments 1 to 157.

Embodiment 168

The method of embodiment 167, wherein the oral dosage form or plurality of dosage forms comprises about 101 mg to about 700 mg citric acid; about 76 mg to about 226 mg magnesium citrate; about 3 mg to about 600 mg phytin; about 0.1 mg to about 15 mg pyridoxine; and about 1 mg to about 251 mg musa.

In general, the invention may alternatively comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group.

Reference throughout the specification to "some embodiments", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. An oral dosage form or plurality of dosage forms comprising citric acid and three ingredients selected from magnesium citrate, phytin, pyridoxine, and musa where in the dosage form or plurality of dosage forms is selected from:
   a. an oral dosage form or plurality of dosage forms wherein citric acid is present in an amount of about 101 mg to about 699 mg, magnesium citrate is present in an amount of about 77 mg to about 227 mg, phytin is present in an amount of about 3.06 mg to about 600 mg, and pyridoxine is present in an amount of about 0.23 mg to about 15.13 mg, wherein the percent inhibition of calcium oxalate crystal formation by the combination of active ingredients is greater than about 89%;
   b. an oral dosage form or plurality of dosage forms wherein citric acid is present in an amount of about 102 mg to about 1052 mg, magnesium citrate is present in an amount of about 2.32 mg to about 201 mg, phytin is present in an amount of about 100 mg to about 600 mg, and musa is present in an amount of about 1.51 mg to about 251 mg, wherein the percent inhibition of calcium oxalate crystal formation by the combination of active ingredients is greater than about 92%;
   c. an oral dosage form or plurality of dosage forms wherein citric acid is present in an amount of about 101 mg to about 1051 mg, magnesium citrate is present in an amount of about 2.14 mg to about 226 mg, pyridoxine is present in an amount of about 0.25 mg to about 10.23 mg, and musa is present in an amount of about 41 mg to about 252 mg, wherein the percent inhibition of calcium oxalate crystal formation by the combination of active ingredients is greater than about 59%; and
   d. an oral dosage form or plurality of dosage forms wherein citric acid is present in an amount of about 101 mg to less than about 700 mg, phytin is present in an amount of about 101 mg to about 600 mg, pyridoxine is present in an amount of about 0.23 mg to about 15.12 mg, and musa is present in an amount of about 1.46 mg to about 252 mg, wherein the percent inhibition of calcium oxalate crystal formation by the combination of active ingredients is greater than about 88%.

2. The oral dosage form or plurality of dosage forms according to claim 1, wherein
   citric acid is present in an amount of about 101 mg to about 699 mg,
   magnesium citrate is present in an amount of about 77 mg to about 227 mg,
   phytin is present in an amount of about 3.06 mg to about 600 mg, and
   pyridoxine is present in an amount of about 0.23 mg to about 15.13 mg.

3. The oral dosage form or a plurality of dosage forms according to claim 2, wherein the percent inhibition of calcium oxalate crystal formation by the combination of active ingredients is greater than about 94%.

4. The oral dosage form or plurality of dosage forms according to claim 1 wherein
   citric acid is present in an amount of about 102 mg to about 1052 mg,
   magnesium citrate is present in an amount of about 2.32 mg to about 201 mg,
   phytin is present in an amount of about 100 mg to about 600 mg, and
   musa is present in an amount of about 1.51 mg to about 251 mg.

5. The oral dosage form or a plurality of dosage forms according to claim 4, wherein the percent inhibition of calcium oxalate crystal formation by the combination of active ingredients is greater than about 97%.

6. The oral dosage form or plurality of dosage forms according to claim 1 wherein
   citric acid is present in an amount of about 101 mg to about 1051 mg, magnesium citrate is present in an amount of about 2.14 mg to about 226 mg,
pyridoxine is present in an amount of about 0.25 mg to about 10.23 mg, and
musa is present in an amount of about 41 mg to about 252 mg.

7. The oral dosage form or a plurality of dosage forms according to claim 6, wherein the percent inhibition of calcium oxalate crystal formation by the combination of active ingredients is greater than about 63%.

8. The oral dosage form or plurality of dosage forms according to claim 1 wherein
citric acid is present in an amount of about 101 mg to less than about 700 mg,
phytin is present in an amount of about 101 mg to about 600 mg,
pyridoxine is present in an amount of about 0.23 mg to about 15.12 mg, and
musa is present in an amount of about 1.46 mg to about 252 mg.

9. The oral dosage form or a plurality of dosage forms according to claim 8, wherein the percent inhibition of calcium oxalate crystal formation by the combination of active ingredients is greater than about 101%.

10. The oral dosage form or plurality of dosage forms according to claim 1 wherein
citric acid is present in an amount of about 350 mg; and three ingredients selected from
  i. magnesium citrate is present in an amount of about 150 mg;
  ii. phytin is present in an amount of about 200 mg;
  iii. pyridoxine is present in an amount of about 5 mg; and
  iv. musa is present in an amount of about 200 mg.

11. The oral dosage form or plurality of dosage forms according to claim 1 wherein
a. the amount of magnesium citrate is selected from:
  i. about 2.03 mg to about 151 mg,
  ii. about 2.03 mg to about 77 mg,
  iii. about 77 mg to about 201 mg,
  iv. about 77 mg to about 151 mg, and
  v. about 151 mg to about 201 mg;
b. the amount of phytin is selected from:
  i. about 100 mg to about 475 mg
  ii. about 100 mg to about 400 mg,
  iii. about 100 mg to about 202 mg,
  iv. about 201 mg to about 475 mg,
  v. about 201 to about 400 mg, and
  vi. about 400 to about 475 mg;
c. the amount of pyridoxine is selected from:
  i. about 0.22 mg to about 10.11 mg,
  ii. about 0.22 mg to about 6.01 mg,
  iii. about 0.22 mg to about 2.69 mg,
  iv. about 2.69 mg to about 15.1 mg,
  v. about 2.69 mg to about 10.11 mg,
  vi. about 2.69 mg to about 6.01 mg,
  vii. about 5.4 mg to about 15.1 mg,
  viii. about 5.4 mg to about 10.11 mg, and
  ix. about 10.11 mg to about 15.1 mg; and,
d. the amount of musa is selected from:
  i. about 1.46 mg to about 168 mg,
  ii. about 1.46 mg to about 85 mg,
  iii. about 1.46 mg to about 42 mg,
  iv. about 42 mg to about 252 mg,
  v. about 42 mg to about 168 mg,
  vi. about 42 mg to about 85 mg,
  vii. about 85 mg to about 252 mg,
  viii. about 85 mg to about 168 mg, and
  ix. about 168 mg to about 252 mg,
e. the amount of citric acid is selected from:
  i. about 101 mg to about 700 mg,
  ii. about 101 mg to about 352 mg,
  iii. about 101 mg to about 177 mg,
  iv. about 177 mg to about 1052 mg,
  v. about 177 mg to about 700 mg,
  vi. about 177 mg to about 352 mg,
  vii. about 351 mg to about 1052 mg,
  viii. about 351 mg to about 700 mg, and
  ix. about 700 mg to about 1052 mg.

12. The oral dosage form or plurality of dosage forms according to claim 1 where there is one oral dosage form.

13. The oral dosage form or plurality of dosage forms according to claim 1, which is a plurality of oral dosage forms.

14. The oral dosage form or plurality of dosage forms according to claim 1, wherein the oral dosage form or plurality of dosage forms is a capsule, an emulsion, or a plurality thereof.

15. A method of promoting kidney health in a subject, comprising administering to a subject the oral dosage form or plurality of dosage forms according to claim 1.

16. The method of claim 15, wherein the oral dosage form or plurality of dosage forms is administered once daily.

17. The method of claim 15, wherein the oral dosage form or plurality of dosage forms is administered twice daily.

18. The method of claim 15, wherein the oral dosage form or plurality of dosage forms comprises
  a. citric acid is present in the amount of about 350 mg;
  b. magnesium citrate is present in an amount of about 150 mg;
  c. phytin is present in an amount of about 200 mg;
  d. pyridoxine is present in an amount of about 5 mg; and
  e. musa is present in an amount of about 200 mg.

19. The method according to claim 18, wherein the percent inhibition of calcium oxalate crystal formation by the combination of active ingredients is greater than about 89%.

20. The method according to claim 15 wherein the oral dosage form or plurality of dosage forms comprises
citric acid is present in an amount of about 102 mg to about 1052 mg,
magnesium citrate is present in an amount of about 2.32 mg to about 201 mg,
phytin is present in an amount of about 100 mg to about 600 mg, and
musa is present in an amount of about 1.51 mg to about 251 mg.

21. The method according to claim 20, wherein the percent inhibition of calcium oxalate crystal formation by the combination of active ingredients is greater than about 92%.

22. The method according to claim 15, wherein the oral dosage form or plurality of dosage forms comprises
citric acid is present in an amount of about 101 mg to about 1051 mg,
magnesium citrate is present in an amount of about 2.14 mg to about 226 mg,
pyridoxine is present in an amount of about 0.25 mg to about 10.23 mg, and
musa is present in an amount of about 41 mg to about 252 mg.

23. The method according to claim 22, wherein the percent inhibition of calcium oxalate crystal formation by the combination of active ingredients is greater than about 59%.

24. The method according to claim 15 wherein the oral dosage form or plurality of dosage forms comprises
- citric acid is present in an amount of about 101 mg to less than about 700 mg,
- phytin is present in an amount of about 101 mg to about 600 mg,
- pyridoxine is present in an amount of about 0.23 mg to about 15.12 mg, and
- musa is present in an amount of about 1.46 mg to about 252 mg.

25. The method according to claim 24, wherein the percent inhibition of calcium oxalate crystal formation by the combination of active ingredients is greater than about 88%.

26. A method of inhibiting calcium oxalate formation, comprising administering to a subject the oral dosage form or plurality of dosage forms according to claim 1.

* * * * *